US007511119B2

(12) United States Patent
Liu et al.

(10) Patent No.: US 7,511,119 B2
(45) Date of Patent: Mar. 31, 2009

(54) PRAME PEPTIDE ANALOGUES

(75) Inventors: Liping Liu, Manassas, VA (US); Adrian Bot, Valencia, CA (US); David C. Diamond, West Hills, CA (US)

(73) Assignee: MannKind Corporation, Valencia, CA (US)

( * ) Notice: Subject to any disclaimer, the term of this patent is extended or adjusted under 35 U.S.C. 154(b) by 0 days.

(21) Appl. No.: 11/455,278

(22) Filed: Jun. 16, 2006

(65) Prior Publication Data

US 2007/0060524 A1     Mar. 15, 2007

Related U.S. Application Data

(60) Provisional application No. 60/691,889, filed on Jun. 17, 2005.

(51) Int. Cl.
A61K 38/04 (2006.01)
A61K 38/00 (2006.01)
A61K 51/00 (2006.01)

(52) U.S. Cl. ............................. 530/327; 530/326; 514/2; 426/1.69

(58) Field of Classification Search ............. 514/2
See application file for complete search history.

(56) References Cited

U.S. PATENT DOCUMENTS

| 5,538,866 | A | 7/1996 | Israeli et al. |
| 5,620,886 | A | 4/1997 | Brichard et al. |
| 5,747,271 | A | 5/1998 | Boon-Falleur et al. |
| 5,804,381 | A | 9/1998 | Chen et al. |
| 5,830,753 | A | 11/1998 | Coulie et al. |
| 5,874,560 | A | 2/1999 | Kawakami et al. |
| 5,935,818 | A | 8/1999 | Israeli et al. |
| 5,994,523 | A | 11/1999 | Kawakami et al. |
| 6,025,470 | A | 2/2000 | Valmori et al. |
| 6,274,145 | B1 | 8/2001 | Chen et al. |
| 6,417,165 | B1 | 7/2002 | Valmori et al. |
| 6,548,064 | B1 | 4/2003 | Tureci et al. |
| 6,605,711 | B1 | 8/2003 | Valmori et al. |
| 6,685,947 | B1 | 2/2004 | Jackson et al. |
| 6,709,844 | B1 | 3/2004 | Levy |
| 6,861,234 | B1 | 3/2005 | Simard et al. |
| 6,977,074 | B2 | 12/2005 | Kündig et al. |
| 6,994,851 | B1 | 2/2006 | Kündig et al. |
| 2003/0046714 | A1 | 3/2003 | Simard et al. |
| 2003/0138808 | A1 | 7/2003 | Simard et al. |
| 2003/0186355 | A1 | 10/2003 | Ossendorp et al. |
| 2003/0215425 | A1 | 11/2003 | Simard et al. |
| 2003/0220239 | A1 | 11/2003 | Simard et al. |
| 2003/0228634 | A1 | 12/2003 | Simard et al. |
| 2004/0180354 | A1 | 9/2004 | Simard et al. |
| 2004/0253218 | A1 | 12/2004 | Eisenbach-Schwartz et al. |
| 2005/0079152 | A1 | 4/2005 | Bot et al. |
| 2005/0118186 | A1 | 6/2005 | Chiang et al. |
| 2005/0287068 | A1 | 12/2005 | Bot et al. |
| 2006/0008468 | A1 | 1/2006 | Chiang et al. |
| 2006/0057673 | A1 | 3/2006 | Liu et al. |
| 2006/0063913 | A1 | 3/2006 | Liu et al. |
| 2006/0094661 | A1 | 5/2006 | Liu et al. |
| 2006/0153844 | A1 | 7/2006 | Kündig et al. |
| 2006/0159689 | A1 | 7/2006 | Chiang et al. |
| 2006/0159694 | A1 | 7/2006 | Chiang et al. |
| 2006/0165711 | A1 | 7/2006 | Bot et al. |
| 2007/0003563 | A1 | 1/2007 | Bot et al. |
| 2007/0004662 | A1 | 1/2007 | Qiu et al. |

FOREIGN PATENT DOCUMENTS

| WO | WO 99/02183 | 1/1999 |
| WO | WO 01/62776 | 8/2001 |
| WO | WO 02/069907 | 9/2002 |
| WO | WO 02/081646 | 10/2002 |
| WO | WO 02/102299 | 12/2002 |
| WO | WO 03/076585 | 9/2003 |
| WO | WO 2004/018666 | 3/2004 |
| WO | WO 2004/022709 | 3/2004 |
| WO | WO 2004/112825 | 12/2004 |
| WO | WO 2006/009920 | 1/2006 |
| WO | WO 2006/014579 A2 | 2/2006 |

OTHER PUBLICATIONS

Online Medical Dictionary, http://cancerweb.ncl.ac.uk/cgi-bin/omd?query=immunogenic, Nov. 18, 1997.*
Falk et al. *Nature.* 351:290-296 (1991).
Kessler et al. *J. Exp. Med.* 193(1):73-88 (2001).
Ayyoub et al. *J. Immunol.* 168(4): 1717-22 (2002).
Ayyoub et al. *Cancer Res.* 63(17): 5601-6 (2003).
Baratin. *J. Peptide Sci.* 8:327-334 (2002).
Blanchet et al. *J. Immunol.* 167:5852-5861 (2001).
Chung et al. *J. Immunother.* 22:279-287 (1999).
Gure et al. *Int. J. Cancer.* 72:965-971 (1997).
Jäger et al. *J. Exp. Med.* 187(2):265-270 (1998).
Morel et al. *Immunity.* 12:107-117 (2000).
Parker et al. *J. Immunol.* 152:163-175 (1994).
Parkhurst et al. *J. Immunol.* 157(6):2539-2548 (1996).
Pascolo et al. *J. Exp. Med.* 185(12):2043-51 (1997).
Probst-Kepper et al. *J. Immunol.* 173:5610-5616 (2004).
Rammensee et al. *MHC Ligands and Peptide Motifs.* New York: Landes Bioscience, 1997.
Regner et al. *Exp. Clin. Immunogenet.* 13(1):30-35 (1996).
Salgaller et al. *Cancer Res.* 55:4972-4979 (1995).
Sasada et al. *Eur. J. Immunol.* 30:1281-1289 (2000).
Schönbach et al. *Nucleic Acids Research.* 28(1):222-224 (2000).
Schönbach et al. *Nucleic Acids Research.* 30(1):226-229 (2002).
Stauss et al. *Proc. Natl. Acad. Sci. USA.* 89:7871-7875 (1992).
Tsai et al. *J. Immunol.* 158:1796-1802 (1997).

(Continued)

Primary Examiner—Andrew D. Kosar
Assistant Examiner—Maury Audet
(74) Attorney, Agent, or Firm—Davis Wright Tremaine LLP

(57) ABSTRACT

Some embodiments relate to analogs of peptides corresponding to class I MHC-restricted T cell epitopes and methods for their generation. These analogs can contain amino acid substitutions at residues that directly interact with MHC molecules, and can confer improved, modified or useful immunologic properties. Additionally, classes of analogs, in which the various substitutions comprise the non-standard residues norleucine and/or norvaline, are disclosed.

26 Claims, 49 Drawing Sheets

OTHER PUBLICATIONS

Valmori et al. *J Immunol.* 160(4): 1750-1758 (1998).
Vertuani et al. *J Immunol.* 172(6): 3501-3508 (2004).
Wagner et al. *Cancer Immunity.* 3:18 (2003).
World Wide Web page of Hans -Georg Rammensee, Jutta Bachmann, Niels Emmerich, Stefan Stevanovic: SYFPEITHI: An Internet Database for MHC Ligands and Peptide Motifs (hypertext transfer protocol access via: syfpeithi. bmi-heidelberg. com/ scripts/ MHCServer. dll/ home.htm) and "bimas. dcrt. nih. gov/ molbio/ hla_bind."
Zhang et al. *J. Mol. Biol.* 281:929-947 (1998).
U.S. Appl. No. 60/580,969, filed Jun. 17, 2004. Title: Combinations of Tumor-Associated Antigens in Diagnotistics for Various Types of Cancers.
U.S. Appl. No. 09/560,465, filed Apr. 28, 2000. Title: Epitope Synchronization in Antigen Presenting Cells.
U.S. Appl. No. 09/561,571, filed Apr. 28, 2000. Title: Epitope Clusters.
U.S. Appl. No. 11/323,520, filed Dec. 29, 2005. Title: Methods to Bypass CD4+ Cells in the Induction of an Immune Response.
U.S. Appl. No. 11/454,300, filed Jun. 16, 2006. Title: Melanoma Antigen Peptide Analogues.
U.S. Appl. No. 11/454,633, filed Jun. 16, 2006. Title: PSMA Peptide Analogues.

\* cited by examiner

| K | A | S | E | K | I | F | Y | V |
|---|---|---|---|---|---|---|---|---|
| F | L | N | L | T | L | | | |
| Y | V | S | V | F | V | | | |
| W | I | T | M | S | I | | | |
| D-Lys | M | Q | Nle | Phe-4F | A | | | |
| Phg | D-Ala | Nle | Nva | Phg | M | | | |
| Cha | D-Leu | Nva | | | Abu | | | |
| Phe (4-F) | D-Val | | | | Nle | | | |
| Phe (4-NO2) | Nal-1 | | | | Nva | | | |
| O-methyl-Tyr | Nal-2 | | | | Aib | | | |
| β-(3-benzothienyl) Ala | Abu | | | | MeLeu | | | |
| | Nle | | | | MeVal | | | |
| | Nva | | | | D-Val | | | |
| | Aib | | | | D-Leu | | | |
| | | | | | -NH2 | | | |

Figure 1A: Overview of the designed nonamer analogs

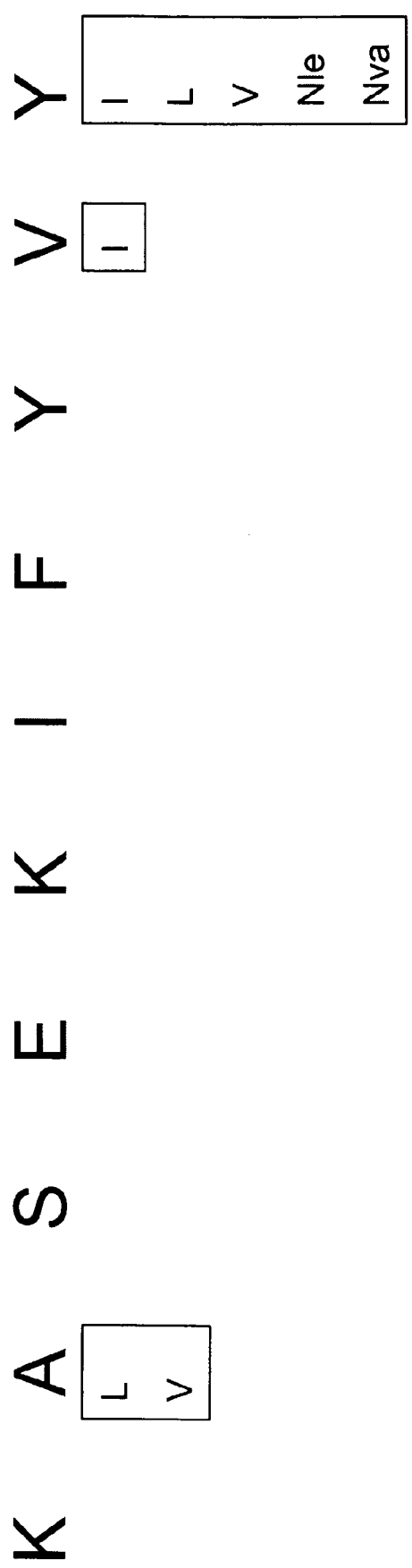
Figure 1B: Overview of the designed decamer analogs

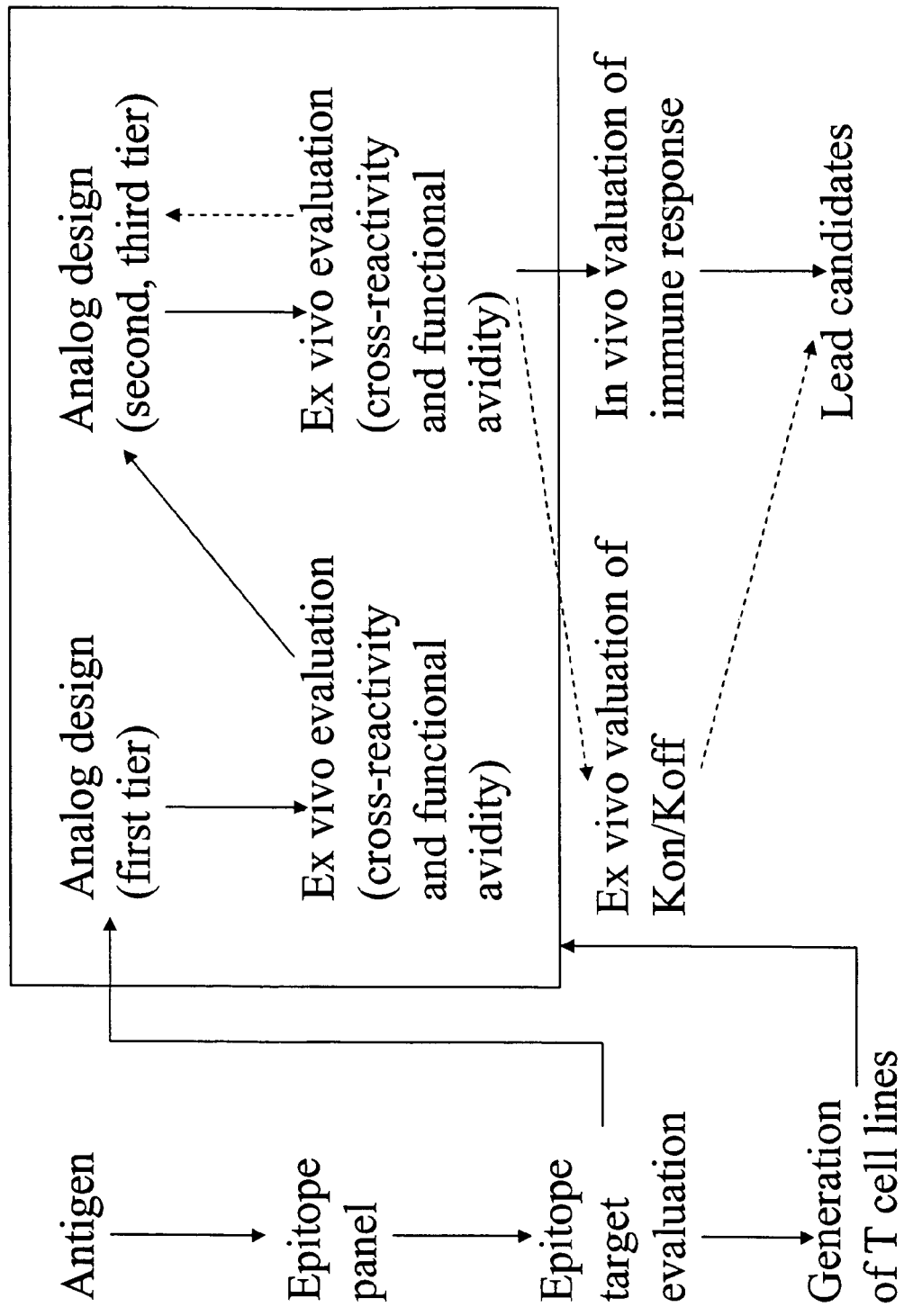
Figure 2: Methodology

Figure 3: Cross-reactivity and functional avidity of analogs substituted at single position

| Category | Number | Peptide name | Sequence | NOTE | Cross-reactivity and fct avidity (native to analogues) * | **Cross-reactivity and fct avidity (Nat to analogues, peak IFNgamma) |
|---|---|---|---|---|---|---|
| Native | 1 | SSX2 41-49 | KASEKIFYV | Native peptide | 1 | 46 |
| N-terminal Primary Anchor | 2 | SSX2 41-49 (A42L) | KLSEKIFYV | | 0.03 | 89 |
| | 3 | SSX2 41-49 (A42V) | KVSEKIFYV | | 0.03 | 65 |
| | 4 | SSX2 41-49 (A42I) | KISEKIFYV | | 3 | 55 |
| | 5 | SSX2 41-49 (A42M) | KMSEKIFYV | | 0.1 | 65 |
| | 6 | SSX2 41-49 (A42a) | KaSEKIFYV | Small letter stands for the corresponding d-Amino acid | 10 | 26 |
| | 7 | SSX2 41-49 (A42v) | KvSEKIFYV | | 3 | 43 |
| | 8 | SSX2 41-49 (A42Nal-1) | KNal-1SEKIFYV | Nal-1 is 1-naphtyl L-Ala | >10 | 12 |
| | 9 | SSX2 41-49 (A42Nal-2) | KNal-2SEKIFYV | Nal-1 is 2-naphtyl L-Ala | 3 | 48 |
| | 10 | SSX2 41-49 (A42Abu) | KAbuSEKIFYV | Abu is L-α-aminobutyric acid | 0.3 | 60 |
| | 11 | SSX2 41-49 (A42Nle) | KNleSEKIFYV | Nle is Norleucine | 0.1 | 69 |
| | 12 | SSX2 41-49 (A42Nva) | KNvaSEKIFYV | Nva is Norvaline | 0.1 | 72 |
| | 13 | SSX2 41-49 (A42Aib) | KAibSEKIFYV | Aib is α-aminoisobutyric acid | 3 | 70 |
| N-terminal Secondary Anchor | 14 | SSX2 41-49 (K41F) | FASEKIFYV | | 0.3 | 59 |
| | 15 | SSX2 41-49 (K41W) | WASEKIFYV | | >10 | 16 |
| | 16 | SSX2 41-49 (K41Y) | YASEKIFYV | | 3 | 53 |
| | 17 | SSX2 41-49(K41k) | kASEKIFYV | k is d-Lys | >10 | 10 |
| | 18 | SSX2 41-49 (K41Phg) | PhgASEKIFYV | Phg is Phenylglycine | 0.1 | 40 |
| | 19 | SSX2 41-49 (K41Cha) | ChaASEKIFYV | Cha is β-cyclohexylalanine | >10 | 18 |
| | 20 | SSX2 41-49 (K41Phe-4F) | Phe(4-F)ASEKIFYV | Phe(4-F) is 4-Fluorophenylalanie | 3 | 49 |
| | 21 | SSX2 41-49 (K41Phe-4NO2) | Phe(4-NO2)ASEKIFYV | Phe(4-NO2) is 4-Nitrophenylalanie | 3 | 46 |
| | 22 | SSX2 41-49 (K41O-methyl Tyr) | O-methyl-TyrASEKIFYV | O-methyl-Tyr is O-methyl-L-tyrosine | 3 | 41 |
| | 23 | SSX2 41-49 (K41β-(3-benzothienyl)Ala) | β-(3-benzothienyl)AlaASEKIFYV | β-(3-benzothienyl)Ala:  | 10 | 23 |
| C-terminal Primary Anchor | 24 | SSX2 41-49 (V49I) | KASEKIFYI | Based on 1st round of cross-reactivity data | 10 | 24 |
| C-terminal amide | 25 | SSX2 41-49-NH2 | KASEKIFYV-NH2 | Exploring the C-terminus anchor residue | >10 | 12 |
| | 26 | SSX2 41-49-NH2 (A42L) | KLSEKIFYV-NH2 | Exploring the C-terminus anchor residue | 3 | 65 |
| | 27 | SSX2 41-49-NH2 (A42V) | KVSEKIFYV-NH2 | Exploring the C-terminus anchor residue | 10 | 49 |
| | | | | | | |

* μM; **ng/ml

Figure 4: Cross-reactivity and functional avidity of analogs substituted at two positions

| Category | Number | Peptide name | Sequence | NOTE | Cross-reactivity and fct avidity (native to analogues) * | **Cross-reactivity and fct avidity (Nat to analogues, peak IFNgamma) | **Cross-reactivity and fct avidity (analogue conc at peak IFNgamma) |
|---|---|---|---|---|---|---|---|
| Native | 1 | SSX2 41-49 | KASEKIFYV | Native peptide | 1 | 46 | 10 |
| N-terminal Primary/Secondary Anchor | 2 | SSX2 41-49 (K41Y, A42V) | YVSEKIFYV | | 0.1 | 69 | 10 |
| | 3 | SSX2 41-49 (K41Y, A42M) | YMSEKIFYV | | 3 | 44 | 10 |
| | 4 | SSX2 41-49 (K41Y, A42I) | YISEKIFYV | | 1 | 52 | 3 |
| | 5 | SSX2 41-49 (K41F, A42L) | FLSEKIFYV | | 0.3 | 50 | 10 |
| | 6 | SSX2 41-49 (K41F, A42V) | FVSEKIFYV | | 0.1 | 61 | 10 |
| | 7 | SSX2 41-49 (K41F, A42M) | FMSEKIFYV | | 3 | 36 | 10 |
| | 8 | SSX2 41-49 (K41F, A42I) | FISEKIFYV | | 0.3 | 51 | 10 |
| | 9 | SSX2 41-49 (K41W, A42L) | WLSEKIFYV | | 0.3 | 43 | 10 |
| | 10 | SSX2 41-49 (K41W, A42V) | WVSEKIFYV | | 1 | 54 | 10 |
| | 11 | SSX2 41-49 (K41W, A42M) | WMSEKIFYV | | 1 | 49 | 10 |
| | 12 | SSX2 41-49 (K41W, A42I) | WISEKIFYV | | 0.1 | 53 | 10 |
| | 13 | SSX2 41-49 (K41k, A42L) | kLSEKIFYV | | 10 | 48 | 10 |
| | 14 | SSX2 41-49 (K41k, A42V) | kVSEKIFYV | | 10 | 52 | 10 |
| N-terminal Primary Anchor, C-terminal Primary Anchor | 16 | SSX2 41-49 (A42V, V49I) | KVSEKIFYI | | 0.3 | 68 | 10 |
| | 17 | SSX2 41-49 (A42L, V49I) | KLSEKIFYI | | 0.03 | 68 | 10 |
| | 18 | SSX2 41-49 (A42a, V49v) | KaSEKIFYv | | ≥10 | ≥15 | 3 |

* µM; **ng/ml

Figure 5: Cross-reactivity and functional avidity of analogs substituted at more than two positions

| Category | Number | Peptide name | Sequence | NOTE | Cross-reactivity and fct avidity (native to analogues)* | *Cross-reactivity and fct avidity (Nat to analogues, peak IFNgamma) | **Cross-reactivity and fct avidity (analogue at peak conc at peak IFNgamma) |
|---|---|---|---|---|---|---|---|
| Native | 1 | SSX2 41-49 | KASEKIFYV | Native peptide | | | |
| N-terminal Primary/Secondary Anchor, C-terminal Primary Anchor | 2 | SSX2 41-49 (K41F, A42V, V49L) | FVSEKIFYL | Exploring the C-terminus anchor residue | 1 | 45 | 10 |
| | 3 | SSX2 41-49 (K41F, A42V, V49I) | FVSEKI Figure 6: Cross-reactivity and functional avidity of decamer analogs encompassing the nominal 41-49 peptide

| Category | Number | Peptide name | Sequence | NOTE | Cross-reactivity and fct avidity (native to analogues)* | Cross-reactivity and fct avidity (Nat to analogues, peak IFNgamma) | Cross-reactivity and fct avidity (analogue conc at peak IFNgamma) |
|---|---|---|---|---|---|---|---|
| Native | 1 | SSX2 41-49 | KASEKIFYV | Native peptide | 1 | 46 | 10 |
| Decamer | 2 | SSX2 41-50 | KASEKIFYVY | Native peptide | | | |
| | 3 | SSX2 41-50 (Y50I) | KASEKIFYVI | | 10 | 25 | 10 |
| | 4 | SSX2 41-50 (Y50L) | KASEKIFYVL | | 10 | 31 | 10 |
| | 5 | SSX2 41-50 (Y50V) | KASEKIFYVV | | | | |
| | 6 | SSX2 41-50 (Y50 (Nle)) | KASEKIFYV(Nle) | | | | |
| | 7 | SSX2 41-50 (Y50 (Nva)) | KASEKIFYV(Nva) | | | | |
| | 8 | SSX2 41-50 (A42V,Y50I) | KVSEKIFYVI | | 10 | 44 | 10 |
| | 9 | SSX2 41-50 (A42V,Y50L) | KVSEKIFYVL | | 10 | 41 | 10 |
| | 10 | SSX2 41-50 (A42L,Y50L) | KLSEKIFYVL | | 3 | 58 | 10 |
| | 11 | SSX2 41-50 (A42V,Y50V) | KVSEKIFYVV | | 10 | 25 | 10 |
| | 12 | SSX2 41-50 (A42L,Y50V) | KLSEKIFYVV | | 10 | 44 | 10 |
| | 13 | SSX2 41-50 (A42V,Y50(Nle)) | KVSEKIFYV(Nle) | | 10 | 55 | 10 |
| | 14 | SSX2 41-50 (A42L,Y50(Nle)) | KLSEKIFYV(Nle) | | 10 | 39 | 10 |
| | 15 | SSX2 41-50 (A42V,Y50(Nva)) | KVSEKIFYV(Nva) | | | | |
| | 16 | SSX2 41-50 (A42L,Y50(Nva)) | KLSEKIFYV(Nva) | | 10 | 40 | 10 |

Spleen — In Vivo Specific Lysis

| | SSX2 Mean | 1ug/ml SEM | SSX2 Mean | 20ug/ml SEM |
|---|---|---|---|---|
| Control | -0.2 | 2.8 | -0.2 | 2.8 |
| SSX 41-49 natural | 50.8 | 13.9 | 71.9 | 17.1 |
| SSX2 A42V | 72.4 | 4.42 | 94.7 | 3.22 |
| SSX2 K41F | 68.2 | 9.5 | 91.3 | 5.4 |
| SSX2 K41Y | 69.2 | 14.45 | 90.7 | 8.45 |
| SSX2 A42V V49I | 56.3 | 28.29 | 74.4 | 27.34 |
| SSX2 K41Y A42V | 46.8 | 23.5 | 67.2 | 29.1 |
| SSX2 K41F A42V E44Na | 53.0 | 7.6 | 70.1 | 14.7 |
| EAA | 0.6 | 2.85 | 1.7 | 1.8 |

Figure 11

| Blood | In Vivo Specific Lysis | | | | MHC Binding (1/RA) | MHC Stability (hrs) |
|---|---|---|---|---|---|---|
| | SSX2 Mean | SSX2 1ug/ml SEM | SSX2 Mean | SSX2 20ug/ml SEM | | |
| Control | -0.01 | 0.88 | 0.3 | 1.61 | - | - |
| SSX 41-49 natural | 59.64 | 15.33 | 73.33 | 15.53 | 1.0 | 11 |
| SSX2 A42V | 79.31 | 3.91 | 90.84 | 0.72 | 2.8 | 20 |
| SSX2 K41F | 74.28 | 11.46 | 89.07 | 3.20 | 1.5 | >24 |
| SSX2 K41Y | 72.49 | 11.69 | 88.21 | 4.02 | 1.7 | >24 |
| SSX2 A42V V49I | 61.27 | 27.62 | 68.84 | 27.86 | 1.1 | |
| SSX2 K41Y A42V | 52.60 | 25.65 | 66.21 | 28.18 | | >24 |
| SSX2 K41F A42V E44Nva | 55.38 | - | 65.98 | - | 3.9 | >24 |
| EAA | 3.06 | 1.26 | 2.61 | 3.96 | | |

Figure 13A

* Min conc (uM) analogue for value > 10xbck
** Maximal conc of cytokine (ng/ml); bkg = 0.046+0.011 ng/ml
Comparable with or more potent than L's C165V
More potent than natural, less potent than L's
Less potent than natural

| Category | Peptide name | Sequence | NOTE | Half-maximal Binding (µM) | Relative affinity (1/RA) | *Cross-reactivity and fct avidity (Nat to analogues, min conc) | **Cross-reactivity and fct avidity (Nat to analogues, peak IFNgamma) |
|---|---|---|---|---|---|---|---|
| Native | NY-ESO-1 157-165 | SLLMMWITQC | Native Peptide | 27.89 | 1.0 | 0.3 | 1.83 |
| N-terminal Primary Anchor | NY-ESO-1 157-165 (S157Y) | YLLMMWITQC | Anchors explore | 26.32 | 1.1 | >10 | 0.43 |
| | NY-ESO-1 157-165 (S157F) | FLLMMWITQC | Anchors explore | | | 10 | 1.9 |
| | NY-ESO-1 157-165(S157K) | KLLMMWITQC | Anchors explore (improve the solubility) | | | 10 | 1.81 |
| N-terminal Primary/Secondary Anchor | NY-ESO-1 157-165 (S157F, L158V) | FVLMMWITQC | Anchors explore | 12.19 | 2.3 | >10 | 0.08 |
| | NY-ESO-1 157-165 (S157F, L158I) | FILMMWITQC | Anchors explore | 27.07 | 1.0 | >10 | 0.17 |
| | NY-ESO-1 157-165 (S157Y, L158V) | YVLMMWITQC | Anchors explore | 24.9 | 1.1 | >10 | 0.28 |
| | NY-ESO-1 157-165 (S157Y, L158I) | YILMMWITQC | Anchors explore | | | | |
| N-terminal secondary and C-terminal primary anchor | NY-ESO-1 157-165 (S157Y, C165V) | YLLMMWITQV | Anchors explore | 1.92 | 14.5 | 0.3 | 0.78 |
| | NY-ESO-1 157-165 (S157Y, C165L) | YLLMMWITQL | Anchors explore | 6.05 | 4.6 | >10 | 0.45 |
| | NY-ESO-1 157-165 (S157Y, C165A) | YLLMMWITQA | Anchors explore | 2.26 | 12.3 | >10 | 0.28 |
| | NY-ESO-1 157-165 (S157Y, C165I) | YLLMMWITQI | Anchors explore | 2.33 | 12.0 | >10 | 0.35 |
| | NY-ESO-1 157-165 (S157F, C165V) | FLLMMWITQV | Anchors explore | 2.95 | 9.5 | 0.001 | 1.67 |
| | NY-ESO-1 157-165 (S157F, C165L) | FLLMMWITQL | Anchors explore | 1.96 | 14.2 | 0.03 | 0.74 |
| | NY-ESO-1 157-165 (S157F, C165A) | FLLMMWITQA | Anchors explore | 1.84 | 15.2 | 1 | 1 |
| | NY-ESO-1 157-165 (S157F, C165I) | FLLMMWITQI | Anchors explore | 2.09 | 13.3 | 0.03 | 0.91 |
| | NY-ESO-1 157-165 (S157K, C165V) | KLLMMWITQV | Anchors explore (improve the solubility) | | | 0.001 | 1.66 |
| | NY-ESO-1 157-165 (S157K, C165L) | KLLMMWITQL | Anchors explore | | | 0.03 | 2.77 |
| | NY-ESO-1 157-165 (S157K, C165A) | KLLMMWITQA | Anchors explore (improve the solubility) | | | 1 | 0.68 |
| | NY-ESO-1 157-165 (S157K, C165I) | KLLMMWITQI | Anchors explore | | | 0.01 | 1.65 |
| | NY-ESO-1 157-165 (S157Y, C165(Abu)) | YLLMMWITQ(Abu) | | | | | |
| | NY-ESO-1 157-165 (S157Y, C165(Nva)) | YLLMMWITQ(Nva) | Anchors explore | | | 0.001 | 1.9 |
| | NY-ESO-1 157-165 (S157Y, C165(Nle)) | YLLMMWITQ(Nle) | Anchors explore | | | 0.001 | 1.5 |

Figure 13B

| Category | Peptide name | Sequence | NOTE | Half-maximal Binding (µM) | Relative affinity (1/RA) | *Cross-reactivity and fct avidity (Nat to analogues, min conc) | **Cross-reactivity and fct avidity (Nat to analogues, peak IFNgamma) |
|---|---|---|---|---|---|---|---|
| N-terminal primary/secondary and C-terminal primary anchor | NY-ESO-1 157-165 (S157Y, L158V, C165V) | YVLMMTQV | Anchors explore | 2.33 | 12.0 | 1 | 0.72 |
| | NY-ESO-1 157-165 (S157Y, L158V, C165L) | YVLMMTQL | Anchors explore | 3.12 | 8.9 | >10 | 0.08 |
| | NY-ESO-1 157-165 (S157Y, L158V, C165A) | YVLMMTQA | Anchors explore | 5.44 | 5.1 | >10 | 0.07 |
| | NY-ESO-1 157-165 (S157Y, L158V, C165I) | YVLMMTQI | Anchors explore | 5.02 | 5.6 | 3 | 0.59 |
| | NY-ESO-1 157-165 (S157Y, L158I, C165V) | YILMMTQV | Anchors explore | 1.13 | 24.7 | 0.1 | 1.51 |
| | NY-ESO-1 157-165 (S157Y, L158I, C165L) | YILMMTQL | Anchors explore | 4.26 | 6.6 | 3 | 1.62 |
| | NY-ESO-1 157-165 (S157Y, L158I, C165A) | YILMMTQA | Anchors explore | 1.11 | 25.1 | >10 | 0.12 |
| | NY-ESO-1 157-165 (S157Y, L158I, C165I) | YILMMTQI | Anchors explore | 2.31 | 12.1 | 3 | 0.81 |
| | NY-ESO-1 157-165 (S157F, L158V, C165V) | FVLMMTQV | Anchors explore | 1.63 | 17.1 | 0.3 | 1.21 |
| | NY-ESO-1 157-165 (S157F, L158V, C165L) | FVLMMTQL | Anchors explore | 1.15 | 24.3 | 0.3 | 0.6 |
| | NY-ESO-1 157-165 (S157F, L158V, C165A) | FVLMMTQA | Anchors explore | 4.26 | 6.5 | >10 | 0.13 |
| | NY-ESO-1 157-165 (S157F, L158V, C165I) | FVLMMTQI | Anchors explore | 4.21 | 6.6 | 3 | 0.55 |
| | NY-ESO-1 157-165 (S157F, L158I, C165V) | FILMMTQV | Anchors explore | 12.28 | 2.3 | 0.3 | 0.81 |
| | NY-ESO-1 157-165 (S157F, L158I, C165L) | FILMMTQL | Anchors explore | 6.17 | 4.5 | >10 | 0.37 |
| | NY-ESO-1 157-165 (S157F, L158I, C165A) | FILMMTQA | Anchors explore | 2.98 | 9.4 | 1 | 0.6 |
| | NY-ESO-1 157-165 (S157F, L158I, C165I) | FILMMTQI | Anchors explore | 3.55 | 7.9 | >10 | 0.38 |
| N-terminal secondary and TCR site | NY-ESO-1 157-165 (S157Y, M160A, C165V) | YLLAMTQV | TCR explore | 5.62 | 5.0 | >10 | 0.14 |
| | NY-ESO-1 157-165 (S157Y, M160V, C165V) | YLVMTQV | TCR explore | 6.9 | 4.0 | >10 | 0.32 |
| | NY-ESO-1 157-165 (S157Y, M160I, C165V) | YLLIMTQV | TCR explore | 3.83 | 7.3 | 0.1 | 0.13 |
| | NY-ESO-1 157-165 (S157Y, M160L, C165V) | YLLNMTQV | TCR explore | 0.83 | 33.6 | 10 | 0.69 |
| | NY-ESO-1 157-165 (S157Y, M160N, C165V) | YLLNMTQV | TCR explore | 6.07 | 4.6 | 10 | 0.54 |
| | NY-ESO-1 157-165 (S157Y, I162A, C165V) | YLLMMATQV | TCR explore | | | 3 | 1.1 |
| | NY-ESO-1 157-165 (S157Y, I162L, C165V) | YLLMMLTQV | TCR explore | | | 3 | 0.68 |
| | NY-ESO-1 157-165 (S157Y, I162L, C165V) | YLLMMLTQV | TCR explore | 0.81 | 34.4 | >10 | 0.08 |
| | NY-ESO-1 157-165 (S157Y, I162T, C165V) | YLLMMTTQV | TCR explore | 6.12 | 4.6 | 3 | 0.81 |
| | NY-ESO-1 157-165 (S157Y, I162V, C165V) | YLLMMVTQV | TCR explore | 4.53 | 6.2 | 10 | 0.64 |
| | NY-ESO-1 157-165 (S157Y, I162N, C165V) | YLLMNTQV | TCR explore | 5.45 | 5.1 | >10 | 0.31 |
| | NY-ESO-1 157-165 (S157Y, Q164A, C165V) | YLLMMTAV | TCR explore | | | 10 | 1.57 |
| | NY-ESO-1 157-165 (S157Y, Q164E, C165V) | YLLMMTEV | TCR explore | | | 10 | 0.49 |
| | NY-ESO-1 157-165 (S157Y, Q164D, C165V) | YLLMMTDV | TCR explore | | | 10 | 0.36 |
| | NY-ESO-1 157-165 (S157Y, Q164N, C165V) | YLLMMTNV | TCR explore | | | >10 | 0.81 |
| | NY-ESO-1 157-165 (S157Y, Q164T, C165V) | YLLMMTTV | TCR explore | | | 3 | 0.49 |
| | NY-ESO-1 157-165 (S157Y, Q164S, C165V) | YLLMMTSV | TCR explore | | | >10 | 0.37 |

Figure 13C

| Category | Peptide name | Sequence | NOTE | Half-maximal Binding (µM) | Relative affinity (1/RA) | *Cross-reactivity and fct avidity (Nat to analogues, min conc) | **Cross-reactivity and fct avidity (Nat fct avidity to analogues, peak IFNgamma) |
|---|---|---|---|---|---|---|---|
| C-terminal amide | NY-ESO-1 157-165-NH2 (S157Y, C165V) | YLLMWITQV-NH2 | Anchors explore | | | 1 | 0.6 |
| | NY-ESO-1 157-165-NH2 (S157Y, C165L) | YLLMWITQL-NH2 | Anchors explore | | | 3 | 0.68 |
| | NY-ESO-1 157-165-NH2 (S157Y, C165A) | YLLMWITQA-NH2 | Anchors explore | | | >10 | 0.04 |
| C-terminal anchor (Ludwig patent) | NY-ESO-1 157-165 (C165V) | SLLMWITQV | Anchors explore | 6.13 | 4.5 | 0.001 | 2.46 |
| | NY-ESO-1 157-165 (C165L) | SLLMWITQL | Anchors explore | | | 0.001 | 2.44 |
| | NY-ESO-1 157-165 (C165A) | SLLMWITQA | Anchors explore | 4.29 | 6.5 | 0.01 | 2.2 |
| | NY-ESO-1 157-165 (C165I) | SLLMWITQI | Anchors explore | 9.99 | 2.8 | 0.001 | 3.44 |
| | NY-ESO-1 157-166 | SLLMWITQCF | Based on the proposal by Ddiamond | | | >10 | 0.19 |
| | NY-ESO-1 157-166 (F166L) | SLLMWITQCL | Based on the proposal by Ddiamond | | | 10 | 0.78 |
| | NY-ESO-1 157-166 (S157Y, C165V, F166L) | YLLMWITQVL | Based on the proposal by Ddiamond | | | 1 | 0.95 |
| | NY-ESO-1 157-166 (S157Y, C165V, F166I) | YLLMWITQVI | Based on the proposal by Ddiamond | | | 1 | 0.65 |
| | NY-ESO-1 157-166 (S157Y, C165V, F166V) | YLLMWITQVV | Based on the proposal by Ddiamond | | | >10 | 0.22 |
| | NY-ESO-1 157-166 (S157Y, C165V, F166(Nle)) | YLLMWITQV(Nle) | Based on the proposal by Ddiamond | | | 10 | 1.68 |
| Decamer | NY-ESO-1 157-166 (S157Y, C165V, F166 (Nva)) | YLLMWITQV(Nva) | Based on the proposal by Ddiamond | | | >10 | 0.18 |
| | | SVLMWITQL | Additional peptides | | | 0.03 | 2.93 |
| | | SVLMWITQI | Additional peptides | | | 0.03 | 2.68 |
| | | SVLMWITQV | Additional peptides | | | 0.001 | 3.84 |
| | | SILMWITQL | Additional peptides | | | 0.001 | 3.25 |
| | | YNleLMWITQV | Additional peptides | | | 0.003 | 2.61 |
| | | WVLMWITQV | Additional peptides | | | 1 | 2.35 |
| | | SVLMWITQA | Additional peptides | | | 0.3 | 1.87 |
| | | SVLMWITQC | Additional peptides | | | 1 | 1.47 |
| | | TVLMWITQV | Additional peptides | | | 0.01 | 3.64 |
| | | YNvaLMWITQV | Additional peptides | | | 0.001 | 2.91 |
| | | SILMWITQC | Additional peptides | | | 0.1 | 2.69 |
| | | SILMWITQA | Additional peptides | | | 0.03 | 2.91 |
| | | SILMWITQV | Additional peptides | | | 0.001 | 3.57 |

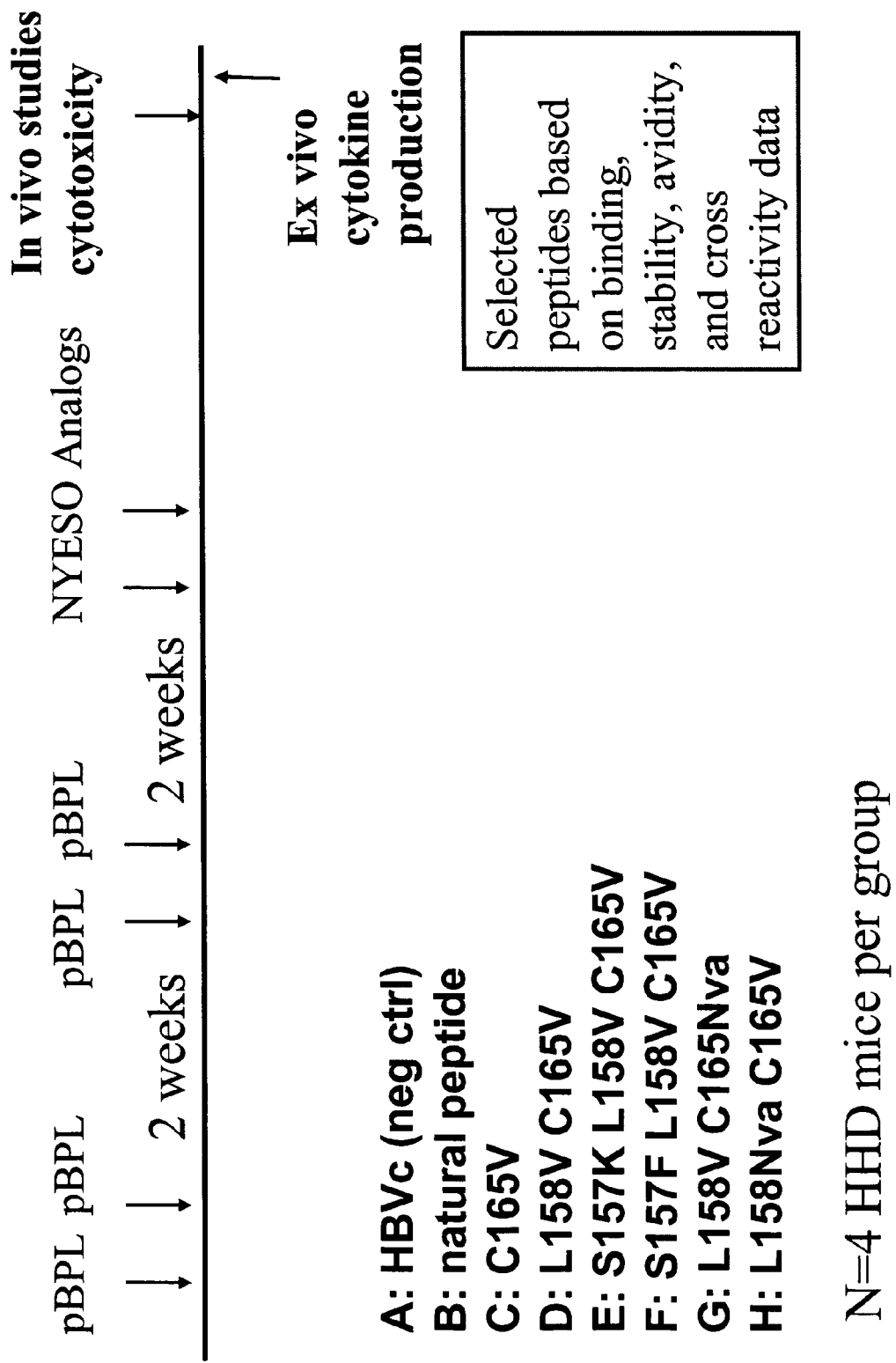

Immunization protocol for HHD Experiment 22:

2 clusters (4 total injections) of pBPL plasmid followed by 1 cluster of NY-ESO analogues Flow cytometry results include PI (vertical) and CFSE (horizontal)

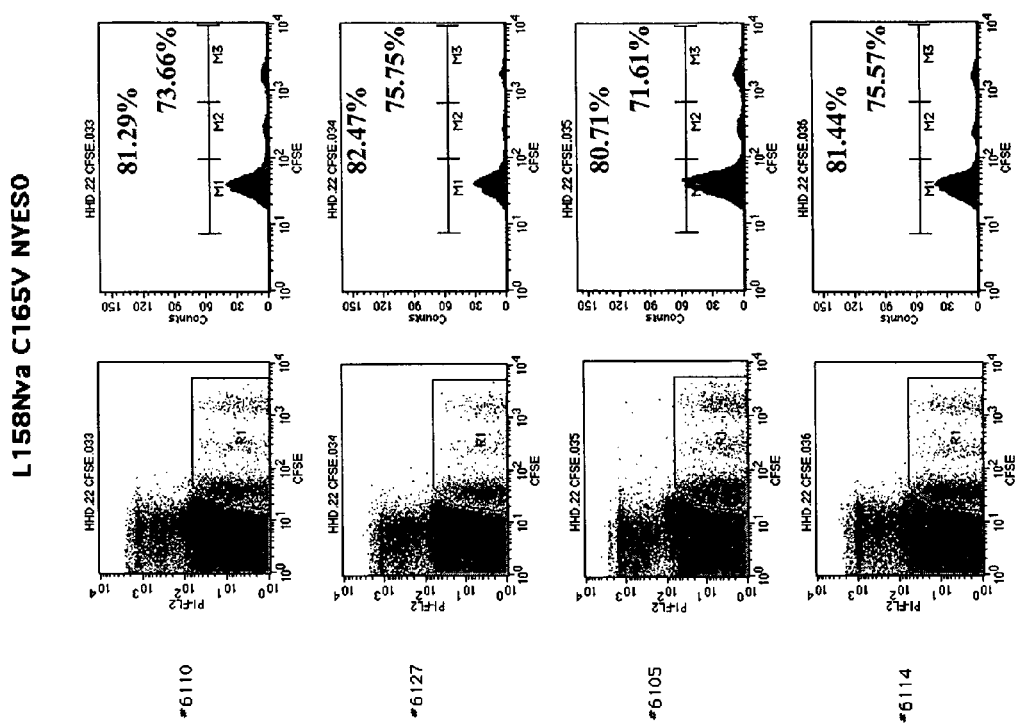
Figure 15C: (L158Nva, C165V)

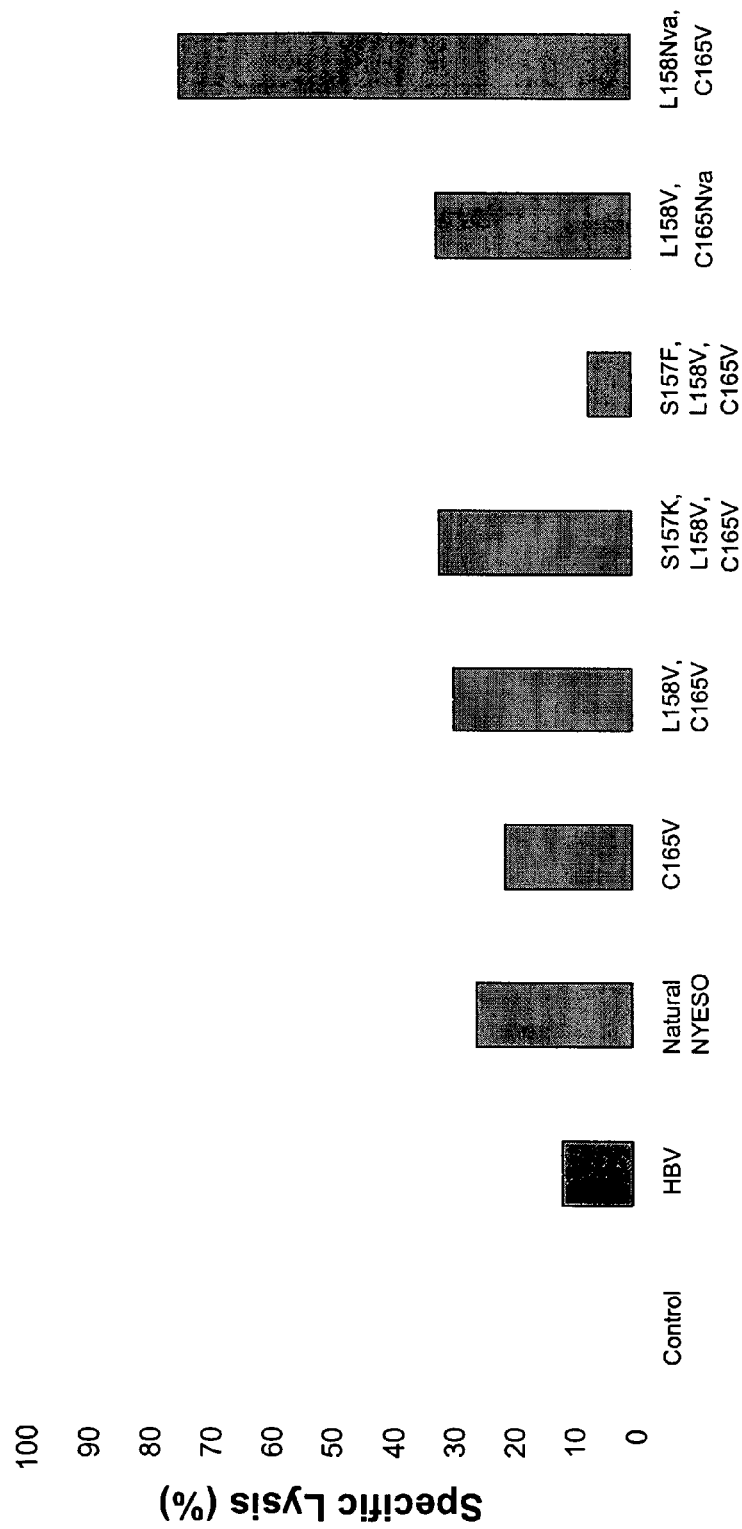
Figure 16A: CFSE in vivo cytotoxicity assay of NY-ESO-1 prime-boost candidates

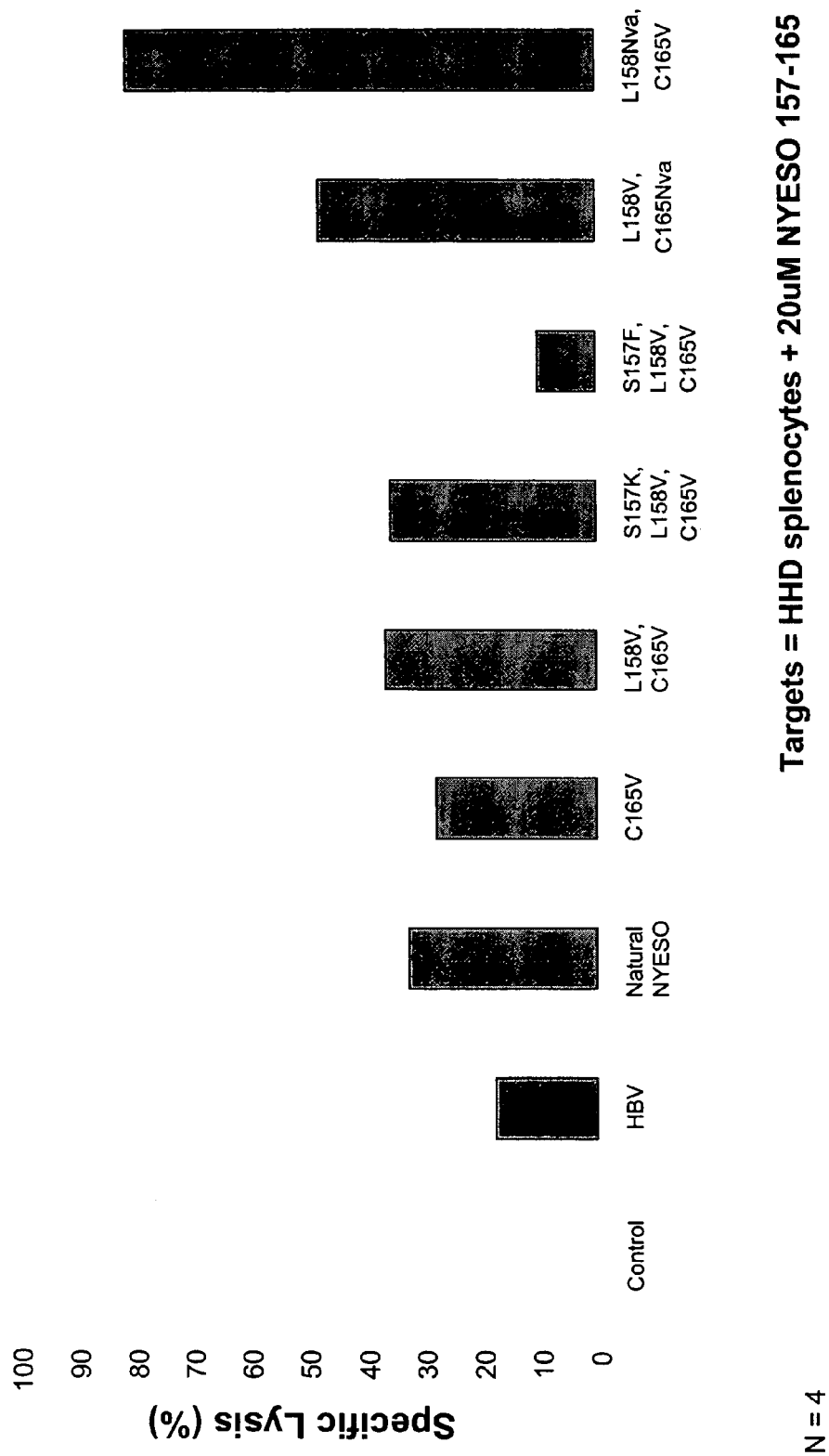
Figure 16B: CFSE in vivo cytotoxicity assay of NY-ESO-1 prime-boost candidates

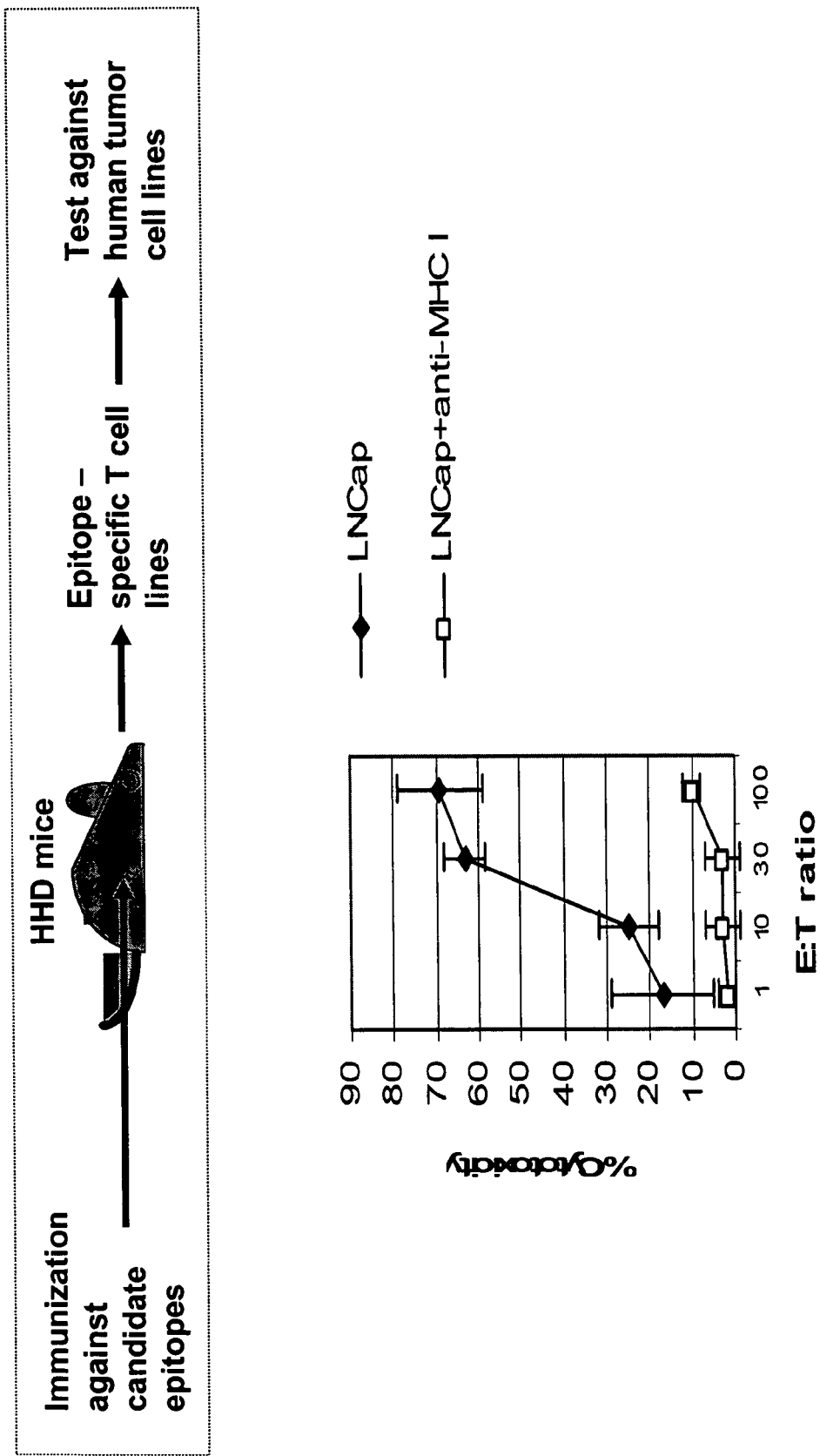
Figure 18: PSMA$_{288-297}$ Epitope Validation – Lysis of Human Tumor Cells by Specific T Cell Lines Figure 19: Single substitution analogs of PSMA$_{288-297}$

| Category | | Peptide name | Sequence | % Binding | ED50 (M) | Stability (t1/2) (hr) | IScore | reactivity (IFN-γ) |
|---|---|---|---|---|---|---|---|---|
| Native | 1 | PSMA 288-297 | GLPSIPVHPI | 86.3 | 1.330E-06 | 5,341 | 0.693 | 27.29 |
| N-terminal primary anchor | 2 | PSMA 288-297 (L289M) | GMPSIPVHPI | 93.2 | 1.072E-06 | 3,340 | 0.605 | -4.99 |
| | 3 | PSMA 288-297 (L289I) | GIPSIPVHPI | 75.3 | 1.314E-06 | 0,948 | 0.159 | 4.39 |
| | 4 | PSMA 288-297 (L289Q) | GQPSIPVHPI | 84.9 | 6.687E-07 | 1,445 | 0.402 | -1.55 |
| | 5 | PSMA 288-297 (L289V) | GVPSIPVHPI | 69.9 | 2.414E-06 | 0,212 | 0.105 | 18.65 |
| | 6 | PSMA 288-297 (L289(Nva)) | G(Nva)PSIPVHPI | 100.0 | 6.946E-07 | 4,342 | 0.81 | 15.26 |
| | 7 | PSMA 288-297 (L289(Nle)) | G(Nle)PSIPVHPI | 65.9 | 1.224E-06 | 0.598 | .189 | 5.36 |
| | 8 | PSMA 288-297 (L289(Abu)) | G(Abu)PSIPVHPI | 74.4 | 9.806E-07 | 9,331 | 0.858 | 13.65 |
| N-terminal secondary anchor | 9 | PSMA 288-297 (G288A) | ALPSIPVHPI | | | | | 8.60 |
| | 10 | PSMA 288-297 (G288S) | SLPSIPVHPI | 87.7 | | 4,337 | 0 | 12.55 |
| | 11 | PSMA 288-297 (G288(Sar)) | (Sar)LPSIPVHPI | 90.4 | 6.851E-07 | 8,785 | 1.037 | 6.41 |
| | 12 | PSMA 288-297 (G288(Abu)) | (Abu)LPSIPVHPI | 101.4 | 4.068E-07 | 7,816 | 1.173 | 15.28 |
| C-terminal primary anchor | 13 | PSMA 288-297 (I297V) | GLPSIPVHPV | 98.6 | 8.344E-07 | 13,123 | 1.312 | 69.80 |
| | 14 | PSMA 288-297 (I297L) | GLPSIPVHPL | 83.8 | 1.166E-06 | 3,256 | 0.54 | 11.57 |
| | 15 | PSMA 288-297 (I297(Nva)) | GLPSIPVHP(Nva) | 92.4 | 1.221E-06 | 10,062 | 1.02 | 40.19 |
| | 16 | PSMA 288-297 (I297(Nle)) | GLPSIPVHP(Nle) | 97.3 | 8.525E-07 | 4,860 | 0.787 | 11.32 |
| C-terminal secondary anchor/TCR exploration | 17 | PSMA 288-297 (P296A) | GLPSIPVHAI | 90.4 | 8.160E-07 | 8,506 | 0.969 | 6.41 |
| | 18 | PSMA 288-297 (P296L) | GLPSIPVHLI | 86.3 | 5.859E-07 | 1,894 | 0.477 | 11.68 |
| | 19 | PSMA 288-297 (P296S) | GLPSIPVHSI | 83.6 | 4.468E-07 | 4,059 | 0.712 | 1.12 |
| | 20 | PSMA 288-297 (P296T) | GLPSIPVHTI | 82.2 | 4.629E-07 | 2,381 | 0.682 | 3.19 |
| TCR exploration/ secondary anchor | 21 | PSMA 288-297 (P290W) | GLWSIPVHPI | 102.7 | 7.770E-07 | 10,788 | 1.243 | 15.19 |

Figure 20: Double substitution analogs of PSMA$_{288-297}$

| Category | | Peptide name | Sequences | % Binding | ED50 (M) | Stability (t1/2) (hr) | iScore | reactivity (IFNγ) |
|---|---|---|---|---|---|---|---|---|
| Native | 1 | PSMA 288-297 | GLPSIPVHPI | 88.3 | 1.330E-06 | 5.341 | 0.693 | 27.29 |
| N-terminal primary anchor and C-terminal primary | 22 | PSMA 288-297 (L289(Nva), I297(Nle)) | G(Nva)PSIPVHP(Nle) | 82.2 | 3.438E-07 | 1.044 | 0.374 | 5.37 |
| | 23 | PSMA 288-297 (L289(Nle), I297(Nva)) | G(Nle)PSIPVHP(Nva) | 88.3 | 5.443E-07 | 4.306 | 0.725 | 13.85 |
| | 24 | PSMA 288-297 (L289(Nva), I297(Nva)) | G(Nva)PSIPVHP(Nva) | 97.3 | 1.197E-06 | 6.356 | 0.649 | 10.81 |
| | 25 | PSMA 288-297 (L289(Nle), I297(Nle)) | G(Nle)PSIPVHP(Nle) | 100.0 | 5.245E-07 | 4.648 | 0.847 | 6.52 |
| | 26 | PSMA 288-297 (L289(Nva), I297V) | G(Nva)PSIPVHPV | 94.8 | 2.195E-06 | 13.695 | 1.0940 | 58.12 |
| | 27 | PSMA 288-297 (L289(Nle), I297V) | G(Nle)PSIPVHPV | 92.4 | 2.271E-06 | 13.332 | 1.053 | 57.46 |
| | 28 | PSMA 288-297 (L289V, I297V) | GVPSIPVHPV | 78.3 | 3.325E-05 | 1.824 | 0.301 | 8.43 |
| | 29 | PSMA 288-297 (L289I, I297V) | GIPSIPVHPV | 94.3 | 1.146E-05 | 2.476 | 0.634 | 0.00 |
| | 30 | PSMA 288-297 (L289V, I297(Nva)) | GVPSIPVHP(Nva) | 96.6 | 8.235E-07 | 14.942 | 1.758 | 0.00 |
| | 31 | PSMA 288-297 (L289I, I297(Nva)) | GIPSIPVHP(Nva) | 81.8 | 2.692E-07 | 2.685 | 0.502 | 0.00 |
| N-terminal secondary anchor and C-terminal primary anchor | 32 | PSMA 288-297 (G288A, I297V) | ALPSIPVHPV | 86.0 | 5.957E-06 | 14.157 | 0.882 | 72.33 |
| | 33 | PSMA 288-297 (G288A, I297(Nva)) | ALPSIPVHP(Nva) | 81.8 | 1.006E-06 | 10.320 | 0.924 | 48.11 |
| | 34 | PSMA 288-297 (G288(Abu), I297V) | (Abu)LPSIPVHPV | 85.1 | 7.885E-07 | 13.518 | 1.185 | 65.68 |
| | 35 | PSMA 288-297 (G288(Abu), I297(Nva)) | (Abu)LPSIPVHP(Nva) | 82.0 | 8.460E-07 | 10.894 | 1.141 | 65.01 |
| C-terminal primary anchor | 36 | PSMA 288-297 (P290W, I297V) | GLWSIPVHPV | 89 | 1.244E-06 | 12.082 | 1.082 | 10.83 |
| | 37 | PSMA 288-297 (P290W, I297(Nva)) | GLWSIPVHP(Nva) | 102.2 | 8.325E-07 | 13.693 | 1.579 | 28.5% |
| N-terminal primary anchor and TCR exploration | 38 | PSMA 288-297 (L289(Nva), P290W) | G(Nva)WSIPVHPI | 101.1 | 1.411E-06 | 13.688 | 1.247 | 41.79 |
| | 39 | PSMA 288-297 (L289V, P290W) | GVWSIPVHPI | 83.7 | 2.184E-06 | 2.316 | 0.409 | 8.46 |
| | 40 | PSMA 288-297 (L289(Nle), P290W) | G(Nle)WSIPVHPI | 105.4 | 1.242E-06 | 10.527 | 1.156 | 21.2 |
| | 41 | PSMA 288-297 (L289I, P290W) | GIWSIPVHPI | 86.7 | 1.839E-07 | 9.687 | 1.202 | 0.00 |

Figure 21:
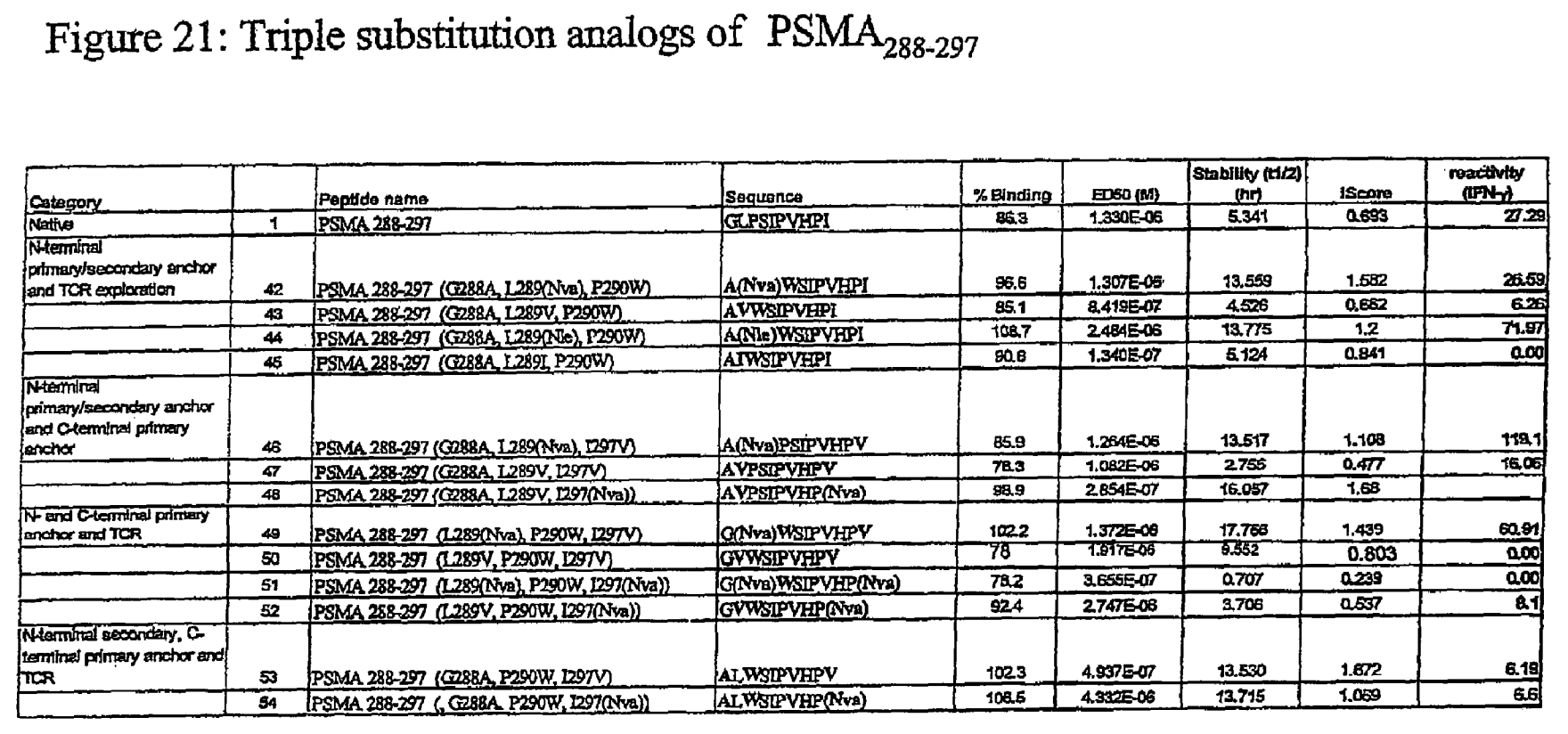

Figure 21: Triple substitution analogs of $PSMA_{288-297}$

| Category | | Peptide name | Sequence | % Binding | ED50 (M) | Stability (t1/2) (hr) | iScore | reactivity (IFN-γ) |
|---|---|---|---

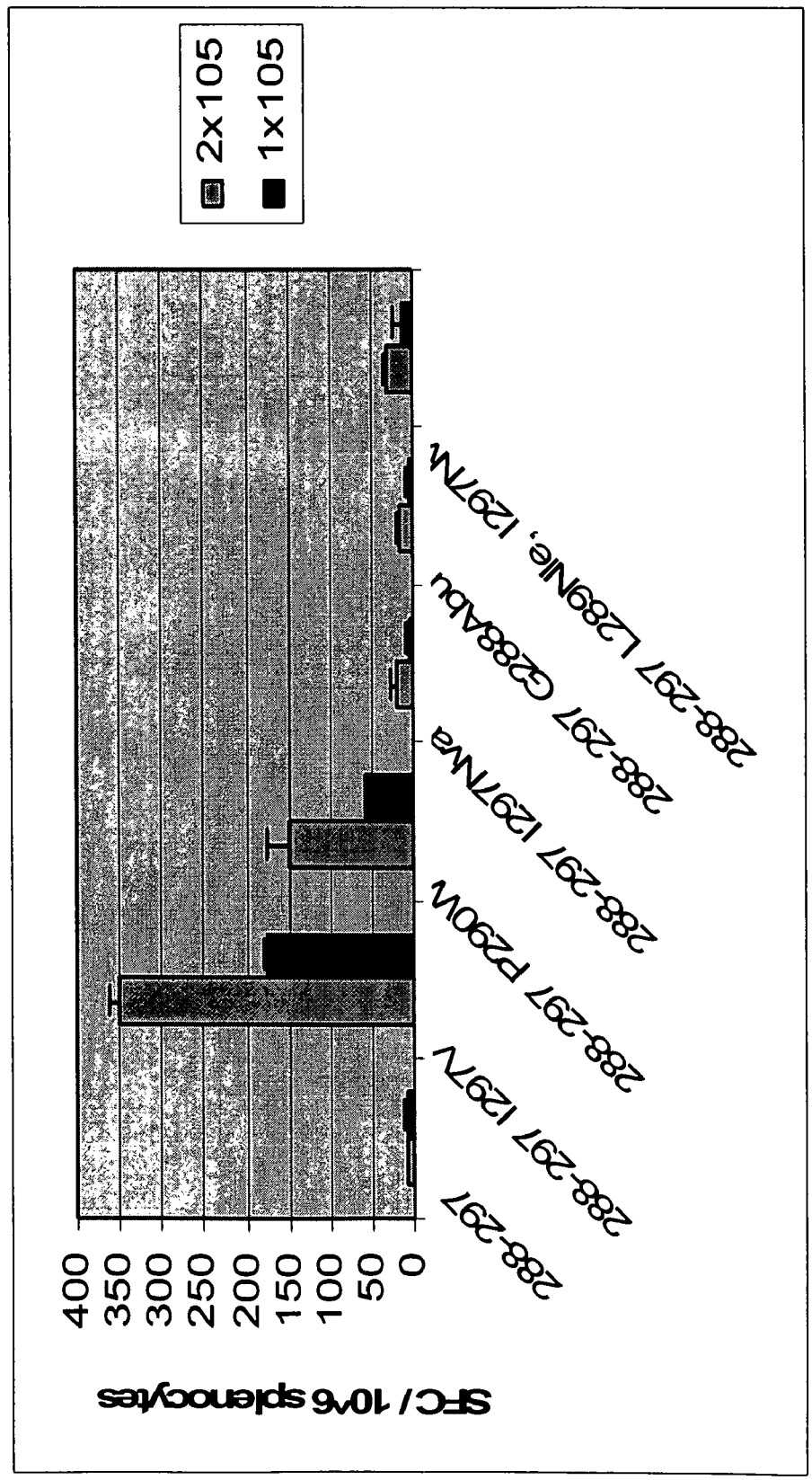
Figure 22: Immunogenicity of various PSMA$_{288-297}$ Analogs Measured by Elispot

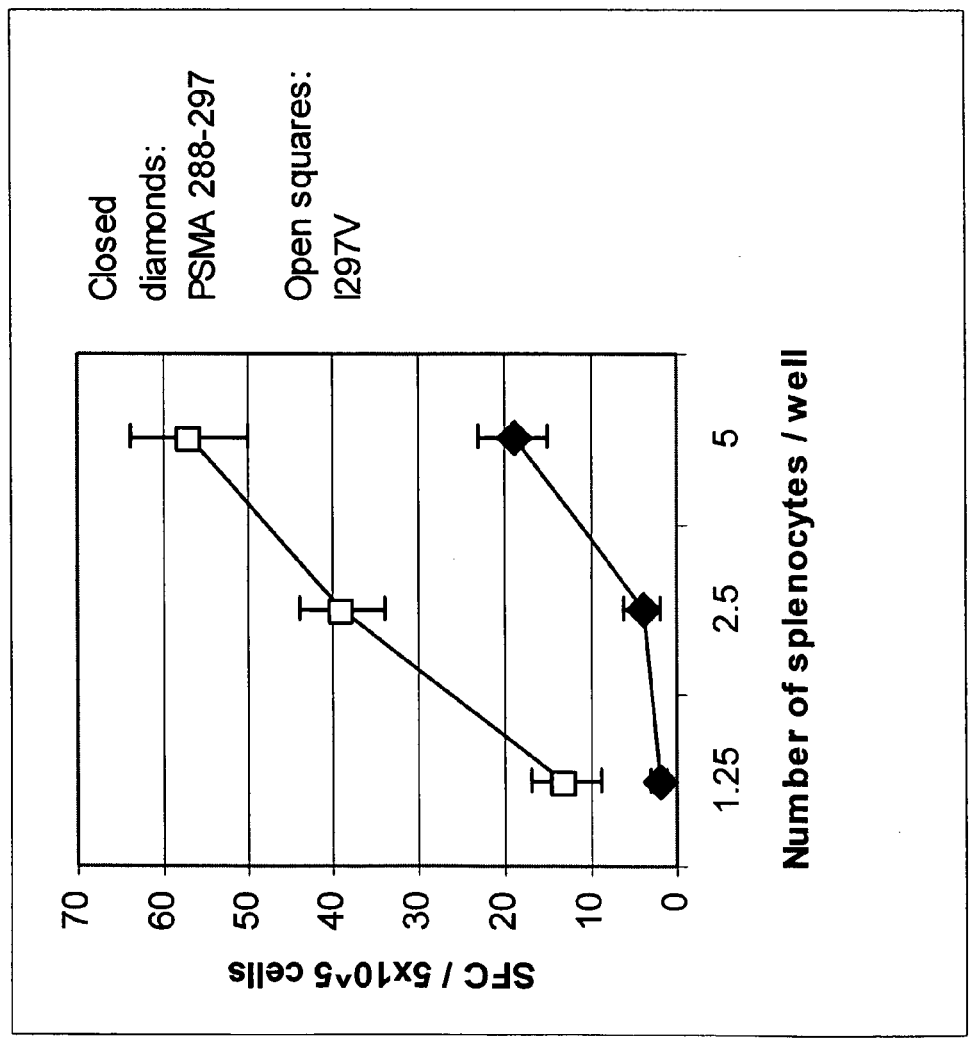
Figure 23: Amplification of anti-PSMA$_{288-297}$ response by the I297V Analog. Measured by Elispot.

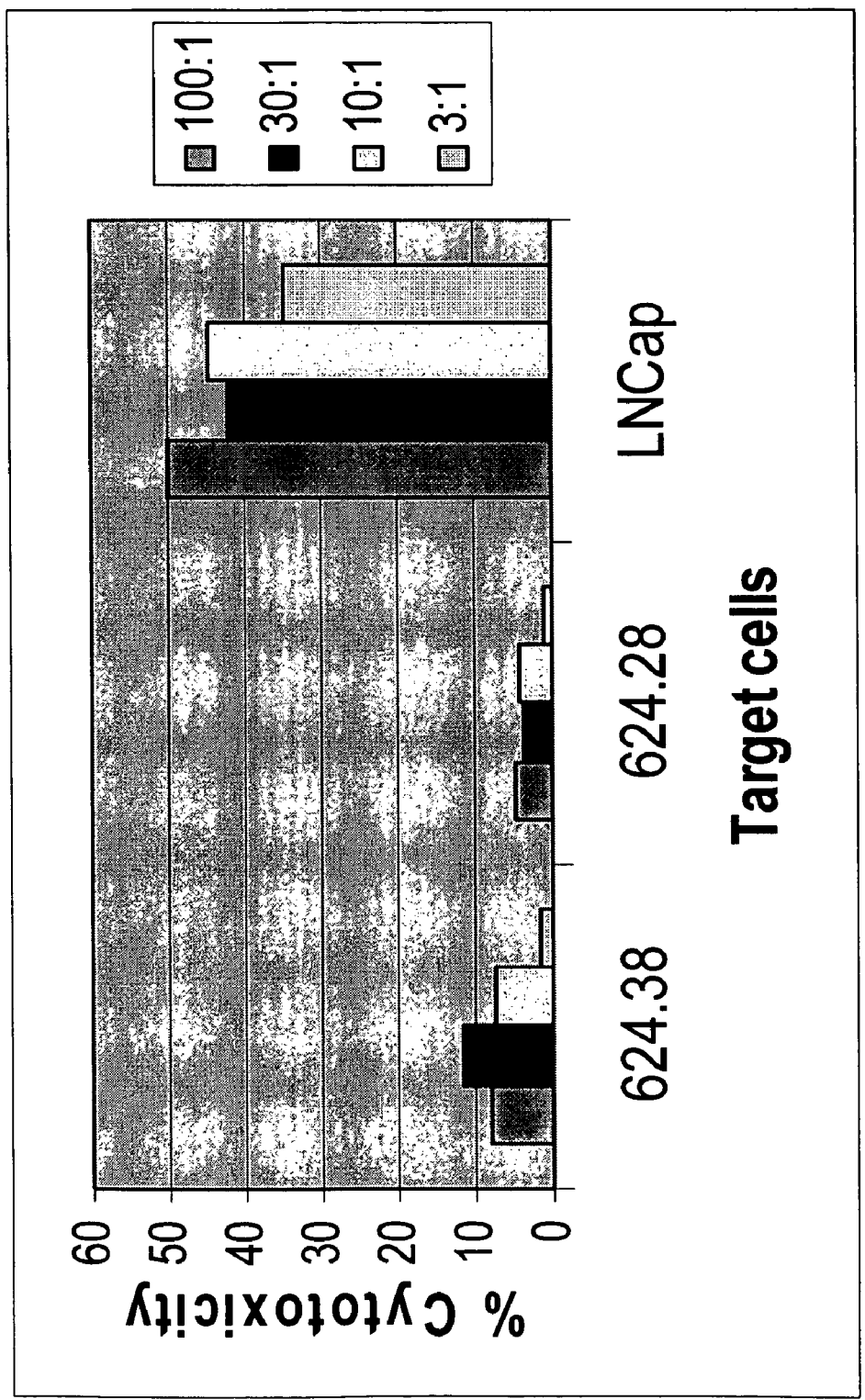
Figure 24: Boosting with I297V Epitope Analog Results in Cytotoxic Immunity against a PSMA+ Human Tumor Cell Line.

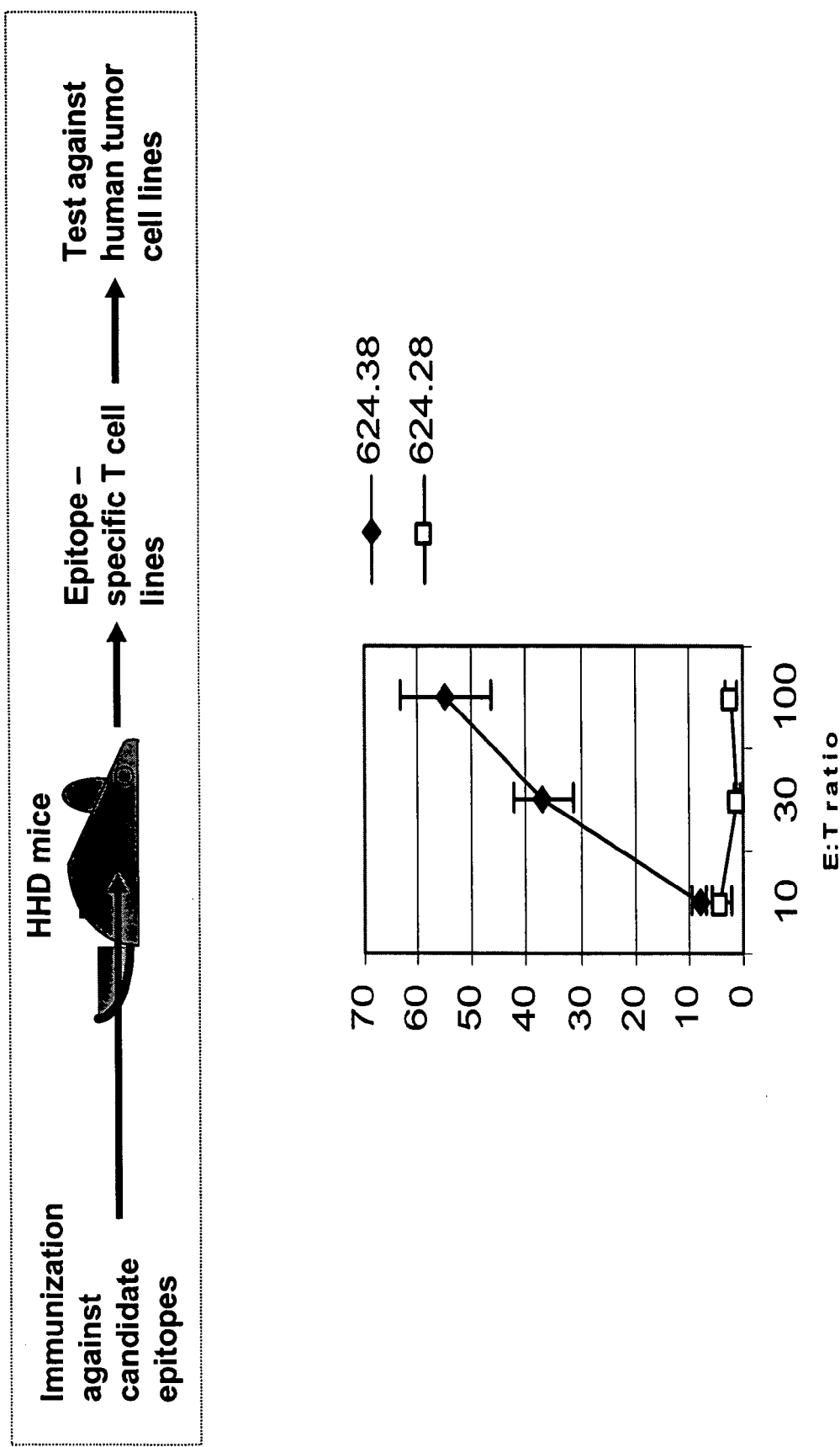
Figure 25: PRAME$_{425-433}$ Epitope Validation – Lysis of Human Tumor Cells by Specific T Cell Lines

Figure 26: Single substitution analogs of PRAME 425-433

| Category | # | Peptide name | Sequence | % Binding (A0201) | Stability (t1/2) (hr) (A0201) | ED50 (mM) (A0201) | iScore (A0201) | Cross-reactivity as normalized IFN-gamma production |
|---|---|---|---|---|---|---|---|---|
| Native | 1 | Prame 425-433 | SLLQHLIGL | 81 | 12.2 | 7.158E-07 | 1.17 | 1.00 |
| N-terminal primary anchor | 2 | Prame 425-433 (L426V) | SVLQHLIGL | 66 | 7.1 | 6.178E-06 | 0.49 | 0.4 |
|  | 3 | Prame 425-433 (L426M) | SMLQHLIGL | 100 | 10.3 | 9.884E-07 | 1.14 | 0.6 |
|  | 4 | Prame 425-433 (L426I) | SILQHLIGL | 76 | 9.4 | 1.628E-06 | 0.80 | . |
|  | 5 | Prame 425-433 (L426(Nle)) | S(Nle)LQHLIGL | 93 | 12.6 | 2.423E-06 | 1.01 | 0.56 |
|  | 6 | Prame 425-433 (L426(Nva)) | S(Nva)LQHLIGL | 92 | 11.4 | 1.911E-06 | 1.00 | 0.8 |
|  | 7 | Prame 425-433 (L426(Abu)) | S(Abu)LQHLIGL | 73 | 8.1 | 4.849E-06 | 0.59 | . |
| N-terminal secondary anchor | 8 | Prame 425-433 (S425K) | KLLQHLIGL | 82 | 10.8 | 4.412E-06 | 0.77 | 0.4 |
|  | 9 | Prame 425-433 (S425F) | FLLQHLIGL | 110 | 17.7 | 4.335E-07 | 1.86 | 0.52 |
|  | 10 | Prame 425-433 (S425Y) | YLLQHLIGL | 99 | 11.8 | 5.496E-07 | 1.34 | 0.8 |
|  | 11 | Prame 425-433 (S425T) | TLLQHLIGL | 88 | 9.3 | 1.452E-06 | 0.92 | 0.81 |
|  | 12 | Prame 425-433 (S425(Orn)) (Orn is L-ornithine) | (Orn)LLQHLIGL | 89 | 10.0 | 2.252E-06 | 0.89 | 0.55 |
|  | 13 | Prame 425-433 (S425(Hse)) (Hse is L-Homoserine) | (Hse)LLQHLIGL | 80 | 10.8 | 1.360E-06 | 1.01 | 0.85 |
| C-terminal primary anchor | 14 | Prame 425-433 (L433V) | SLLQHLIGV | 80 | 12.6 | 7.310E-06 | 0.74 | . |
|  | 15 | Prame 425-433 (L433I) | SLLQHLIGI | 75 | 11.9 | 3.349E-06 | 0.79 | . |
|  | 16 | Prame 425-433 (L433A) | SLLQHLIGA | 80 | 13.6 | 8.430E-06 | 0.85 | . |
|  | 17 | Prame 425-433 (L433(Nle)) | SLLQHLIG(Nle) | 98 | 14.8 | 7.768E-07 | 1.40 | 0.72 |
|  | 18 | Prame 425-433 (L433(Nva)) | SLLQHLIG(Nva) | 92 | 17.2 | 1.663E-06 | 1.26 | 0.52 |
|  | 19 | Prame 425-433 (L433(Abu)) | SLLQHLIG(Abu) | 81 | 12.3 | 3.411E-06 | 0.65 | . |
| C-terminal amide | 20 | Prame 425-433-NH2 | SLLQHLIGL-NH2 | 89 | 3.0 | 1.384E-06 | 0.53 | 0.6 |
| TCR exploitation | 21 | Prame 425-433 (G432A) | SLLQHLIAL | 88 | 12.4 | 1.726E-06 | 1.02 | . |
|  | 22 | Prame 425-433 (G432S) | SLLQHLISL | 71 | 10.7 | 4.367E-06 | 0.69 | . |
|  | 23 | Prame 425-433 (G432(Sar)) Sar is sarcosine | SLLQHLI(Sar)L | 74 | 9.2 | 2.368E-06 | 0.73 | . |
|  | 24 | Prame 425-433 (L427(Nle)) | SL(Nle)QHLIGL | 81 | 12.3 | 2.493E-06 | 0.90 | 0.24 |
|  | 25 | Prame 425-433 (L427(Nva)) | SL(Nva)QHLIGL | 78 | 11.7 | 3.153E-06 | 0.81 | . |
|  | 26 | Prame 425-433 (L427(Abu)) | SL(Abu)QHLIGL | 74 | 10.1 | 8.258E-06 | 0.60 | . |
|  | 27 | Prame 425-433 (L430(Nle)) | SLLQH(Nle)IGL | 81 | 11.2 | 4.740E-06 | 0.77 | . |
|  | 28 | Prame 425-433 (L430(Nva)) | SLLQH(Nva)IGL | 74 | 11.4 | 7.265E-06 | 0.66 | 0.61 |
|  | 29 | Prame 425-433 (L430(Abu)) | SLLQH(Abu)IGL | 78 | 10.6 | 5.140E-06 | 0.70 | 0.44 |

Figure 27A: Double substitution analogs of PRAME 425-433

| Category | | Peptide name | Sequence | % Binding (A0201) | Stability (t1/2) (hr) (A0201) | ED50 (mM) (A0201) | iScore (A0201) | Cross-reactivity as normalized IFN-gamma production |
|---|---|---|---|---|---|---|---|---|
| Native | 1 | Prame 425-433 | SLLQHLIGL | 81 | 12.2 | 7.158E-07 | 1.17 | 1.00 |
| N-terminal primary/secondary anchor | 30 | Prame 425-433 (S425F, L426(Nva)) | F(Nva)LQHLIGL | 106 | 11.7 | 4.618E-07 | 1.46 | * |
| | 31 | Prame 425-433 (S425Y, L426(Nva)) | Y(Nva)LQHLIGL | 96 | 9.4 | 1.660E-06 | 0.97 | * |
| | 32 | Prame 425-433 (S425T, L426(Nva)) | T(Nva)LQHLIGL | 87 | 10.7 | 2.386E-06 | 0.92 | * |
| | 33 | Prame 425-433 (S425(Hse), L426(Nva)) | (Hse)(Nva)LQHLIGL | 90 | 13.6 | 1.449E-06 | 1.12 | * |
| | 34 | Prame 425-433 (S425(Orn), L426(Nva)) | (Orn)(Nva)LQHLIGL | 88 | 12.3 | 6.019E-06 | 0.85 | * |
| | 35 | Prame 425-433 (S425F, L426(Nle)) | F(Nle)LQHLIGL | 118 | 11.4 | 5.661E-07 | 1.52 | * |
| | 36 | Prame 425-433 (S425Y, L426(Nle)) | Y(Nle)LQHLIGL | 110 | 11.5 | 5.572E-07 | 1.44 | * |
| | 37 | Prame 425-433 (S425T, L426(Nle)) | T(Nle)LQHLIGL | 100 | 12.6 | 2.554E-06 | 1.07 | * |
| | 38 | Prame 425-433 (S425(Hse), L426(Nle)) | (Hse)(Nle)LQHLIGL | 81 | 10.9 | 2.546E-06 | 0.84 | * |
| | 39 | Prame 425-433 (S425(Orn), L426(Nle)) | (Orn)(Nle)LQHLIGL | 80 | 9.9 | 4.704E-06 | 0.83 | * |
| | 40 | Prame 425-433 (S425F, L426M) | FMLQHLIGL | 100 | 12.8 | 1.160E-06 | 1.24 | * |
| | 41 | Prame 425-433 (S425Y, L426M) | YMLQHLIGL | 109 | 11.7 | 2.861E-07 | 1.62 | * |
| | 42 | Prame 425-433 (S425T, L426M) | TMLQHLIGL | 83 | 9.2 | 2.011E-06 | 0.89 | * |
| | 43 | Prame 425-433 (S425(Hse), L426M) | (Hse)MLQHLIGL | 93 | 11.7 | 4.874E-06 | 0.86 | * |
| | 44 | Prame 425-433 (S425(Orn), L426M) | (Orn)MLQHLIGL | 86 | 10.5 | 2.951E-06 | 0.90 | * |
| | 45 | Prame 425-433 (S425F, L426I) | FILQHLIGL | 98 | 10.3 | 1.152E-07 | 1.65 | * |
| | 46 | Prame 425-433 (S425Y, L426I) | YILQHLIGL | 87 | 10.1 | 7.155E-07 | 1.07 | * |
| | 47 | Prame 425-433 (S425T, L426I) | TILQHLIGL | 75 | 8.1 | 3.321E-06 | 0.65 | * |
| | 48 | Prame 425-433 (S425(Hse), L426I) | (Hse)ILQHLIGL | 75 | 9.9 | 2.774E-06 | 0.72 | * |
| | 49 | Prame 425-433 (S425(Orn), L426I) | (Orn)ILQHLIGL | 84 | 8.8 | 1.952E-06 | 0.81 | * |

Figure 27B: Double substitution analogs of PRAME 425-433

| Category | | Peptide name | Sequence | % Binding (A0201) | Stability (t1/2) (hr) (A0201) | ED50 (mM) (A0201) | IScore (A0201) | Cross-reactivity as normalized IFN-gamma production |
|---|---|---|---|---|---|---|---|---|
| Native | 1 | Prame 425-433 | SLLQHLIGL | 81 | 12.2 | 7.158E-07 | 1.17 | 1.00 |
| N-terminal primary anchor and C-terminal primary anchor | 50 | Prame 425-433 (L426(Nva),L433(Nva)) | S(Nva)LQHLIG(Nva) | 91 | 13.2 | 2.936E-06 | 0.99 | * |
| | 51 | Prame 425-433 (L426(Nva),L433(Nle)) | S(Nva)LQHLIG(Nle) | 93 | 13.7 | 8.475E-07 | 1.27 | 0.69 |
| | 52 | Prame 425-433 (L426(Nva),L433V) | S(Nva)LQHLIGV | 88 | 16.0 | 2.980E-06 | 1.08 | * |
| | 53 | Prame 425-433 (L426(Nle),L433(Nva)) | S(Nle)LQHLIG(Nva) | 90 | 12.5 | 1.125E-06 | 1.13 | * |
| | 54 | Prame 425-433 (L426(Nle),L433(Nle)) | S(Nle)LQHLIG(Nle) | 100 | 12.4 | 9.950E-07 | 1.26 | * |
| | 55 | Prame 425-433 (L426(Nle),L433V) | S(Nle)LQHLIGV | 83 | 13.9 | 2.481E-06 | 1.07 | * |
| | 56 | Prame 425-433 (L426M,L433(Nva)) | SMLQHLIG(Nva) | 99 | 13.4 | 6.878E-07 | 1.37 | * |
| | 57 | Prame 425-433 (L426M,L433(Nle)) | SMLQHLIG(Nle) | 104 | 11.2 | 6.148E-07 | 1.84 | * |
| | 58 | Prame 425-433 (L426M,L433V) | SMLQHLIGV | 97 | 15.5 | 9.401E-07 | 1.38 | * |
| N-terminal secondary anchor and C-terminal primary anchor | 59 | Prame 425-433 (S425K,L433V) | KLLQHLIGV | 77 | 14.2 | 8.038E-06 | 0.74 | * |
| | 60 | Prame 425-433 (S425F,L433V) | FLLQHLIGV | 110 | 16.3 | 7.180E-07 | 1.64 | * |
| | 61 | Prame 425-433 (S425Y,L433V) | YLLQHLIGV | 91 | 14.8 | 2.816E-06 | 1.19 | * |
| | 62 | Prame 425-433 (S425T,L433V) | TLLQHLIGV | 85 | 17.2 | 8.722E-06 | 1.02 | * |
| | 63 | Prame 425-433 (S425(Orn),L433V) | (Orn)LLQHLIGV | 79 | 12.9 | 2.740E-06 | 0.89 | * |
| | 64 | Prame 425-433 (S425(Hse),L433V) | (Hse)LLQHLIGV | 77 | 10.2 | 6.849E-06 | 0.67 | * |
| | 65 | Prame 425-433 (S425F,L433(Nle)) | FLLQHLIGNle | 88 | 23.3 | 1.538E-07 | 2.14 | 1.18 |
| | 66 | Prame 425-433 (S425T,L433(Nle)) | TLLQHLIGNle | 88 | 13.9 | 1.251E-06 | 1.15 | 0.75 |

Figure 28: Triple substitution analogs of PRAME$_{425-433}$

| Category | | Peptide name | Sequence | % Binding | ED50 (M) | Stability (t1/2) (hr) | iScore | Cross-reactivity as normalized IFN-γ production |
|---|---|---|---|---|---|---|---|---|
| Native | 1 | Prame 425-433 | SLLQHLIGL | 81 | 7.158E-07 | 12.2 | 1.17 | 1.00 |
| N-terminal primary/secondary anchor and C-terminal primary anchor | 67 | Prame 425-433 (S425F, L426(Nva), L433(Nle)) | FNvaLQHLIGNle | 108 | 1.158E-07 | 25.3 | 2.78 | 0.82 |
| | 68 | Prame 425-433 (S425T, L426(Nva), L433(Nle)) | TNvaLQHLIGNle | 118 | 2.844E-07 | 19.6 | 2.24 | 0.91 |
| | 69 | Prame 425-433 (S425F, L426M, L433(Nle)) | FMLQHLIGNle | 124 | 1.803E-07 | 13.1 | 2.05 | ND |
| | 70 | Prame 425-433 (S425T, L426M, L433(Nle)) | TMLQHLIGNle | 97 | 6.802E-07 | 13.6 | 1.36 | ND |

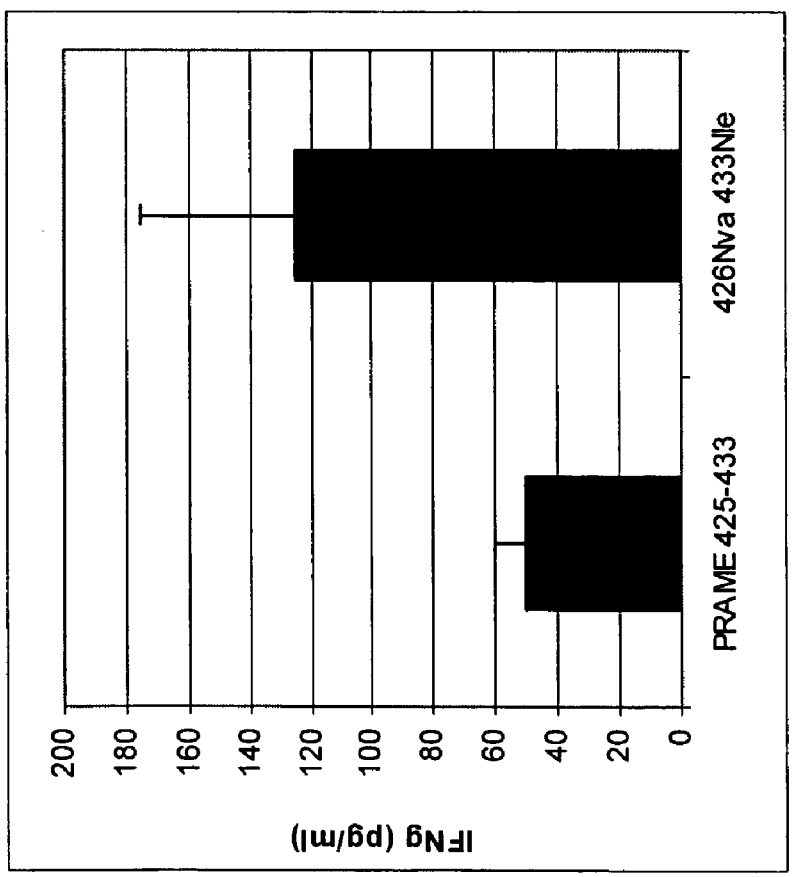
Figure 29: Immunogenicity of a PRAME$_{425-433}$ Analog Measured by Elispot

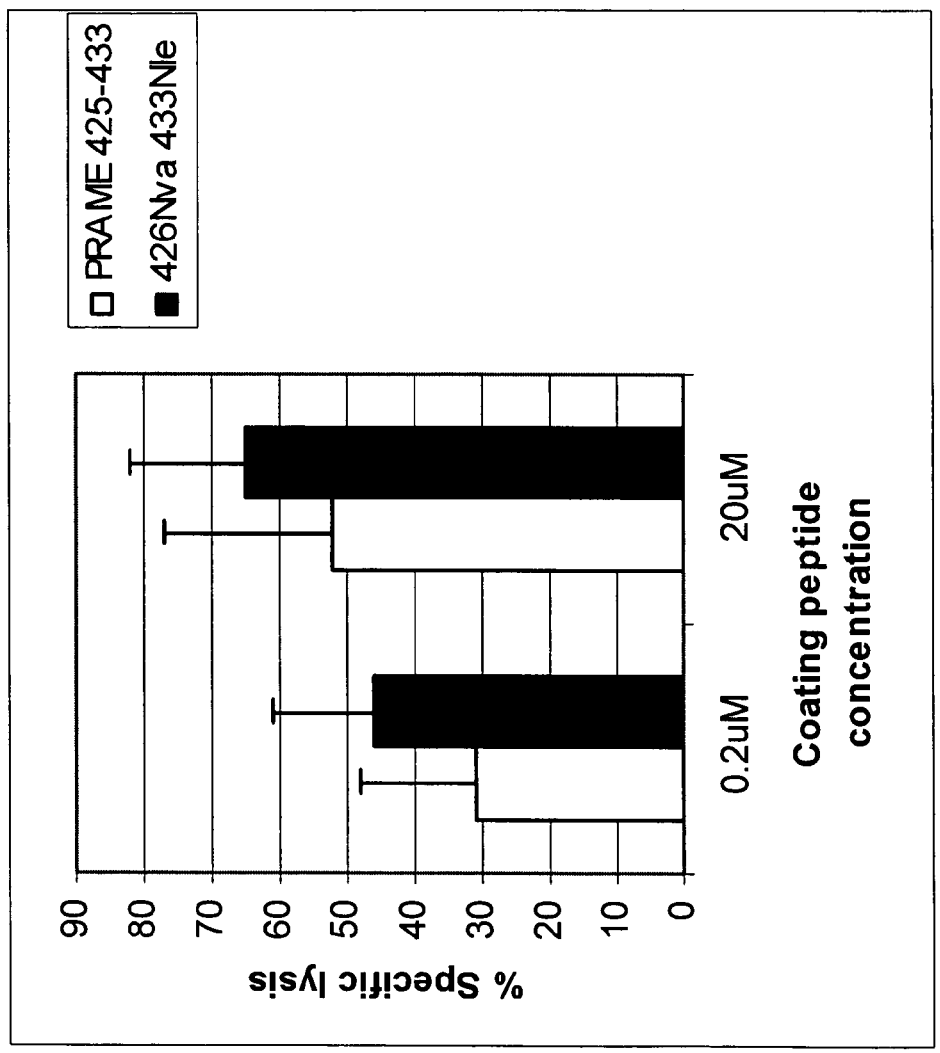
Figure 30: Boosting with the L426Nva L433Nle Epitope Analog Results in *in vivo* Cytotoxicity Against Native Epitope Co

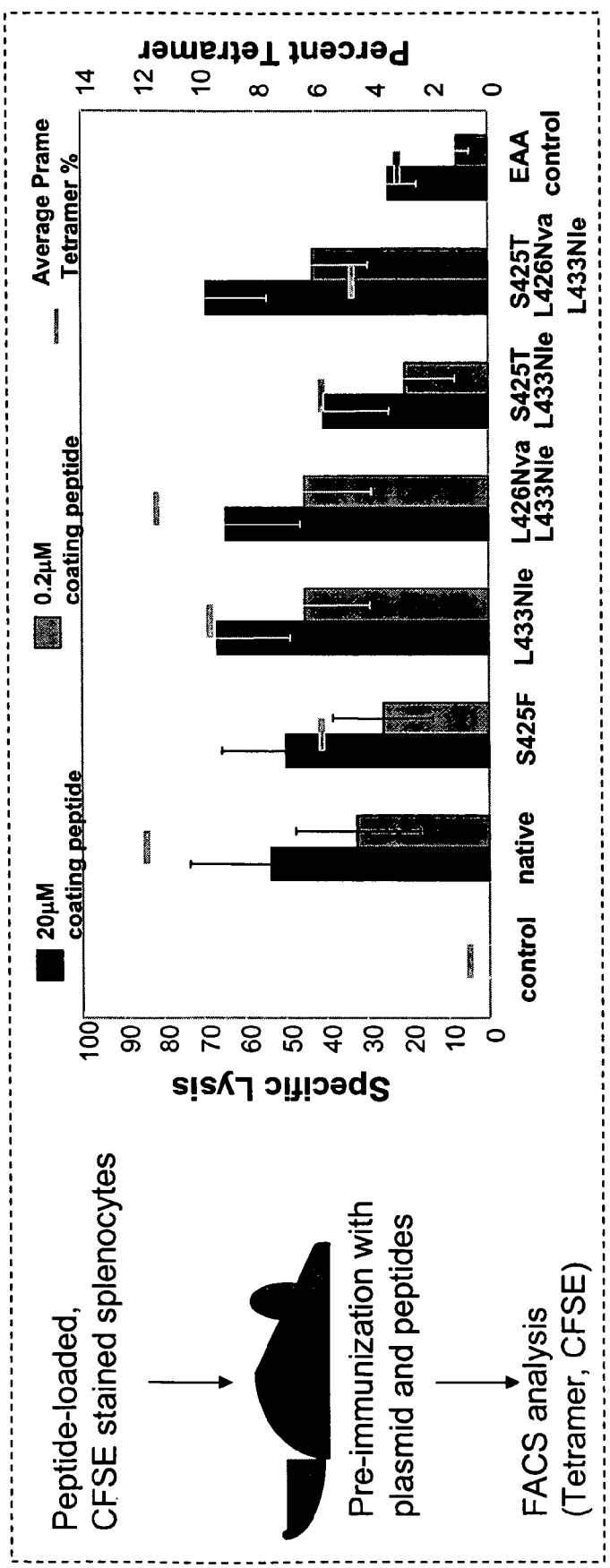
Figure 31: *In Vivo* Evaluation of PRAME Analogs

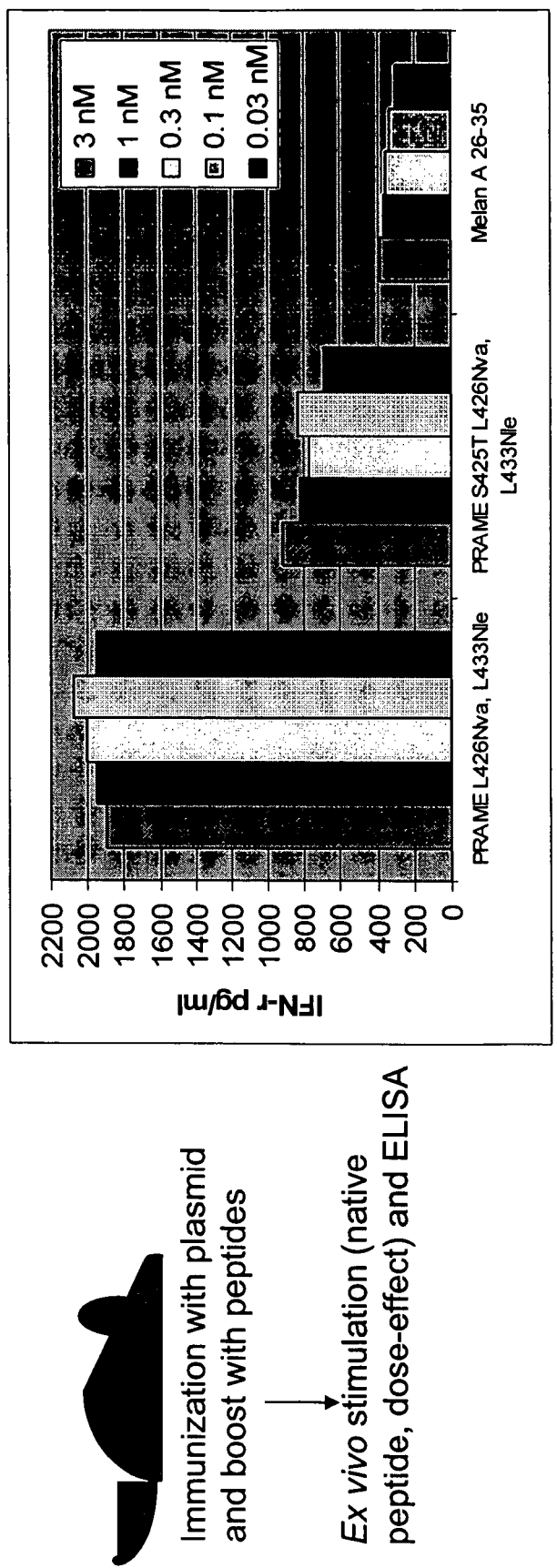
Figure 32: *Ex vivo* cytokine production of analog-induced, native epitope re-stimulated T cells.

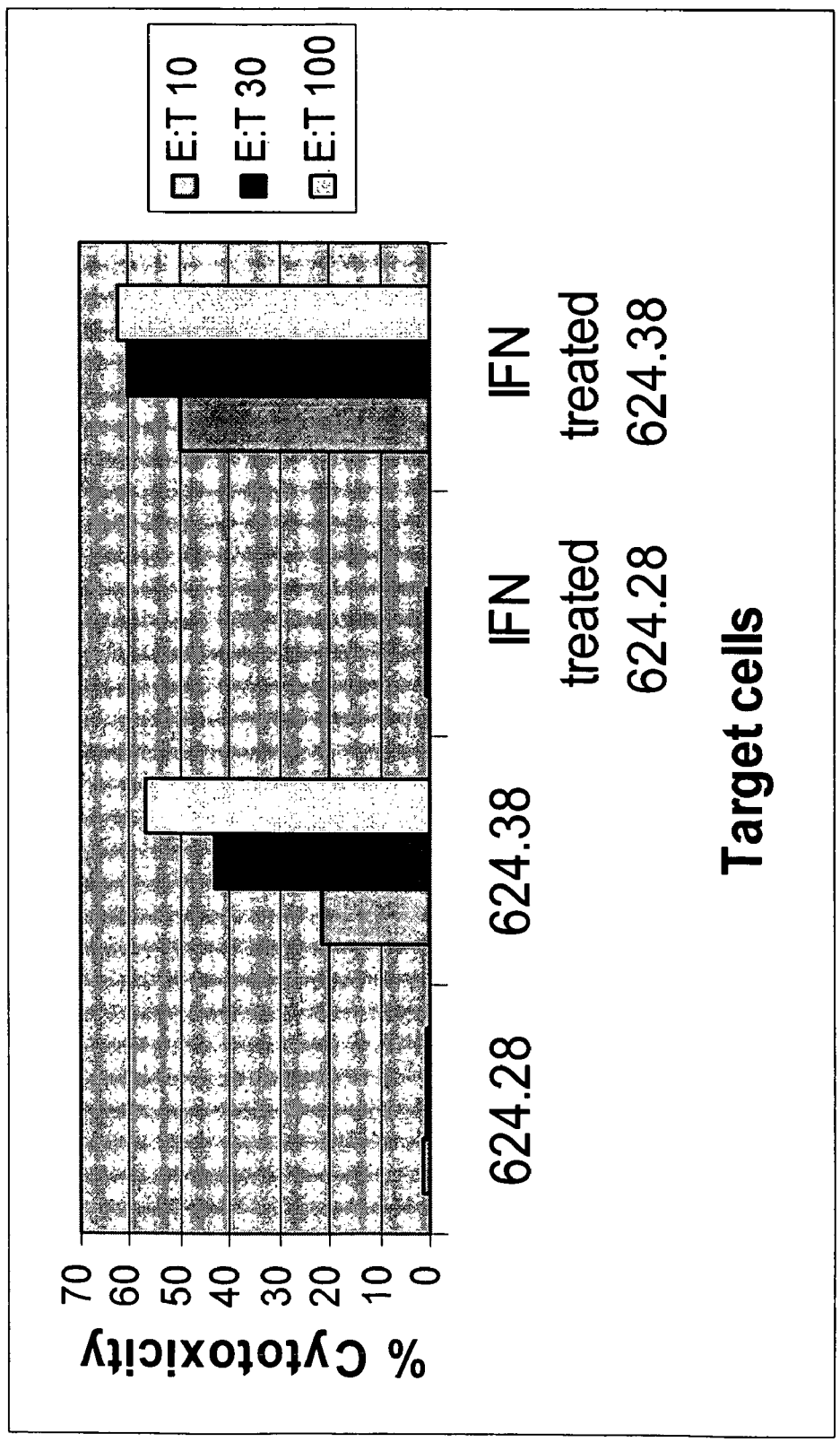
Figure 33: Boosting with the L426Nva L433Nle Analogue Results in Cytotoxic Immunity against a Human Tumor Cell Line

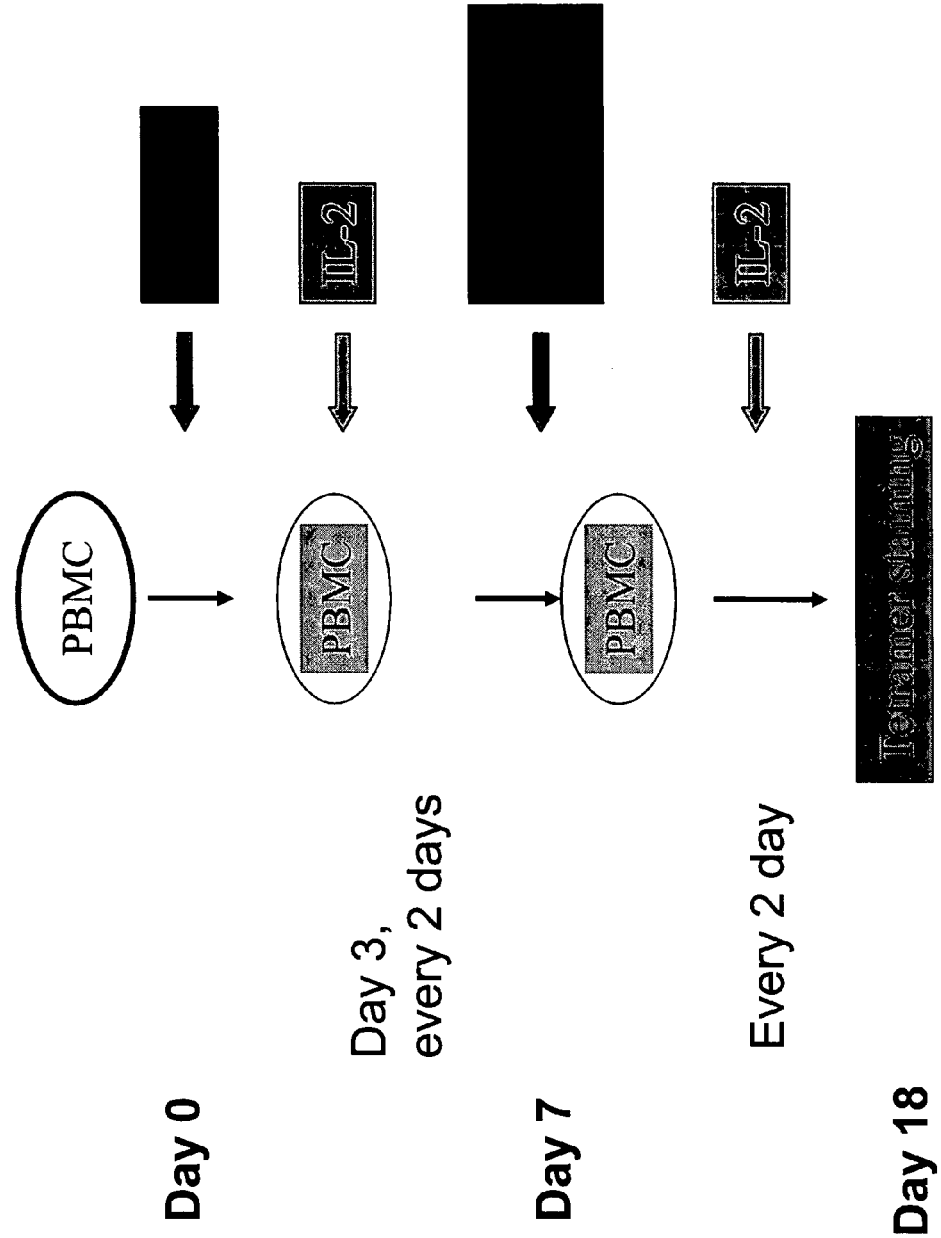
Figure 34: In vitro immunization

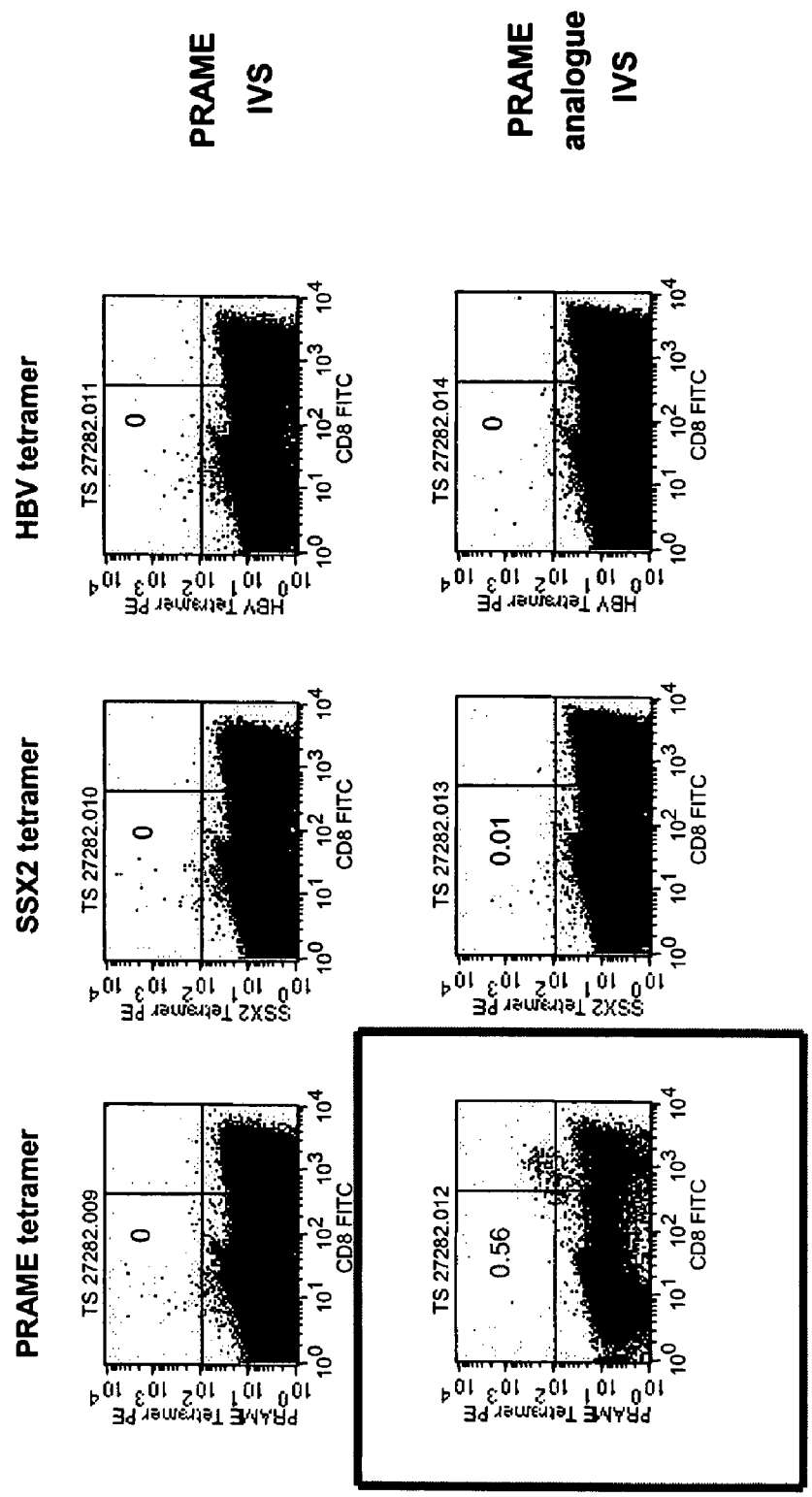
Figure 35: *In vitro* Immunization with a PRAME Analog Generates Tetramer+ Cells

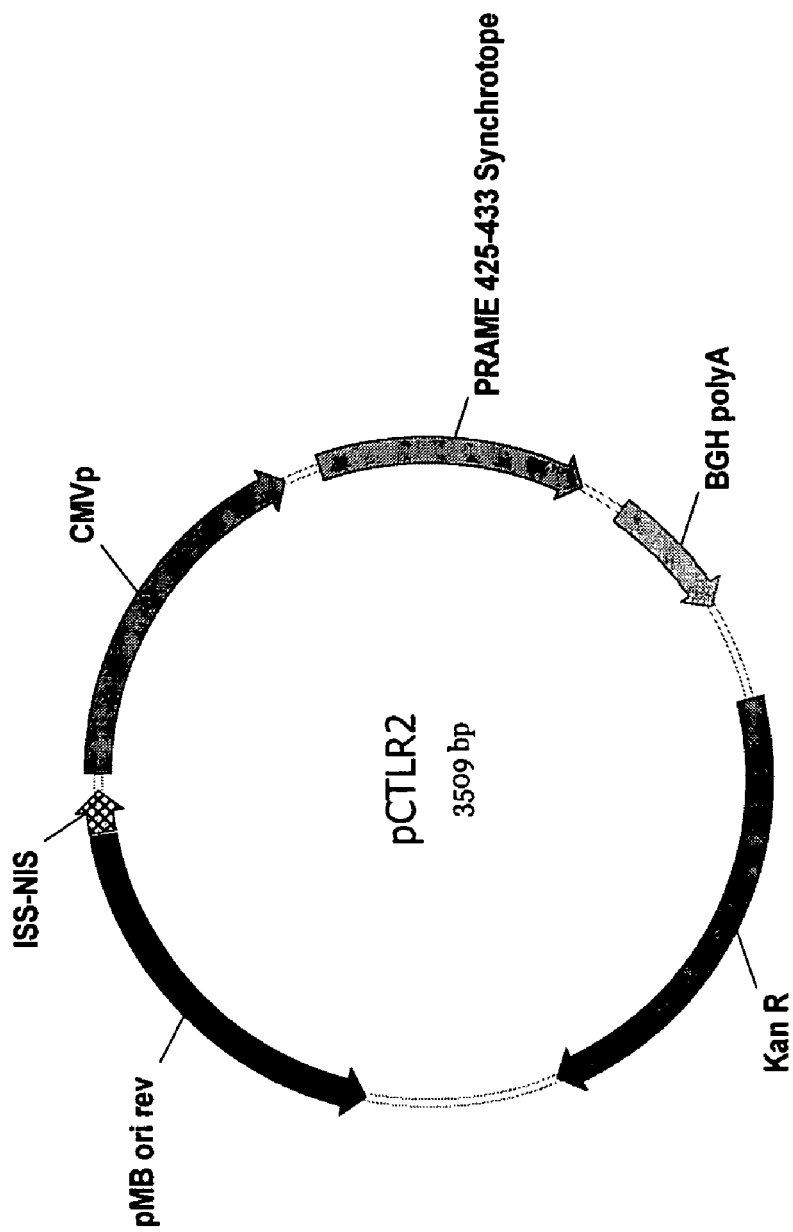
Figure 36: pCTLR2, A Plasmid expressing the PRAME$_{425-433}$ Epitope

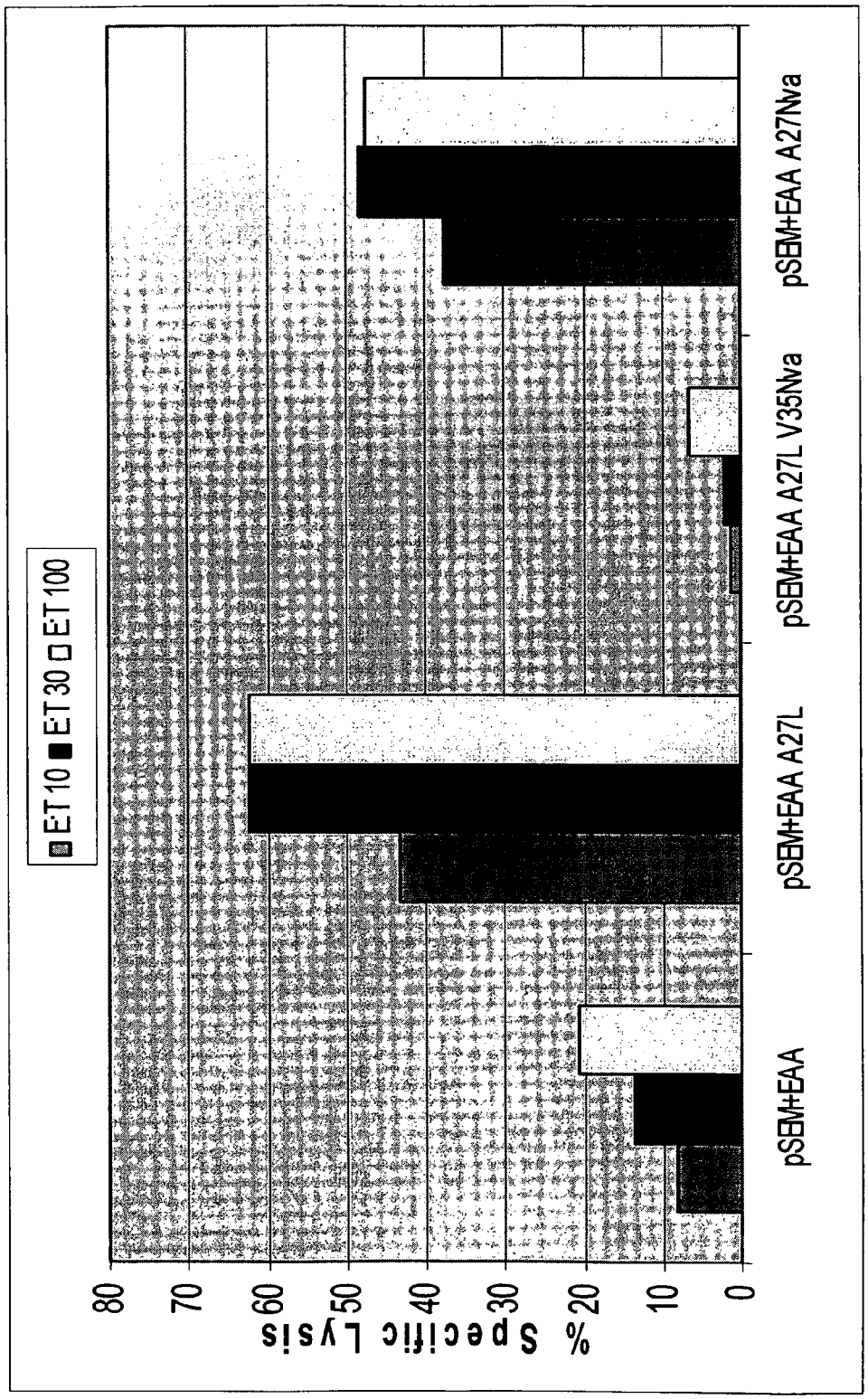
Figure 37: Lysis of 624.38 cells by T cells primed with plasmid DNA and boosted with peptide

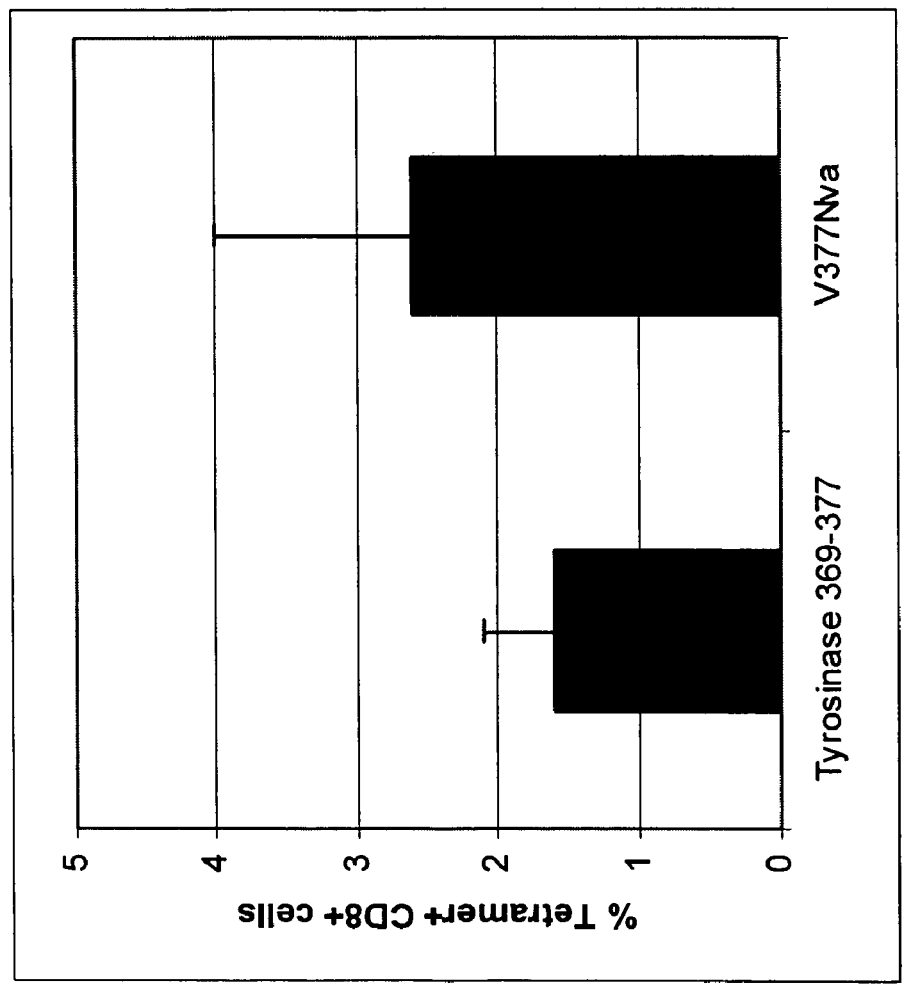
Figure 38: Tyr$_{369-377}$ Tetramer Staining (plasmid prime, peptide boost)

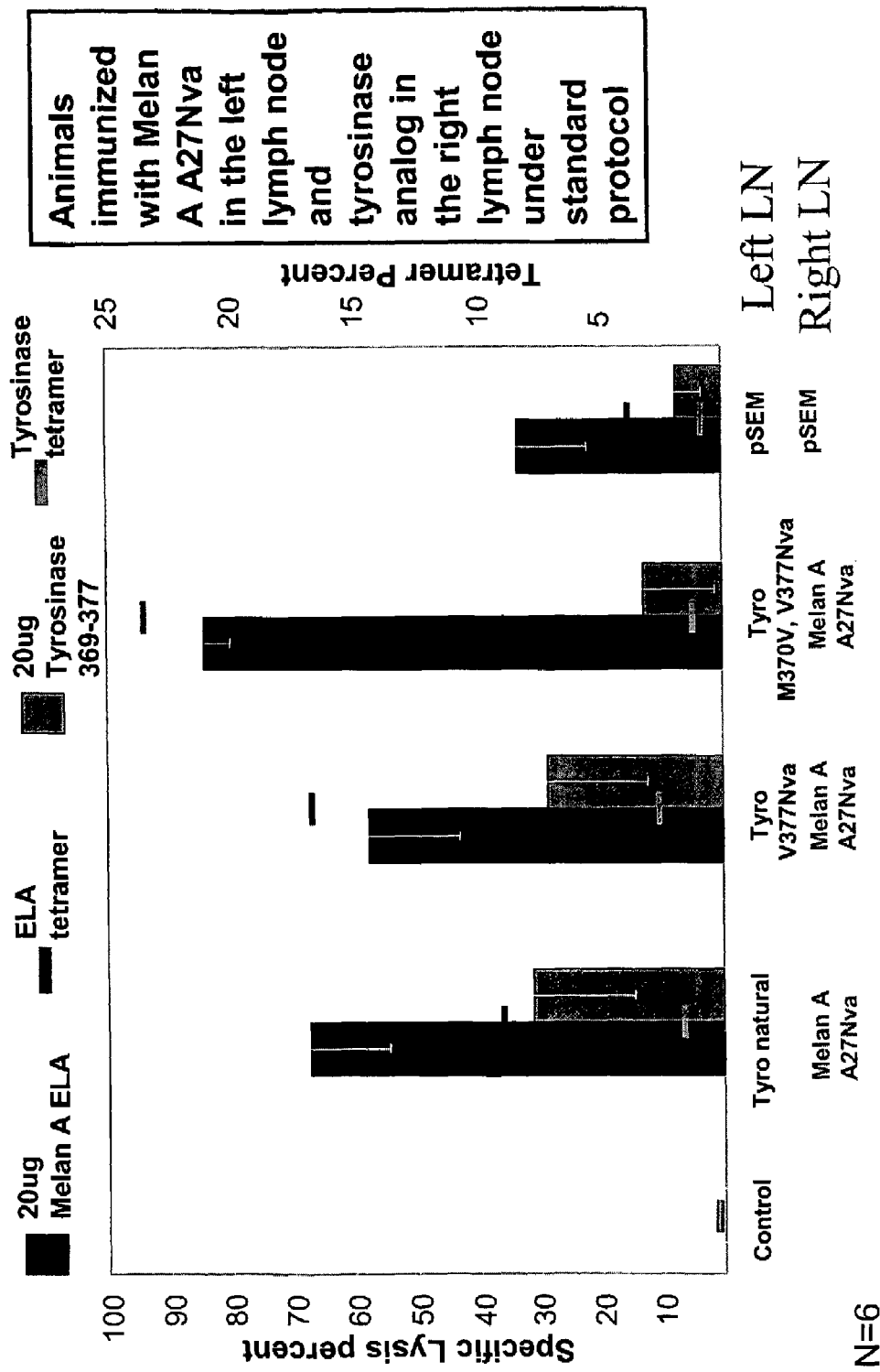
Figure 39: CFSE *in vivo* challenge with multivalent Melan A A27Nva/Tyrosinase analog immunized animals

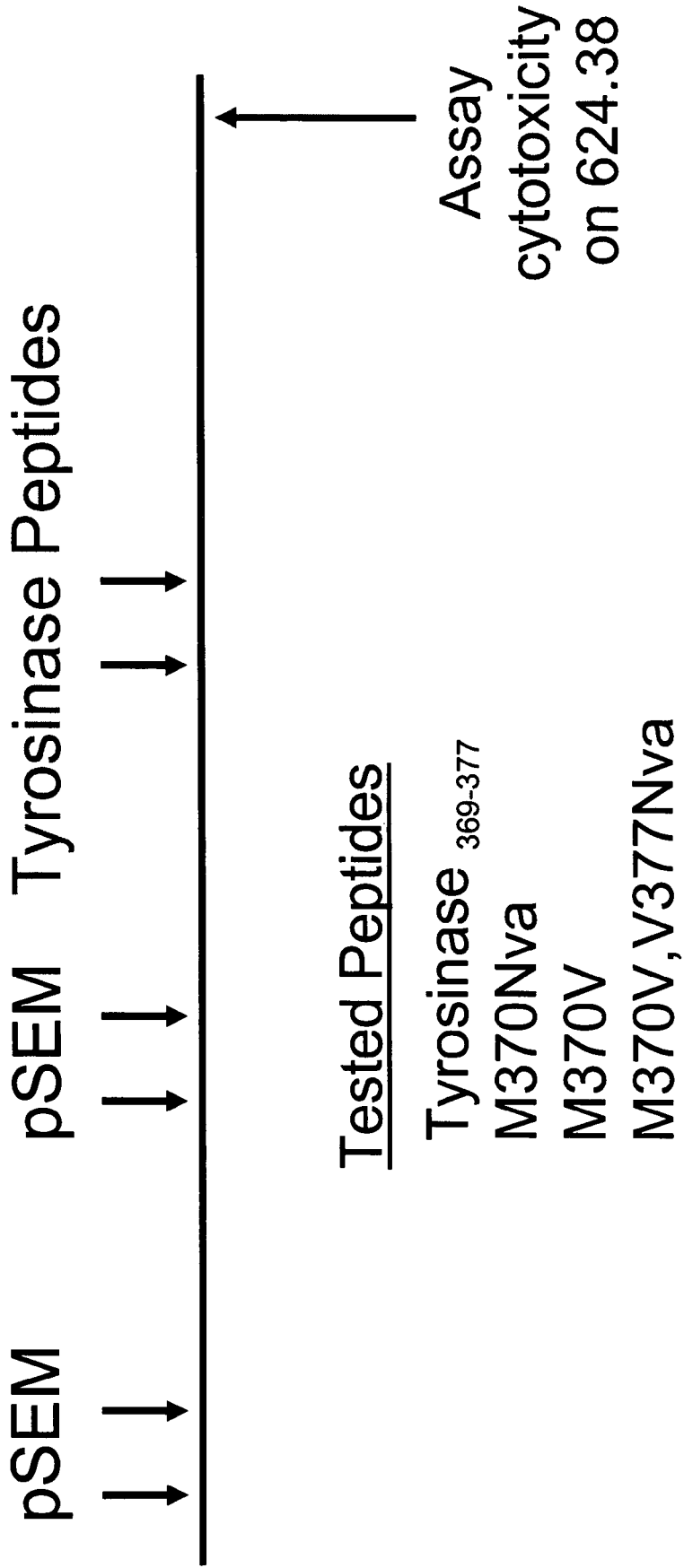
Figure 40: Schematic of Analog Immunogenicity Evaluation Protocol

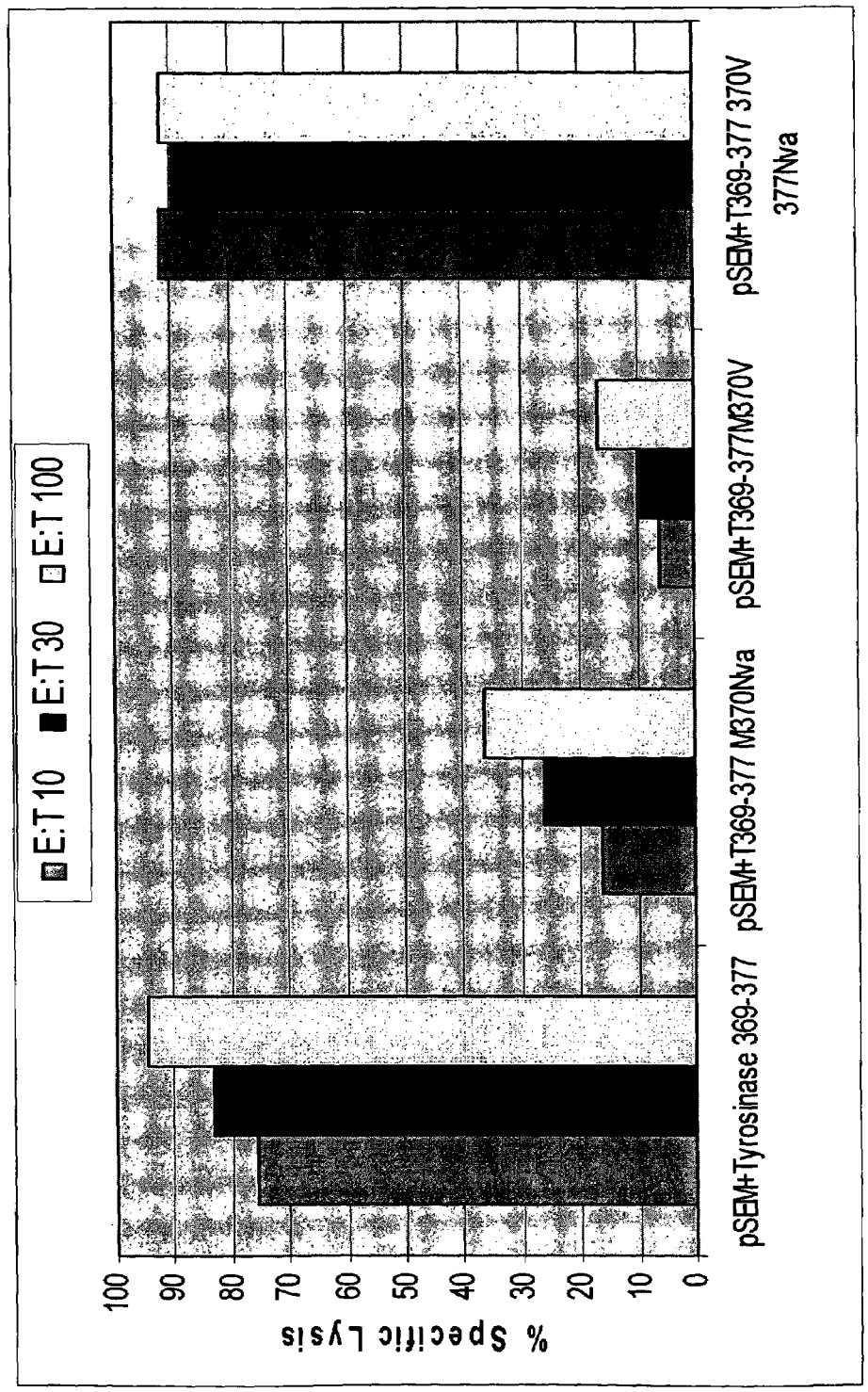
Figure 41: Immune Response against 624.38 Cells Effector Cells from HHD Primed with pSEM and Boosted with $Tyr_{369-377}$ Analogs

PRAME PEPTIDE ANALOGUES

CROSS-REFERENCE TO RELATED APPLICATIONS

The present application claims the benefit of the filing date of U.S. Provisional Patent Application Ser. No. 60/691,889, filed on Jun. 17, 2005, the entire text of which is incorporated herein by reference without disclaimer.

SEQUENCE LISTING

The present application includes a Sequence Listing provided in electronic format on duplicate copies of a CD-ROM marked "COPY 1 REPLACEMENT Nov. 1, 2006" and "COPY 2 REPLACEMENT Nov. 1, 2006." The duplicate copies of the CD-ROM each contain a file entitled "MANNK.052A -Substitute Sequence Listing.txt" created on Nov. 1, 2006, which is 100 kilobytes in size. The information on these duplicate CD-ROMs is incorporated herein by reference in its entirety.

BACKGROUND OF THE INVENTION

1. Field of the Invention

In certain embodiments, the invention disclosed herein relates to analogs of peptides corresponding to class I MHC-restricted T cell epitopes and methods for their generation. These analogs can contain amino acid substitutions at residues that directly interact with MHC molecules and can confer improved, modified or useful immunologic properties. In particular, epitope analogs from the tumor-associated antigens SSX-2, NY-ESO-1, PRAME, PSMA, tyrosinase, and melan-A are identified. Additionally, classes of analogs, in which the various substitutions comprise the non-standard residues norleucine and/or norvaline, are disclosed.

2. Description of the Related Art

The Major Histocompatibility Complex and T Cell Target Recognition

T lymphocytes (T cells) are antigen-specific immune cells that function in response to specific antigen signals. B lymphocytes and the antibodies they produce are also antigen-specific entities. However, unlike B lymphocytes, T cells do not respond to antigens in a free or soluble form. For a T cell to respond to an antigen, it requires the antigen to be bound to a presenting complex comprised of major histocompatibility complex (MHC) proteins.

MHC proteins provide the means by which T cells differentiate native or "self" cells from foreign cells. MHC molecules are a category of immune receptors that present potential peptide epitopes to be monitored subsequently by the T cells. There are two types of MHC, class I MHC and class II MHC. CD4+ T cells interact with class II MHC proteins and predominately have a helper phenotype while CD8+ T cells interact with class I MHC proteins and predominately have a cytolytic phenotype, but each of them can also exhibit regulatory, particularly suppressive, function. Both MHC class I and II are transmembrane proteins with a majority of their structure on the external surface of the cell. Additionally, both classes of MHC have a peptide binding cleft on their external portions. It is in this cleft that small fragments of proteins, native or foreign, are bound and presented to the extracellular environment.

Cells called antigen presenting cells (APCs) display antigens to T cells using the MHC. T cells can recognize an antigen, if it is presented on the MHC. This requirement is called MHC restriction. If an antigen is not displayed by a recognizable MHC, the T cell will not recognize and act on the antigen signal. T cells specific for the peptide bound to a recognizable MHC bind to these MHC-peptide complexes and proceed to the next stages of the immune response.

SUMMARY OF THE INVENTION

SSX-2$_{41-49}$ Analog Embodiments

Embodiments include analogs of the MHC class I-restricted T cell epitope SSX-2$_{41-49}$, KASEKIFYV (SEQ ID NO. 1), polypeptides comprising these analogs that can be processed by pAPC to present the epitope analogs, and nucleic acids that express the analogs. The analogs can have similar or improved immunological properties compared to the wild-type epitope.

One particular embodiment relates to an isolated SSX-2 peptide having a sequence comprising one or more amino acid substitutions of the sequence KASEKIFYV (SEQ ID NO:1), in an amount sufficient to elicit cytokine production from a T cell line generated by immunization against an epitope with the sequence KASEKIFYV (SEQ ID NO:1). In one aspect, the amount sufficient is less than 10 µM. In a further aspect, the amount is less than 3 µM. In yet a further aspect, the amount is less than 1 µM. In one aspect, the one or more amino acid substitutions can include at least one standard amino acid substitution. "Standard amino acid" as used herein includes any of the 20 genetically encoded amino acids. Thus, in one aspect, the at least one standard amino acid substitution can, for example Tyr, Val, Leu, Ala, Ile, Met, Trp, Phe, Asp, Asn, or Ser. In a further aspect, the one or more amino acid substitution can include at least one non-standard amino acid substitution. Non-standard amino acids include, for example, but not limited to, any of the following: norleucine (Nle), norvaline (Nva), phenylglycine (Phg), 4-fluorophenylalanine (Phe(4-F)), 4-nitrophenylalanine (Phe(4-NO$_2$)), α-aminobutyric acid (Abu), α-aminoisobutyric acid (Aib), methyl-leucine (MeLeu), methylvaline (MeVal), β-(3-benzothienyl)-alanine (β-(3-benzothienyl)Ala), O-methyltyorosine (O-methyl-Tyr), cyclohexylalanine (Cha), β-(1-napthyl)-alanine (Nal-1), β-(2-napthyl)-alanine (Nal-2), D-stereoisomer of a standard amino acid, or amino acids wherein the carboxy terminus has been modified to the amide (indicated by —NH2). Thus, in one aspect, the at least one non-standard amino acid substitution can be Nle, Nva, Abu, or a D-stereoisomer of a standard amino acid. In a further aspect, the one or more amino acid substitution can include a modified terminal amino acid. In one aspect, the modified terminal amino acid can be an amidated C-terminal amino acid. In a further aspect at least one of the substitutions can be the addition of an amino acid, wherein the addition is a C-terminal addition. In a further aspect, the peptide further can include the substitution of conserved amino acids at any site, but preferably at the P3, P5, or P7 sites which are not expressly involved in any MHC interactions.

A further embodiment relates to an isolated peptide of 9 amino acids, P1 to P9, which can include one amino acid at each site. For example, P1 can be K, F, Y, W, Phg, Phe(4-F), Phe(4-NO$_2$), MeTyr, β-(3-benzothienyl)-Ala, or D-Lys; P2 can be A, L, V, I, M, D-Ala, Nal-2, Abu, Aib, Nle, or Nva; P3 can be S; P4 can be E, Q, Nle, or Nva; P5 can be K; P6 can be I, L, V, Nle, or Nva; P7 can be F; P8 can be Y, F, Phe(4-F); and PΩ (P-omega) at P9 can be V, I, A, Nva, MeVal, or Abu. In some instances, the sequence is not KASEKIFYV (SEQ ID NO. 1).

A further embodiment relates to an isolated peptide of 9 amino acids, P1 to P9, which can include one amino acid at each site. For example, P1 can be K, F, Y, W, Phg, Phe(4-F), Phe(4-NO$_2$), MeTyr, β-(3-benzothienyl)-Ala, or D-Lys; P2 can be V, L, M, Abu, Nle, or Nva; P3 can be S; P4 can be E, Q, Nle, or Nva; P5 can be K: P6 can be I, L, V, Nle, or Nva; P7 can be F; P8 can be Y, F, Phe(4-F); and PΩ at P9 can be V, I, A, Nva, MeVal, Abu, or V—NH$_2$.

A further embodiment relates to an isolated peptide of 9 amino acids, P1 to P9, which can include one amino acid at each site. For example, P1 can be K, F, Y, W, Phg, Phe(4-F), Phe(4-NO$_2$), MeTyr, β-(3-benzothienyl)-Ala, or D-Lys; P2 can be A, L, V, M, Abu, Nle, or Nva; P3 can be S; P4 can be E, Q, Nle, or Nva; P5 can be K; P6 can be I, L, V, Nle, or Nva; P7 can be F; P8 can be Y, F, Phe(4-F); P9 can be V; and PΩ at P10 can be I or L.

A further embodiment relates to an isolated peptide of 9 amino acids, P1 to P9, which can include one amino acid at each site. For example, P1 can be K, F, Y, W, Phg, Phe(4-F), Phe(4-NO$_2$), MeTyr, β-(3-benzothienyl)-Ala, or D-Lys; P2 can be V; P3 can be S; P4 can be E, Q, Nle, or Nva; P5 can be K: P6 can be I, L, V, Nle, or Nva; P7 can be F; P8 can be Y, F, Phe(4-F); P9 can be V; and PΩ at P10 can be I, L, V, or Nle.

A further embodiment relates to an isolated peptide of 9 amino acids, P1 to P9, which can include one amino acid at each site. For example, P1 can be K, F, Y, W, Phg, Phe(4-F), Phe(4-NO$_2$), MeTyr, β-(3-benzothienyl)-Ala, or D-Lys; P2 can be L; P3 can be S; P4 can be E, Q, Nle, or Nva; P5 can be K: P6 can be I, L, V, Nle, or Nva; P7 can be F; P8 can be Y, F, Phe(4-F); P9 can be V; and PΩ at P10 can be I, L, V, Nle or Nva.

A further embodiment relates to an isolated peptide having the sequence: K{L, V, M, I, D-Ala, D-Val, Nal-2, Aib, Abu, Nle, or Nva}SEKIFYV (SEQ ID NO. 2); or {F, Phg, Y, Phe(4-F), Phe(4-NO$_2$), O-methyl-Tyr, or P-(3-benzothienyl-Ala}ASEKIFYV (SEQ ID NO. 3); or {Y, F, or W}{V, M, or I}SEKIFYV (SEQ ID NO. 4); or {F or W}LSEKIFYV (SEQ ID NO. 5); or K{A, V, or L}SEKIFYI (SEQ ID NO. 6); or K{L or V}SEKIFYV-NH$_2$ (SEQ ID NO. 7); or FVSEKIFY{I, A, Nva, Abu, or MeVal} (SEQ ID NO. 8); or FVS{Q, Nle, or Nva}KIFYV (SEQ ID NO. 9); or FVSEK{L, V, Nle, or Nva}FYV (SEQ ID NO. 10); or FVSEKIF{F or Phe(4-F)}V (SEQ ID NO. 11); or KASEKIFYV{I or L} (SEQ ID NO. 12); or KVSEKIFYV {I, L, V, or Nle} (SEQ ID NO. 13); or KLSEKIFYV {L, V, Nle, or Nva} (SEQ ID NO. 14).

A further embodiment relates to an isolated peptide having the sequence: K{L, V, M, Abu, Nle, or Nva} SEKIFYV (SEQ ID NO. 15); or {F or Phg}A SEKIFYV (SEQ ID NO. 16; or YVSEKIFYV (SEQ ID NO. 17); or F{L, V, or I}SEKIFYV (SEQ ID NO. 18); or W{L or I}SEKIFYV (SEQ ID NO. 19); or K{V or L}SEKIFYI (SEQ ID NO. 20); or FVSEKIFY{I or Nva} (SEQ ID NO. 21).

A further embodiment relates to an isolated peptide having the sequence: K{V or L}SEKIFYV (SEQ ID NO. 22); or {F or Y}ASEKIFYV (SEQ ID NO. 23); or FVSEKIFYI (SEQ ID NO. 24).

A further embodiment relates to a class I MHC/peptide complex wherein the peptide has the sequence of any of the peptides in the embodiments described above and elsewhere herein. In one aspect, the complex can be cross-reactive with a T cell receptor (TCR) that recognizes a class I MHC/SSX-2$_{41-49}$ complex. In a further aspect, the complex can be an HLA-A2/SSX-2$_{41-49}$ complex.

A further embodiment relates to an immunogenic composition that can include any of the peptide embodiments described above and elsewhere herein. In one aspect the peptide can have, for example, the sequence: K{L, V, M, Abu, Nle, or Nva}SEKIFYV (SEQ ID NO. 15); or {F or Phg}A SEKIFYV (SEQ ID NO. 16); or YVSEKIFYV (SEQ ID NO. 17); or F{L, V, or I}SEKIFYV (SEQ ID NO. 18); or W{L or I}SEKIFYV (SEQ ID NO. 19); or K{V or L}SEKIFYI (SEQ ID NO. 20); or FVSEKIFY{I or Nva} (SEQ ID NO. 21), or K{V or L}SEKIFYV (SEQ ID NO. 22); or {F or Y}ASEKIFYV (SEQ ID NO. 23); or FVSEKIFYI (SEQ ID NO. 24).

Some further embodiments relate to analogs of the MHC class I-restricted T cell epitope NY-ESO-1$_{157-165}$, SLLMWITQC (SEQ ID NO.25), polypeptides that include these analogs that can be processed by pAPC to present the epitope analogs, and nucleic acids that express the analogs. The analogs can have similar or improved immunological properties compared to the wild-type epitope.

One embodiment relates to an isolated NY-ESO-1$_{157-165}$ peptide having a sequence comprising one or more amino acid substitutions of the sequence SLLMWITQC (SEQ ID NO: 25), in an amount sufficient to elicit cytokine production from a T cell line generated by immunization against an epitope with the sequence SLLMWITQC (SEQ ID NO: 25). For example, in one aspect, the amount sufficient can be less than 10 µM. In a further aspect, the amount can be less than 3 µM. Also, in a further aspect, the amount can be less than 1 µM. In a further aspect, the amount is less than 0.3 µM. In one aspect, the one or more amino acid substitution can include at least one standard amino acid. In a further aspect, the one or more amino acid substitution can include at least one non-standard amino acid. In a further aspect, the one or more amino acid substitution can include a modified terminal amino acid. In one aspect, the modified terminal amino acid can be an amidated C-terminal amino acid. In a further aspect, at least one of the substitutions can be the addition of an amino acid, wherein the addition is a C-terminal addition.

One embodiment relates to an isolated peptide having a sequence in which:
P1 is S, F, K, or W;
P2 is L, I, V, Nle, or Nva;
P3 is L;
P4 is M, L, or N;
P5 is W;
P6 is I, A, L, V, or N;
P7 is T;
P8 is Q, E, D, or T;
PΩ at P9 is C, V, I, L, A, Nva, Nle, V—NH$_2$, or L-NH$_2$; and
wherein the sequence is not SLLMWITQ{C, V, I, L, or A} (SEQ ID NO. 26), FVLMWITQA (SEQ ID NO. 27), or FILMWITQ{L or I} (SEQ ID NO. 28).

Another embodiment relates to an isolated peptide having a sequence in which:
P1 is Y;
P2 is L, V, I, Nle, or Nva;
P3 is L;
P4 is M, L, or N;
P5 is W;
P6 is I, A, L, V, or N;
P7 is T;
P8 is Q, E, D, or T;
PΩ at P9 is V, I, L, Nva, Nle, V—NH$_2$, or L-NH$_2$; and
wherein the sequence is not YVLMWITL (SEQ ID NO. 29) or YLLMWIT{I or L} (SEQ ID NO. 30).

A further embodiment relates to an isolated decamer peptide having a sequence {S or Y}LLMWITQ{C or V}{L, I or Nle} (SEQ ID NO. 31).

Yet another embodiment relates to an isolated peptide having a sequence SILMWITQ{C, V, L, or A} (SEQ ID NO. 32), YLLMWITQ{Nva or Nle}(SEQ ID NO. 33), F{L or V}LMWITQ{V, L, or I} (SEQ ID NO. 34), Y{I, Nva, or Nle}LMWITQV (SEQ ID NO. 35), YLLLWITQV (SEQ ID NO. 36), or TVLMWITQV (SEQ ID NO. 37).

A further embodiment relates to an isolated peptide having a sequence {S or F}VLMWITQV (SEQ ID NO. 38), SLMWITQNva (SEQ ID NO. 39), or SNvaLMWITQV (SEQ ID NO. 40).

Still another embodiment relates to an isolated peptide having a sequence SNvaLMWITQV (SEQ ID NO. 40).

Some embodiments relate to an isolated peptide. The peptide can include or consist essentially of a sequence in which:
P0 is X, XX, or XXX, wherein X specifies any amino acid or no amino acid; and
P1 is K, F, Y, W, Phg, Phe(4-F), Phe(4-NO$_2$), MeTyr, β-(3-benzothienyl)-Ala, or D-Lys; and
P2 is A, L, V, I, M, D-Ala, Nal-2, Abu, Aib, Nle, or Nva; and
P3 is S; and
P4 is E, Q, Nle, or Nva; and
P5 is K: and
P6 is I, L, V, Nle, or Nva; and
P7 is F; and
P8 is Y, F, Phe(4-F); and
PΩ at P9 is V, I, A, Nva, MeVal, Abu, or V—NH$_2$, or P9 is V, and PΩ at P10 is I, L, V, Nle or Nva; and
PΩ+1 is X, XX, or XXX, wherein X specifies any amino acid or no amino acid; and
wherein the sequence is not KASEKIFYV (SEQ ID NO. 1);

The isolated peptide can include or consist essentially of the sequence:
K{L, V, M, I, D-Ala, D-Val, Nal-2, Aib, Abu, Nle, or Nva}SEKIFYV (SEQ ID NO. 2); or
{F, Phg, Y, Phe(4-F), Phe(4-NO$_2$), O-methyl-Tyr, or β-(3-benzothienyl-Ala}ASEKIFYV (SEQ ID NO. 3); or
{Y, F, or W}{V, M, or I}SEKIFYV (SEQ ID NO. 4); or
{F or W}LSEKIFYV (SEQ ID NO. 5); or
K{A, V, or L}SEKIFYI (SEQ ID NO. 6); or
K{L or V}SEKIFYV-NH$_2$ (SEQ ID NO. 7); or
FVSEKIFY{I, A, Nva, Abu, or MeVal} (SEQ ID NO. 8); or
FVS{Q, Nle, or Nva}KIFYV (SEQ ID NO. 9); or
FVSEK{L, V, Nle, or Nva}FYV (SEQ ID NO. 10); or
FVSEKIF{F or Phe(4-F)}V (SEQ ID NO. 11); or
KASEKIFYV{I or L} (SEQ ID NO. 12); or KVSEKIFYV {I, L, V, or Nle} (SEQ ID NO. 13); or
KLSEKIFYV {L, V, Nle, or Nva} (SEQ ID NO. 14).

The isolated peptide can include or consist essentially of the sequence:
K{L, V, M, Abu, Nle, or Nva} SEKIFYV (SEQ ID NO. 15); or
{F or Phg}A SEKIFYV (SEQ ID NO. 16); or
YVSEKIFYV (SEQ ID NO. 17); or
F{L, V, or I}SEKIFYV (SEQ ID NO. 18); or
W{L or I}SEKIFYV (SEQ ID NO. 19); or
K{V or L}SEKIFYI (SEQ ID NO. 20); or
FVSEKIFY{I or Nva} (SEQ ID NO. 21).

Also, the isolated peptide can include or consist essentially of the sequence:
K{V or L}SEKIFYV (SEQ ID NO. 22); or
{F or Y}ASEKIFYV (SEQ ID NO. 23); or
FVSEKIFYI (SEQ ID NO. 24); or
KVSEKIFYV (SEQ ID NO. 41).

Further, the isolated peptide can include or consist essentially of the sequence KVSEKIFYV (SEQ ID NO. 41).

The isolated peptide can have affinity for a class I MHC peptide binding cleft. The MHC can be, for example, HLA-A2.

Some embodiments relate to a class I MHC/peptide complex wherein the peptide can have the sequence of any of the peptides described above or elsewhere herein. The class I MHC/peptide complex can be cross-reactive with a TCR that recognizes a class I MHC/SSX-2$_{41-49}$ complex. The class I MHC/peptide complex can be an HLA-A2/SSX-2$_{41-49}$ complex.

Other embodiments relate to a polypeptide that includes a peptide as described above and elsewhere herein, embedded within a liberation sequence.

Still further embodiments relate to immunogenic compositions that include a peptide as described above or elsewhere herein.

Other embodiments relate to nucleic acids encoding or nucleic acid means for expressing a polypeptide as described above or elsewhere herein. Also, some embodiments relate to immunogenic compositions that include such nucleic acids or nucleic acid means.

Some embodiments relate to methods of inducing, maintaining, or amplifying a CTL response. The methods can include intranodal administration of a composition as described above and elsewhere herein.

Other embodiments relate to methods of entraining a class I MHC-restricted T cell response, which methods can include intranodal administration a composition as described above or elsewhere herein. The methods can further include administration of an immunopotentiating agent.

Further embodiments relate to methods of inducing, maintaining, or entraining a CTL response, which methods can include intranodal administration of a composition as described above and elsewhere herein.

Some embodiments relate to isolated peptides that include 1 to 3 amino acid substitutions in the sequence KASEKIFYV (SEQ ID NO. 1) having an affinity for a class I MHC binding cleft that is similar to or greater than the affinity of KASEKIFYV (SEQ ID NO. 1) for said class I MHC binding cleft. The halftime of dissociation can be similar to or greater than the halftime of dissociation of KASEKIFYV (SEQ ID NO. 1) from said class I MHC binding cleft. The isolated peptide can be recognized by T cells with specificity for the peptide KASEKIFYV (SEQ ID NO. 1).

Still further embodiments relate to isolated peptides that include or consist essentially of a sequence in which:
P1 is K, F, Y, W, Phg, Phe(4-F), Phe(4-NO$_2$), MeTyr, β-(3-benzothienyl)-Ala, or D-Lys; and
P2 is A, L, V, I, M, D-Ala, Nal-2, Abu, Aib, Nle, or Nva; and
P3 is S; and
P4 is E, Q, Nle, or Nva; and
P5 is K: and
P6 is I, L, V, Nle, or Nva; and
P7 is F; and
P8 is Y, F, Phe(4-F); and
PΩ at P9 is V, I, A, Nva, MeVal, or Abu;
wherein the sequence is not KASEKIFYV (SEQ ID NO. 1);
or
P1 is K, F, Y, W, Phg, Phe(4-F), Phe(4-NO$_2$), MeTyr, β-(3-benzothienyl)-Ala, or D-Lys; and
P2 is V, L, M, Abu, Nle, or Nva; and
P3 is S; and
P4 is E, Q, Nle, or Nva; and
P5 is K: and
P6 is I, L, V, Nle, or Nva; and
P7 is F; and
P8 is Y, F, Phe(4-F); and
PΩ at P9 is V, I, A, Nva, MeVal, Abu, or V—NH$_2$;
or
P1 is K, F, Y, W, Phg, Phe(4-F), Phe(4-NO$_2$), MeTyr, β-(3-benzothienyl)-Ala, or D-Lys; and P2 is A, L, V, M, Abu, Nle, or Nva; and
P3 is S; and
P4 is E, Q, Nle, or Nva; and
P5 is K: and
P6 is I, L, V, Nle, or Nva; and
P7 is F; and
P8 is Y, F, Phe(4-F); and
P9 is V; and
PΩ at P10 is I or L;
or
P1 is K, F, Y, W, Phg, Phe(4-F), Phe(4-NO$_2$), MeTyr, β-(3-benzothienyl)-Ala, or D-Lys; and
P2 is V; and
P3 is S; and
P4 is E, Q, Nle, or Nva; and
P5 is K: and
P6 is I, L, V, Nle, or Nva; and
P7 is F; and
P8 is Y, F, Phe(4-F); and
P9 is V; and
PΩ at P10 is I, L, V, or Nle;
or
P1 is K, F, Y, W, Phg, Phe(4-F), Phe(4-NO$_2$), MeTyr, β-(3-benzothienyl)-Ala, or D-Lys; and
P2 is L; and
P3 is S; and
P4 is E, Q, Nle, or Nva; and
P5 is K: and
P6 is I, L, V, Nle, or Nva; and
P7 is F; and
P8 is Y, F, Phe(4-F); and
P9 is V; and
PΩ at P10 is I, L, V, Nle or Nva.

Some embodiments relate isolated peptides that include or consist essentially of a sequence in which:
P0 is X, XX or XXX, wherein X specifies any amino acid or no amino acid; and
P1 is S, F, K, W or Y; and
P2 is L, I, V, Nle, or Nva; and
P3 is L; and
P4 is M, L, or N; and
P5 is W; and
P6 is I, A, L, V, or N; and
P7 is T; and
P8 is Q, E, D, or T; and
PΩ at P9 is C, V, I, L, A, Nva, Nle, V—NH$_2$, or L-NH$_2$; and
PΩ+1 is X, XX, XXX, wherein X specifies any amino acid or no amino acid; and
wherein the sequence is not SLLMWITQ{C, V, I, L, or A} (SEQ ID NO. 26), FVLMWITQA (SEQ ID NO. 27), FILMWITQ{L or I} (SEQ ID NO. 28), YVLMWITL (SEQ ID NO. 29) or YLLMWIT{I or L} (SEQ ID NO. 30).
P1 is S, F, K, or W;
P2 is L, I, V, Nle, or Nva;
P3 is L;
P4 is M, L, or N;
P5 is W;
P6 is I, A, L, V, or N;
P7 is T;
P8 is Q, E, D, or T;
PΩ at P9 is C, V, I, L, A, Nva, Nle, V—NH$_2$, or L-NH$_2$; and
wherein the sequence is not SLLMWITQ{C, V, I, L, or A} (SEQ ID NO. 26), FVLMWITQA (SEQ ID NO. 27), or FILMWITQ{L or I} (SEQ ID NO. 28);
or
P1 is Y;
P2 is L, V, I, Nle, or Nva;
P3 is L;
P4 is M, L, or N;
P5 is W;
P6 is I, A, L, V, or N;
P7 is T;
P8 is Q, E, D, or T;
PΩ at P9 is V, I, L, Nva, Nle, V, V—NH$_2$, or L-NH$_2$; and
wherein the sequence is not YVLMWITL (SEQ ID NO. 29) or YLLMWIT{I or L} (SEQ ID NO. 30).

A further embodiment relates to a class I MHC/peptide complex wherein the peptide can have the sequence of any of the peptides in the embodiments described above or elsewhere herein. In one aspect, the complex can be cross-reactive with a TCR that recognizes a class I MHC/NY-ESO-1$_{157-165}$ complex. In a further aspect, the complex can be an HLA-A2/NY-ESO-1$_{157-165}$ complex.

In one aspect of the above embodiments, the peptide can have affinity for a class I MHC peptide binding cleft, such as HLA-A2.

A further embodiment relates to a polypeptide comprising the peptide sequence of any of the embodiments described herein in association with a liberation sequence.

A further embodiment relates to an immunogenic composition that includes any of the peptide embodiments described herein. In one aspect, the peptide can have a sequence as set forth herein.

A further embodiment relates to a nucleic acid encoding any of the peptide embodiments described herein, but preferably those which do not have non-standard amino acid substitutions. In a further aspect, the nucleic acid can be encoded in a vector.

A further embodiment relates to an immunogenic composition that includes a nucleic acid encoding any of the peptide embodiments disclosed herein.

A further embodiment relates to a method of inducing a CTL response comprising intranodally administering of any of the compositions or peptides of the embodiments disclosed herein. In a further aspect, the method can allow for maintaining a CTL response. In a further aspect, the method can allow for amplifying a class I MHC-restricted T cell response. In a further aspect, the method can allow for entraining a class I MHC-restricted T cell response. In a further aspect, the method also can include administering an immunopotentiating agent.

Some embodiments relate to isolated peptides having a sequence comprising one to three or four amino acid substitutions in a native epitope sequence, wherein a concentration of the peptide required to elicit cytokine production from a T cell line generated by immunization against an epitope with the sequence is not more than a particular concentration, for example, 10 μM, 1 μM, 0.3 μM, and the like. The one to three or four amino acid substitutions can include at least one standard amino acid substitution and/or at least one non-standard amino acid substitution, and the like. The at least one non-standard amino acid can be any of those described herein, for example, a D-stereoisomer of a standard amino acid, Nva, or Nle. The one to three or four amino acid substitutions can include a modified terminal amino acid, and the modified terminal amino acid can be an amidated C-terminal amino acid. One of the substitutions can be the addition of an amino acid, for example, the addition can be a C-terminal addition.

Other embodiments relate to peptides having an amino acid sequence that includes at least one difference from a sequence of a segment of a target-associated antigen, the segment having known or predicted affinity for the peptide binding cleft of a MHC protein, wherein the at least one difference can be a Nle or Nva residue replacing a residue at an MHC-binding motif anchor position in said segment. The anchor position can be a primary anchor position, for example, P2 or PΩ. The anchor position can be an auxiliary anchor position. The difference can include a Nle or Nva residue replacing a hydrophobic residue in said segment. In some aspects I, L, or V can be a preferred residue in the MHC-binding motif anchor position. In some aspects the peptide can have a length of about 8 to about 14 amino acids, or more preferably a length of 9 to 10 amino acids, for example.

The MHC protein can be a human MHC protein, for example, class I HLA protein. The MHC protein can be, for example, a type such as HLA-A2, A3, A24, A30, A66, A68, A69, B7, B8, B15, B27, B35, B37, B38, B39, B40, B48, B51, B52, B53, B 60, B61, B62, B63, B67, B70, B71, B75, B77, C4, Cw1, Cw3, Cw4, Cw6, Cw7, and Cw10. In some aspects, the MHC protein can be HLA-A2 or A24. The MHC can have an anchor residue binding pocket, wherein the pocket is homologous to the B- or F-pocket of HLA-A*0201. The MHC residues responsible for forming binding pockets, and which binding pockets accommodate epitope anchor residues and thus define the binding specificity of the MHC molecule, are well understood in the art. One compilation of such information is found at the FIMM (Functional Immunology) website at the hypertext transfer protocol (http://) "sdmc.lit.org.sg:8080/fimm/." (See also Schönbach C., Koh J. L. Y., Sheng X., Wong L., and V. Brusic. FIMM, a database of functional molecular immunology. *Nucleic Acids Research*, 2000, Vol. 28, No. 1 222-224; Schönbach C., Koh J L, Flower D R, Wong L., and Brusic V. FIMM, a database of functional molecular immunology; update 2002. *Nucleic Acids Research*, 2002, Vol. 30, No. 1 226-229; and Zhang, C. et al., *J. Mol. Biol.* 281:929-947, 1998; each of which is hereby incorporated by reference in its entirety). Also, the peptide can have at least one binding characteristic that is substantially the same as, or better than, a corresponding characteristic of said segment for said MHC. For example, the binding characteristic can be elevated compared with that of said segment. In some embodiments, the binding characteristic can be affinity or stability of binding for example.

The peptide can have an immunogenicity that is substantially the same as, or better than, the immunogenicity of the segment. The immunogenicity can be increased. The immunogenicity can evoke an immune response that is cross-reactive to said segment or can evoke a CTL response. The immunogenicity can be assessed, for example, using an MHC-tetramer assay, a cytokine assay, a cytotoxicity assay, by measuring an immune response recognizing the peptide, by measuring an immune response recognizing said segment, using an in vitro immunizations system, or any other suitable method. The immunization system can include human cells. The immunogenicity can be assessed using an in vivo immunization system, for example, one that includes a transgenic mouse. The peptide can have an at least similar binding characteristic as said segment for said MHC. For example, in some aspects what is considered to be "similar" can be determined based upon the instant disclosure. In some particular aspects, "similarity" can be based upon, for example, peptide concentration for half-maximal binding, relative affinity, stability (half time of dissociation) and cross-reactivity/functional avidity. As an example, a peptide can be considered similar if it has results or characteristics that are within two-fold, even threefold, four, five or 10-fold of the value for the native peptide. For example, for cross-reactivity/functional avidity, a similar result can be one where the data are within three and 10-fold of the native peptide. As another example, percentage of binding values can be considered similar when within 2, 3, 4, 5, 6, 7, 10, 15 or 20% of the native peptide. In some aspects, $ED_{50}$ values can be considered similar when within 2- or 3-fold of native sequence. Similar halftime of dissociation can be, for example, within 2- or 3- fold. As still another example, a cross-reactivity value that is about 2-fold different from wild-type can be considered similar. These similar values are exemplary only and given in the context of some aspects of some embodiments. Other "similar" values can be determined based upon the experiments and teachings herein.

The peptides can be immunologically cross-reactive with the segment. Thus, the cross-reactivity can be assessed by immunizing with the segment and assaying recognition of the peptide. Alternatively, the cross-reactivity can be assessed by immunizing with the peptide and assaying recognition of the segment.

The peptide as described above and elsewhere herein can be modified to include two differences, for example. In some instances, each difference independently can include a Nle or Nva residue. In some instances, one difference can is not a Nle or Nva substitution. Also, the peptide as described above and elsewhere herein can include three or more differences.

The target-associated antigen can be a tumor-associated antigen. The target-associated antigen can be a pathogen-associated antigen.

Other embodiments relate to immunogenic composition that include the instant peptides as described above and elsewhere herein. Further embodiments relate to methods of immunization that include administering such compositions to a mammal, for example, administering directly to the lymphatic system of the mammal.

Still other embodiments relate to methods of making a T cell epitope analogue. The methods can include providing an amino acid sequence of a segment of a target-associated antigen, the segment can have known or predicted affinity for the peptide binding cleft of a MHC protein; changing at least one amino acid of the sequence corresponding to an anchor position of a MHC binding motif to Nle or Nva; and synthesizing a peptide comprising the changed sequence. The synthesis can be, for example, chemical synthesis or any other synthetic method.

Some embodiments relate to T cell epitope peptide analogues wherein the analogue differs from a native epitope peptide by replacement of at least one native residue corresponding to an anchor position of a MHC binding motif with a Nle or Nva residue.

Some embodiments relate to isolated peptides including or consisting essentially of a sequence in which:
P0 is X, XX, or XXX, wherein X specifies any amino acid or no amino acid; and
P1 is G, A, S, Abu, or Sar; and
P2 is L, M, I, Q, V, Nva, Nle, or Abu; and
P3 is P or W; and
P4 is S; and
P5 is I; and
P6 is P; and
P7 is V; and
P8 is H; and
P9 is P, A, L, S, or T; and
PΩ at P10 is I, L, V, Nva, or Nle; and
PΩ+1 is X, XX, or XXX, wherein X specifies any amino acid or no amino acid; and
wherein the sequence is not GLPSIPVHPI (SEQ ID NO. 42).

The isolated peptide can include or consist essentially of the sequence:
{S, Sar, or Abu}LPSIPVHPI (SEQ ID NO. 43); or
G{M or Nle}PSIPVHPI (SEQ ID NO. 44); or
G{L, I, Nva, or Nle}WSIPVHPI (SEQ ID NO. 45); or GLWSIPVHP{Nva or V} (SEQ ID NO. 46); or
GLPSIPVH{A or S}I (SEQ ID NO. 47); or
GLPSIPVHP{V, L, Nva, or Nle} (SEQ ID NO. 48); or
G{Nle}PSIPVHP{Nva, or Nle} (SEQ ID NO. 49); or
G{Nva}PSIPVHP{Nva} (SEQ ID NO. 50); or
G{V, Nva, or Nle}PSIPVHPV (SEQ ID NO. 51); or
{Sar or Abu}LPSIPVHP{V or Nva} (SEQ ID NO. 52); or
A{V, I, Nva, or Nle}WSIPVHPI (SEQ ID NO. 53); or
AVPSIPVHP{V or Nva} (SEQ ID NO. 54); or
A{Nva}PSIPVHPV (SEQ ID NO. 55); or
ALWSIPVHP{V or Nva} (SEQ ID NO. 56); or
GVWSIPVHP{V or Nva} (SEQ ID NO. 57); or
G{Nva}WSIPVHPV (SEQ ID NO. 58).

Also, the isolated peptide can include or consist essentially of the sequence:
{Abu}LPSIPVHPI (SEQ ID NO. 59); or
G{V, Nva, or Abu}PSIPVHPI (SEQ ID NO. 60); or
GLPSIPVHP{V or Nva} (SEQ ID NO. 61); or
GLWSIPVHP{I or Nva} (SEQ ID NO. 62); or
G{Nle}PSIPVHP{Nva} (SEQ ID NO. 63); or
G{Nle or Nva}PSIPVHPV (SEQ ID NO. 64); or
{A or Abu}LPSIPVHP{V or Nva} (SEQ ID NO. 65); or
G{Nva}WPSIPVHP{I or V} (SEQ ID NO. 66); or
A{Nva or Nle}WSIPVHPI (SEQ ID NO. 67); or
A{V or Nva}PSIPVHPV (SEQ ID NO. 68).

In particular, the isolated peptide can include or consist essentially of the sequence:
{Abu}LPSIPVHPI (SEQ ID NO. 59); or
GLPSIPVHP{V or Nva} (SEQ ID NO. 61); or
GLWSIPVHPI (SEQ ID NO. 69); or
G{Nle}PSIPVHP{Nva} (SEQ ID NO. 63).

Preferably, the isolated peptide can include or consist essentially of the sequence: GLPIPVHPV (SEQ ID NO. 70).

The peptide can have affinity for a class I MHC peptide binding cleft, and the class I MHC can be, for example, HLA-A2.

Further embodiments relate to class I MHC/peptide complexes wherein the peptide has the sequence of a peptide as described above and elsewhere herein. The class I MHC/peptide complex can be cross-reactive with a TCR that recognizes a class I MHC/PSMA$_{288-297}$ complex. The class I MHC/peptide complex can be an HLA-A2/PSMA$_{288-297}$ complex.

Some embodiments relate to polypeptides that include a peptide sequence as described above and elsewhere herein embedded within a liberation sequence.

Further embodiments relate to immunogenic compositions that include a peptide as described above and elsewhere herein.

Still other embodiments relate to a nucleic acid encoding or a nucleic acid means for expressing a polypeptide as described above and elsewhere herein, as well as immunogenic compositions that include the nucleic acids or nucleic acid means.

Some other embodiments relate to methods of inducing, maintaining, or amplifying a CTL response. The methods can include intranodal administration of a composition as described above and elsewhere herein.

Also, some methods relate to methods of entraining a class I MHC-restricted T cell response, which methods can include intranodal administration of a composition as described above and elsewhere herein. The methods can also include administration of an immunopotentiating agent.

Other embodiments relate to isolated peptides that include 1 to 3 substitutions in the sequence GLPSIPVHPI (SEQ ID NO. 42) and which have an affinity for a class I MHC binding cleft that is similar to or greater than the affinity of GLPSIPVHPI (SEQ ID NO. 42) for the class I MHC binding cleft. The halftime of dissociation can be similar to or greater than the halftime of dissociation of GLPSIPVHPI (SEQ ID NO. 42) from the class I MHC binding cleft. The isolated peptide can be recognized by T cells with specificity for the peptide GLPSIPVHPI (SEQ ID NO. 42).

Some embodiments relate to isolated peptides that include or consist essentially of a sequence in which:
P0 is X, XX, or XXX, wherein X specifies any amino acid or no amino acid; and
P1 is S, K, F, Y, T, Orn, or Hse; and
P2 is L, V, M, I, Nva, Nle, or Abu; and
P3 is L, Nva, Nle or Abu; and
P4 is Q; and
P5 is H; and
P6 is L, Nva, Nle, or Abu; and
P7 is I; and
P8 is G, A, S, or Sar; and
PΩ at P9 is L, V, I, A, Nle, Nva, Abu, or L-NH$_2$; and
PΩ+1 is X, XX, or XXX, wherein X specifies any amino acid or no amino acid; and
wherein the sequence is not SLLQHLIGL (SEQ ID NO. 71).

The isolated peptide can include or consist essentially of the sequence:
{K, F, Y, T, Orn, or Hse}LLQHLIGL (SEQ ID NO. 72); or
S{V, M, I, Nva, Nle, or Abu}LQHLIGL (SEQ ID NO. 73); or
SL{Nva, Nle or Abu}QHLIGL (SEQ ID NO. 74); or
SLLQH{Nva, Nle or Abu}IGL (SEQ ID NO. 75); or
SLLQHLI{A, S, or Sar}L (SEQ ID NO. 76); or
SLLQHLIG{V, I, A, Nle, Nva, Abu, or L-NH$_2$} (SEQ ID NO. 77); or
{F, Y, T, Orn, or Hse} {Nva, Nle, M, or I}LQHLIGL (SEQ ID NO. 78); or
S{Nva, Nle, or M}LQHLIG{Nva, Nle, or V} (SEQ ID NO. 79); or
{K, F, Y, T, Orn, or Hse}LLQHLIGV (SEQ ID NO. 80); or
{F or T}LLQHLIG{Nle} (SEQ ID NO. 81); or
{F or T} {Nva or M}LQHLIG{Nle} (SEQ ID NO. 82).

Also, the isolated peptide can include or consist essentially of the sequence:
{F, Y, T, Orn, or Hse}LLQHLIGL (SEQ ID NO. 83); or
S{Nva, Nle, or M}LQHLIGL (SEQ ID NO. 84); or
SLLQHLIG{Nle, Nva, or L-NH$_2$} (SEQ ID NO. 85); or
SLLQH{Nva or Abu}IGL (SEQ ID NO. 86); or
S{Nva}LQHLIG{Nle} (SEQ ID NO. 87); or {F or T} {L or Nva}LQHLIG{Nle} (SEQ ID NO. 88).

Further, the isolated peptide can include or consist essentially of the sequence:
S{L or Nva}LQHLIG{Nle} (SEQ ID NO. 89); or
T{Nva}LQHLIG{Nle} (SEQ ID NO. 90).

The isolated can include or consist essentially of the sequence S{Nva}LQHLIG{Nle} (SEQ ID NO. 87).

The isolated peptide can have affinity for a class I MHC peptide binding cleft, and for example, the class I MHC can be HLA-A2.

Embodiments relate to class I MHC/peptide complexes wherein the peptide can have the sequence of a peptide as disclosed above, and elsewhere herein. The class I MHC/peptide complex can be cross-reactive with a TCR that recognizes a class I MHC/PRAME$_{425-433}$ complex. The class I MHC/peptide complex can be an HLA-A2/PRAME$_{425-433}$ complex.

Other embodiments relate to polypeptides that include a peptide sequence as described above and described elsewhere herein in association with a liberation sequence.

Further embodiments relate to immunogenic compositions that include a peptide as described above and described elsewhere herein.

Some embodiments relate to a nucleic acid encoding and a nucleic acid means for expressing a polypeptide as described above and described elsewhere herein, as well as immunogenic compositions that include such nucleic acids and means.

Still other embodiments relate to methods of inducing, maintaining, or amplifying a CTL response, which methods can include intranodal administration of a composition as described above and described elsewhere herein. Some embodiments relate to methods of entraining a class I MHC-restricted T cell response, which can include intranodal administration of a composition as described above and described elsewhere herein. In some embodiments, the methods further include administration of an immunopotentiating agent.

Some embodiments relate to isolated peptides that include 1 to 3 substitutions in the sequence SLLQHLIGL (SEQ ID NO. 71), having an affinity for a class I MHC binding cleft that is similar to or greater than the affinity of SLLQHLIGL (SEQ ID NO. 71) for said class I MHC binding cleft. The halftime of dissociation can be similar to or greater than the halftime of dissociation of SLLQHLIGL (SEQ ID NO. 71) from said class I MHC binding cleft. The isolated peptide can be recognized by T cells with specificity for the peptide SLLQHLIGL (SEQ ID NO. 71).

Further embodiments relate to methods to generate and resulting compositions representing peptides that are immune active and carry unnatural amino acids at one or multiple MHC anchor residues.

A further embodiment of the present invention relates to the pSEM plasmid and immunogenic peptides expressed by this plasmid corresponding to Melan-A$_{26-35}$ and/or tyrosinase$_{369-377}$ epitopes. The pSEM plasmid encodes the Melan-A and tyrosinase epitopes in a manner that allows for their expression and presentation by pAPCs. Details of the pSEM plasmid are disclosed in U.S. Patent Application Publication No. 20030228634, which is incorporated herein by reference in its entirety.

In particular embodiments of the invention, there is provided an isolated peptide analogue of an immunogenic peptide expressed by a pSEM plasmid consisting essentially of the sequence: E{A, L, Nva, or Nle}AGIGILT{V, Nva, or Nle} (SEQ ID NO. 91); or Y{M, V, Nva, or Nle}DGTMSQ{V, Nva, or Nle} (SEQ ID NO. 92); and wherein the sequence is not E{A or L}AGIGILTV (SEQ ID NO. 93) or YMDGTMSQV (SEQ ID NO. 94). The isolated peptide analogue of the invention may be selected from the group consisting of ELAGIGILTNva (SEQ ID NO. 95), ENvaAGIGILTV (SEQ ID NO. 96), YVDGTMSQNva (SEQ ID NO. 97), YVDGTMSQV (SEQ ID NO. 98) and YMDGTMSQNva (SEQ ID NO. 99).

In other embodiments the isolated peptide analogue is an analogue consisting essentially of the amino acid sequence ENvaAGIGILTV (SEQ ID NO. 96). In yet other embodiments the isolated peptide analogue is an analogue consisting essentially of the amino acid sequence YMDGTMSQNva (SEQ ID NO. 97). In further embodiments the peptide has affinity for a class I MHC peptide binding cleft. The class I MHC is HLA-A2.

Other embodiments of the invention relate to an isolated peptide analogue comprising one to three substitutions in the sequence EAAGIGILTV (SEQ ID NO. 100) having an affinity for a class I MHC binding cleft that is similar to or greater than the affinity of EAAGIGILTV (SEQ ID NO. 100) for the class I MHC binding cleft. In still other embodiments, the halftime of dissociation is similar to or greater than the halftime of dissociation of EAAGIGILTV (SEQ ID NO. 100) from the class I MHC binding cleft. In other embodiments, the isolated peptide is recognized by T cells with specificity for the peptide EAAGIGILTV (SEQ ID NO. 100).

In yet another embodiment, the invention relates to an isolated peptide analogue comprising one to three substitutions in the sequence YMDGTMSQV (SEQ ID NO. 94) having an affinity for a class I MHC binding cleft that is similar to or greater than the affinity of YMDGTMSQV (SEQ ID NO. 94) for the class I MHC binding cleft. In yet other embodiments, the halftime of dissociation is similar to or greater than the halftime of dissociation of YMDGTMSQV (SEQ ID NO. 94) from the class I MHC binding cleft. In other embodiments, the isolated peptide is recognized by T cells with specificity for the peptide YMDGTMSQV (SEQ ID NO. 94).

Embodiments of the invention also relate to a class I MHC/peptide complex wherein the peptide has the sequence of the peptide of: E{A, L, Nva, or Nle}AGIGILT{V, Nva, or Nle} (SEQ ID NO. 91); or Y{M, V, Nva, or Nle}DGTMSQ{V, Nva, or Nle} (SEQ ID NO. 92); and wherein the sequence is not E{A or L}AGIGILTV (SEQ ID NO. 93) or YMDGTMSQV (SEQ ID NO. 94). In other embodiments, the class I MHC/peptide complex is cross-reactive with a TCR that recognizes a class I MHC/Melan-A$_{26-35}$ complex. The class I MHC/peptide complex of is an HLA-A2/Melan-A$_{26-35}$ complex.

In still yet another embodiment, the class I MHC/peptide complex is cross-reactive with a TCR that recognizes a class I MHC/Tyrosinase$_{369-377}$ complex. The class I MHC/peptide complex is an HLA-A2/Tyrosinase$_{369-377}$ complex.

Some embodiments of invention relate to a polypeptide comprising the peptide sequence of E{A, L, Nva, or Nle}AGIGILT{V, Nva, or Nle} (SEQ ID NO. 91); or Y{M, V, Nva, or Nle}DGTMSQ{V, Nva, or Nle} (SEQ ID NO. 92) embedded within a liberation sequence; wherein the sequence is not E{A or L}AGIGILTV (SEQ ID NO. 93) or YMDGTMSQV (SEQ ID NO. 94). In yet a further embodiment, the invention relates to an immunogenic composition comprising any of the peptides of E{A, L, Nva, or Nle}AGIGILT{V, Nva, or Nle} (SEQ ID NO. 91); or Y{M, V, Nva, or Nle}DGTMSQ{V, Nva, or Nle} (SEQ ID NO. 92); and wherein the sequence is not E{A or L}AGIGILTV (SEQ ID NO. 93) or YMDGTMSQV (SEQ ID NO. 94). The invention also relates to an immunogenic composition comprising a polypeptide comprising any of the peptides of E{A, L, Nva, or Nle}AGIGILT{V, Nva, or Nle} (SEQ ID NO. 91); or Y{M, V, Nva, or Nle}DGTMSQ{V, Nva, or Nle} (SEQ ID NO. 92), and to a nucleic acid encoding such a polypeptide. Embodiments of invention further relate to an immunogenic composition comprising the nucleic acid.

The immunogenic compositions of the invention may be administered as the entraining portion of an immunization strategy against a cancer such as glioblastoma and melanoma, but is not limited to such. In addition, peptides corresponding to the Melan-A$_{26-35}$ and tyrosinase$_{369-377}$ epitopes and epitope analogues can be administered as the amplification portion of the same immunization strategy. In preferred embodiments, the peptide analogues E{A, L, Nva, or Nle}AGIGILT{V, Nva, or Nle} (SEQ ID NO. 91); or Y{M, V, Nva, or Nle}DGTMSQ{V, Nva, or Nle} (SEQ ID NO. 92) may be utilized in the amplification step. The entrain-and-amplify protocol employed in the present invention is as disclosed in greater detail in U.S. Patent Publication No. 20050079152, and U.S. Provisional Patent Application No. 60/640,402, both entitled METHODS TO ELICIT, ENHANCE AND SUSTAIN IMMUNE RESPONSES AGAINST MHC CLASS I-RESTRICTED EPITOPES, FOR PROPHYLACTIC OR THERAPEUTIC PURPOSES, each of which is incorporated herein by reference in its entirety.

Thus, in one embodiment, a method of inducing, maintaining, or amplifying a CTL response is provided. The method can include intranodal administration of an immunogenic composition comprising a nucleic acid encoding a polypeptide comprising the peptide sequence of an immunogenic peptide expressed by a pSEM plasmid consisting essentially of the sequence: E{A, L, Nva, or Nle}AGIGILT{V, Nva, or Nle} (SEQ ID NO. 91); or Y{M, V, Nva, or Nle}DGTMSQ{V, Nva, or Nle} (SEQ ID NO. 92). In further embodiments, there is provided a method of entraining a class I MHC-restricted T cell response comprising intranodal administration of the immunogenic composition and an immunopotentiating agent. In yet other embodiments, there is provided a method of inducing, maintaining, or entraining a CTL response comprising intranodal administration of any immunogenic composition disclosed herein.

BRIEF DESCRIPTION OF THE DRAWINGS

FIGS. 1A and B summarize substitutions for SSX-$2_{41-49}$ analogs at each individual amino acid position for nonamers and decamers, respectively (SEQ ID NO: 1).

FIG. 2 is a schematic diagram of the methodology of a preferred embodiment for identifying analogs.

FIG. 3 is a table showing the cross-reactivity and functional avidity of SSX-$2_{41-49}$ analogs substituted at a single position. The sequence depicted in row 1, col. 4 is SEQ ID NO: 1; the sequences depicted in rows 2-13, col. 4 are SEQ ID NOS: 102-114, respectively; the sequences depicted in rows 14-16 are SEQ ID NO: 115, 116, and 117, respectively; the sequence depicted in row 17 is SEQ ID NO: 118; the sequence depicted in row 18 is SEQ ID NO: 119; the sequence depicted in row 19 is SEQ ID NO: 120; the sequence depicted in row 20 is SEQ ID NO: 121; the sequence depicted in row 21 is SEQ ID NO: 122; the sequence depicted in row 22 is SEQ ID NO: 123; the sequence depicted in row 23 is SEQ ID NO: 124; the sequence depicted in row 24 is SEQ ID NO: 12; the sequence depicted in row 25 is SEQ ID NO: 173; the sequence depicted in row 26 is SEQ ID NO: 174; and the sequence depicted in row 27 is SEQ ID NO: 175.

FIG. 4 is a table showing the cross-reactivity and functional avidity of SSX-$2_{41-49}$ analogs substituted at two positions. The sequence depicted in row 1, col. 4 is SEQ ID NO: 1; the sequences depicted in rows 2-14, col. 4 are SEQ ID NOS: 126-138, respectively; and the sequences depicted in rows 16-18 are SEQ ID NOS; 148, 149 and 150, respectively.

FIG. 5 is a table showing the cross-reactivity and functional avidity of SSX-$2_{41-49}$ analogs substituted at more than two positions. The sequence depicted in row 1, col. 4 is SEQ ID NO: 1; the sequences depicted in rows 2-10 are SEQ ID NOS: 139-147, respectively; the sequences depicted in rows 11-28 are SEQ ID NOS: 152-168, respectively; and the sequences depicted in rows 30-31 are SEQ ID NOS: 171 and 172, respectively.

FIG. 6 is a table showing the cross-reactivity and functional avidity of SSX-$2_{41-49}$ decamer analogs encompassing the nominal 41-49 peptide. The sequence depicted in row 1, col. 4 is SEQ ID NO: 1; the sequences depicted in rows 2-8 are SEQ ID NOS: 177-183, respectively; and the sequences depicted in rows 9-16 are SEQ ID NOS: 185-192, respectively.

FIG. 7 is a timeline showing the injection schedule of the SSX-$2_{41-49}$ analogs.

FIG. 8 is a bar graph showing the activity of the SSX-$2_{41-49}$ A42V, A42L analogs and wild-type in lysis of tumor cells.

FIG. 9 is a timeline showing the injections schedule for in vivo cytoxicity studies and ex vivo cytotoxicity studies as well as the SSX-$2_{41-49}$ analog peptide used for the boost.

FIG. 10 is a table showing the in vivo specific lysis results for a number of the analogs as compared to a control (wild-type peptide) and EAA (Melan A 26-35).

FIG. 11 is a table showing the in vivo specific lysis results for a number of the SSX-$2_{41-49}$ analogs as compared to a control (wild-type peptide) and EAA as well as MHC binding and MHC stability.

FIG. 12 is a bar graph showing the percent specific lysis of tumor cells (624.38 human tumor cells) achieved following immunization with a number of analogs as compared to a wild-type control.

FIGS. 13A-C are tables summarizing the substitutions at each individual amino acid position for nonamers and decamers, respectively, as well as the results obtained for each. The peptides depicted in col. 3, beginning in the first row and continuing to the last row of the table, are SEQ ID NOS: 25 and 201-281, respectively.

FIG. 14 is a timeline showing the injection schedule used for analysis and testing of the NY-ESO-1 analogs.

FIGS. 15A-C show the specific elimination of target cells as measured by removing the spleens and PBMC from challenged animals and measuring CFSE fluorescence by flow cytometry.

FIGS. 16A and B are bar graphs showing the in vivo cytotoxicity against target cells coated with wild-type peptide after boost with NY-ESO-1 analogs.

FIGS. 17A and B are bar graphs showing an ex vivo analysis of the ability of the analogs to trigger enhanced immunity against the wild-type epitope as assessed by cytokine production.

FIG. 18 illustrates a protocol for validating the antigenicity of the $PSMA_{288-297}$ epitope, as well as the results of the testing.

FIG. 19 is a table showing the cross-reactivity and functional avidity of $PSMA_{288-297}$ analogs substituted at a single position. The peptides depicted in col. 4, beginning in the first row and continuing to the last row of the table, are SEQ ID NOS: 352-372, respectively.

FIG. 20 is a table showing the cross-reactivity and functional avidity of $PSMA_{288-297}$ analogs substituted at two positions. The peptides depicted in col. 4, beginning in the first row and continuing to the last row of the table, are SEQ ID NOS: 373-393, respectively.

FIG. 21 is a table showing the cross-reactivity and functional avidity of $PSMA_{288-297}$ analogs substituted at more than two positions. The peptides depicted in col. 4, beginning in the first row and continuing to the last row of the table, are SEQ ID NOS: 394-407, respectively.

FIG. 22 is a bar graph showing the immunogenicity of various $PSMA_{288-297}$ analogs measured by Elispot.

FIG. 23 is a line graph showing the amplification of anti-$PSMA_{288-297}$ response by the I297V analog measured by Elispot.

FIG. 24 is a bar graph showing the results of boosting with the I297V analog. The assay showed that the boosting resulted in cytotoxic immunity against a $PSMA^+$ human tumor line.

FIG. 25 illustrates a protocol for validating the antigenicity of the $PRAME_{425-433}$ epitope, as well as the results of the testing.

FIG. 26 is a table showing the cross-reactivity and functional avidity of PRAME$_{425\text{-}433}$ analogs substituted at a single position. The peptide depicted in col. 4, row 1, is SEQ ID NO: 71. The peptides depicted in col. 4, beginning in the second row and continuing to the last row of the table, are SEQ ID NOS: 282-310, respectively.

FIGS. 27 A and B are tables showing the cross-reactivity and functional avidity of PRAME$_{425\text{-}433}$ analogs substituted at two positions. The peptide depicted in col. 4, row 1, of the table in both FIGS. 27A and 27B is SEQ ID NO: 71. The peptides depicted in col. 4, beginning in the second row and continuing to the last row of the table in FIG. 27A, are SEQ ID NOS: 311-347, respectively. The peptides depicted in col. 4, beginning in the second row and continuing to the last row of the table in FIG. 27B, are SEQ ID NOS: 331-347, respectively.

FIG. 28 is a table showing the cross-reactivity and functional avidity of PRAME$_{425\text{-}433}$ analogs substituted at more than two positions. The peptide depicted in col. 4, row 1, is SEQ ID NO: 71. The peptides depicted in col. 4, beginning in the second row and continuing to the last row of the table, are SEQ ID NOS: 348-351, respectively.

FIG. 29 is a bar graph showing the immunogenicity of a PRAME$_{425\text{-}433}$ analog measured by Elispot.

FIG. 30 shows the results of boosting with the L426Nva L433Nle analog. The assay showed that the boosting resulted in cytotoxic immunity against native epitope coated cells.

FIG. 31 shows a protocol for the in vivo evaluation of PRAME analogs, as well as a bar graph showing the results of the evaluation.

FIG. 32 shows a protocol for the ex vivo stimulation of cytokine production in analog induced, native epitope re-stimulated T cells and a bar graph showing the results of the evaluation.

FIG. 33 is a bar graph showing the results of boosting with the L426Nva L433Nle analog. The assay showed that the boosting resulted in cytotoxic immunity against a human tumor cell line.

FIG. 34 depicts a protocol for in vitro immunization to PRAME$_{425\text{-}433}$.

FIG. 35 shows the tetramer analysis results after in vitro immunization with PRAME$_{425\text{-}433}$ analogs.

FIG. 36 depicts the structure of the plasmid, pCTLR2, a plasmid that expresses the PRAME$_{425\text{-}433}$ epitope.

FIG. 37 is a bar graph showing the assay results for an experiment in which humor tumor cells (624.38) were lysed by T cells primed with plasmid DNA and boosted with peptides.

FIG. 38 is a bar graph showing the tetramer analysis results after plasmid prime with Tyr$_{369\text{-}377}$ and peptide boost with the V377Nva analog.

FIG. 39 is a bar graph showing in vivo response against analogues Tyrosinase and Melan A epitopes.

FIG. 40 is a timeline showing a Tyrosinase analogues immunogenicity evaluation protocol.

FIG. 41 is a bar graph showing the immune response results against 624.38 cells contacted with effector cells from HHD primed with plasmid and boosted with Tyr$_{369\text{-}377}$ analogs.

DETAILED DESCRIPTION OF THE PREFERRED EMBODIMENT

Figure 7:
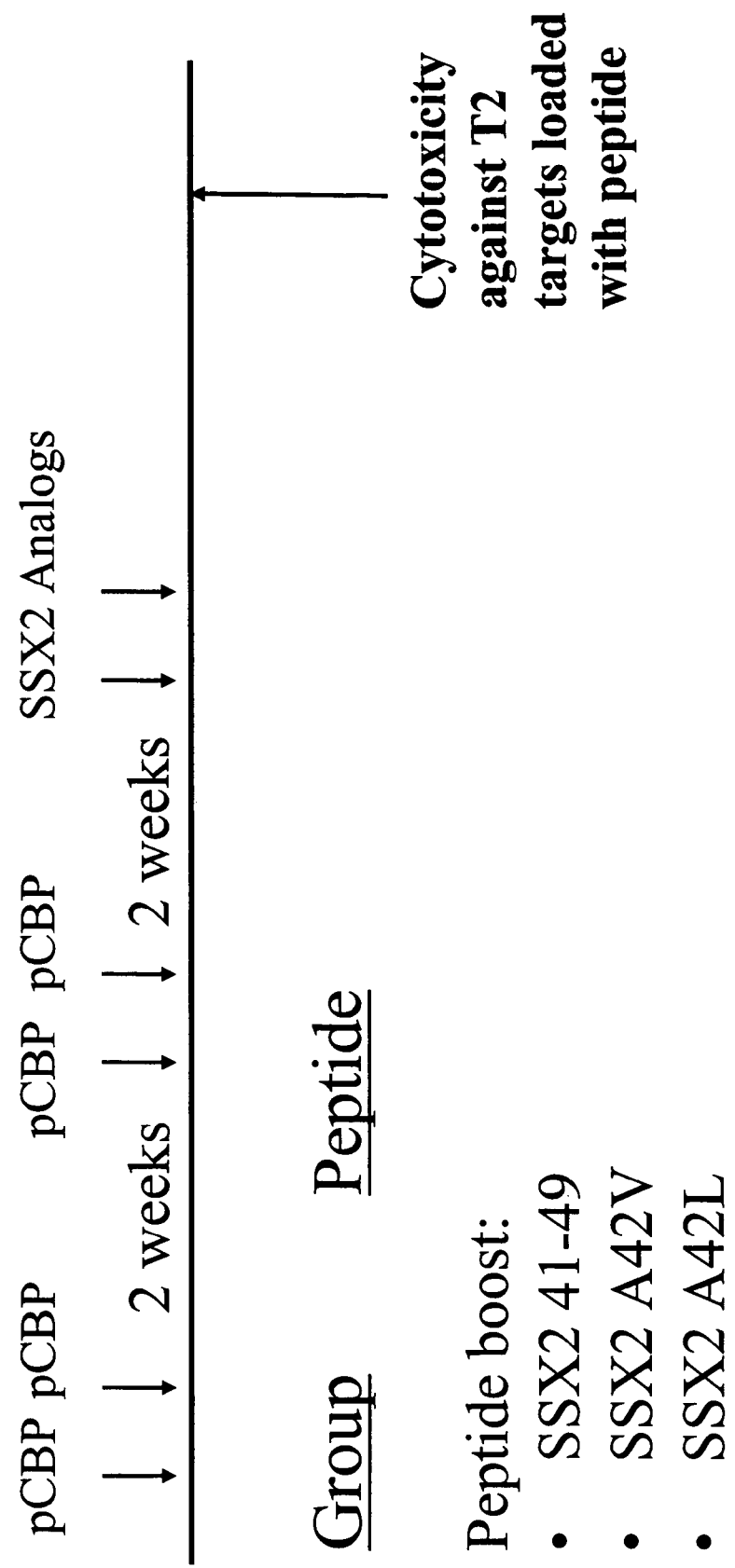

Peptides encompassing T cell epitopes are usually poor immunogens or immune modulators due to one of multiple factors: a suboptimal pharmacokinetics profile, limited binding to MHC molecules (reduced $K_{on}$ and increased $K_{off}$), or decreased intrinsic recognition by T cells present in the normal immune repertoire (e.g., through various forms of tolerance). Various strategies have been pursued to improve the immunologic properties of peptides, particularly the screening and use of peptides in which the sequence differs from the natural epitope. Such analogs are known by various names in the art, such as heteroclytic peptides and altered peptide ligands (APL). The generation of such analogs has most often utilized amino acids from the standard set of genetically encoded residues (see for example Valmori, D. et al., *J. Immunol.* 160:1750-1758, 1998). Use of non-standard amino acids has typically been associated with efforts to improve the biochemical stability of the peptide (see, for example, Blanchet, J.-S. et al., *J. Immunol.* 167:5852-5861, 2001).

Generally, analogs can be categorized into the following two main classes: (1) modification of peptide anchor residues to achieve better HLA binding profiles and higher immune responses, and (2) modification of peptide anchor residues and TCR contact residues to circumvent T cell tolerance for self-antigens.

Some embodiments of the invention described herein relate to analogs that have at least one of the following retained or improved properties, including but not limited to:

1. Cross-reactivity and functional avidity to TCR;
2. Affinity for and stability of binding to MHC class I;
3. In vivo effect on immunity assessed by cytotoxicity;
4. In vivo effect on immunity assessed by ex vivo production of IFN-gamma; and/or
5. Increased resistance to proteolysis.

Some embodiments relate to peptide sequences, including analogs, wherein the amino acids of the sequence are referred to with a position designator, for example P1, P2, P3, PΩ, etc. In addition, the peptide sequences can be referred to as including a P0 and/or PΩ+1 designator. In some aspects, P0 can be X, XX, or XXX, wherein X is any amino acid or no amino acid. Similarly, in some aspects, PΩ+1 can be X, XX, or XXX, wherein X is any amino acid or no amino acid. Thus, for example, XXX can mean any combination of any amino acid residues or no amino acid residues. Thus, these embodiments can encompass polypeptides having up to three additional amino acids (with any combination of amino acid residues) on the N-terminus or C-terminus of the specified sequence. Also, in some aspects, the embodiments can encompass no additional amino acid residues on the N-terminus or the C-terminus.

The MHC residues responsible for forming binding pockets, and which binding pockets accommodate epitope anchor residues and thus define the binding specificity of the MHC molecule, are well understood in the art. One compilation of such information is found at the FIMM (Functional Immunology) web site at the hypertext transfer protocol (http://) "sdmc.lit.org.sg:8080/fimm/", which is hereby incorporated by reference in its entirety. (See also Schönbach C., Koh J. L. Y., Sheng X., Wong L., and V. Brusic. FIMM, a database of functional molecular immunology. Nucleic Acids Research, 2000, Vol. 28, No. 1 222-224; and Schönbach C., Koh J L, Flower D R, Wong L., and Brusic V. FIMM, a database of functional molecular immunology; update 2002. Nucleic Acids Research, 2002, Vol. 30, No. 1 226-229; each of which is hereby incorporated by reference in its entirety).

The phrase "liberation sequence," as used herein, refers to a peptide comprising or encoding an epitope or an analog, which is embedded in a larger sequence that provides a context allowing the epitope or analog to be liberated by immunoproteasomal processing, directly or in combination with N-terminal trimming or other physiologic processes. In some aspects, the analog or epitope can be designed or engineered.

Other embodiments relate to epitope arrays and other polypeptides that include the epitope analog sequences that can be processed to liberate the analog. Further embodiments relate to nucleic acids, particularly DNA plasmids, encoding such polypeptides, or simply an analog, and their expression therefrom. The analogs, the polypeptides comprising them, and the encoding nucleic acids can all be components of immunogenic compositions, particularly compositions suitable for intralymphatic delivery, all of which relate to further embodiments.

Peptide analogs with improved immunologic properties can be designed by modifying the anchor residues involved in the interaction with MHC molecules, so as to increase the binding and stabilize the formation of MHC-peptide complexes. Such modifications can be guided by knowledge of the binding motif or preferred anchor residues of the restricting MHC molecule. There further exist various rules, indexes and algorithms that can be used to predict the properties of analogs bearing various substitutions with the limitation that the substitution is selected from the standard set of genetically encodable amino acids.

However, there are no databases or algorithms to predict the outcome of replacing anchor residues with non-standard amino acids and their usefulness is previously not well explored. It is herein disclosed that the non-standard amino acids norleucine (Nle) and norvaline (Nva) can be advantageously substituted into the anchor residue positions of MHC-binding peptides. It is preferred that they be placed in a position favorably occupied by a hydrophobic or a large amino acid, especially I, L, or V.

MHC-binding motifs are generally defined in terms of preferred residue side chains at nominal positions within a span of 8 to 10 amino acids (see for example Rammensee et al., "MHC Ligands and Peptide Motifs," (Molecular Biology Intelligence Unit), Springer-Verlag, Germany, 1997 Landes Bioscience, Austin, Tex.; and Parker, et al., "Scheme for ranking potential HLA-A2 binding peptides based on independent binding of individual peptide side-chains," J. Immunol. 152:163-175. Website algorithms are also available which can be used to predict MHC binding. See for example, the world wide web page of Hans-Georg Rammensee, Jutta Bachmann, Niels Emmerich, Stefan Stevanovic: SYFPEITHI: An Internet Database for MHC Ligands and Peptide Motifs (hypertext transfer protocol access via: syfpeithi.bmi-heidelberg.com/scripts/MHCServer.dll/home.htm) and "bimas.dcrt.nih.gov/molbio/hla_bind." For class I-restricted epitopes the C-terminal position, PΩ, is typically a primary anchor. The 2nd position, P2, is also often a primary anchor or, alternatively, P3 and/or P5 can serve this role. Positions P2 through P7 have all been recognized as secondary or auxiliary anchor positions for one or another MHC (see Rammensee et al., and see Table 6 from U.S. Patent Application Publication No. 20030215425 (U.S. patent application Ser. No. 10/026,066, filed on Dec. 7, 2001, entitled EPITOPE SYNCHRONIZATION IN ANTIGEN PRESENTING CELLS; which is incorporated herein by reference in its entirety for all of its disclosure). For class II-restricted epitopes, P1, P4, P6, P7, and P9 have been recognized as anchor positions. The foregoing is intended as a general guide and should be considered exemplary and not exhaustive or limiting. Many analyses and compilations of binding motifs, anchor residues, and the like are available in the scientific and patent literature and over the internet. Their conventions and results further provide those of skill in the art useful guidance regarding the design of epitope analogs, when coupled with the teaching herein.

The length of the peptide actually bound to the presenting MHC molecule can be longer than the nominal motif sequence. The ends of the binding cleft for class II MHC molecules are open so that the bound peptide can be extended at either end of the core motif. In contrast, the binding cleft is closed at both ends in class I MHC molecules so that the ends of the bound peptide must generally correspond to the motif, however, significant variation in length can be accommodated through bulging and folding of the central region of the bound peptide, so that peptides of up to at least about 14 amino acids in length can be presented (see for example Probst-Kepper, M. et al., J. Immunol. 173:5610-5616, 2004).

Epitope analogs can have improved $K_{on}$ and $K_{off}$ related to the interaction with class I MHC molecules, as well as preserved or increased interaction with T cell receptors recognizing the original epitope, modified or improved in vivo or ex vivo activity reflected in enhanced expansion of specific T cell populations, improved cytokine production by specific T cells, or in vivo or in vitro cytotoxicity against targets carrying natural epitopes, mediated by T cells that reacted with the peptide. In addition, such analogs can interact in a more optimal fashion with multiple distinct MHC class I molecules.

Such peptide analogs with improved immune properties can encompass one or multiple substitutions, including one or multiple non-standard amino acid substitutions. Among non-standard amino acid substitutions, substitutions for primary anchor residues consisting of norvaline or norleucine are preferred because, as exemplified below, they can not only improve the interaction with MHC class I, but can also preserve cross-reactivity with TCR specific for the native epitope and show improved in vivo immune profile. For example, mutating the P2 amino acid residue from A, L or V to norvaline or norleucine improved immune properties and is thus preferred. In addition, modifying the C terminal residue to norvaline or preferably norleucine, improved immune features of the analogs. In addition, analogs that encompass multiple substitutions at primary and/or secondary anchor residues including norvaline and/or norleucine at P2 or PΩ can be associated with improved immune properties.

Certain uses of norvaline (Nva) and norleucine (Nle) are mentioned in U.S. Pat. No. 6,685,947; PCT Publication Nos. WO 03/076585 A2 and WO 01/62776 A1; and U.S. Patent Publication No. 20040253218A1. None of these references teaches the general usefulness of Nva or Nle substituted at an anchor position of a MHC-biding peptide to improve an immunological property. The '218 publication teaches that the substituted residues should be incorporated at TCR-interacting positions and not at MHC-interacting positions.

In still another embodiment of the invention, the peptide is an analog of a peptide derived from an NS-specific antigen that is immunogenic but not encephalitogenic. The most suitable peptides for this purpose are those in which an encephalitogenic self-peptide is modified at the T-cell receptor (TCR) binding site and not at the MHC binding site(s), so that the immune response is activated but not anergized (Karin et al., 1998; Vergelli et al, 1996).

Others have also suggested a variety of non-standard amino acids may be substituted without destroying the usefulness of the peptide (see for example WO 02/102299A). Non-standard amino acids have also been used to investigate interaction between TCR and the MHC-peptide complex (see for example WO 03/076585A and Sasada, T. et al. Eur. J. Immunol. 30:1281-1289, 2000). Baratin showed some usefulness of Nle and Abu at non-anchor positions and Nle at an anchor position in a p53 peptide presented by the murine MHC molecule H2-Db (J. Peptide Sci. 8:327-334, 2002). Each of these forgoing documents is hereby incorporated by reference in its entirety.

HL-A2.1-restricted peptides incorporating Nle disclosed in WO 01/62776 are derived from CEA, p53, and MAGE-3. In the CEA peptide I(Nle)GVLVGV (SEQ ID NO: 198) and the p53 peptide S(Nle)PPPGTRV (SEQ ID NO: 101), Nle is present at the P2 position. No teaching about the general usefulness of norleucine is provided and no disclosure is provided indicating how or if these substitutions altered the properties of the analogs as compared to the native sequence.

Some of the instant embodiments relate to epitope analogs that incorporate Nva and/or Nle at a position promoting binding to MHC. Some embodiments specifically exclude the use Nle and/or Nva in HLA-A2.1-restricted epitopes, HLA-A2.1 epitopes from CEA, p53, and/or MAGE-3, or other peptides derived from MAGE-3, CEA, and/or p53. In some embodiments, one or more of the specific sequences as disclosed in the above patent references are specifically excluded. In other embodiments, analogs of murine or other non-human MHC-restricted epitopes are excluded. Other exemplary embodiments include the use of Nle and/or Nva at P3, P5, and/or PΩ anchor positions, in an auxiliary anchor position, to make an analog of a non-A2- or non-A2.1-HLA restricted epitope, in an anchor position of a peptide that is not derived from an oncogene or oncofetal protein, and in an anchor position of a peptide derived from a CT antigen.

In general, such analogs may be useful for immunotherapy and/or prophylaxis of various diseases, such as infectious, cancerous or inflammatory, as single agents or in combination therapies. This is due to their optimized interaction with MHC molecules and T cell receptors key to onset and regulation of immune responses.

Analog Production

The analogs may be produced using any method known to one of skill in the art, including manufacturing the peptides using a method of peptide synthesis or expressing nucleic acids that code for the desired peptide analogs. Thus, when the analogs include one or more non-standard amino acids, it is more likely that they will be produced by a method of peptide production. When the analogs include only one or more substitutions with standard amino acids, they can be expressed from an expression vector using any method known to one of skill in the art. Alternatively, the peptides can be expressed using a method of gene therapy.

Analog Testing

To evaluate usefulness and/or activity, and/or improved properties of the analogs and to compare the analogs in any way to the wild-type, one or more of the following assays were conducted: peptide binding affinity for HLA-A*0201; peptide-HLA-A*0201 complex stability assay; a cross-reactivity assay (recognition of peptide analogs by wild-type, peptide-specific CTL or recognition of wild-type peptide by CTL generated using peptide analogs); an immunogenicity assay, such as an IFN-γ secretion assay, a cytotoxicity assay, and/or an Elispot assay; an antigenicity assay, such as an in vitro tumor cell lysis assay, an ex vivo tumor cell lysis, and an in vivo tumor cell lysis; and a proteolysis assays to identify increased resistance to proteolysis. Details of exemplary assays are presented in the Examples below.

The Using the above methodologies, useful and/or improved analogs were identified. To be useful, an analog may not necessarily be found to be improved in the identified assays. For example, a useful peptide can contain other properties such as being useful in a tolerized patient or resistant to proteolysis. To be improved, a peptide can be found to have a clear improvement in binding to the TCR, binding to the MHC molecule, and an improved immune response or any other biological activity. In some instances, a useful peptide does not appear to be improved when using a murine test system, but because of the differences in the human immune system, is determined to be improved when tested in a human. In some cases, the usefulness can stem from a potential to break tolerance in a tolerized human. In some instances, the usefulness can stem from the ability to use the peptide as a base for further substitutions to identify improved analogs.

Uses of the Analogs

Useful methods for using the disclosed analogs in inducing, entraining, maintaining, modulating and amplifying class I MHC-restricted T cell responses, and particularly effector and memory CTL responses to antigen, are described in U.S. Pat. No. 6,994,851 (Feb. 7, 2006) and U.S. Pat No. 6,977,074 (Dec. 20, 2005) both entitled "A Method of Inducing a CTL Response"; U.S. Provisional Application No. 60/479,393, filed on Jun. 17, 2003, entitled "METHODS TO CONTROL MHC CLASS I-RESTRICTED IMMUNE RESPONSE"; and U.S. patent application Ser. No. 10/871,707 (Pub. No. 2005 0079152) and Provisional U.S. Patent Application No. 60/640,402 filed on Dec. 29, 2004, both entitled "METHODS TO ELICIT, ENHANCE AND SUSTAIN IMMUNE RESPONSES AGAINST MHC CLASS I-RESTRICTED EPITOPES, FOR PROPHYLACTIC OR THERAPEUTIC PURPOSE". The analogs can also be used in research to obtain further optimized analogs. Numerous housekeeping epitopes are provided in U.S. application Ser. No. 10/117,937, filed on Apr. 4, 2002 (Pub. No. 20030220239 A1), and Ser. No. 10/657,022 (20040180354), and in PCT Application No. PCT/US2003/027706 (Pub. No. WO04022709A2), filed on Sep. 5, 2003; and U.S. Provisional Application Nos. 60/282,211, filed on Apr. 6, 2001; 60/337,017, filed on Nov. 7, 2001; 60/363,210 filed on Mar. 7, 2002; and 60/409,123, filed on Sep. 5, 2002; each of which applications is entitled "EPITOPE SEQUENCES". The analogs can further be used in any of the various modes described in those applications. Epitope clusters, which can comprise or include the instant analogs, are disclosed and more fully defined in U.S. patent application Ser. No. 09/561,571, filed on Apr. 28, 2000, entitled EPITOPE CLUSTERS. Methodology for using and delivering the instant analogs is described in U.S. patent applications Ser. No. 09/380,534 and U.S. Pat. No. 6,977,074 (Issued Dec. 20, 2005) and in PCT Application No. PCTUS98/14289 (Pub. No. WO9902183A2), each entitled A "METHOD OF INDUCING A CTL RESPONSE". Beneficial epitope selection principles for such immunotherapeutics are disclosed in U.S. patent application Ser. No. 09/560,465, filed on Apr. 28, 2000, Ser. No. 10/026,066 (Pub. No. 20030215425 A1), filed on Dec. 7, 2001, and Ser. No. 10/005,905 filed on Nov. 7, 2001, all entitled "EPITOPE SYNCHRONIZATION IN ANTIGEN PRESENTING CELLS"; U.S. Pat. No. 6,861,234 (issued 01, Mar. 2005; application Ser. No. 09/561,074), entitled "METHOD OF EPITOPE DISCOVERY"; U.S. Pat. No. 09/561,571, filed Apr. 28, 2000, entitled EPITOPE CLUSTERS; Ser. No. 10/094,699 (Pub. No. 20030046714 A1), filed Mar. 7, 2002, entitled "ANTI-NEOVASCULATURE PREPARATIONS FOR CANCER"; application Ser. No. 10/117,937 (Pub. No. 20030220239 A1) and PCTUS02/11101 (Pub. No. WO02081646A2), both filed on Apr. 4, 2002, and both entitled "EPITOPE SEQUENCES"; and application Ser. Nos. 10/657,022 and PCT Application No. PCT/US2003/027706 (Pub. No. WO04022709A2), both filed on Sep. 5, 2003, and both entitled "EPITOPE SEQUENCES". Aspects of the overall design of vaccine plasmids are disclosed in U.S. patent application Ser. No. 09/561,572, filed on Apr. 28, 2000, entitled "EXPRESSION VECTORS ENCODING EPITOPES OF TARGET-ASSOCIATED ANTIGENS" and U.S. Pat. No. 10/292,413 (Pub. No.20030228634 A1), filed on Nov. 7, 2002, entitled "EXPRESSION VECTORS ENCODING EPITOPES OF TARGET-ASSOCIATED ANTIGENS AND METHODS FOR THEIR DESIGN"; Ser. No. 10/225,568 (Pub No. 2003-0138808), filed on Aug. 20, 2002, PCT Application No. PCT/US2003/026231 (Pub. No. WO 2004/018666), filed on Aug. 19, 2003, both entitled "EXPRESSION VECTORS ENCODING EPITOPES OF TARGET-ASSOCIATED ANTIGENS"; and U.S. Pat. No. 6,709,844, entitled "AVOIDANCE OF UNDESIRABLE REPLICATION INTERMEDIATES IN PLASMID PROPAGATION". Specific antigenic combinations of particular benefit in directing an immune response against particular cancers are disclosed in Provisional U.S. patent Application Ser. No. 60/479,554, filed on Jun. 17, 2003 and U.S. patent application Ser. No. 10/871,708, filed on Jun. 17, 2004 and PCT Patent Application No. PCT/US2004/019571 (Pub. No. WO 2004/112825), all entitled "COMBINATIONS OF TUMOR-ASSOCIATED ANTIGENS IN VACCINES FOR VARIOUS TYPES OF CANCERS". Antigens associated with tumor neovasculature (e.g., PSMA, VEGFR2, Tie-2) are also useful in connection with cancerous diseases, as is disclosed in U.S. patent application Ser. No. 10/094,699 (Pub. No. 20030046714A1), filed Mar. 7, 2002, entitled "ANTI-NEOVASCULATURE PREPARATIONS FOR CANCER". Methods to trigger, maintain, and manipulate immune responses by targeted administration of biological response modifiers are disclosed U.S. Provisional Application No. 60/640,727, filed on Dec. 29, 2004. Methods to bypass CD4+ cells in the induction of an immune response are disclosed in U.S. Provisional Application No. 60/640,821, filed on Dec. 29, 2004. Exemplary diseases, organisms and antigens and epitopes associated with target organisms, cells and diseases are described in U.S. patent application Ser. No. 6,977,074 (issued Dec. 20, 2005) filed Feb. 2, 2001 and entitled "METHOD OF INDUCING A CTL RESPONSE". Exemplary methodology is found in U.S. Provisional Application No. 60/580,969, filed on Jun. 17, 2004, and U.S. Patent Application No. 2006-0008468-A1, published on Jan. 12, 2006, both entitled "COMBINATIONS OF TUMOR-ASSOCIATED ANTIGENS IN DIAGNOTISTICS FOR VARIOUS TYPES OF CANCERS". Methodology and compositions are also disclosed in U.S. Provisional Application No. 60/640, 598, filed on Dec. 29, 2004, entitled "COMBINATIONS OF TUMOR-ASSOCIATED ANTIGENS TN COMPOSITIONS FOR VARIOUS TYPES OF CANCER". The integration of diagnostic techniques to assess and monitor immune responsiveness with methods of immunization including utilizing the instant analogs is discussed more fully in Provisional U.S. Patent Application No. 60/580,964 filed on Jun. 17, 2004 and U.S. Patent Application No. US-2005-0287068-A1, published on Dec. 29, 2005) both entitled "IMPROVED EFFICACY OF ACTIVE IMMUNOTHERAPY BY INTEGRATING DIAGNOSTIC WITH THERAPEUTIC METHODS". Immunogenic polypeptide encoding vectors are disclosed in U.S. patent application Ser. No. 10/292,413 (Pub. No. 20030228634 A1), filed on Nov. 7, 2002, entitled EXPRESSION VECTORS ENCODING EPITOPES OF TARGET-ASSOCIATED ANTIGENS AND METHODS FOR THEIR DESIGN, and in U.S. Provisional Application No. 60/691,579, filed on Jun. 17, 2005, and the corresponding U.S. patent application Ser. No. 11/454,616, filed on the same date as the present application, both entitled "METHODS AND COMPOSITIONS TO ELICIT MULTIVALENT IMMUNE RESPONSES AGAINST DOMINANT AND SUBDOMINANT EPITOPES EXPRESSED ON CANCER CELLS AND TUMOR STROMA"). Additional useful disclosure, including methods and compositions of matter, is found in U.S. Provisional Application No. 60/691,581, filed on Jun. 17, 2005, entitled "MULTIVALENT ENTRAIN-AND-AMPLIFY IMMUNOTHERAPEUTICS FOR CARCINOMA." Further methodology, compositions, peptides, and peptide analogs are disclosed in U.S. Provisional Application Nos. 60/581,001 and 60/580,962, both filed on Jun. 17, 2004, and respectively entitled "SSX-2 PEPTIDE ANALOGS" and "NY-ESO PEPTIIDE ANALOGS." Each of the applications and patents mentioned in the above paragraphs is hereby incorporated by reference in its entirety for all that it teaches. Additional analogs, peptides and methods are disclosed in U.S. Patent Application Publication No. 20060063913, entitled "SSX-2 PEPTIDE ANALOGS"; and U.S. Patent Publication No. 2006-0057673 A1, published on Mar. 16, 2006, entitled "EPITOPE ANALOGS"; and PCT Application Publication No. WO/2006/009920, entitled "EPITOPE ANALOGS"; all filed on Jun. 17, 2005, as well as in U. S. Provisional Patent Application No. 60/691,889, filed on Jun. 17, 2005 entitled EPITOPE ANALOGS; and U.S. patent application Ser. No. 11/454,633, entitled PSMA PEPTIDE ANALOGUES and U.S. patent application Ser. No. 11/454,300, entitled MELANOMA ANTIGEN PEPTIDE ANALOGUES, each of which is hereby incorporated by reference in its entirety. Exemplary immunogenic products are disclosed in U.S. Provisional Patent Application No. 60/691,581, filed on Jun. 17, 2005 and U.S. patent application Ser. No. 11/455,279, filed on date even with the instant application, each entitled MULTIVALENT ENTRAIN-AND-AMPLIFY IMMUNOTHERAPEUTICS FOR CARCINOMA, and each incorporated by reference in its entirety. Further methodology and compositions are disclosed in U.S. Provisional Application No. 60/581,001, filed on Jun. 17, 2004, entitled "SSX-2 PEPTIDE ANALOGS", and to U.S. Provisional Application No. 60/580,962, filed on Jun. 17, 2004, entitled "NY-ESO PEPTIDE ANALOGS"; each of which is incorporated herein by reference in its entirety. Other applications that are expressly incorporated herein by reference are: U.S. patent application Ser. No. 11/156,253 (Publication No.), filed on Jun. 17, 2005, entitled "SSX-2 PEPTIDE ANALOGS"; U.S. patent application Ser. No. 11/155, 929, filed on Jun. 17, 2005, entitled "NY-ESO-1 PEPTIDE ANALOGS" (Publication No. ); U.S. patent application Ser. No. 11/321,967, filed on Dec. 29, 2005, entitled "METHODS TO TRIGGER, MAINTAIN AND MANIPULATE IMMUNE RESPONSES BY TARGETED ADMINISTRATION OF BIOLOGICAL RESPONSE MODIFIERS INTO LYMPHOID ORGANS"; U.S. patent application Ser. No. 11/323,572, filed on Dec. 29, 2005, entitled "METHODS TO ELICIT ENHANCE AND SUSTAIN IMMUNE REPONSES AGAINST MCH CLASS I RESTRICTED EPITOPES, FOR PROPHYLACTIC OR THERAPEUTIC PURPOSES"; U.S. patent application Ser. No. 11/323,520, filed Dec. 29, 2005, entitled "METHODS TO BYPASS CD4+ CELLS IN THE INDUCTION OF AN IMMUNE RESPONSE"; U.S. patent application Ser. No. 11/323,049, filed Dec. 29, 2005, entitled "COMBINATION OF TUMOR-ASSOCIATED ANTIGENS IN COMPOSITIONS FOR VARIOUS TYPES OF CANCERS"; U.S. patent application Ser. No. 11,323,964, filed Dec. 29, 2005, entitled "COMBINATIONS OF TUMOR-ASSOCIATED ANTIGENS IN DIAGNOSTICS FOR VARIOUS TYPES OF CANCERS." As an example, without being limited thereto each reference is incorporated by reference for what it teaches about class I MHC-restricted epitopes, analogs, the design of analogs, uses of epitopes and analogs, methods of using and making epitopes, the design and use of nucleic acid vectors for their expression, and formulations.

Antigens

There are many antigens, epitopes of which can be recognized by T cells in an MHC-restricted manner, for which manipulation of an immune response directed against them has therapeutic or prophylactic potential. The principles for making analogs of MHC-binding peptides described herein are generally applicable to any of these antigens and their epitopes. A particular focus of the present disclosure is epitopes from the tumor-associated antigens (TuAA) SSX-2, NY-ESO-1, PRAME, PSMA, tyrosinase, and Melan-A.

SSX-2, also know as Hom-Mel-40, is a member of a family of highly conserved cancer-testis antigens (Gure, A. O. et al. *Int. J. Cancer* 72:965-971, 1997, which is hereby incorporated by reference in its entirety). Its identification as a TuAA antigen is taught in U.S. Pat. No. 6,025,191 entitled "ISOLATED NUCLEIC ACID MOLECULES THAT ENCODE A MELANOMA SPECIFIC ANTIGEN AND USES THEREOF", which is hereby incorporated by reference in its entirety. Cancer-testis antigens are found in a variety of tumors, but are generally absent from normal adult tissues except testis. SSX-2 is expressed in many different types of tumors, including synovial sarcomas, melanoma, head and neck cancers, breast, colon and ovarian cancers. In addition to its widespread expression in a variety of cancers, it is also immunogenic in patients with late stage disease. Further, there is evidence of spontaneous humoral and cellular immune responses towards this antigen in metastatic tumor patients (Ayyoub M, et al., *Cancer Res.* 63(17): 5601-6, 2003; Ayyoub M, et al. *J Immunol.* 168(4): 1717-22, 2002), which is incorporated herein by reference in its entirety. Two HLA-A2 restricted T cell epitopes have been identified recently using reverse T-cell immunology, namely SSX-2$_{41-49}$ (Ayyoub M, et al. *J. Immunol.* 168(4): 1717-22, 2002; U.S. Pat. No. 6,548,064, entitled "ISOLATED PEPTIDES CONSISTING OF AMINO ACID SEQUENCES FOUND IN SSX OR NY-ESO-1 MOLECULES, THAT BIND TO HLA MOLECULE"; U.S. patent application Ser. No. 10/117,937 (Publication No. US 2003-0220239 A1), entitled "EPITOPE SEQUENCES") and SSX-2$_{103-111}$ (Wagner C, et al. *Cancer Immunity* 3:18, 2003), each of which is incorporated herein by reference in its entirety. The C-termini of both epitopes can be efficiently generated by in vitro proteasome digestion. Isolated HLA-A*0201/SSX-2$_{41-49}$ multimer$^+$ CD8$^+$ T cells from tumor-infiltrated lymph nodes of SSX-2 positive patients exhibited high functional avidity and can effectively recognize SSX-2 positive tumors; however, the spontaneously occurring immunological responses were not sufficient for stopping tumor growth, possibly because these immune response did not develop until fairly late in the disease progression, and the activated T cells were not numerous enough. U.S. Pat. No. 6,548,064 (which is incorporated herein by reference in its entirety) further describes substituting a T or A residue at both the P2 and PΩ position of an SSX-2 epitope.

NY-ESO-1 is a cancer-testis antigen found in a wide variety of tumors and is also known as CTAG-1 (Cancer-Testis Antigen-1) and CAG-3 (Cancer Antigen-3). NY-ESO-1 as a tumor-associated antigen (TuAA) is disclosed in U.S. Pat. No. 5,804,381 entitled "ISOLATED NUCLEIC ACID MOLECULE ENCODING AN ESOPHAGEAL CANCER ASSOCIATED ANTIGEN, THE ANTIGEN ITSELF, AND USES THEREOF," which is hereby incorporated by reference in its entirety. Paralogous locus encoding antigens with extensive sequence identity, LAGE-1a/s and LAGE-1b/L, have been disclosed in publicly available assemblies of the human genome, and have been concluded to arise through alternate splicing. Additionally, CT-2 (or CTAG-2, Cancer-Testis Antigen-2) appears to be either an allele, a mutant, or a sequencing discrepancy of LAGE-1b/L. Due to the extensive sequence identity, many epitopes from NY-ESO-1 can also induce immunity to tumors expressing these other antigens. The proteins are virtually identical through amino acid 70. From residues 71-134 the longest run of identity between NY-ESO-1 and LAGE is 6 residues, but potentially cross-reactive sequences are present. From residues 135-180, NY-ESO and LAGE-1a/s are identical except for a single residue, but LAGE-1b/L is unrelated due to the alternate splice. The CAMEL and LAGE-2 antigens appear to derive from the LAGE-1 mRNA, but from alternate reading frames, thus giving rise to unrelated protein sequences. More recently, GenBank Accession AF277315.5, *Homo sapiens* chromosome X clone RP5-865E18, RP5-1087L19, complete sequence, which is incorporated herein by reference in its entirety, reports three independent loci in this region that are labeled as LAGE1 (corresponding to CTAG-2 in the genome assemblies), plus LAGE2-A and LAGE2-B (both corresponding to CTAG-1 in the genome assemblies).

NY-ESO-1$_{57-165}$ is identified as an HLA-A2 restricted epitope in U.S. Pat. No. 6,274,145 entitled "ISOLATED NUCLEIC ACID MOLECULE ENCODING CANCER ASSOCIATED ANTIGEN, THE ANTIGEN ITSELF, AND USES THEREOF", and U.S. patent application Ser. No. 10/117,937 (Pub. No. 20030220239) entitled "EPITOPE SEQUENCES" reports that this C-terminus is generated by the housekeeping proteasome in an in vitro assay. Analogs substituting A, V, L, I, P, F, M, W, or G at PΩ, alone or in combination with A at another position, are disclosed in U.S. Pat. Nos. 6,417,165 and 6,605,711, both entitled "NY-ESO-1-PEPTIDE DERIVATIVES AND USES THEREOF". Each of the references described in this paragraph is incorporated herein by reference in its entirety.

PRAME, also known as MAPE, DAGE, and OIP4, was originally observed as a melanoma antigen. Subsequently, it has been recognized as a CT antigen, but unlike many CT antigens (e.g., MAGE, GAGE, and BAGE) it is expressed in acute myeloid leukemias. PRAME is a member of the MAPE family which consists largely of hypothetical proteins with which it shares limited sequence similarity. The usefulness of PRAME as a TuAA is taught in U.S. Pat. No. 5,830,753 entitled "ISOLATED NUCLEIC ACID MOLECULES CODING FOR TUMOR REJECTION ANTIGEN PRECURSOR DAGE AND USES THEREOF", which is hereby incorporated by reference in its entirety. U.S. patent application Ser. No. 10/181,499 (Publication No. US 2003-0186355 A1), entitled "METHODS FOR SELECTING AND PRODUCING T CELL PEPTIDE EPITOPES AND VACCINES INCORPORATING SAID SELECTED EPITOPES" (which is incorporated herein by reference in its entirety) identifies a variety of potential epitopes, including PRAME$_{425-433}$, using in vitro digestion with immunoproteasome.

PSMA (prostate-specific membranes antigen), a TuAA described in U.S. Pat. No. 5,538,866 entitled "PROSTATE-SPECIFIC MEMBRANES ANTIGEN," which is hereby incorporated by reference in its entirety, is expressed by normal prostate epithelium and, at a higher level, in prostatic cancer. It has also been found in the neovasculature of non-prostatic tumors. PSMA can thus form the basis for vaccines directed to both prostate cancer and to the neovasculature of other tumors. This later concept is more fully described in U.S. Patent Publication No. 20030046714; PCT Publication No. WO 02/069907; and a provisional U.S. patent application Ser. No. 60/274,063 entitled "ANTI-NEOVASCULAR VACCINES FOR CANCER", filed Mar. 7, 2001, and U.S. application Ser. No. 10/094,699 (Publication No. US 2003-0046714 A1), filed on Mar. 7, 2002, entitled "ANTI-NEOVASCULAR PREPARATIONS FOR CANCER," each of which are hereby incorporated by reference in its entirety. The teachings and embodiments disclosed in said publications and applications provide supporting principals and embodiments related to and useful in connection with the present invention. Briefly, as tumors grow they recruit ingrowth of new blood vessels. This is understood to be necessary to sustain growth as the centers of unvascularized tumors are generally necrotic and angiogenesis inhibitors have been reported to cause tumor regression. Such new blood vessels, or neovasculature, express antigens not found in established vessels, and thus can be specifically targeted. By inducing CTL against neovascular antigens the vessels can be disrupted, interrupting the flow of nutrients to (and removal of wastes from) tumors, leading to regression.

Alternate splicing of the PSMA mRNA also leads to a protein with an apparent start at $Met_{58}$, thereby deleting the putative membrane anchor region of PSMA as described in U.S. Pat. No. 5,935,818, entitled "ISOLATED NUCLEIC ACID MOLECULE ENCODING ALTERNATIVELY SPLICED PROSTATE-SPECIFIC MEMBRANES ANTIGEN AND USES THEREOF" which is hereby incorporated by reference in its entirety. A protein termed PSMA-like protein, Genbank accession number AF261715, which is hereby incorporated by reference in its entirety, is nearly identical to amino acids 309-750 of PSMA and has a different expression profile. Thus, the more preferred epitopes are those with an N-terminus located from amino acid 58 to 308. $PSMA_{288-297}$ was identified as possessing an HLA-A2 binding motif in WO 01/62776, entitled "HLA BINDING PEPTIDES AND THEIR USES", which is hereby incorporated by reference in its entirety. Its production in vitro by digestion with a housekeeping proteasome and actual binding to HLA-A2 was disclosed in U.S. Patent Application Publication No. 20030220239 entitled "EPITOPE SEQUENCES".

Tyrosinase is a melanin biosynthetic enzyme that is considered one of the most specific markers of melanocytic differentiation. Tyrosinase is expressed in few cell types, primarily in melanocytes, and high levels are often found in melanomas. The usefulness of tyrosinase as a TuAA is taught in U.S. Pat. No. 5,747,271, entitled "METHOD FOR IDENTIFYING INDIVIDUALS SUFFERING FROM A CELLULAR ABNORMALITY SOME OF WHOSE ABNORMAL CELLS PRESENT COMPLEXES OF HLA-A2/TYROSINASE DERIVED PEPTIDES, AND METHODS FOR TREATING SAID INDIVIDUALS," which is hereby incorporated by reference in its entirety.

Melan-A, also called MART-1 (Melanoma Antigen Recognized by T cells), is another melanin biosynthetic protein expressed at high levels in melanomas. The usefulness of Melan-A/MART-1 as a TuAA is taught in U.S. Pat. Nos. 5,874,560 and 5,994,523, both entitled "MELANOMA ANTIGENS AND THEIR USE IN DIAGNOSTIC AND THERAPEUTIC METHODS", as well as U.S. Pat. No. 5,620,886, entitled "ISOLATED NUCLEIC ACID SEQUENCE CODING FOR A TUMOR REJECTION ANTIGEN PRECURSOR PROCESSED TO AT LEAST ONE TUMOR REJECTION ANTIGEN PRESENTED BY HLA-A2", each of which is hereby incorporated by reference in its entirety. The immunodominant HLA-A2 restricted epitope from this TuAA is Melan-$A_{26-35}$. It has been shown to be produced by the housekeeping proteasome (Morel, S. et al., *Immunity* 12:107-117, 2000, which is hereby incorporated by reference in its entirety). Various analogs incorporating standard amino acids, including an improved analog substituting L at P2, are disclosed in U.S. Pat. No. 6,025,470, entitled "ISOLATED NONA-AND DECAPEPTIDES WHICH BIND TO HLA MOLECULES, AND THE USE THEREOF", which is hereby incorporated by reference in its entirety. The use of analogs incorporating non-standard amino acids with a primary goal of improving biochemical stability is reported by Blanchet, J.-S. et al., *J. Immunol.* 167:5852-5861, 2001, which is hereby incorporated by reference in its entirety.

SSX-2 41-49 Analogs

As noted above, the natural immune response to SSX-2 in cancer patients, including the response to SSX-$2_{41-49}$, may not be effective in controlling cancer. Additionally, wild-type SSX-$2_{41-49}$ is only a moderately immunogenic peptide, which can further limit its clinical potential. Stronger SSX-2 specific immune responses induced by the use of superagonist analogs results in clinical benefits for patients with SSX-2 positive tumors.

Thus, in one embodiment, the analogs can be used in compositions to stimulate the immune response of a subject to mount an immune response against a target cell displaying the target antigen. The embodiment can have utility in the treatment and prevention of neoplastic and viral disease.

Because the wild-type SSX-$2_{41-49}$ is only a moderately immunogenic peptide, which may prevent it from eliminating tumors effectively in vivo, a method was used to de novo design SSX-$2_{41-49}$ variants that were more potent or had a variety of improved properties. By using a more immunogenic SSX-2 analog peptide, it was possible to stimulate a stronger immune response and/or to amplify the naturally occurring immune response to achieve a better chance of clinical response. Thus, the binding properties (affinity and HLA-A*0201/peptide complexes stability), immunogenicity, antigenicity and cross-reactivity to the wild-type epitope were analyzed for each of the analogs to identify an improved property. In some embodiments, by improved property it is meant generally, that the analog can be better used for some purpose than the wild-type. Thus, the analog need not exhibit improved binding, stability, or activity to be improved and may even show a reduced ability to mediate certain parts of the process, but still be improved for use in another way. For example, analogs that retain some activity, but not all activity can be better in human systems that are tolerized to the wild-type antigen.

Previously, modifications of natural tumor-associated peptide epitopes by incorporating favorable anchor residues have generated analogs with improved binding profiles with HLA molecules and enhanced immunogenicity. One of the most successful examples is the A27L peptide analog of Melan-A 26-35 epitope. Valmori et al., "Enhanced generation of specific tumor-reactive CTL in vitro by selected Melan-A/MART-1 immunodominant peptide analogs," *J Immunol.* 1998, 160(4): 1750-8, which is hereby incorporated by reference in its entirety. The original epitope failed to form a stable complex with HLA-A2 molecules because it lacked an optimum anchor amino acid residue at position 2. The modified A27L Melan A 26-35 peptide analog has demonstrated unequivocally increased binding profiles with HLA-A2 molecules and greater immunogenicity than its wild-type counterpart. Immunizing patients with this analog generated strong T cell immune responses that were able to recognize the wild-type epitope presented at the cell surfaces. Similar modifications have been obtained successfully with many other tumor-associated epitopes, such as GP100 209-217

(Parkhurst et al., "Improved induction of melanoma-reactive CTL with peptides from the melanoma antigen gp100 modified at HLA-A*0201-binding residues," *J Immunol*. 1996, 157(6): 2539-48; which is hereby incorporated by reference in its entirety), and Her-2 369-377 (Vertuani et al., "Improved immunogenicity of an immunodominant epitope of the HER-2/neu protooncogene by alterations of MHC contact residues," *J. Immunol*. 2004, 172(6): 3501-8; which is hereby incorporated by reference in its entirety).

Methods are disclosed herein that can be used for the identification and production of analogs to a Synovial sarcoma X breakpoint 2 (SSX-2) wild-type sequence. Using the methods disclosed herein, a panel of 95 novel SSX-$2_{41-49}$ analogs based on the wild-type sequence from amino acids 241-249 were identified with a variety of improved properties. The improved properties include, but are not limited to, binding to class I MHC and T cell receptor (TCR) molecules, and biological responses such as IFN-γ secretion, cytotoxicity, and tumor cell lysis. Peptides with improved potency that retained cross-reactivity with the wild-type epitope were also identified. Among these analogs, some were demonstrated to be the superagonist variants of the wild-type SSX-$2_{41-49}$ peptide, some of which were shown to have much higher affinity with HLA-A*0201 molecule, and the peptide-HLA complex possessed extended stability. These analogs induced enhanced CTL immune responses in HHD transgenic mice immunized with them. The resulting CTLs could effectively lyse A2+ and SSX-2+tumor cell lines both in vivo and in vitro, indicating that the CTLs generated using the analogs were able to recognize the wild-type SSX-$2_{41-49}$ epitope that naturally presented at the cell surfaces. In comparison with the wild-type SSX-$2_{41-49}$ epitope, the analogs are better candidates for the development of cancer vaccines.

Accordingly, embodiments of the invention disclosed herein include families of one or more peptides of 9 or 10 amino acids in length related by sequence to amino acids 41-49 of the human cancer testis (CT) antigen SSX-2 (SSX-$2_{41-49}$). The individual peptide embodiments have one to several defined amino acid substitutions in the wild-type sequence. The substituted amino acids are, variously, other members of the standard set of amino acids commonly genetically encoded, derivatives thereof, their D-stereoisomers, or other non-standard L-amino acids. These analogs are useful for investigating the interaction of the wild-type epitope with class I MHC and TCR molecules and other components of the immune response, and for designing additional analogs with further optimized immunologic properties. Some embodiments of the analogs have at least similar immunologic properties to the wild-type epitope in the HLA-transgenic mouse model in which they have been tested. Such peptides can be useful in humans, as SSX-2 is a self-antigen to which a degree of tolerance may be expected, and the amino acid differences of the analogs can help to stimulate populations of T cells that have avoided negative selection but are cross-reactive with the wild-type epitope. Various peptide embodiments can have one or more improved immunologic properties in that they possess greater affinity for MHC or greater stability of binding to MHC, elicit greater cytokine production or require lower peptide concentrations to elicit similar cytokine production from T cells that recognize the wild-type epitope, are more immunogenic, can induce or amplify a cross-reactive cytolytic response to the wild-type epitope, and/or can break tolerance.

In one embodiment, the analogs can have at least one substitution at a residue selected from the group consisting of, P1, P2, P4, P6, P8, P9 and P10. In a further embodiment, the analogs can have at least two substitutions at residues selected from the group consisting of: P1, P2, P4, P6, P8, P9 and P10. In a further embodiment, the analogs can have at least three substitutions at residues selected from the group consisting of: P1, P2, P4, P6, P8, P9 and P10. In a further embodiment, the analogs can have substitutions at positions P2 and P9. In a further embodiment, the peptides can have substitutions at residues P1, P2, and P9. In a further embodiment, the peptide analogs can have substitutions at residues P1, P2, and P4. In a further embodiment, the peptide analogs can have substitutions at residues P1, P2, and P6. In a further embodiment, the peptide analogs can have substitutions at residues P1, P2, and P8. In one embodiment, two substitutions can produce improved properties. In a further embodiment, one substitution can produce improved properties. In a further embodiment, three substitutions can produce improved properties. In a further embodiment, the one or more substitutions can produce improved properties but are still recognized by a TCR that recognizes the wild-type sequence (still cross-reactive with the wild-type sequence).

One embodiment relates to epitope arrays and other polypeptides comprising the epitope analog sequences that can be processed to liberate the analog. Further embodiments relate to nucleic acids, particularly DNA plasmids, encoding such polypeptides, or simply an analog, and their expression therefrom. The analogs, the polypeptides comprising them, and the encoding nucleic acids can all be components of immunogenic compositions, particularly compositions suitable for intralymphatic delivery, that constitute further embodiments.

Analog Design

Embodiments relate to SSX-$2_{41-49}$ peptides containing substitutions of the sequence KASEKIFYV (SEQ ID NO. 1) (See FIG. 1). In a further embodiment, the analog can be generally an analog of the SSX-$2_{41-50}$ decamer peptide with the sequence KASEKIFYVY (SEQ ID NO. 1). The residues or amino acids that make up the peptide are referred to herein as P1-P9 or P1-P10 to designate the position within the peptide as numbered from the N— to the C-terminus, P1 corresponding to the N-terminal Lysine and P9 corresponding to the C-terminal Valine in the nonamer. Alternatively, the residues may be referred to by the primary activity of the molecule that they are involved in. For example, residue P2 is described as the N-terminal primary anchor molecule, while P9 (or P10 in the decamer) is described as the primary C-terminal anchor. Residues P4, P6 and P8 are primarily involved in TCR interactions. Substitutions can use any amino acids, including standard and non-standard amino acids, known to one of skill in the art. A number of exemplary amino acids are disclosed herein, however, the substitutions disclosed herein are not meant to be a list that includes all imagined substitutions, but are exemplary of the substitutions that are possible. One of skill in the art may find a number of other non-standard amino acids in catalogs and references that may be purchased or chemically produced for use with the analogs herein.

A number of possible analogs were produced by modification of peptide anchor residues to achieve better HLA binding profiles and higher immune responses, including at the N-terminal primary anchor (P2 position), at the N-terminal secondary anchor (P1 position), at the N-terminal primary and secondary anchor (P1 and P2 positions), and at the N-terminal primary/secondary anchor (P1 and P2 positions) and C-terminal primary anchor (P9 position). Further, peptides with modifications at the anchor residues and TCR contact residues were produced to circumvent T cell tolerance for self-antigens, these modifications included modifications at the N-terminal primary/secondary anchor (P1 and P2 positions) and secondary TCR recognition sites (P4, P6 and/or P8 positions), modifications at the N-terminal primary/secondary anchors (P1 and P2 position), and modifications at the C-terminal primary anchor (P9) and at secondary TCR recognition sites (P4, P6 and/or P8 positions). Further, decamer analogs were produced.

The choice of which residues would best produce analogs with improved properties involved analysis of studies of MHC peptide interactions, studies of TCR peptide interactions and previous analogs that were known in the art. Some residues are primarily involved in a specific interaction and some are secondarily or even tertiarily involved. Thus, the knowledge of how the residues are involved in the binding to these molecules was involved in the analysis. Further, some of the wild-type residues are preferred, meaning that they work well for the intended interaction, while others are non-preferred, meaning that they work poorly for the interaction. Thus, in one embodiment, the non-preferred residues can be substituted. For example, the valine at the C-terminus is generally a preferred anchor residue because it produces a strong interaction with the HLA molecule and, thus, it was less preferred to substitute this residue. However, modifications of wild-type tumor-associated peptide epitopes by incorporating favorable anchor residues have generated analogs with improved binding profiles with HLA molecules and enhanced immunogenicity. One of the most successful examples is the A27L peptide analog of Melan-A 26-35 epitope (Valmori D, et al. $J.$ $Immunol.$ 160(4): 1750-8, 1998; which is hereby incorporated by reference in its entirety). The original epitope failed to form a stable complex with HLA-A2 molecules as it lacked an optimal anchor residue at position 2. In contrast, the modified Melan $A_{26-35}$ A27L peptide analog demonstrated unequivocally increased binding profiles with HLA-A2 molecules and greater immunogenicity than its wild-type counterpart. Immunizing patients with this analog generated strong T cell immune responses that were able to recognize the wild-type epitope presented at the cell surfaces. Similar modifications were obtained successfully with many other tumor-associated epitopes such as GP100 209-217 (Parkhurst M R, et al. $J$ $Immunol.$ 157(6): 2539-48, 1996; which is hereby incorporated by reference in its entirety), Her-2 369-377 (Vertuani S, et al. $J.$ $Immunol.$ 172(6): 3501-8, 2004; which is hereby incorporated by reference in its entirety).

The choice of how many residues to substitute involves a desire to substitute better residues while still retaining enough of the qualities of the epitope that it will still be recognized by T cells that recognize the wild-type epitope. Thus, in one embodiment, one or two substitutions can be made to the wild-type peptide. In a further embodiment, more than two substitutions can be made to the wild-type peptide, while still retaining cross-reactivity with the wild-type peptide.

Generally, the part of the peptide that is involved in TCR recognition is desirably substituted to produce improved immunogenicity while still cross-reacting with the wild-type epitope. In one example, a peptide that shows increased immunogenicity is preferred. Because the P2 position or second amino acid at the N-terminal end is believed to be primarily involved in the process of producing improved immunogenicity, primarily through improved binding properties, it is a preferred substitution site and a number of modifications were made in the exemplary analogs to identify desirable substitutions. Similar considerations apply to the carboxy-terminal position, PΩ, which also can be important for MHC binding.

Thus, in one embodiment, the analog can include a substitution at the P2 residue that substitutes a more hydrophobic residue for the wild-type alanine. In a further embodiment, the hydrophobic residue also can possess a more bulky side chain. In a further embodiment, the residue at P1 can be substituted with a more hydrophobic residue. In a further embodiment, residues P1 and P2 both can be substituted with more hydrophobic residues. In further embodiments, at least one residue at P1, P2, and P9 can be substituted. In a further embodiment, at least two residues at P1, P2 and P9 can be substituted. In a further embodiment at least two residues at P1, P2, P9, P4, and P6 can be substituted including one or more residues involved in TCR binding.

In some embodiments, substitutions of those residues only secondarily involved in binding to TCR or the MHC molecule can be advantageous. For example, substitution of secondary TCR binding amino acids can generate analogs that still bind and produce a response and do not interfere with the binding to the MHC molecule, but preferably overcome the tolerance issues of self-antigens. This is useful because a patient who has cancer may be partially tolerized to the antigen. Thus, in order to overcome that tolerance, an analog that retains some activity can be preferable to an analog with more improved immunogenicity, because it will be less likely to be recognized as "self" by the immune system.

In addition to substituting amino acids at various positions of the defined nominal epitope, length variants can also be used as analogues. Most typically, additional amino acid residues are added to or removed from one, the other, or both ends of a peptide. In some cases, additional terminal residues are removed by proteolysis after administration to a subject, regenerating the nominal epitope or an analogue of the same length before binding with MHC. In other cases, the peptide of altered length is truly antigenically cross-reactive, as described in Example 20 or exemplified by the relationship between Melan-$A_{27-35}$ and Melan-$A_{26-35}$. It is to be understood that individual embodiments specifically including or excluding any particular amino acid at any of these additional terminal positions (in some places herein termed P0 and PΩ+1) are within the scope of the invention disclosed herein. When an analogue is said to consist essentially of a sequence it is to be understood that such short length variants that are either trimmed or that retain cross-reactivity are intended. In some embodiments, insertions of smaller amino acids (e.g., glycine, alanine, or serine), especially between the anchor positions, can behave similarly to changes in TCR-interacting residues.

1. N-Terminal Proximal Primary Anchor Modification (P2)

The N-terminal primary anchor is the second N-terminal amino acid of the peptide and is the N-terminal proximal primary anchor. It is primarily involved in the interaction with the MHC molecule and substitutions can result in improved binding and stability. However, it may be secondarily involved in TCR interactions also. Thus, substitutions at this site can result in a peptide with improved interaction with MHC molecules as well as improved interaction with the TCR.

The alanine found at this position in the wild-type sequence is generally believed to be non-preferred for the interaction with the MHC molecule. Thus, preferred embodiments of the analogs have a substitution at this position. In one embodiment, the original Ala 42 found in the wild-type sequence can be substituted with a more hydrophobic amino acid. Any more hydrophobic amino acid can be used including any that is available or known to one of skill in the art, including standard amino acids and non-standard amino acids. In a further embodiment, the original Ala 42 is substituted with a more hydrophobic amino acid also possessing a bulky side chain. Examples of more hydrophobic amino acids include, but are not limited to: Leu, Val, Ile, Met, α-aminobutyric acid, Norleucine and Norvaline. Table 1 is a summary of the N-terminal proximal primary anchor modifications and the results for each.

TABLE 1

N-TERMINAL PROXIMAL PRIMARY ANCHOR MODIFICATION

| Catergory | Peptide name | Sequence | SEQ ID NO. | Predictive Scores (R/NIH) | Half-maximal Binding (mM) | Relative affinity (1/RA) | Stability (T½) (Hrs) | Cross-reactivity and fct avidity (native to analogs)* |
|---|---|---|---|---|---|---|---|---|
| Native peptide | SSX2 41-49 | KASEKIFYV | 1 | 22/1017 | 14.64 | 1.0 | 11 | 1 |
| N-terminal Primary Anchor | SSX2 41-49 (A42L) | KLSEKIFYV | 102 | 28/73228 | 8.89 | 1.6 | 19 | 0.03 |
| | SSX2 41-49 (A42V) | KVSEKIFYV | 103 | 22/6407 | 5.2 | 2.8 | 20 | 0.03 |
| | SSX2 41-49 (A42I) | KISEKIFYV | 104 | 26/10068 | 8.8 | 1.7 | 22.5 | 3 |
| | SSX2 41-49 (A42M) | KMSEKIFYV | 105 | 26/52887 | 8.8 | 1.7 | 22.5 | 0.1 |
| | SSX2 41-49 (A42(D-Ala)) | K(D-Ala)SEKIFYV | 106 | NA | N/B | N/B | N/B | 10 |
| | SSX2 41-49 (A42(D-Leu)) | K(D-Leu)SEKIFYV | 107 | NA | N/B | N/B | N/B | N/T |
| | SSX2 41-49 (A42(D-Val)) | K(D-Val)SEKIFYV | 108 | NA | N/B | N/B | N/B | 3 |
| | SSX2 41-49 (A42(Nal-1)) | KNal-1SEKIFYV | 109 | NA | N/B | N/B | N/B | >10 |
| | SSX2 41-49 (A42(Nal-2)) | KNal-2SEKIFYV | 110 | NA | 13.9 | 1.1 | N/A | 3 |
| | SSX2 41-49 (A42(Abu)) | KAbuSEKIFYV | 111 | NA | 7.56 | 1.9 | N/A | 0.3 |
| | SSX2 41-49 (A42(Nle)) | KNleSEKIFYV | 112 | NA | 5.82 | 2.5 | 24 | 0.1 |
| | SSX2 41-49 (A42(Nva)) | KNvaSEKIFYV | 113 | NA | 11.4 | 1.3 | N/A | 0.1 |
| | SSX2 41-49 (A42(Aib)) | KAibSEKIFYV | 114 | NA | 18.4 | 0.8 | N/A | 3 |

2. N-Terminal Secondary Anchor Modification (P1)

The N-terminal secondary anchor is the first amino acid at the N-terminus. This residue is Lys 41 and is defined as a secondary anchor residue in interacting with the HLA-A*0201 molecule. However, it is also engaged in the interaction with the T cell receptors to a certain degree. Therefore, modifications of this position can generate some heteroclitic analogs that are more immunogenic and more suitable for the development of tumor vaccines. Although the lysine at this position is generally considered to be favored, substitutions can result in highly improved properties.

Thus, in one embodiment, the original Lys 43 found in the wild-type sequence can be substituted with a more hydrophobic amino acid. Any more hydrophobic amino acid can be used, including any that is available or known to one of skill in the art, including standard amino acids and non-standard amino acids. In a further embodiment, the Lys 43 can be substituted with an aromatic amino acid. Examples of more hydrophobic amino acids include, but are not limited to: Phe, Tyr, Trp, and D-Lys. Table 2 is a summary of N-terminal secondary anchor modifications and the results for each.

TABLE 2

N-TERMINAL SECONDARY ANCHOR MODIFICATIONS

| Category | Peptide name | Sequence | SEQ ID NO. | Predictive Scores (R/NIH) | Half-maximal Binding (mM) | Relative affinity (1/RA) | Stability (T½) (Hrs) | Cross-reactivity and fct avidity (native to analogs)* |
|---|---|---|---|---|---|---|---|---|
| Native | SSX2 41-49 | KASEKIFYV | 1 | 22/1017 | 14.64 | 1.0 | 11 | 1 |
| N-terminal Secondary Anchor | SSX2 41-49 (K41F) | FASEKIFYV | 115 | 23/1336 | 9.55 | 1.5 | >24 | 0.3 |
| | SSX2 41-49 (K41W) | WASEKIFYV | 116 | 22/1336 | 27.07 | 0.5 | N/A | >10 |
| | SSX2 41-49 (K41Y) | YASEKIFYV | 117 | 21/1336 | 8.74 | 1.7 | >24 | 3 |
| | SSX2 41-49(K41(D-Lys)) | (D-Lys)ASEKIFYV | 118 | NA | N/B | N/B | N/B | >10 |
| | SSX2 41-49 (K41(Phg)) | PhgASEKIFYV | 119 | NA | 5.83 | 2.5 | >24 | 0.1 |
| | SSX2 41-49 (K41(Cha)) | ChaASEKIFYV | 120 | NA | N/B | N/B | N/B | >10 |
| | SSX2 41-49 (K41(Phe-4F)) | Phe(4-F)ASEKIFYV | 121 | NA | 6.72 | 2.2 | >24 | 3 |
| | SSX2 41-49 (K41(Phe-4NO2)) | Phe(4-NO2)ASEKIFYV | 122 | NA | 12.8 | 1.1 | N/A | 3 |
| | SSX2 41-49 (K41(O-methyl Tyr)) | O-methyl-TyrASEKIFYV | 123 | NA | 19.5 | 0.8 | 20 | 3 |
| | SSX2 41-49 (K41(b-(3-benzothienyl)Ala)) | b-(3-benzothienyl)AlaASEKIFYV | 124 | NA | 24.1 | 0.6 | N/A | 10 |

3. N-Terminal Primary and Secondary Modifications (P2 and P1)

In one embodiment, both primary and secondary anchor residues were substituted to result in improved binding affinity to the HLA molecule. In a further embodiment, the double substitution produced improved stability of binding to the HLA molecule. In further embodiments, the binding and/or stability was not improved and may have even been reduced, but other properties of the molecule were improved, such as activity or recognition by a tolerized individual. Table 3 is a summary of N-terminal primary and secondary anchor modifications and the results for each.

TABLE 3

N-TERMINAL PRIMARY AND SECONDARY ANCHOR MODIFICATION

| Category | Peptide name | Sequence | SEQ ID NO. | Predictive Scores (R/NIH) | Half-maximal Binding (mM) | Relative affinity (1/RA) | Stability (T½) (Hrs) | Cross-reactivity and fct avidity (native to analogs)* |
|---|---|---|---|---|---|---|---|---|
| Native N-terminal Primary/ Secondary Anchor | SSX2 41-49 | KASEKIFYV | 1 | 22/1017 | 14.64 | 1.0 | 11 | 1 |
| | SSX2 41-49 (K41Y, A42L) | YLSEKIFYV | 125 | 29/96243 | 11.8 | 1.2 | >24 | N/T |
| | SSX2 41-49 (K41Y, A42V) | YVSEKIFYV | 126 | 23/8421 | 14.6 | 1.0 | >24 | 0.1 |
| | SSX2 41-49 (K41Y, A42M) | YMSEKIFYV | 127 | 27/69508 | 25 | 0.6 | >24 | 3 |
| | SSX2 41-49 (K41Y, A42I) | YISEKIFYV | 128 | 27/13233 | 6.5 | 2.3 | N/A | 1 |
| | SSX2 41-49 (K41F, A42L) | FLSEKIFYV | 129 | 28/96243 | 4.9 | 3.0 | >24 | 0.3 |
| | SSX2 41-49 (K41F, A42V) | FVSEKIFYV | 130 | 22/8421 | 4.675 | 3.1 | 24 | 0.1 |
| | SSX2 41-49 (K41F, A42M) | FMSEKIFYV | 131 | 26/69508 | 6.58 | 2.2 | >24 | 3 |
| | SSX2 41-49 (K41F, A42I) | FISEKIFYV | 132 | 26/13233 | 5.368 | 2.7 | >24 | 0.3 |
| | SSX2 41-49 (K41W, A42L) | WLSEKIFYV | 133 | 27/96243 | 4.472 | 3.3 | >24 | 0.3 |
| | SSX2 41-49 (K41W, A42V) | WVSEKIFYV | 134 | 21/8421 | 4.82 | 3.0 | >24 | 1 |
| | SSX2 41-49 (K41W, A42M) | WMSEKIFYV | 135 | 25/69508 | 5.13 | 2.9 | >24 | 1 |
| | SSX2 41-49 (K41W, A42I) | WISEKIFYV | 136 | 25/13233 | 6.98 | 2.1 | >24 | 0.1 |
| | SSX2 41-49 (K41(D-Lys), A42L) | (D-Lys)LSEKIFYV | 137 | N/A | 2.5 | 5.9 | 15 | 10 |
| | SSX2 41-49 (K41(D-Lys), A42V) | (D-Lys)VSEKIFYV | 138 | N/A | 24.5 | 0.6 | N/A | 10 |

4. N-Terminal Primary/Secondary Anchor and C-Terminal Primary Modification (P2, P1 and P9)

The C-terminal Val of the wild-type peptide is generally a preferred anchor residue and primarily involved in the interaction with the MHC molecule. However, substitutions were carried out to identify which amino acids improve the analogs having primary and secondary N-terminal modifications. These C-terminal substitutions can be used in the absence of one or more N-terminal modifications also.

These modifications were shown to improve binding affinity and stability and in some cases resulted in analogs with decreased cross-reactivity. Thus, in some embodiments, the substitution to the C-terminus resulted in a peptide with improved binding and/or stability without decreased cross-reactivity. However, in other embodiments the substitution to the C-terminus resulted in a peptide with improved binding and/or stability with equal or decreased cross-reactivity. Each of the molecules can be of use in certain cases or in certain patients. In one embodiment, the valine at the C-terminus is substituted with a large aliphatic amino acid. Table 4 is a summary of N-terminal primary/secondary anchor and C-terminal primary modifications and the results for each.

TABLE 4

N-TERMINAL PRIMARY/SECONDARY ANCHOR AND C-TERMINAL PRIMARY MODIFICATIONS

| Category | Peptide name | Sequence | SEQ ID NO. | Predictive Scores (R/NIH) | Half-maximal Binding (mM) | Relative affinity (1/RA) | Stability (T½) (Hrs) | Cross-reactivity and fct avidity (native to analogs)* |
|---|---|---|---|---|---|---|---|---|
| Native | SSX2 41-49 | KASEKIFYV | 1 | 22/1017 | 14.64 | 1.0 | 11 | 1 |
| N-terminal Primary/ Secondary Anchor, C-terminal Primary Anchor | SSX2 41-49 (K41F, A42V, V49L) | FVSEKIFYL | 139 | 22/2586 | 10.7 | 1.4 | 17 | >10 |
| | SSX2 41-49 (K41F, A42V, V49I) | FVSEKIFYI | 140 | 20/1263 | 9 | 1.6 | 24 | 0.3 |
| | SSX2 41-49 (K41F, A42V, V49A) | FVSEKIFYA | 141 | 16/601 | 6.9 | 2.1 | 16 | 1 |
| | SSX2 41-49 (K41F, A42V, V49M) | FVSEKIFYM | 142 | 16/601 | 17.8 | 0.8 | 22 | >10 |
| | SSX2 41-49 (K41F, A42V, V49Nle) | FVSEKIFY(Nle) | 143 | N/A | 5.59 | 2.6 | >24 | >10 |
| | SSX2 41-49 (K41F, A42V, V49Nva) | FVSEKIFY(Nva) | 144 | N/A | 1.89 | 7.7 | 20 | 0.1 |
| | SSX2 41-49 (K41F, A42V, V49MeVal) | FVSEKIFY(MeVal) | 145 | N/A | 17.9 | 0.8 | 22 | 10 |
| | SSX2 41-49 (K41F, A42V, V49Aib) | FVSEKIFY(Aib) | 146 | N/A | N/A | N/A | N/A | >10 |
| | SSX2 41-49 (K41F, A42V, V49Abu) | FVSEKIFY(Abu) | 147 | N/A | 3.43 | 4.3 | 20 | 1 |
| N-terminal Primary Anchor, C-terminal Primary Anchor | SSX2 41-49 (A42V, V49I) | KVSEKIFYI | 148 | 20/961 | 13.9 | 1.1 | N/A | 0.3 |

TABLE 4-continued

N-TERMINAL PRIMARY/SECONDARY ANCHOR AND C-TERMINAL PRIMARY MODIFICATIONS

| Category | Peptide name | Sequence | SEQ ID NO. | Predictive Scores (R/NIH) | Half-maximal Binding (mM) | Relative affinity (1/RA) | Stability (T½) (Hrs) | Cross-reactivity and fct avidity (native to analogs)* |
|---|---|---|---|---|---|---|---|---|
| | SSX2 41-49 (A42L, V49I) | KLSEKIFYI | 149 | 26/10984 | 5.682 | 2.6 | N/A | 0.03 |
| | SSX2 41-49 (A42a, V49v) | K(D-Ala)SEKIFY(D-Val) | 150 | N/A | N/B | N/B | N/B | >10 |
| C-terminal Primary Anchor | SSX2 41-49(V49I) | KASEKIFYI | 151 | 20/152.56 | 14 | 1.0 | N/A | 10 |

5. N-Terminal Primary/Secondary Anchor and TCR Residues Modification

The TCR sites are generally recognized as residues P4, P6, and P8 and are the primary residues involved in the binding to the TCR. However, other residues may also be involved in the interaction to a lesser extent. In one embodiment, one or more of the sites primarily involved in TCR interaction can be substituted to increase the interaction. Preferably, these substitutions can generate heteroclitic analogs that do not interfere with binding to the MHC molecule, but overcome the tolerance issues of the wild-type peptides. In a further embodiment, at least one TCR substitution can be included with at least one substitution at position P1, P2, and/or P9. In a further embodiment, the substitution at any one or more of the P4, P6, and P8 positions can be a polar amino acid. In a further embodiment, the substitution can be an aromatic amino acid at position P8. In a further embodiment, the substitution can be an amino acid with a large aliphatic side chain at position P6. In a further embodiment, the substitution can be an amino acid which has a larger side chain to preserve the interaction. Table 5 is a summary of N-terminal primary/secondary anchor and TCR residues modifications and the results for each.

TABLE 5

| N-TERMINAL PRIMARY/SECONDARY ANCHOR AND TCR SITES MODIFICATION | | | | | | | | |
|---|---|---|---|---|---|---|---|---|
| Catergory | Peptide name | Sequence | SEQ ID NO. | Predictive Scores (R/NIH) | Half-maximal Binding (mM) | Relative affinity (1/RA) | Stability (T½) (Hrs) | Cross-reactivity and fct avidity (native to analogs)* |
| Native | SSX2 41-49 | KASEKIFYV | 1 | 22/1017 | 14.64 | 1.0 | 11 | 1 |
| N-terminal Primary/ Secondary Anchor, TCR sites | SSX2 41-49 (K41F, A42V, E44D) | FVSDKIFYV | 152 | 21/8421 | 13.18 | 1.1 | N/A | >10 |
| | SSX2 41-49 (K41F, A42V, E44N) | FVSNKIFYV | 153 | 20/2054 | 8.97 | 1.6 | N/A | >10 |
| | SSX2 41-49 (K41F, A42V, E44S) | FVSSKIFYV | 154 | 20/2054 | 17.5 | 0.8 | N/A | >10 |
| | SSX2 41-49 (K41F, A42V, E44T) | FVSTKIFYV | 155 | 20/2054 | 12.94 | 1.1 | N/A | >10 |
| | SSX2 41-49 (K41F, A42V, E44Q) | FVSQKIFYV | 156 | 20/2054 | 40.8 | 0.4 | N/A | 10 |
| | SSX2 41-49 (K41F, A42V, E44Nle) | FVS(Nle)KIFYV | 157 | N/A | 13 | 1.1 | N/A | 10 |
| | SSX2 41-49 (K41F, A42V, E44Nva) | FVS(Nva)KIFYV | 158 | N/A | 3.8 | 3.9 | >24 | 3 |
| | SSX2 41-49 (K41F, A42V, I46L) | FVSEKLFYV | 159 | 22/8421 | 7.8 | 1.9 | 24 | 3 |
| | SSX2 41-49 (K41F, A42V, I46V) | FVSEKVFYV | 160 | 22/8421 | N/A | N/A | 24 | 1 |
| | SSX2 41-49 (K41F, A42V, I46M) | FVSEKMFYV | 161 | 18/8421 | 9.2 | 1.6 | 22 | >10 |
| | SSX2 41-49 (K41F, A42V, I46Nle) | FVSEK(Nle)FYV | 162 | N/A | 12.8 | 1.1 | 19 | 10 |
| | SSX2 41-49 (K41F, A42V, I46Nva) | FVSEK(Nva)FYV | 163 | N/A | 6.21 | 2.4 | >24 | 1 |
| | SSX2 41-49 (K41F, A42V, Y48T) | FVSEKIFTV | 164 | 24/1531 | 3.9 | 3.8 | 24 | >10 |
| | SSX2 41-49 (K41F, A42V, Y48F) | FVSEKIFFV | 165 | 22/8421 | 8.8 | 1.7 | 20 | 10 |
| | SSX2 41-49 (K41F, A42V, Y48S) | FVSEKIFSV | 166 | 24/1531 | 3.8 | 3.9 | 20 | >10 |
| | SSX2 41-49 (K41F, A42V, Y48(Phe-4F)) | FVSEKIF(Phe-4F)V | 167 | N/A | 10.6 | 1.4 | 24 | 10 |
| | SSX2 41-49 (K41F, A42V, Y48Phg) | FVSEKIF(Phg)V | 168 | N/A | 5.85 | 2.5 | >24 | >10 |
| | SSX2 41-49 (K41F, A42V, I46L, Y48T) | FVSEKLFTV | 169 | 24/1531 | 5.67 | 2.6 | 24 | >10 |
| | SSX2 41-49 (K41F, A42V, I46L, Y48S) | FVSEKLFSV | 170 | 24/1531 | N/A | N/A | N/A | N/T |
| N-terminal Primary/ Secondary Anchor, C-terminal Primary Anchor, TCR sites | SSX2 41-49 (K41F, A42V, I46L, Y48T, V49A) | FVSEKLFTA | 171 | 18/109 | 6.3 | 2.3 | 12 | >10 |
| | SSX2 41-49 (K41F, A42V, I46L, Y48S, V49A) | FVSEKLFSA | 172 | 18/109 | 6.2 | 2.4 | N/A | >10 |

6. C-Terminal Amide

In some embodiments, the C-terminal residue can be modified to contain an amide in the place of the free carboxylic acid. Thus, for example, if the peptide is a 9-mer (nonamer) the P9 residue can be modified. If the peptide is a 10-mer (decamer) the P10 residue can be modified. Preferably this results in a peptide or analog that has increased stability in biological media, including but not limited to blood, lymph, and CNS. Preferably, the peptides can retain the other necessary activities to result in an analog usable for vaccination or as an immunogen. Table 6 is a summary of C-terminal amide modifications and the results for each.

TABLE 6

C-TERMINAL AMIDE

| Catergory | Peptide name | Sequence | SEQ ID NO. | Predictive Scores (R/NIH) | Half-maximal Binding (mM) | Relative affinity (1/RA) | Stability (T½) (Hrs) | Cross-reactivity and fct avidity (native to analogs)* |
|---|---|---|---|---|---|---|---|---|
| Native | SSX2 41-49 | KASEKIFYV | 1 | 22/1017 | 14.64 | 1.0 | 11 | 1 |
| C-terminal amide | SSX2 41-49-NH2 | KASEKIFYV-NH2 | 173 | N/A | N/B | N/B | N/T | >10 |
|  | SSX2 41-49-NH2 (A42L) | KLSEKIFYV-NH2 | 174 | N/A | N/B | N/B | N/T | 3 |
|  | SSX2 41-49-NH2 (A42V) | KVSEKIFYV-NH2 | 175 | N/A | N/B | N/B | N/T | 10 |

7. Decamers

The length of typical MHC binding peptides can vary from about 8 to about 11 amino acids in length. However, most of the previously used HLA-A*0201 are 9-mers (nonamers) or 10-mers (decamers). Thus, in one embodiment, the analog can be an analog of the wild-type sequence SSX-$2_{41\text{-}50}$. However, because the wild-type 10-mer does not have the correct binding motif and showed no immunological activity, a 10-mer was created by substituting amino acids at the P10 position and identifying the effect of various wild-type and analogs (see FIG. 1B).

8. Remaining Residues

With reference to FIGS. 1A and 1B, any residues can also be substituted with conservative amino acids. Conservative substitutions can be paired with any of the above substitutions that can produce an effect. Alternatively, conservative substitutions can be specifically at residues that are not believed to be involved in any of the activities at a primary, secondary, or even tertiary level. Such residues include P3, P5 and P7. For example, the Serine at position P3 can be substituted with an alanine or threonine to produce an analog. Typically, such conservative substitutions do not significantly affect the activity of the analog, however, in some embodiments they can increase certain activities or decrease certain activities.

NY-ESO-$1_{157\text{-}165}$ Analogs

Many features regarding a variety of embodiments and aspects of analog design are disclosed above, either generally or as applied to the SSX-2 epitope. It is to be understood that such disclosure is also applicable to this and subsequent epitopes. Explicit restatement of such disclosure will be minimized for the sake of brevity.

Embodiments relate to analogs of the MHC class I-restricted T cell epitope NY-ESO-$1_{157\text{-}165}$, SLLMWITQC (SEQ ID NO. 25), polypeptides comprising these analogs that can be processed by pAPC to present the epitope analogs, and nucleic acids that express the analogs. The analogs can have similar or improved immunological properties compared to the wild-type epitope.

One embodiment relates to methods to derivatize and improve analogs of NY-ESO-$1_{157\text{-}165}$, along with specific sequences that encompass substitutions. The analogs can contain at least one substitution, but can have multiple substitutions comprising standard or non-standard amino acids singly or in various combinations. The analogs can result in peptides with retained or improved properties.

The epitope NY-ESO-$1_{57\text{-}165}$ has been shown to be presented by NY-ESO-1 expressing cell lines, by measuring the epitope specific T cell activity against such cells (Jaeger, E. et al., *J. Exp. Med.* 187:265-270, 1998; U.S. Pat. No. 6,274,145, entitled "ISOLATED NUCLEIC ACID MOLECULE ENCODING CANCER ASSOCIATED ANTIGEN, THE ANTIGEN ITSELF, AND USES THEREOF", each of which is incorporated herein by reference in its entirety. Methodologies to improve the physico-chemical properties of the peptide NY-ESO-$1_{157\text{-}165}$ have been described in U.S. Pat. No. 6,417,165, entitled "NY-ESO-1-PEPTIDE DERIVATIVES, AND USES THEREOF", which is incorporated herein by reference in its entirety, and can consist of replacement of the terminal cysteine with other amino acids that preserve or enhance the interaction with MHC and are devoid of the deleterious property of disulfide C—C bond formation interfering with the activity. However, sole manipulation of the C terminal cysteine residue ignores the advantages of optimizing multiple residues throughout the peptide for major histocompatibility (MHC) and/or T cell Receptor (TCR) binding. Thus, beyond the practicality of mutating the Cys residue, there is considerable opportunity in mutating additional amino acids throughout the peptide. For example, substitutions can be used to further optimize the binding to MHC and/or TCR in a fashion that enables more effective application in clinics.

Embodiments relate to families of one or more peptides of 9 or 10 amino acids in length related by sequence to amino acids 157-165 of the human cancer testis (CT) antigen NY-ESO-1 (NY-ESO-$1_{157\text{-}165}$).

Analog Design

The analog is generally an analog of the NY-ESO-$1_{157\text{-}165}$, with the sequence SLLMWITQC (SEQ ID NO: 25). Analysis of whether wild-type amino acids are preferred or non-preferred used previous analyses of other peptide-MHC or TCR interactions. For example, the Cysteine at the C-terminus is generally a non-preferred anchor residue because it does not produce a strong interaction with the HLA molecule and, thus, it was highly preferred to substitute this residue. However, although the Serine at position P1 is generally preferred, it was found that substituting an aromatic could produce a peptide with improved properties. Further the Leucine at position P2 is generally acceptable, but substituting a hydrophobic and/or bulky amino acid resulted in a peptide with improved properties. The residues are primarily involved in the interaction with the TCR (P4, P6 and P8) showed a preference generally for some polarity, and in the case of P8 an aromatic generally produced peptides with favorable properties.

One preferred embodiment relates to an analog that has a substitution at the P2 position. In one such embodiment, the substitution can be a hydrophobic residue. In a further embodiment, the substitution can be a bulky hydrophobic residue. In another embodiment, the residue at P1 can be substituted with a more hydrophobic residue. In a further embodiment, residues P1 and P2 can be both substituted with more hydrophobic residues. In further embodiments, at least one residue at P1, P2, and P9 can be substituted. In a further embodiment, at least two residues at P1, P2 and P9 can be substituted. In a further embodiment, at least two residues at P1, P2, P9, P4, and P6 can be substituted, including one or more residues involved in TCR binding. In a further embodiment, the residue at P8 can be substituted with an aromatic residue. Examples of the following substitutions are shown in FIGS. 13A-13C.

1. N-Terminal Proximal Primary Anchor Modification (P2)

The N-terminal primary anchor is the second N-terminal amino acid of the peptide, thus, it is the N-terminal proximal primary anchor. Although the original Leucine 158 is not considered "non-preferred" for binding to the MHC molecule, substitutions can produce a peptide with improved binding. Thus, in one embodiment, the original Leu 158 found in the wild-type sequence can be substituted with a similarly or more hydrophobic amino acid. Any hydrophobic amino acid can be used, including one that is available to or that is known to one of skill in the art, including standard amino acids and non-standard amino acids. In a further embodiment, the original Leu 158 can be substituted with a more hydrophobic amino acid also possessing a bulky side chain. Examples of more hydrophobic amino acids include, but are not limited to: Leu, Val, Ile, Met, α-aminobutyric acid, Norleucine and Norvaline. Further, a naphthal side chain can also be substituted. Preferably, the substitution results in improved binding and stability with the HLA molecule. However, this residue may be secondarily or tertiarily involved in TCR interactions, and substitutions can also result in improved recognition by the TCR.

2. N-Terminal Secondary Anchor Modification (P1)

The N-terminal secondary anchor is the first amino acid at the N-terminus or P1. This residue is involved in a number of interactions. The residue of Ser 157 was defined as a secondary anchor residue in interacting with HLA-A*0201 molecule. It is also engaged in the interaction with the T cell receptors to a certain degree. Therefore, modifications of this position generate some heteroclitic analogs that are more immunogenic and more suitable for the development of tumor vaccines. Thus, substitutions can result in a variety of improved qualities.

Although the Serine is not considered "non-preferred," a number of substitutions can result in improved qualities of the peptide. Thus, in one embodiment, the original Ser 157 found in the wild-type sequence can be substituted with a more hydrophobic amino acid. Any more hydrophobic amino acid can be used, including one that is available to or that is known to one of skill in the art, including standard amino acids and non-standard amino acids. Examples of more hydrophobic amino acids include, but are not limited to: Phe, Tyr, Trp, and D-Lys.

3. N-Terminal Primary and Secondary Modifications (P2 and P1)

In one embodiment, both primary and secondary anchor residues were substituted to result in improved binding affinity to the HLA molecule. In a further embodiment, the double substitution produced improved stability of binding to the HLA molecule. In further embodiments, the binding and/or stability was not improved and may have even been reduced, but other properties of the molecule were improved, such as activity or recognition by a tolerized individual.

4. N-Terminal Primary/Secondary Anchor and C-Terminal Primary Modification (P2, P1 and P9)

The C-terminal cysteine of the wild-type peptide is generally a non-preferred anchor residue. Because this residue is generally primarily involved in the interaction with the MHC molecule, it can be preferred to substitute residues that result in a stronger interaction with the MHC molecule. Thus, substitutions were shown to improve binding affinity and stability and in some cases resulted in analogs with decreased cross-reactivity. In some embodiments, the substitution to the C-terminus can result in a peptide with improved binding and/or stability without decreased cross-reactivity. However, in other embodiments, the substitution to the C-terminus can result in a peptide with improved binding and/or stability with equal or decreased cross-reactivity. Because substitution of this residue has been previously shown to provide improved peptides, it can be preferable produce peptides that are more improved in the interaction with the MHC molecule as well as other interactions, such as the recognition by the TCR. Thus, in some embodiments, the C-terminal substitution can be paired with at least one other substitution. Examples of amino acid substitutions to the C-terminus include, but are not limited to, valine, lysine, alanine, and isoleucine.

5. N-Terminal Primary/Secondary Anchor and TCR Residue Modifications

The primary residues involved in the interaction with the TCR are generally recognized as residues P4, P6, and P8. However, other residues may also be involved in the interaction to a lesser extent. In one embodiment, one or more of the sites primarily involved in TCR interaction can be substituted to result in an improved interaction. Preferably, these substitutions generate heteroclitic analogs that do not interfere with binding to the MHC molecule, but overcome the tolerance issues of the wild-type peptides. In one embodiment, at least one TCR substitution can be included with at least one substitution at position P1, P2, and/or P9. In one embodiment, amino acids with some polarity can be substituted at P4, P6, and P8. In a further embodiment, aromatic amino acids can be substituted at the P8 position.

6. C-Terminal Amide

In some embodiments, the C-terminal residue can be modified to contain an amide in the place of the free carboxylic acid. Thus, for example if the peptide is a 9-mer (nonamer) the P9 residue can be modified. If the peptide is a 10-mer (decamer) the P10 residue can be modified. Preferably, this results in a peptide or analog that has increased stability in biological media, including but not limited to blood, lymph, and CNS. Preferably, the peptides retain their other activities to result in an analog usable for vaccination or as an immunogen.

7. Decamers

The length of typical MHC binding peptides varies from about 8 to about 11 amino acids in length. However, most of the previously used HLA-A*0201 are 9-mers (nonamers) or 10-mers (decamers). Thus, in one embodiment, the analog can be a 10-mer of the wild-type sequence NY-ESO-$1_{157-166}$. However, because the wild-type 10-mer does not have the correct binding motif and showed no immunological activity, a 10-mer was created by substituting amino acids at the P10 position and identifying the effect of various modifications (see FIGS. 13A-13C). In one embodiment, the residues that were added or substituted for the wild-type at the C-terminus can be selected from the group consisting of norvaline, leucine, isoleucine, valine, and alanine.

8. Remaining Residues

With reference to FIGS. 13A and 13C, any residues can also be substituted with conservative amino acids. Conservative substitutions can be paired with any of the above substitutions that can produce an effect. Alternatively, conservative substitutions can be specifically at residues that are not believed to be involved in any of the activities at a primary, secondary, or even tertiary level. Such residues can include P3, P5 and/or P7. Conservative substitutions are known to those of skill in the art, but, for example, the Leucine at position P3 can be substituted with an alanine or threonine to produce an analog. Typically, such conservative substitutions do not significantly affect the activity of the analog. However, in some embodiments they may increase certain activities or decrease certain activities. Because of the known interactions, it is unlikely that such conservative substitutions will have a significant effect on any of the activities.

PSMA$_{288-297}$ Analogs

Many features regarding the variety of embodiments and aspects of analog design are disclosed above, either generally or as applied to particular epitopes. It is to be understood that such disclosure is also applicable to this and subsequent epitopes. Explicit restatement of such disclosure will be minimized for the sake of brevity.

Some embodiments relate to analogs of the MHC class I-restricted T cell epitope PSMA$_{288-297}$, GLPSIPVHPI (SEQ ID NO. 42), polypeptides comprising these analogs that can be processed by pAPC to present the epitope analogs, and nucleic acids that express the analogs. The analogs can have similar or improved immunological properties compared to the wild-type epitope. Evidence validating the presentation of this epitope by human cancer cells is presented in Example 32 below.

One embodiment relates to methods to derivatize and improve analogs of PSMA$_{288-297}$, along with specific sequences that encompass substitutions. The analogs can contain at least one substitution, but can have multiple substitutions comprising standard or non-standard amino acids singly or in various combinations. The analogs can result in peptides with retained or improved properties.

Embodiments relate to families of one or more peptides of 9 or 10 amino acids in length related by sequence to amino acids 288-297 of the human PSMA.

Analog Design

In some embodiments, the PSMA$_{288-297}$ analog can contain substitutions of the sequence GLPSIPVHPI (SEQ ID NO. 42). Reference to binding motif data, such as presented in table 7 in example 2 below, indicates that the P2 anchor residue can make the largest individual contribution to affinity of any position in an A2.1-restricted epitope. In this case, the amino acid at the P2 position is the optimally preferred leucine. The PΩ anchor residue, isoleucine, is favorable. In vitro binding studies using the T2 cell assay system (not shown) have indicated that the native peptide has generally superior binding characteristics, particularly as compared to the SSX-2 and NY-ESO-1 epitopes. The epitope exhibited significant binding at relatively low concentrations, although this was paired with a relatively shallow rise toward saturation. The wild-type epitope can be improved. Analyses such as those represented by tables 7 and 8 are averages and the behavior of a given residue in a particular sequence may diverge from the average. Consistent with the favorable results obtained with Nle and Nva for the SSX-2 and NY-ESO-1 epitopes discussed above, Nle and Nva also can be successfully used for the instant PSMA epitope. Finally, even similar binding characteristics, if paired with alterations that help circumvent whatever tolerance to the epitope may exist, can increase the effective immunogenicity of the peptide. In the transgenic mouse model, the native peptide is poorly immunogenic (see Example 35 for instance) which may reflect tolerance to the epitope; the region of PSMA from which this epitope is derived is identical between mouse and human PSMA.

1. N-Terminus Proximal Primary Anchor Modification (P2)

As noted above, although the native residue at the P2 position of this epitope is generally the optimal residue among genetically encoded amino acids. The effect of substituting other preferred or bulky hydrophobic residues were examined for potential improvement of binding, tolerance breaking and cross-reactive immunity. Exemplary substitutions can include Met, Ile, Gln, Val, Nva, Nle, and aminobutyric acid (Abu).

2. N-Terminal Secondary Anchor Modification (P1)

The N-terminal secondary anchor is the first amino acid at the N-terminus. The native Gly is only marginally preferred at this position. Various observations (see tables 7 and 8 for example) show that amino acids with potential to improve the epitope include Ala, Ser, Abu and sarkosine (Sar, that is, N-methylglycine).

3. C-Terminal Primary Anchor Modification (PΩ)

The native Ile at this position is generally a preferred but not optimal residue. Substitution at this position can improve binding. Exemplary substitutions can include Val, Leu, Nva, and Nle.

4. Secondary Anchors and TCR Exploration

The penultimate position (PΩ-1) can serve both as a secondary anchor and a TCR interacting position. Substitution of Ala, Leu, Ser, or Thr can have a primary effect on TCR interaction, though it can also contribute to improved binding. P3 is another position that can effect both binding and immunogenicity. Substitution of Trp at this position can improve both.

Further embodiments relate to combinations of substitutions at multiple positions in order to combine, synergize, and counteract the various effects obtained with the single substitutions.

PRAME$_{425-433}$ Analogs

Many features regarding a variety of embodiments and aspects of analog design are disclosed above, either generally or as applied to particular epitopes. It is to be understood that such disclosure is also applicable to this and subsequent epitopes. Explicit restatement of such disclosure will be minimized for the sake of brevity.

Embodiments include analogs of the MHC class I-restricted T cell epitope PRAME$_{425-433}$, SLLQHLIGL (SEQ ID NO. 71), polypeptides comprising these analogs that can be processed by pAPC to present the epitope analogs, and nucleic acids that express the analogs. The analogs can have similar or improved immunological properties compared to the wild-type epitope. Evidence validating the presentation of this epitope by human cancer cells is presented in Example 39 below.

One embodiment relates to methods to derivatize and improve analogs of PRAME$_{425-433}$, along with specific sequences that encompass substitutions. The analogs can contain at least one substitution, but can have multiple substitutions comprising standard or non-standard amino acids singly or in various combinations. The analogs can result in peptides with retained or improved properties.

Some embodiments relate to families of one or more peptides of 9 or 10 amino acids in length related by sequence to amino acids 425-433 of the human PRAME sequence.

Analog Design

Some embodiments relate to analogs of the PRAME$_{425-433}$ which can contain substitutions of the sequence SLLQH-LIGL (SEQ ID NO. 71). Reference to binding motif data, such as those presented in Table 7 in Example 2 below, indicates that the P2 anchor residue can make the largest individual contribution to affinity of any position in an A2.1-restricted epitope. In this case, the amino acid at the P2 position is the optimally preferred leucine. The PΩ anchor residue, leucine, is favorable, though not as strongly preferred, nor is the wild type PΩ residue necessarily the most preferred for that position. Analyses such as those reported in Tables 7 and 8 are averages and the behavior of a given residue in a particular sequence can diverge from the average. Consistent with the favorable results obtained with Nle and Nva for the other epitopes, similar improvements can be obtained substituting Nle and Nva with this sequence. Finally, even similar binding characteristics, if paired with alterations that help circumvent whatever tolerance to the epitope may exist, can increase the effective immunogenicity of the peptide.

The rationale for various substitutions has been set forth above. The particular substitutions investigated for the PRAME$_{425-433}$ epitope follow the same logic and are disclosed in the Examples 40-48 and FIGS. 25-27. Substitutions were made at the primary anchor positions P2 and PΩ (P9), the secondary anchor positions P1 and PΩ-1 (P8). Substitutions were also made in the TCR interacting positions (in addition to secondary anchor positions) P3 and P6. Selected substitutions have impact on binding and/or stability of MHC class I—peptide complexes; a key feature in determining the immunological properties of peptides. In addition, due to T cell repertoire considerations and to circumvent mechanisms responsible for the limited immunity to native epitopes, substitutions that retain the capability of analogs to interact with T cell receptors recognizing native peptides can be of practical value.

EXAMPLES

The following examples provide analogs and methods of identifying analogs. The analogs can be used, for example, as immunogens, vaccines, and/or for the treatment of a variety of cancers. The analogs were produced as in Example 1. SSX-2$_{41-49}$ analogs were identified as shown in Example 2 and are listed in Example 3. The analogs were tested for improved properties as shown in Examples 4-21. The testing of NY-ESO-1$_{157-165}$ analogs for improved properties is presented in Examples 22-30. The testing of PSMA analogues for improved properties is presented in Examples 33-38. The testing of PRAME$_{425-433}$ analogues for improved properties is presented in Examples 40-48.

Example 1

Peptide Synthesis, Purification and Characterization

Peptides were synthesized on either a Symphony multiple peptide synthesizer (PTI technologies, MA) or an ABI 433A peptide synthesizer (Applied Biosystems, Foster City, Calif.) at 0.05-0.1 mmole scale using standard Fmoc solid phase chemistry. C-terminal free acid peptides were synthesized using pre-load PEG-PS resins (on Symphony) or Wang resin (on ABI). C-terminal amidated peptides were synthesized on Fmoc-PAL-PEG-PS resin. All resins were purchased from Applied Biosystems (Foster City, Calif.). The Fmoc-amino acids used in peptide syntheses were purchased from Novabiochem (San Diego, Calif.) and AnaSpec (San Jose, Calif.). Post-synthesis cleavage was carried on by the standard protocol.

Peptide purification was carried out on either semi-preparative HPLC columns or SPE cartridges (Phenomenex, Torrance, Calif.). The purity of all peptides was >90%. The identity of each peptide was verified by Maldi-TOF MS (Voyager DE, Applied Biosystems) and analytical HPLCs (Varian or Shimazu) using a Synergi C12 column (Phenomenex, Torrance, Calif.).

Example 2

De Novo Designed SSX-2$_{41-49}$ Analogs

Structural modification of a moderately antigenic peptide can considerably improve peptide-MHC binding, CTL recognition, and/or immunogenicity. General guidelines regarding how to modify a wild-type epitope in order to achieve a peptide analog with enhanced potency are known in the art. An appreciated strategy is to optimize the residues at the so-called anchor positions for binding to the particular MHC molecule at issue. In the case of HLA-A2, a marked preference for hydrophobic residues at the P2 and PΩ positions has been observed, particularly L and M at P2, and V at PΩ. (PΩ denotes the C-terminal residue of the epitope. For HLA-A2, that is P9 or P10 depending on the length of the peptide.) Replacing the P1 position with aromatic residues, such as F, Y and W can also be advantageous.

TABLE 7

Coefficients used by the BIMAS algorithm
(Algorithm available by hypertext transfer protocol:
//bimas.cit.nih.gov/molbio/hla_bind/)
9-mer Coefficient Table for HLA_A_0201

| Amino Acid Type | Position | | | | | | | | |
|---|---|---|---|---|---|---|---|---|---|
| | 1st | 2nd | 3rd | 4th | 5th | 6th | 7th | 8th | 9th |
| A | 1.000 | 1.000 | 1.000 | 1.000 | 1.000 | 1.000 | 1.000 | 1.000 | 1.000 |
| C | 1.000 | 0.470 | 1.000 | 1.000 | 1.000 | 1.000 | 1.000 | 1.000 | 1.000 |
| D | 0.075 | 0.100 | 0.400 | 4.100 | 1.000 | 1.000 | 0.490 | 1.000 | 0.003 |
| E | 0.075 | 1.400 | 0.064 | 4.100 | 1.000 | 1.000 | 0.490 | 1.000 | 0.003 |
| F | 4.600 | 0.050 | 3.700 | 1.000 | 3.800 | 1.900 | 5.800 | 5.500 | 0.015 |

TABLE 7-continued

Coefficients used by the BIMAS algorithm
(Algorithm available by hypertext transfer protocol:
//bimas.cit.nih.gov/molbio/hla_bind/)
9-mer Coefficient Table for HLA_A_0201

| Amino Acid Type | Position | | | | | | | | |
|---|---|---|---|---|---|---|---|---|---|
| | 1st | 2nd | 3rd | 4th | 5th | 6th | 7th | 8th | 9th |
| G | 1.000 | 0.470 | 1.000 | 1.000 | 1.000 | 1.000 | 0.130 | 1.000 | 0.015 |
| H | 0.034 | 0.050 | 1.000 | 1.000 | 1.000 | 1.000 | 1.000 | 1.000 | 0.015 |
| I | 1.700 | 9.900 | 1.000 | 1.000 | 1.000 | 2.300 | 1.000 | 0.410 | 2.100 |
| K | 3.500 | 0.100 | 0.035 | 1.000 | 1.000 | 1.000 | 1.000 | 1.000 | 0.003 |
| L | 1.700 | 72.000 | 3.700 | 1.000 | 1.000 | 2.300 | 1.000 | 1.000 | 4.300 |
| M | 1.700 | 52.000 | 3.700 | 1.000 | 1.000 | 2.300 | 1.000 | 1.000 | 1.000 |
| N | 1.000 | 0.470 | 1.000 | 1.000 | 1.000 | 1.000 | 1.000 | 1.000 | 0.015 |
| P | 0.022 | 0.470 | 1.000 | 1.000 | 1.000 | 1.000 | 1.000 | 1.000 | 0.003 |
| Q | 1.000 | 7.300 | 1.000 | 1.000 | 1.000 | 1.000 | 1.000 | 1.000 | 0.003 |
| R | 1.000 | 0.010 | 0.076 | 1.000 | 1.000 | 1.000 | 0.200 | 1.000 | 0.003 |
| S | 1.000 | 0.470 | 1.000 | 1.000 | 1.000 | 1.000 | 1.000 | 1.000 | 0.015 |
| T | 1.000 | 1.000 | 1.000 | 1.000 | 1.000 | 1.000 | 1.000 | 1.000 | 1.500 |
| V | 1.700 | 6.300 | 1.000 | 1.000 | 1.000 | 2.300 | 1.000 | 0.410 | 14.000 |
| W | 4.600 | 0.010 | 8.300 | 1.000 | 1.000 | 1.700 | 7.500 | 5.500 | 0.015 |
| Y | 4.600 | 0.010 | 3.200 | 1.000 | 1.000 | 1.500 | 1.000 | 5.500 | 0.015 |
| final constant | 0.069 | | | | | | | | |

TABLE 8

Scoring Pattern for HLA-A*0201 used by the SYFPEITHI Algorithm
(9-mers)
(Algorithm available by hypertext transfer protocol:
//syfpeithi.bmi-heidelberg.com/scripts/MHCServer.dll/home.htm)

| AA | P1 | P2 | P3 | P4 | P5 | P6 | P7 | P8 | P9 |
|---|---|---|---|---|---|---|---|---|---|
| A | 2 | 6 | 2 | 0 | 0 | 0 | 2 | 1 | 6 |
| C | 0 | 0 | 0 | 0 | 0 | 0 | 0 | 0 | 0 |
| D | -1 | 0 | 0 | 1 | 0 | 0 | 0 | 0 | 0 |
| E | -1 | 0 | -1 | 2 | 0 | 0 | 0 | 2 | 0 |
| F | 1 | 0 | 1 | -1 | 1 | 0 | 0 | 0 | 0 |
| G | 1 | 0 | 0 | 2 | 2 | 0 | 0 | 1 | 0 |
| H | 0 | 0 | 0 | 0 | 0 | 0 | 1 | 0 | 0 |
| I | 2 | 8 | 2 | 0 | 0 | 6 | 0 | 0 | 8 |
| K | 1 | 0 | -1 | 0 | 1 | 0 | -1 | 2 | 0 |
| L | 2 | 10 | 2 | 0 | 1 | 6 | 1 | 0 | 10 |
| M | 0 | 8 | 1 | 0 | 0 | 0 | 0 | 0 | 6 |
| N | 0 | 0 | 1 | 0 | 0 | 0 | 1 | 0 | 0 |
| P | 0 | 0 | 0 | 2 | 1 | 0 | 1 | 0 | 0 |
| Q | 0 | 0 | 0 | 0 | 0 | 0 | 0 | 0 | 0 |
| R | 0 | 0 | 0 | 0 | 0 | 0 | 0 | 0 | 0 |
| S | 2 | 0 | 0 | 0 | 0 | 0 | 0 | 2 | 0 |
| T | 0 | 6 | -1 | 0 | 0 | 2 | 0 | 2 | 6 |
| V | 1 | 6 | 0 | 0 | 0 | 6 | 2 | 0 | 10 |
| W | 0 | 0 | 1 | 0 | 0 | 0 | 0 | 0 | 0 |
| X | 0 | 0 | 0 | 0 | 0 | 0 | 0 | 0 | 0 |
| Y | 2 | 0 | 1 | -1 | 1 | 0 | 1 | 0 | 0 |

Adapted from: Rammensee, Bachmann, Stevanovic: *MHC ligands and peptide motifs*. Landes Bioscience 1997

Example 3

The following analogs were produced using the predictions in Example 1.

TABLE 9

| Catergory | SEQ ID Number | Peptide name | Sequence |
|---|---|---|---|
| wild-type | 1 | SX-2 41-49 | KASEKIFYV |
| N-terminal Primary Anchor | 102 | SSX-2 41-49 (A42L) | KLSEKIFYV |
| | 103 | SSX-2 41-49 (A42V) | KVSEKIFYV |
| | 104 | SSX-2 41-49 (A42I) | KISEKIFYV |
| | 105 | SSX-2 41-49 (A42M) | KMSEKIFYV |
| | 106 | SSX-2 41-49 (A42(D-Ala)) | K(D-Ala)SEKIFYV |
| | 107 | SSX-2 41-49 (A42(D-Leu)) | K(D-Leu)SEKIFYV |
| | 108 | SSX-2 41-49 (A42(D-Val)) | K(D-Val)SEKIFYV |
| | 109 | SSX-2 41-49 (A42(Nal-1)) | KNal-1SEKIFYV |
| | 110 | SSX-2 41-49 (A42(Nal-2)) | KNal-2SEKIFYV |
| | 111 | SSX-2 41-49 (A42(Abu)) | KAbuSEKIFYV |
| | 112 | SSX-2 41-49 (A42(Nle)) | KNleSEKIFYV |
| | 113 | SSX-2 41-49 (A42(Nva)) | KNvaSEKIFYV |
| | 114 | SSX-2 41-49 (A42(Aib)) | KAibSEKIFYV |

TABLE 9-continued

| Catergory | SEQ ID Number | Peptide name | Sequence |
|---|---|---|---|
| N-terminal Secondary Anchor | 115 | SSX-2 41-49 (K41F) | FASEKIFYV |
| | 116 | SSX-2 41-49 (K41W) | WASEKIFYV |
| | 117 | SSX-2 41-49 (K41Y) | YASEKIFYV |
| | 118 | SSX-2 41-49 (K41(D-Lys)) | (D-Lys)ASEKIFYV |
| | 119 | SSX-2 41-49 (K41(Phg)) | PhgASEKIFYV |
| | 120 | SSX-2 41-49 (K41(Cha)) | ChaASEKIFYV |
| | 121 | SSX-2 41-49 (K41(Phe-4F)) | Phe(4-F)ASEKIFYV |
| | 122 | SSX-2 41-49 (K41(Phe-4NO2)) | Phe(4-NO$_2$)ASEKIFYV |
| | 123 | SSX-2 41-49 (K41(O-methyl Tyr)) | O-methyl-TyrASEKIFYV |
| | 124 | SSX-2 41-49 (K41(β-(3-benzothienyl)Ala)) | β-(3-benzothienyl)AlaASEKIFYV |
| N-terminal Primary/ Secondary Anchor | 125 | SSX-2 41-49 (K41Y, A42L) | YLSEKIFYV |
| | 126 | SSX-2 41-49 (K41Y, A42V) | YVSEKIFYV |
| | 127 | SSX-2 41-49 (K41Y, A42M) | YMSEKIFYV |
| | 128 | SSX-2 41-49 (K41Y, A42I) | YISEKIFYV |
| | 129 | SSX-2 41-49 (K41F, A42L) | FLSEKIFYV |
| | 130 | SSX-2 41-49 (K41F, A42V) | FVSEKIFYV |
| | 131 | SSX-2 41-49 (K41F, A42M) | FMSEKIFYV |
| | 132 | SSX-2 41-49 (K41F, A42I) | FISEKIFYV |
| | 133 | SSX-2 41-49 (K41W, A42L) | WLSEKIFYV |
| | 134 | SSX-2 41-49 (K41W, A42V) | WVSEKIFYV |
| | 135 | SSX-2 41-49 (K41W, A42M) | WMSEKIFYV |
| | 136 | SSX-2 41-49 (K41W, A42I) | WISEKIFYV |
| | 137 | SSX-2 41-49 (K41(D-Lys), A42L) | (D-Lys)LSEKIFYV |
| | 138 | SSX-2 41-49 (K41(D-Lys), A42V) | (D-Lys)VSEKIFYV |
| N-terminal Primary/ Secondary Anchor, C-terminal Primary Anchor | 139 | SSX-2 41-49 (K41F, A42V, V49L) | FVSEKIFYL |
| | 140 | SSX-2 41-49 (K41F, A42V, V49I) | FVSEKIFYI |
| | 141 | SSX-2 41-49 (K41F, A42V, V49A) | FVSEKIFYA |
| | 142 | SSX-2 41-49 (K41F, A42V, V49M) | FVSEKIFYM |
| | 143 | SSX-2 41-49 (K41F, A42V, V49Nle) | FVSEKIFY(Nle) |
| | 144 | SSX-2 41-49 (K41F, A42V, V49Nva) | FVSEKIFY(Nva) |
| | 145 | SSX-2 41-49 (K41F, A42V, V49MeVal) | FVSEKIFY(MeVal) |
| | 176 | SSX-2 41-49 (K41F, A42V, V49MeLeu) | FVSEKIFY(MeLeu) |
| | 146 | SSX-2 41-49 (K41F, A42V, V49Aib) | FVSEKIFY(Aib) |
| | 147 | SSX-2 41-49 (K41F, A42V, V49Abu) | FVSEKIFY(Abu) |
| N-terminal Primary/ Secondary Anchor, TCR sites | 152 | SSX-2 41-49 (K41F, A42V, E44D) | FVSDKIFYV |
| | 153 | SSX-2 41-49 (K41F, A42V, E44N) | FVSNKIFYV |
| | 154 | SSX-2 41-49 (K41F, A42V, E44S) | FVSSKIFYV |
| | 155 | SSX-2 41-49 (K41F, A42V, E44T) | FVSTKIFYV |
| | 156 | SSX-2 41-49 (K41F, A42V, E44Q) | FVSQKIFYV |
| | 157 | SSX-2 41-49 (K41F, A42V, E44(Nle)) | FVS(Nle)KIFYV |
| | 158 | SSX-2 41-49 (K41F, A42V, E44(Nva)) | FVS(Nva)KIFYV |
| | 159 | SSX-2 41-49 (K41F, A42V, I46L) | FVSEKLFYV |
| | 160 | SSX-2 41-49 (K41F, A42V, I46V) | FVSEKVFYV |
| | 161 | SSX-2 41-49 (K41F, A42V, I46M) | FVSEKMFYV |
| | 162 | SSX-2 41-49 (K41F, A42V, I46(Nle)) | FVSEK(Nle)FYV |
| | 163 | SSX-2 41-49 (K41F, A42V, I46(Nva)) | FVSEK(Nva)FYV |
| | 164 | SSX-2 41-49 (K41F, A42V, Y48T) | FVSEKIFTV |
| | 165 | SSX-2 41-49 (K41F, A42V, Y48F) | FVSEKIFFV |
| | 166 | SSX-2 41-49 (K41F, A42V, Y48S) | FVSEKIFSV |
| | 167 | SSX-2 41-49 (K41F, A42V, Y48(Phe-4F)) | FVSEKIF(Phe4-F)V |
| | 168 | SSX-2 41-49 (K41F, A42V, Y48(Phg)) | FVSEKIF(Phg)V |
| | 169 | SSX-2 41-49 (K41F, A42V, I46L,Y48T) | FVSEKLFTV |
| | 170 | SSX-2 41-49 (K41F, A42V, I46L,Y48S) | FVSEKLFSV |
| N-terminal Primary/ Secondary Anchor, C-Terminal Primary Anchor, TCR sites | 171 | SSX-2 41-49 (K41F, A42V, I46L,Y48T,V49A) | FVSEKLFTA |
| | 172 | SSX-2 41-49 (K41F, A42V, I46S,Y48S,V49A) | FVSEKLFSA |
| N-terminal Primary Anchor, C-terminal Primary Anchor | 148 | SSX-2 41-49 (A42V, V49I) | KVSEKIFYI |
| | 149 | SSX-2 41-49 (A42L, V49I) | KLSEKIFYI |
| | 150 | SSX-2 41-49 (A42(D-Ala), V49(D-Val)) | K(D-Ala)SEKIFY(D-Val) |
| | 199 | SSX-2 41-49 (A42(D-Leu), V49(D-Val)) | K(D-Leu)SEKIFY(D-Val) |
| | 200 | SSX-2 41-49 (A42(D-Val), V49(D-Val)) | K(D-Val)SEKIFY(D-Val) |
| C-terminal Primary Anchor | 151 | SSX-2 41-49 (V49I) | KASEKIFYI |

TABLE 9-continued

| Catergory | SEQ ID Number | Peptide name | Sequence |
|---|---|---|---|
| C-terminal amide | 173 | SSX-2 41-49-NH2 | KASEKIFYV-NH2 |
| | 174 | SSX-2 41-49-NH2 (A42L) | KLSEKIFYV-NH2 |
| | 175 | SSX-2 41-49-NH2 (A42V) | KVSEKIFYV-NH2 |
| Decamers | 177 | SSX-2 41-50 | KASEKIFYVY |
| | 178 | SSX-2 41-50 (Y50I) | KASEKIFYVI |
| | 179 | SSX-2 41-50 (Y50L) | KASEKIFYVL |
| | 180 | SSX-2 41-50 (Y50V) | KASEKIFYVV |
| | 181 | SSX-2 41-50 (Y50(Nle)) | KASEKIFYV(Nle) |
| | 182 | SSX-2 41-50 (Y50(Nva)) | KASEKIFYV(Nva) |
| | 183 | SSX-2 41-50 (A42V,Y50I) | KVSEKIFYVI |
| | 184 | SSX-2 41-50 (A42L,Y50I) | KLSEKIFYVI |
| | 185 | SSX-2 41-50 (A42V,Y50L) | KVSEKIFYVL |
| | 186 | SSX-2 41-50 (A42L,Y50L) | KLSEKIFYVL |
| | 187 | SSX-2 41-50 (A42V,Y50V) | KVSEKIFYVV |
| | 188 | SSX-2 41-50 (A42L,Y50V) | KLSEKIFYVV |
| | 189 | SSX-2 41-50 (A42V,Y50(Nle)) | KVSEKIFYV(Nle) |
| | 190 | SSX-2 41-50 (A42L,Y50(Nle)) | KLSEKIFYV(Nle) |
| | 191 | SSX-2 41-50 (A42V,Y50(Nva)) | KVSEKIFYV(Nva) |
| | 192 | SSX-2 41-50 (A42L,Y50(Nva)) | KLSEKIFYV(Nva) |
| | 193 | SSX-2 41-50 (A42V,V49I,Y50I) | KVSEKIFYII |
| | 194 | SSX-2 41-50 (A42L,V49I,Y50I) | KLSEKIFYII |
| | 195 | SSX-2 41-50 (V49I,Y50I) | KASEKIFYII |

Abbreviations for non-standard amino acids are as follows: Nle, norleucine; Nva, norvaline; Phg, phenylglycine; Phe(4-F), 4-fluorophenylalanine; Phe(4-NO$_2$), 4-nitrophenylalanine; Abu, α-aminobutyric acid; Aib, α-aminoisobutyric acid; MeLeu, methyl-leucine; MeVal, methylvaline; β-(3-benzothienyl)Ala, β-(3-benzothienyl)-alanine; O-methyl-Tyr, O-methyltyorosine; Cha, cyclohexylalanine; Nal-1, β-(1-napthyl)-alanine; Nal-2, β-(2-napthyl)-alanine; —NH2 indicates that the carboxy terminus has been modified to the amide.

Examples 4-21

Testing of SSX-2$_{41-49}$ Analogs

The analogs produced in Example 3 were tested for activity, such as binding and biological effect as follows in Examples 4-21:

Example 4

Peptide Binding Using T2 Cells

The affinity of peptide analogs and the wild-type epitope to HLA-A*0201 was evaluated using a T2 cell based assay (Regner M, et al., *Exp Clin Immunogenet.* 1996; 13(1):30-5; which is hereby incorporated by reference in its entirety).

For the binding assay, in brief, T2 cells that lack expression of TAP and thus do not assemble stable MHC class I on the cell surface, were pulsed with different concentrations of peptides (controls or analogs) overnight at 37° C., washed extensively, stained with fluorescently tagged antibody recognizing MHC class I (A2 allele) and run through a FacsScan analyzer. The difference between the MFI (mean fluorescence intensity) corresponding to a given concentration of analog and the negative control (non-MHC binder) is a function of how many stabilized complexes between MHC and peptide are displayed on the surface of T2 cells. Thus, at limiting concentrations of peptide, it is a measurement of $K_{on}$ mostly and at saturation levels of peptide it is a measurement of both $K_{on}$ and $K_{off}$. The binding was quantified by two factors that are mathematically related: half maximal binding (the peptide concentration giving 50% of the signal corresponding to saturation) and relative affinity (1/RA). Relative affinity, RA, is binding normalized to a reference (wild-type peptide); for example, the ratio between half maximal binding of control relative to peptide analog. The higher the 1/RA index and the lower the half maximal binding, the higher the $K_{on}$ of the interaction between the analog and the MHC.

Fifty three analogs identified with these binding parameters were determined to be improved relative to the wild-type peptide. These improved binders carry one, two, three or multiple substitutions (including standard and/or non-standard amino acids) involving positions that are known to participate in the interaction with MHC and/or TCR. However, the overall effect on MHC binding was dependent on the modification. Such peptide analogs can be useful in therapeutic compositions or as a platform to further derive therapeutic compositions.

Example 5

Peptide Stability Using T2 Cells

Peptide stability ($K_{off}$) on MHC generally cannot be solely inferred from binding ($K_{on}$). In addition to binding, the stability of peptides on MHC class I is notoriously important with regard to the immunological properties of such peptides, as the activation of T cells depends on the duration of "signal 1" (MHC peptide complex interaction with T cell receptor). For the stability assay, in brief, T2 cells that lack expression of TAP, and thus do not assemble stable MHC class I on the cell surface, were pulsed with a concentration of peptide (controls or analogs) known to achieve maximal loading of MHC class I ("saturation") overnight at 37° C., washed extensively, and chased for different intervals in the presence of emetine, which blocks endogenous protein synthesis. After extensive washing, the cells were stained with fluorescently tagged antibody recognizing MHC class I (A2 allele) and run through a FacsScan analyzer. The difference between the MFI (mean fluorescence intensity) corresponding to a given concentration of analog and the negative control (non-MHC binder) is a function of how many stabilized complexes between MHC and peptide are displayed on the surface of T2 cells. The decay of the signal over time was mathematically expressed as stability index 50% relative to the binding at 0 hours (at the beginning of the chase interval).

Such improved analogs can carry one, two, three or multiple substitutions (including standard and/or non-standard amino acids) involving positions that are known to participate in the interaction with MHC and/or TCR, with an overall effect on MHC stability that is dependent on the modification. Such peptide analogs can be useful in therapeutic compositions or as a platform to further derive therapeutic compositions. Forty three of the analogs had increased stability relative to the natural peptide.

The analogs that showed both improved binding and stability are useful in improved compositions or as a platform to generate improved compositions of therapeutic benefit.

Example 6

Evaluation of Immunologic Properties of Analogs: Cross-Reactivity and Functional Avidity The immunologic properties of peptides can be described as a function of binding to MHC molecules ($K_{on}$ and $K_{off}$) and TCR (affinity of interaction between TCR and MHC-peptide complexes). Modifications of primary MHC anchor residues generally have a significant degree of predictability in regard to overall impact on binding to MHC molecules.

Modifications of secondary MHC anchor residues can impact the affinity of interaction of the MHC-peptide complex to TCR along with the $K_{on}$ and $K_{off}$ relative to peptide-MHC interaction.

A methodology was devised to allow rapid and rational screening of peptide analogs in a fashion coherent with proposed methods of use and modeling the overall immunologic properties ($K_{on}$ and $K_{off}$ relative to MHC interaction and TCR binding properties in an integrated fashion). In some instances, the method included generating T cell lines against a natural (non-mutated) epitope (SSX-$2_{41-49}$), and using an immunization strategy potent enough to generate a useful response in transgenic mice carrying human MHC (such as the A2 allele). Peptide analogs were interrogated ex vivo in the presence of competent APCs and the functional impact of T cells specific for natural (non-mutated) epitopes measured. The evaluation was done at various concentrations of analog, because the expected effect was biphasic in the case of cross reactive peptides (activating at limited concentrations and inhibiting at higher concentrations, due to antigen-induced cell death, AICD). Measurement of the following three parameters were used to define basic and useful characteristics of peptide analogs:

1. Minimal required concentration of peptide analog to trigger effects indicative of T cell activation (e.g. cytokine production);
2. Maximal (peak value) effect (e.g. cytokine production) at any analog concentration;
3. Analog concentration at peak value of activating effect (e.g., cytokine concentration)

For example, analogs that result in reduced values associated with parameters #1 and 3 but increased #2, can be useful. Use of natural epitope and unrelated non-cross reactive peptides as references is valuable in identifying classes of analogs of potential value. Analogs that display properties quantitatively comparable to or even modestly attenuated from those of natural epitopes are still deemed useful in light of the fact that while they retain cross-reactivity, they may display immunologic properties that are distinct from those of the natural peptide—for example, lower propensity to induce AICD or ability to break tolerance or restore responsiveness in vivo.

Some advantages of this screening strategy include the practicality and rapidity, use of more relevant polyclonal T cell lines instead of potentially biased T cell clones as a read out, and the composite value, integrating parameters such as $K_{on}$, $K_{off}$ and TCR affinity that can translate into cross-reactivity and functional avidity of peptide-MHC complexes relative to TCR. These parameters can be predictive of the in vivo immunologic properties and thus can delineate useful panels of peptide analogs to undergo further evaluation, optimization and practical applications. Analogs that bind to MHC and retain cross-reactivity against TCR specific for the nominal wild-type peptide are predicted to trigger a measurable effect in this assay. The overall methodology is presented in FIG. 2.

The method used for the generation of T cell lines was the following: HHD transgenic mice carrying an A2 human allele (Pascolo et al., *J Exp Med.* 185(12):2043-51, 1997, which is hereby incorporated herein by reference in its entirety) were immunized with 50 µg of SSX-2 natural epitope (41-49) admixed with 25 µg of pIpC at day 0, 4, 14 and 18 by bilateral administration into the inguinal lymph nodes. At 7 days after the last boost, the mice were sacrificed and a suspension of splenocytes prepared at $5 \times 10^6$ million cells/ml in complete HL-1 medium. Cells were incubated with different concentrations of peptide for 48 hours in flat-bottomed 96-well plates (2001 l/well) and for an additional 24 hours with rIL-2 at 10 U/ml added to the wells. The supernatant was harvested and the concentration of IFN-gamma assessed by standard methods such as ELISA.

Example 7

Cross-Reactivity and Functional Avidity of Analogs Substituted at Single Position The strategy from above (Example 6, FIG. 2) was applied to scan through a library of analogs bearing single substitutions relative to the natural SSX-$2_{41-49}$ epitope (KASEKI-FYV (SEQ ID NO. 1)) in its wild-type version (FIG. 3). Strong inverse correlation was found between the minimal required amount of analog to elicit IFN-gamma production ex vivo and the maximal amount of cytokine production at any concentration of analog.

Substitution of $A_{42}$ with L, V or M improved on the immunologic properties of the peptide assessed in this assay. L and V mutants were active. M was more active than the natural epitope. The I mutant retained cross-reactivity to the TCR recognizing the wild-type epitope.

Replacement of the A at position 42 with non-standard amino acids Abu, Nle or Nva improved on the immunologic properties of the peptide relative to the wild-type epitope, both in terms of the minimal amount of analog required to trigger cytokine production and the peak amount of cytokine produced. Mutants encompassing D-Ala, D-Val, Nal-2 or Aib display retained cross-reactivity and reduced immune activity in this assay relative to the natural peptide, but can still be useful for further derivitization to adjust or enhance their properties. An Nal-1 at position 42 abrogated the activity.

Changes of the first residue $K_{41}$ showed that, while replacement with F or Phg improved on the activity, W, D-Lys, and Cha obliterated the immunologic properties in this assay.

Replacement of K with Y, Phe-4F, Phe(4-NO2), O-methyl-Tyr or beta-(3-benzothienyl-Ala) retained activity.

Modification of position $V_{49}$ (C-terminal residue) by replacement with I retained the activity at a lower level compared to the original epitope. Modification of the last residue by addition of an NH2 moiety obliterated the activity of the peptide that was subsequently rescued by modifying the A at position 42 with L or V. This directly illustrates that analogs with activity that is lower than that of the wild-type peptide are still useful for further derivatization.

Example 8

Cross-Reactivity and Functional Avidity of Analogs Substituted at Two Positions

The strategy from Example 6 (FIG. 2) was applied to scan through a library of analogs bearing two substitutions, relative to the wild-type SSX-2$_{41-49}$ epitope in its wild-type version (FIG. 4).

Coordinated modifications at position 1 and 2 had a variable effect on the activity of analogs. For example, substitution of K41 with Y, F or W corroborated with substitution of A42 with V, M or I, and resulted in preserved or enhanced activity of the analogs relative to the wild-type peptide. Such doubly mutated peptides offer an increased opportunity to impact the interaction with TCR in a fashion that results in tolerance breaking (thus being useful for practical application), since the P1 residue participates to a certain extent in binding to TCR. Combinations between the following: Y (position 41) with V (at position 42), W (position 41) with I or L (at position 42), and F (position 41) with L, V, I (at position 42) resulted in analogs that were more active relative to the wild-type peptide. Combinations between Y at position 41 and I at position 42, or W at position 41 and V or M at 42, conferred an activity similar to that of wild-type peptide. Replacement of K with D-lysine at position 41 reduced resulted in analogs with retained activity in this assay. Such peptides can be very useful since the metabolic degradation of such peptides encompassing non-standard amino acids is decreased in vivo.

Combinations between V or L at position 42 and I at position 49 resulted in increased activity over the natural peptide.

Example 9

Cross-Reactivity and Functional Avidity of Analogs Substituted at Multiple Positions The strategy from Example 6 (FIG. 2) was applied to scan through a library of analogs bearing three or more substitutions relative to the natural SSX-2$_{41-49}$ epitope in its wild-type version (FIG. 5).

F and V at positions 41 and 42 respectively, combined with I or A at position 49 resulted in improved or similar activity relative to the wild-type epitope. In contrast, L or M at position 49 resulted in heavily diminished activity.

Triple mutants comprising the non-standard amino acids Nva, Abu or MeVal at the last position resulted in retention or improvement of immune activity. Such peptides are extremely useful due to increased in vivo stability and resistance to enzymatic degradation.

Modification of amino acid residues within the putative TCR binding region can result in peptides of considerable value that retain binding to MHC along with cross-reactivity. Such peptides are useful for restoration of immune responsiveness or tolerance breaking because their conformation in the MHC groove is slightly different from that of natural peptides. Additional substitutions at position 44 (Q, Nva or Nle), position 46 (L, V, Nle or Nva) or 48 (F or Phe-4F) resulted in active analogs, whereas D, N, S or T at position 44, M at 46 or T, S, Phg at position 48 or L at position 46 with T at 48 resulted in analogs devoid of activity. Finally, two analogs with 5 substitutions showed no activity (FIG. 5).

Example 10

Cross-Reactivity and Functional Avidity of Decamers Encompassing the Natural Peptide and Mutated at Various Positions The strategy from Example 6 (FIG. 2) was applied to scan through a library of analogs of a decamer encompassing the nominal SSX-2$_{41-49}$ peptide (FIG. 6).

The decamer SSX-2$_{41-50}$ was significantly less active in stimulating the T cell line specific for the 41-49 nonamer, relative to the latter. Modification of the Y residue at position 50 to I or L, but to a lesser or no extent to V, Nle or Nva, resulted in restoration of activity in this assay. Further optimization of the activity of decameric analogs was obtained by modification of the A at position 2 with L or V. The A42L substitution rescued the activity of the Y50Nva decamer. Peptide analogs of similar or reduced activity in vitro (but retained cross-reactivity) compared with the natural peptide are still useful for induction or boost of immune responses due to: i) more limited AICD; ii) potentially higher in vivo activity due to increased stability on class I MHC and/or slightly modified interaction with TCR which can be important for tolerance breaking.

Example 11

Figure 8:
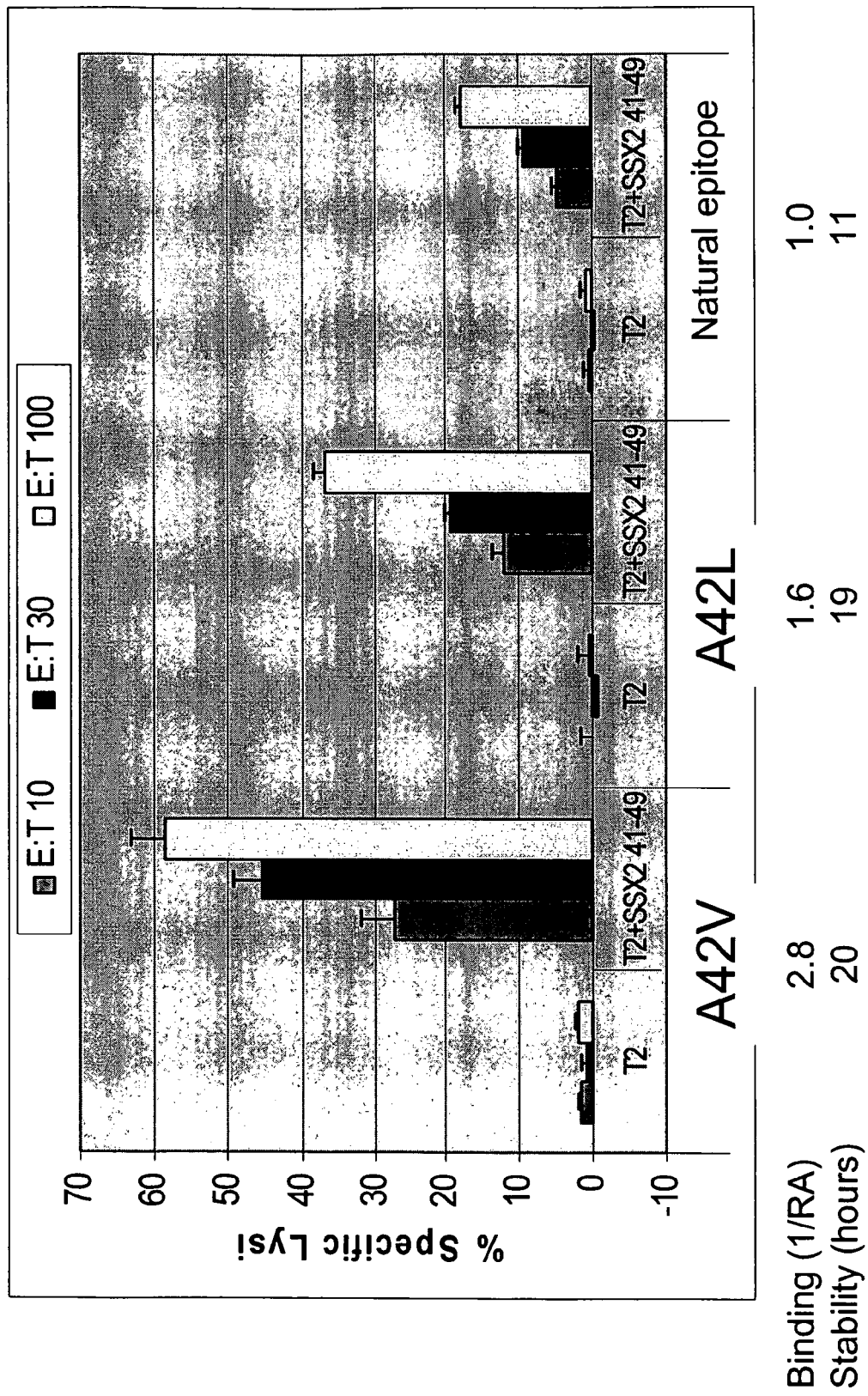

Use of Analogs to Trigger Enhanced Immunity Against Natural Epitope, Assessed Ex Vivo Three groups of mice (n=4) were immunized with a plasmid expressing SSX-2$_{41-49}$ natural epitope by direct inoculation into the inguinal lymph nodes with 25 µg in 25 µl of PBS/each lymph node at day 0, 3, 14 and 17. This was followed by two additional peptide boosts (similar amount) at day 28 and 31. The schedule of immunization is shown in FIG. 7. One week after the boost, splenocytes were stimulated ex vivo with SSX-2$_{41-49}$ natural peptide and tested against $^{51}$Cr-labeled target cells (T2 cells) at various E:T ratios (FIG. 8). The results showed that the analog A42V triggered a higher response against target cells expressing the natural peptide, compared to the analog A42L or the wild-type peptide itself, as boost agents. This correlated with the binding and stability parameters determined by ex vivo experimentation.

Example 12

Figure 9:
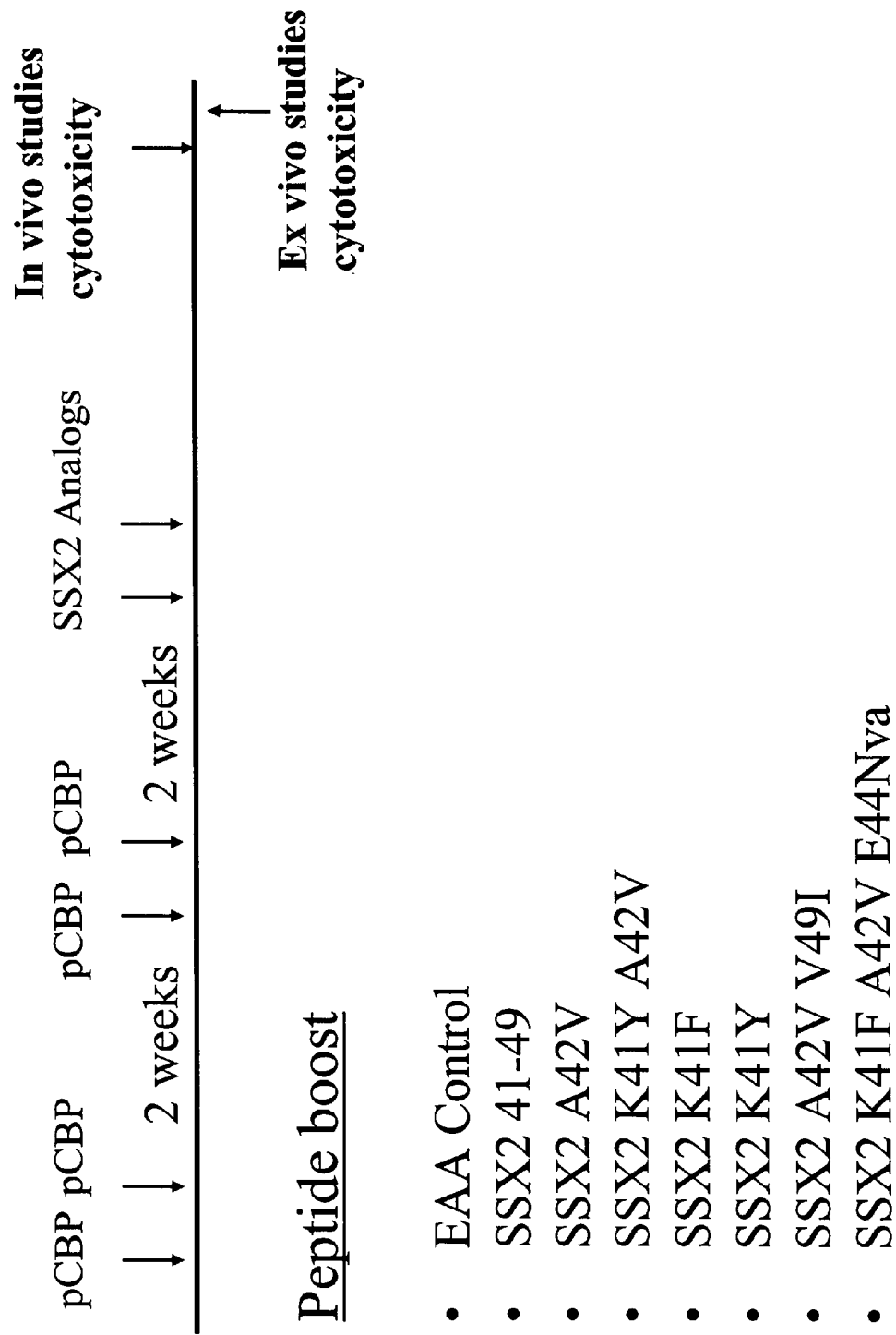

Use of Analogs to Trigger Enhanced Immunity Against Natural Epitope, Assessed In Vivo Eight groups of mice (n=4) were immunized with plasmid expressing SSX-2$_{41-49}$ natural epitope, by direct inoculation into the inguinal lymph nodes with 25 µg in 25 µl of PBS/each lymph node at day 0, 3, 14 and 17. This was followed by two additional peptide boosts (similar amount) at day 28 and 31, using a negative control peptide (Melan A 26-35 "EAA"), natural peptide or analogs as shown in FIG. 9.

To evaluate the in vivo response against natural peptide, splenocytes were isolated from littermate control HHD mice and incubated with 20 μg/mL or 1 μg/ml of natural peptide for 2 hours. These cells were then stained with CFSE$^{hi}$ fluorescence (4.0 μM or 11 M for 15 minutes) and intravenously co-injected into immunized mice with an equal number of control splenocytes stained with CFSE$^{lo}$ fluorescence (0.4 μM). Eighteen hours later the specific elimination of target cells was measured by removing spleen and PBMC from challenged animals and measuring CFSE fluorescence by flow cytometry. The relative depletion of the populations corresponding to peptide loaded splenocytes was calculated relative to the control (unloaded) population and expressed as % specific lysis. FIG. 10 (spleen) and 11 (blood) show the in vivo cytotoxicity elicited by the regimens described in FIG. 7. Three of the tested peptides, A42V, K41F and K41Y, showed increased activity relative to the natural peptide, both in spleen and blood, against target cells coated with 20 μg/ml as well as 1 μg/ml of natural peptide (FIG. 11).

Example 13

Use of Analogs to Trigger Enhanced Responses Against Tumor Cells

Eight groups of mice (n=4) were immunized with plasmid expressing SSX-2$_{41-49}$ natural epitope by direct inoculation into the inguinal lymph nodes with 25 ug in 25 ul of PBS/each lymph node at day 0, 3, 14 and 17. This was followed by two additional peptide boosts (similar amount) at day 28 and 31, using a negative control peptide (Melan A 26-35 "EAA"), natural peptide or analogs as shown in FIG. 9.

Figure 12:
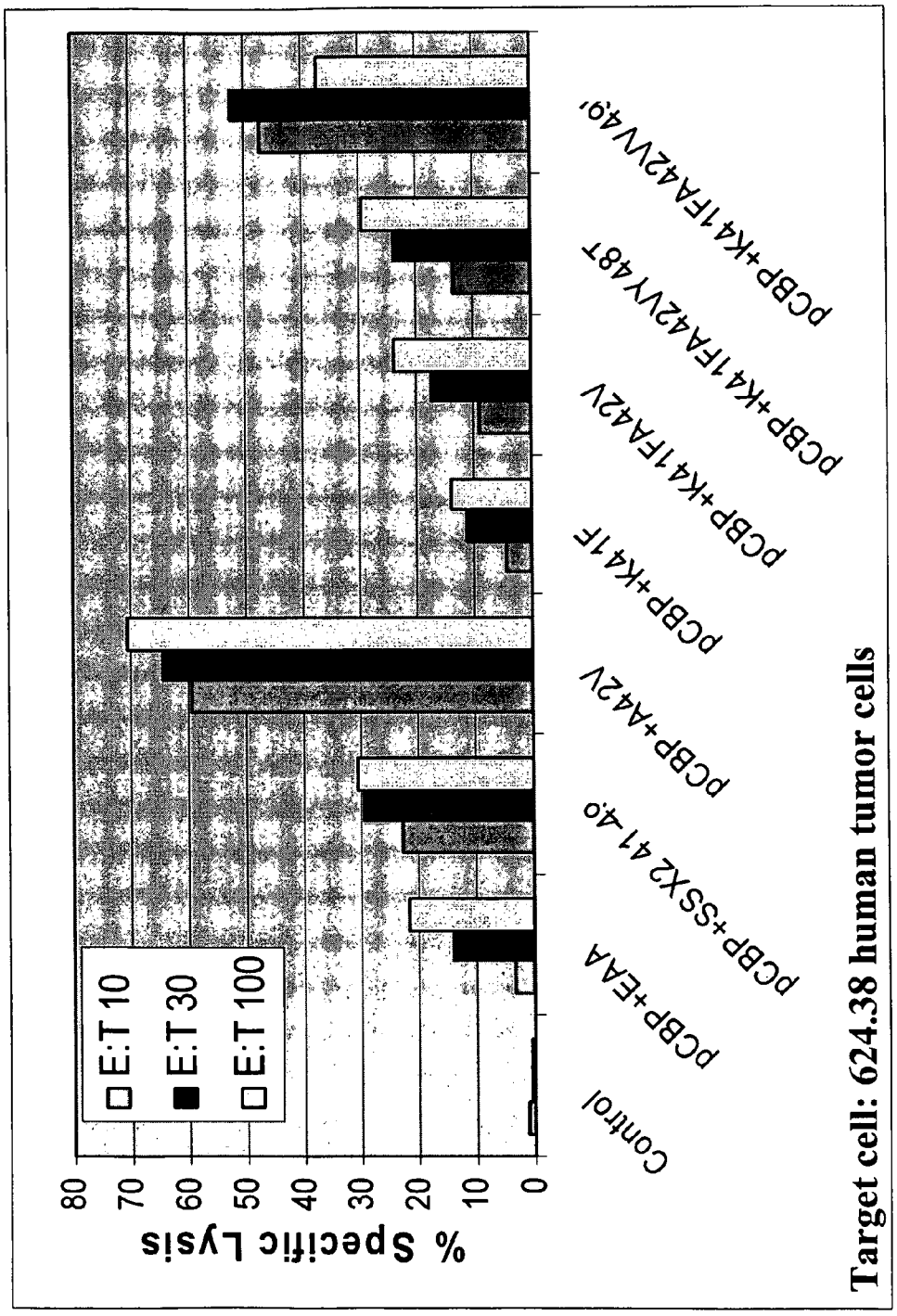
Figure 15A:
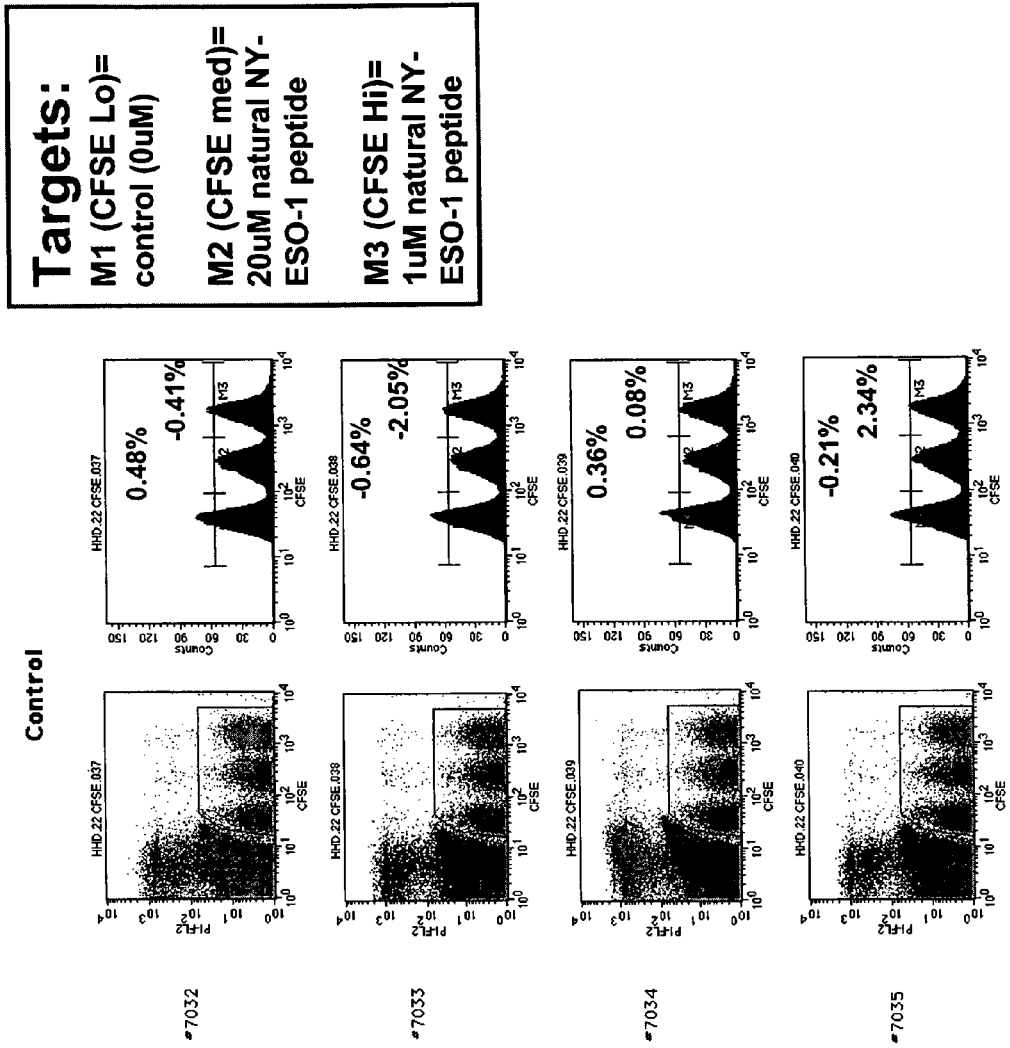
Figure 15B:
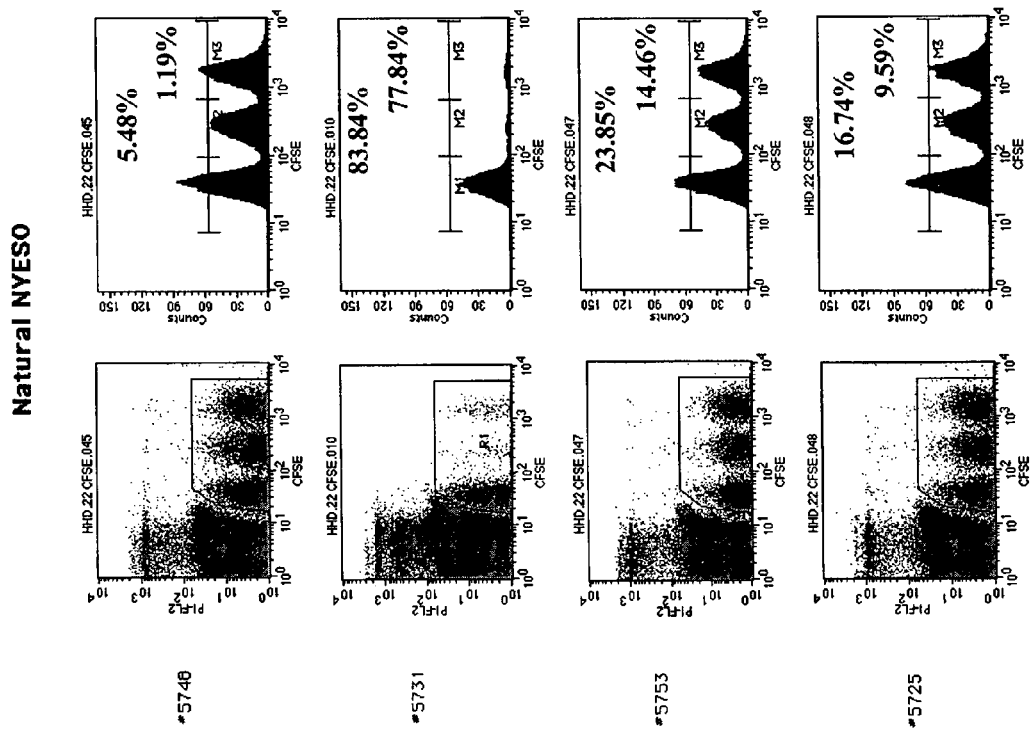
Figure 17A:
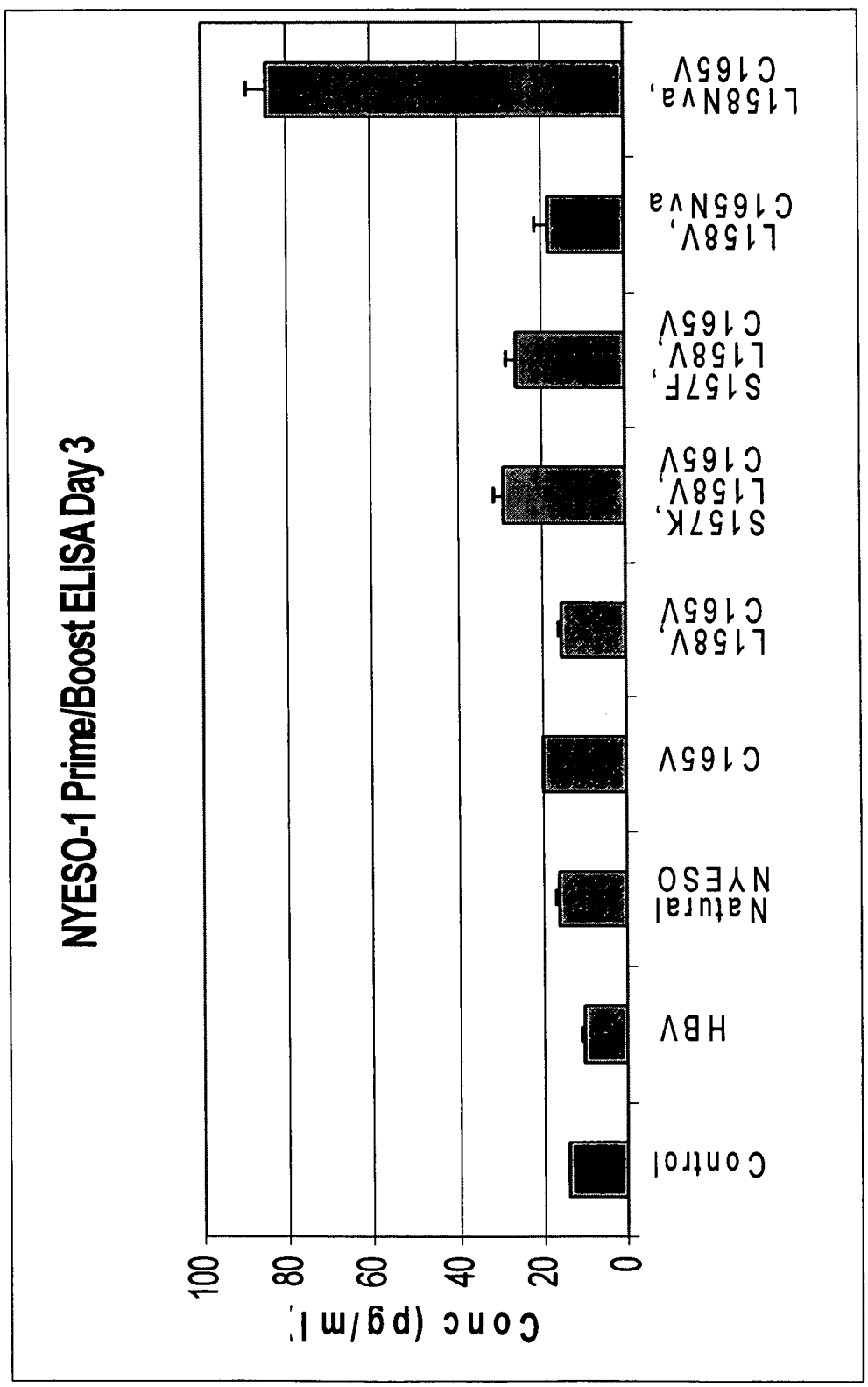
Figure 17B:
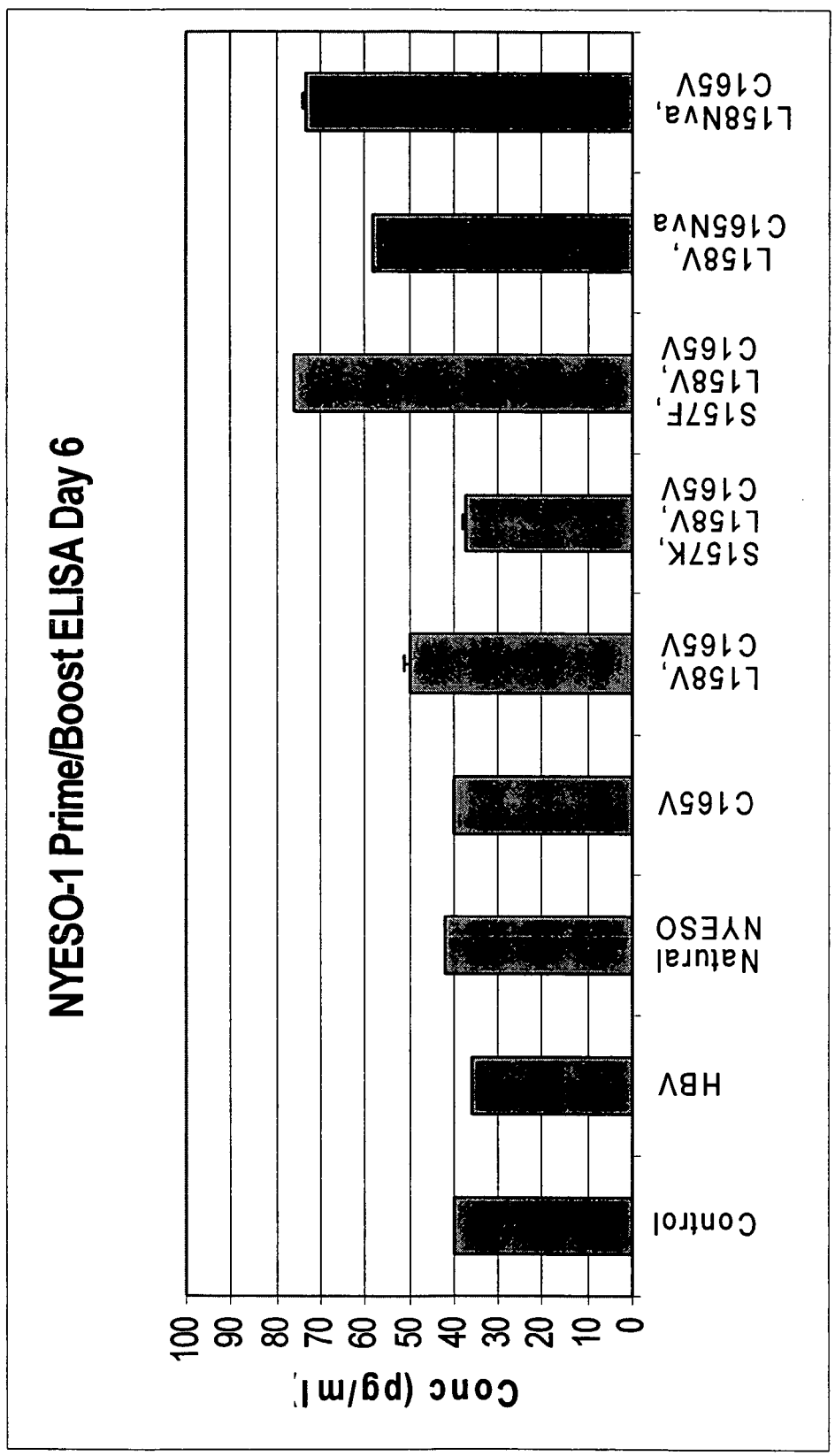

One week after the boost, splenocytes were stimulated ex vivo with SSX-2$_{41-49}$ wild-type peptide and tested against $^{51}$Cr-labeled human tumor cells (624.38 melanoma cells) at various E:T ratios (FIG. 12). Analogs A42V and K41F A42V V49I elicited immune responses that mediated increased cytotoxicity against human tumor cells expressing the natural SSX-2$_{41-49}$ epitope.

Example 14

N-Terminal Proximal Primary Anchor Modification(2$^{nd}$ AA)

When the substituted analogs shown in Table 3 were tested, the analogs showed improved binding and stability profiles in comparison with the wild-type peptide epitope. However, the magnitude of improvement for each analog varied, and the substitution of A42V showed the highest improvement in terms of binding affinity with HLA-A*0201 molecule. Further, the stability of the A42V-HLA-A*0201 complex was better than the complex formed between wild-type peptide and HLA-A*0201: the T1/2 extended from 11.5 hrs to 20 hrs. The peptides with 42 A to L, V and M substitutions were able to induce the IFN-γ secretion of wild-type peptide specific CTL at remarkably lower concentrations. The 42A to I substitution generated an analog with improved binding and stability profile. The residue at the P2 position can also be engaged in the interaction with TCR to a certain degree. This observation was also supported by the results with the 42 A to Aib analog, which possessed a similar binding affinity with HLA-A*0201 relative to the wild-type epitope.

Example 15

N-Terminal Secondary Anchor Modification (1$^{ST}$ AA)

The N-terminal secondary anchor is the first amino acid at the N-terminus. Thus, in one embodiment, the original Lys 43 found in the wild-type sequence is substituted with a more hydrophobic and bulky amino acid. Any more hydrophobic and bulky amino acid also can be used, including any available to or that is known to one of skill in the art, including standard amino acids and non-standard amino acids. Examples of more hydrophobic amino acids include, but are not limited to: Phe, Tyr, Trp, and D-Lys.

The residue of Lys 41 was defined as a secondary anchor residue in interacting with HLA-A*0201 molecule, and it also engaged in the interaction with the T cell receptors to a certain degree. Therefore, modifications of this position can generate some heteroclitic analogs that are more immunogenic and more suitable for the development of tumor vaccines.

As shown in Table 3, replacing Lys 41 with Tyr, Phe or Phe derivatives (Phenylglycine, Para-fluorophenylalanine, Para-nitrophenylalanine) resulted in analogs that have higher affinity with the HLA-A*0201 molecule and form more stable complexes. On the other hand, the Lys to Trp or Trp derivatives analogs have shown significantly decreased affinity with the HLA-A*0201 molecule, although based on the predicted algorithms, the Trp analog should have a similar affinity to that of the Tyr and Phe analogs. The experimental data demonstrate the limitation of the predicted algorithms. For examples: Lys 41 to Phg substitution resulted in an analog with improved affinity and extended stability with the HLA-A*0201 molecule. The para-nitrophenylalanine analog was shown to induce the IFN-γ secretion of the wild-type peptide specific CTL at a much lower concentration, although its affinity with the HLA-A*0201 molecule was about the same as that of wild-type peptide.

Example 16

N-Terminal Primary/Secondary Anchor Modification

When both primary and secondary anchor residues at the N-terminal were modified, a general trend was that resulting analogs demonstrated improved affinity and extended stability with the HLA-A*0201 molecule (Table 3), with only a few exceptions: (K41 Y, A42V), (K41 Y, A42M) and (K41(D-Lys), A42V). Additionally, they had very good cross-reactivity with the wild-type peptide specific CTL. Combining the K41 W substitution with A42V or A42L improved the binding/stability profile. These analogs also had desirable cross-reactivity activity with the wild-type peptide. The combination modifications of N-terminal primary anchor and secondary anchor changed the peptide structure and conformation to a greater degree.

Example 17

N-Terminal Primary/Secondary Anchor and C-Terminal Primary Modification

The C-terminal Val of the wild-type peptide was a preferred anchor residue. However, improved potency was observed when it was mutated to Ile, having one additional —CH2 group. Similar improvement was also observed with a Val to Abu substitution. The other analogs showed improved binding affinity and stability with the MHC molecule. The results of these analogs indicated that the peptide C-terminal anchor residue also plays a critical role in the recognition of T cells. (Table 4).

Example 18

N-Terminal Primary/Secondary Anchor and TCR Sites Modification

Substitutions of secondary TCR binding amino acid residues generated heteroclitic analogs that did not interfere with the binding to the MHC molecule, but overcame the tolerance issues of self-antigens. By combining the substitutions of N-terminal primary/secondary anchor residues (K41 F and A42V) and the TCR sites, analogs were generated with improved binding affinity and stability (Table 6). Some of these analogs induced the IFN-γ production of the wild-type peptide specific CTL at lower concentrations, such as K41F, A42V, E44(Nva)/(Nle) mutants and K41F, A42V, 146L/(Nva)/(Nle) mutants.

Example 19

N-Terminal Amide

Replacing the peptide's free carboxylic acid C-terminus with an amide improved the peptide's stability in biological media by conferring stability to proteolysis and conferred dipeptidyl carboxypeptidase resistance to the peptide. However, some of the resultant analogs lost a significant amount of their affinity with MHC molecules, as well as immunogenicity and antigenicity. Unexpectedly, although the three analogs disclosed herein at Table 7 lost their binding capability with MHC molecule, SSX-2$_{41-49}$-NH2 (A42V) retained its reactivity with wild-type peptide specific CTLs as indicated by its capability of inducing the secretion of IFN-γ at a similar concentration to that of the wild-type peptide. SSX-2$_{41-49}$—NH2 (A42L) was, however, able to stimulate the IFN-γ production at a lower concentration.

Example 20

Decamers

The length of typical MHC binding peptides varies from 8-mer to 11-mer, and most HLA-A*0201 binding peptides are 9-mers or 10-mers. In previous observations, a 9-mer and 10-mer from a natural sequence were both found to possess a binding motif for the same MHC, and had the same N-terminus. From the standpoint of proteasomal processing they are distinct epitopes, but were nonetheless antigenically cross-reactive. In the case of the wild-type epitope SSX-2$_{41-49}$, the epitope is a 9-mer peptide and the 10-mer peptide, SSX-2$_{41-50}$, lacks the appropriate MHC binding motif and showed no immunological activity. The wild-type epitope was therefore lengthened to a 10-mer with amino acids that could create the appropriate binding motif. As shown in Table 8, while many 10-mer analogs have a lower binding affinity with the HLA-A*0201 molecule, analogs SSX-2$_{41-50}$ (A42L, Y50L/V/Nle/Nva) showed improved binding affinity with the HLA-A*0201 molecule. Two 10-mer analogs in particular, A42L and Y50 Nle/Nva, were able to induce IFN-γ production from T cells immunized against the wild-type peptide at lower concentrations than the wild-type peptide.

Example 21

Use of Analogs to Overcome Tolerization

One aspect in which the analogs can represent an improvement over the wild-type epitope is in increased immunogenicity in a human system and tolerance breaking. Differences in the TCR repertoire, whether due to germ line differences or differences in negative selection, have the potential to give anomalous results. To address such issues, the analogs were used in an in vitro immunization of HLA-A2$^+$ blood to generate CTL. Techniques for in vitro immunization, even using naive donors, are known in the field, for example, Stauss et al., *Proc. Natl. Acad. Sci. USA* 89:7871-7875, 1992; Salgaller et al., *Cancer Res.* 55:4972-4979, 1995; Tsai et al., *J. Immunol.* 158:1796-1802, 1997; and Chung et al., *J. Immunother.* 22:279-287, 1999; each of which is hereby incorporated by reference in their entirety.

Specifically, PBMCs from normal donors were purified by centrifugation in Ficoll-Hypaque from buffy coats. All cultures were carried out using autologous plasma (AP) to avoid exposure to potential xenogeneic pathogens and recognition of FBS peptides. To favor the in vitro generation of peptide-specific CTL, autologous dendritic cells (DCs) were employed as APCs. DCs were generated and the CTLs were induced with DCs and peptides from PBMCs as described in Keogh et al., 2001, which is incorporated herein by reference in its entirety. Briefly, monocyte-enriched cell fractions were cultured for 5 days with GM-CSF and IL-4 and were cultured for 2 additional days in culture media with 2 μg/ml CD40 ligand to induce maturation. $2 \times 10^6$ CD8+-enriched T lymphocytes/well and $2 \times 10^5$ peptide-pulsed DCs/well were co-cultured in 24-well plates in 2 ml RPMI supplemented with 10% AP, 10 ng/ml IL-7 and 20 IU/ml IL-2. Cultures were restimulated on days 7 and 14 with autologous irradiated peptide-pulsed DCs. Immunogenicity was assayed using the in vitro cytotoxicity and cytokine production assays described herein.

Examples 22-30

Testing of Ny-Eso-1$_{157-165}$ Analogs

The analogs listed in FIG. 13 were tested for activity, such as binding and biological effect as follows in Examples 22-30:

Example 22

Cross-Reactivity and Functional Avidity of Analogs Substituted at a Single Position (FIGS. 13 A-C)

The strategy from above (Example 6) was applied to scan through a library of analogs bearing single substitutions relative to the wild-type NY-ESO-1$_{157-165}$ epitope in its native (or wild-type) version (FIG. 13). A strong inverse correlation was found between the minimal required amount of analog to elicit IFN-gamma production ex vivo and the maximal amount of cytokine production at any concentration of analog.

Substitution of S157 with F or K resulted in analogs that partially retained MHC binding and cross-reactivity with the T cells specific for the nominal epitope. Substitution of L158 with I improved the immunologic features of the peptide as assessed by this methodology; whereas L158V resulted in partial retention of activity. Modification of C165 with any of the amino acids V, L, A, or I resulted in improved immune properties.

Peptides that have substitutions in the N-terminal position or elsewhere, and present with retained but not increased activity in this assay relative to the wild-type peptide, can be useful in humans. In addition, they are material for further derivatization to improve on their properties, as described below.

Example 23

Cross-Reactivity and Functional Avidity of Analogs Substituted at Two Positions (FIG. 13A-C)

The strategy from Example 6 was applied to scan through a library of analogs bearing two substitutions relative to the wild-type NY-ESO-$1_{157-165}$ epitope. Simultaneous semi-conservative modifications at position 2 and 9 were found to have profound effects on the immune properties of analogs, depending on the precise identity of the analogs. Combining L158I with C165V or C165L further increased activity relative to the wild-type peptide. Similarly, L158V improved on the activity of the C165V or C165L analogs, further increasing such activity relative to wild-type peptide. L158V partially retained the activity of C165A or C165I analogs, showing an interesting effect of double mutation of primary anchor residues. Similarly, L158I partially retained the activity of the C165A analog.

Simultaneous modifications at positions 1 and 9 had profound effects on the immune properties of analogs, depending on the precise identity of the analogs. S157Y combined with C165Nva (norvaline) or Nle (norleucine) at position 9 resulted in substantially improved activity over S157Y alone or the wild-type peptide. The C165V mutant also rescued the activity of the S157Y mutant. V—NH2 or L-NH2 at position 9 partially rescued the activity of the S157Y analog, however, A-NH2 failed to do so. Combinations between S157F and V, L, I, and to a lesser extent A at the $9^{th}$ position retained strong activity of the analog and may be more useful than single mutants at position 9 due to the participation of the first residue in the interaction with TCR. Combinations between S157K and V, L, I and to a lesser extent A at the $9^{th}$ position, retained strong activity of the analog and may be more useful than single mutants at position 9 due to the participation of the first residue in the interaction with TCR and the overall beneficial effect on the peptide solubility of K at position 1.

Example 24

Cross-Reactivity and Functional Avidity of Analogs Substituted at multiple positions (FIG. 13A-C)

The strategy from Example 6 was applied to scan through a library of analogs bearing multiple substitutions relative to the wild-type NY-ESO-1 epitope.

L158Nva or L158Nle considerably improved on the activity of the S157Y C165V mutant. Combinations between V or I at position 158 and V, L, A or I at 165 partially restored the potency of analogs relative to the wild-type peptide. S157Y L158I C165V displayed increased activity relative to the wild-type peptide and S157V with C165V or C165I; and S157I with C165L or I retained MHC binding and cross-reactivity with T cells specific for the wild-type peptide.

Triple substitutions comprising Y and V at positions 157 and 165, respectively, in addition to L or N at 160; A, L, V, or N at 162; or E, D or T at 164, retained the activity of the peptide in this cross-reactivity assay, making these analogs useful compounds for breaking T cell tolerance in vivo as positions 160, 162 and 164 participate in the interaction with TCR.

Triple substitutions comprising 157F and 158V plus V, L, or I at the position 165 showed activity in the assay described in Example 2. In addition, triple mutants encompassing S157F and L158I plus V or A at position 165 retained activity. Together, these data underline the complex interactive and non-linear nature of multiple substitutions.

Finally, triple mutants comprising S157W and to a higher extent S157T together with 158V and 165V, showed retained or increased activity, respectively, relative to the wild-type peptide.

Example 25

Cross-Reactivity and Functional Avidity of Decamers Encompassing the Wild-Type Peptide and Mutated at Various Positions (FIG. 13A-C)

The strategy from Example 6 was applied to scan through a library of analogs of a decamer encompassing the nominal NY-ESO-$1_{157-165}$ peptide. While the decamer itself lacked significant in vitro activity, various substitutions at this position partially rescued activity, such as L at 166, or L, I, Nle at 166 combined with Y at 157 and V at 165.

Peptide analogs with similar or reduced activity in vitro (but with retained cross-reactivity) compared to the wild-type peptide are still useful for induction or boost of immune responses due to: i) more limited AICD (antigen-induced cell death); ii) higher in vivo activity due to increased stability on class I MHC and/or slightly modified interaction with TCR. Thus, these analogs are useful for breaking tolerance.

Example 26

Evaluation of Immunologic Properties of Analogs: Peptide Binding to MHC Class I Molecules (FIG. 13A-C)

The affinity of peptide analogs and the wild-type epitope to HLA-A*0201 was evaluated by T2 cell based assay (Regner M, et al., *Exp Clin Immunogenet*. 1996; 13(1):30-5, which is incorporated herein by reference in its entirety). For the binding assay, in brief, T2 cells that lack expression of TAP, and thus do not assemble stable MHC class I on the cell surface, were pulsed with different concentrations of peptides (controls or analogs) overnight at 37° C., washed extensively, stained with fluorescently tagged antibody recognizing MHC class I (A2 allele), and run through a FacsScan analyzer. Peptides that bind A2 stabilize its presence at the cell surface. The difference between the MFI (mean fluorescence intensity) corresponding to a given concentration of analog and the negative control (a non-MHC binding peptide) is a function of how many stabilized complexes between MHC and peptide are displayed on the surface of T2 cells. Thus, at limiting concentrations of peptide, this is a measurement of $K_{on}$ mostly and at saturation levels of peptide that is a measurement of both $K_{on}$ and $K_{off}$.

In FIG. 13, the binding is quantified by two factors that are mathematically related: Half maximal binding (the peptide concentration giving 50% of the signal corresponding to saturation) and relative affinity (1/RA), that is binding normalized to a reference (wild-type peptide)—i.e., the ratio between half maximal binding of control relative to peptide analog. The higher the 1/RA index and the lower the half maximal binding, the higher the $K_{on}$ of the interaction between an analog and the MHC molecules. In FIG. 13, there are 39 analogs described with such binding parameters improved relative to the wild-type peptide. Such improved binders carry one, two, three, or more substitutions of standard and/or non-standard amino acids at positions that are known to participate in the interaction with MHC and/or TCR, with an overall effect on MHC binding that is dependent on precise/conjugated modification. Such peptide analogs are useful in therapeutic compositions or as a platform to further derive therapeutic compositions.

Example 27

Method of Immunization (FIG. 14)

Eight groups of mice (n=4) were immunized with a plasmid expressing the wild-type NY-ESO-$1_{157-165}$ epitope by direct inoculation into the inguinal lymph nodes with 25 μg in 25 μl of PBS into each lymph node at days 0, 3, 14 and 17. This was followed by two peptide boosts (similar amount) at day 28 and 31, using a negative control peptide (HBVc), wild-type peptide or analog as shown in FIG. 14.

Example 28

Use of Analogs to Trigger Enhanced Immunity Against Wild-Type Epitope, Assessed In Vivo (FIGS. 15A-C)

To evaluate the in vivo responses obtained against the wild-type epitope, splenocytes were isolated from littermate control HHD mice and incubated with 20 μg/mL or 1 μg/ml of wild-type peptide for 2 hours. These cells were then stained with $CFSE^{hi}$ and $CFSE^{med}$ fluorescence (4.0 μM or 1 μM, respectively, for 15 minutes) and intravenously co-injected into immunized mice with an equal number of control splenocytes stained with $CFSE^{lo}$ fluorescence (0.4 μM). Eighteen hours later the specific elimination of target cells was measured by removing the spleens and PBMC from challenged animals and measuring CFSE fluorescence by flow cytometry. The relative depletion of the populations corresponding to peptide loaded splenocytes was calculated relative to the control (unloaded) population and expressed as % specific lysis. FIG. 15A shows the lack of in vivo cytotoxicity in mice receiving the negative control peptide. FIG. 15B shows the variable cytotoxicity in mice immunized with plasmid and amplified with wild-type peptide. FIG. 15C shows the substantial, constant cytotoxicity in mice immunized with plasmid and amplified with the analog L158Nva C165V.

Example 29

Comparison of Various Analogs in Triggering Enhanced Immunity Against the Wild-Type Epitope, Assessed In Vivo (FIGS. 16A-B)

In the context of the immunization protocol described in Example 8 and using the methodology described in the Example 9, in vivo cytotoxicity against target cells coated with limited (1 μM; FIG. 16A) or supraoptimal amounts of wild-type peptide (20 μM, FIG. 16B) was evaluated subsequent to the entrain and amplify protocol using plasmid and peptide analog respectively for the two stages. Results expressed as average % specific lysis +/− SE showed that the analog L158V C165Nva induced the highest activity and that the analogs L158V C165V, L158V C165Nva and S157K L158V C165V showed an effect in the same range with wild-type peptide or the C165V mutant. Because multiple substitutions can alter the TCR binding site, such analogs can be more useful than the wild-type peptide in breaking tolerance against a self epitope. In addition, the S157K triple mutant can ameliorate the poor solubility of the wild-type peptide or other analogs with direct practical implications.

Example 30

Use of Analogs to Trigger Enhanced Immunity Against the Wild-Type Epitope, Assessed Ex Vivo by Cytokine Production (FIGS. 17A-B)

In the context of the immunization protocol described in Example 27, and following the challenge described in Example 28, splenocytes were isolated, pooled and stimulated in vitro with 10 μM of wild-type peptide NY-ESO-$1_{157-165}$ for 3 and 6 days, respectively. Supernatants were harvested and the concentration of IFN-γ measured by ELISA.

Analog L158Nva C165V induced T cells that produced large levels of IFN-gamma more rapidly upon ex vivo stimulation (FIG. 17A). Other analogs such as S157F L158V C165V, L158V C165Nva, and L158V C165V induced T cells that produced increased amounts of IFN-gamma upon ex vivo re-stimulation with wild-type peptide (FIG. 17B). In contrast, C165V failed to induce increased capability of T cells to produce IFN-γ, relative to the wild-type peptide following the protocols described in Examples 27-28.

Example 31

Characterization of Binding and Stability by ELISA (Itopia Testing)

Avidin-coated microtiter plates containing class I monomer loaded with a so-called placeholder peptide were used to evaluate peptide binding, affinity and off-rate. The monomer-coated plates were supplied as part of the iTopia Epitope Discovery System Kit (Beckman Coulter, Inc., San Diego, Calif., USA). Assay buffers, anti-MHC-FITC mAb and beta2-microglobulin and control peptides were also supplied with the kits.

Binding Assay:

Native peptide and analogs were first evaluated for their ability to bind each MHC molecule by binding assay. This assay measures the ability of individual peptides to bind HLA molecules under standardized optimal binding conditions. Monomer-coated plates were first stripped, releasing the placeholder peptide and leaving only the MHC heavy chain bound to the plate. Test peptides were then introduced under optimal folding conditions, along with the anti-MHC-FITC mAb. Plates were incubated for 18 hours at 21° C. The anti-MHC-FITC mAb binds preferentially to a refolded MHC complex. Therefore, the fluorescence intensity resulting from each peptide was related to the peptide's ability to form complex with MHC molecule. Each peptide's binding was evaluated relative to the positive control peptide provided in the kit, and the results were expressed "% binding". The analogs identified as 'better-binders' relative to the native peptide were subsequently analyzed in the affinity and off-rate assays.

Affinity Assay:

For the affinity assay, after the initial stripping of the placeholder peptide, increasing concentrations (range $10^{-4}$ to $10^{-8}$ M) of each test peptides for a given allele were added to a series of wells and incubated under the conditions described previously. Plates were read on the fluorometer. Sigmoidal dose response curves were generated using Prism software.

The amount of peptide required to achieve 50% of the maximum was recorded as $ED_{50}$ value.

Off-Rate Assay:

For the off-rate assay, the plates were washed after 18 hrs incubation at 21° C. to remove excess peptide. The plates were then incubated on the allele-specific monomer plates at 37° C. The plates were measured at multiple time points (0, 0.5, 1, 1.5, 2, 4, 6 and 8 hrs) for relative fluorescence intensity. The time required for 50% of the peptide to dissociate from the MHC monomer is defined as the T1/2 value (hrs).

iScore Calculation:

The iScore is a multi-parameter calculation provided within the iTopia software. Its value was calculated based on the binding, affinity and stability data.

Example 32

Validation of the Antigenicity of $PSMA_{288-297}$

HHD transgenic mice (n=4) were immunized with $PSMA_{288-297}$ peptide (25 μg in 25 μl of PBS, plus 12.5 μg of pI:C to each lymph node) at day 0, 3, 14 and 17. One week after the boost, splenocytes were stimulated ex vivo with the native $PSMA_{288-297}$ peptide and tested against $^{51}$Cr-labeled human tumor cells ($PSMA^+$ $A2^+$ LnCap cells, or as negative control, LnCap cells coated with MHC class I-blocking antibody) at various E:T ratios. The results, expressed as % specific lysis (mean±SEM), showed that PSMA-specific T cells were able to lyse human tumor cells in a fashion dependent on MHC class I availability, confirming display of the PSMA epitope on MHC class I of tumor cells in a fashion allowing immune mediated attack (FIG. 18).

Examples 33-38

Testing of $PSMA_{288-297}$ Analogs

The analogs listed in FIGS. 19 and 20 were tested for various properties such as improved affinity and stability of binding, cross-reactivity with the native epitope, and immunogenicity as follows in Examples 33-38.

Example 33

Cross-Reactivity and Functional Avidity of Analogs Substituted at Single Position Using the procedures described in Example 31, the binding characteristics of $PSMA_{288-297}$ and analogs were assessed in comparison to each other (see FIG. 19). The positive control for binding was melan-$A_{26-35}$ A27L. Cross reactivity with the native epitope was assessed by using the analog peptides to stimulate IFN-gamma secretion from a T cell line specific for the native epitope, essentially as described in Example 6. The data shown in FIG. 19 was generated by stimulating with 10 μg/ml of analog (approximately 10 μM). This concentration generally resulted in maximal or near-maximal IFN-gamma production for the analogs and thus was chosen to represent cross-reactivity.

The observed affinities of the analogs are reported in FIG. 19 as $ED_{50}$s. Met, Ile, Gln, Val, Nva, Nle, and Abu were substituted at the P2 position, and generally resulted in similar affinity. The Nle and Met substitutions also maintained similar stability of binding, measured as half-time of dissociation in hours. The Val, Nva, and Abu analogs elicited a similar level of IFN-gamma production.

Val, Leu, Nva, and Nle were substituted for the Ile at the PΩ primary anchor position. All four had similar binding affinity. The Val and Nva substitutions improved the stability of binding and increased the amount of IFN-gamma produced, indicating cross-reactivity and that the analogs can have improved immunogenicity.

The Ser, Ala, Sar, and Abu substitutions at P1 maintained similar binding characteristics but had marginally similar cross-reactivity. The Ala, Leu, Ser, and Thr substitutions at the PΩ-1 position also maintained similar binding characteristics. Finally, the Trp substitution at P3 exhibited affinity and stability of binding that were both increased about twofold and IFN-gamma production that was within twofold of the native peptide, all generally similar values.

Example 34

Cross-Reactivity and Functional Avidity of Analogs Substituted at Two Positions

The pattern seen above, that substitutions in this epitope did not greatly impair binding affinity, continued with the double substitutions examined (FIG. 20) which uniformly displayed similar or improved binding affinity compared to the native peptide. Among the analogs with substitutions at both primary anchor positions, those with Nva of Nle at P2 and Val at PΩ, and Val at P2 and Nva at PΩ displayed improved binding stability and the former two increased IFN-gamma production (data not shown for the $3^{rd}$ analog). The Val and Nva substitutions at PΩ were also paired with Ala and Abu substitutions at P1. These analogs all had robust binding stability and IFN-gamma production that was improved compared to the single PΩ substitutions, thus further improving the P1 substitutions. The PΩ Nva substitution was also able to maintain better cross-reactivity than PΩ V when combined with the P3 Trp substitution, although the various binding parameters were generally similar.

Example 35

Cross-Reactivity and Functional Avidity of Analogs Substituted at Three Positions Triple substitutions at P1, P2, and P3; P1, P2, and PQ; P2, P3, and PΩ; and P1, P3, and PΩ were made (FIG. 21). In all cases, the P1 substitution was Ala, the P3 substitution was Trp, and the PΩ substitution Val or Nva. As above, affinity at least similar to the native peptide was maintained. For the P1, P2, P3 class Nva and Nle at P2 improved the stability of binding. This P2 Nva analog elicited a similar amount of IFN-gamma while the Nle analog showed a substantial increase.

For the P1, P2, PΩ class, Nva and Val at P2 and PΩ in either combination improved binding stability. This P2 Nva PΩ Val analog also showed a substantial increase in IFN-gamma production. (Data not shown). Val at both P2 and PQ in this triple substitution showed binding stability and IFN-gamma production that was nearly halved from that of the native peptide.

For the P2, P3, PΩ group, only the Nva/W/V analog showed improved binding or IFN-gamma production. For the two P1, P3, PΩ analogs examined PΩ of Val or Nva improved binding stability.

Example 36

Cross-Reactive Immunogenicity of Various Analogs

Groups of HHD transgenic mice (n=8) were immunized with peptide (natural epitope PSMA$_{288-297}$, or analogs bearing substitutions at primary or secondary anchor residues) by direct inoculation into the inguinal lymph nodes, with 25 μg in 25 μl of PBS+12.5 μg of pI:C to each lymph node at day 0, 3, 14 and 17.

Mice were sacrificed at 10 days after the last boost, and splenocytes prepared and assessed for IFN-γ production by ELISPOT analysis. Various numbers of splenocytes/well were stimulated with 10 μg/ml of native peptide in ELISPOT plates coated with anti-IFN-γ antibody. At 48 hours after incubation, the assay was developed and the frequency of cytokine-producing T cells that recognized native PSMA$_{288-297}$ peptide was automatically counted. The data is represented in FIG. 22 as the number of spot forming colonies/well (mean of triplicates±SD). The data show increased priming of immune responses against the native epitope achieved by the I297V and P290W analogs, with the other analogs showing slightly higher (but significant) activity than the native peptide (I297Nva or G288Abu or L289Nle I297Nva). To the extent that the poor immunogenicity of the native epitope reflects tolerance, the improved activity of these analogs represents tolerance breaking.

Example 37

Amplification by the I297V Analog of the Response to PSMA$_{288-297}$ Induced by Plasmid Two groups of HHD transgenic mice (n=8) were immunized with plasmid expressing PSMA$_{288-297}$ by direct inoculation into the inguinal lymph nodes with 25 μg in 25 μl of PBS to each lymph node at day 0, 3, 14 and 17. This was followed by two peptide boosts (25 μg) at day 28 and 31 with either the natural peptide or the I297V analog.

Mice were sacrificed at 10 days after the last boost, and splenocytes prepared and assessed for IFN-γ production by ELISPOT analysis. Various numbers of splenocytes/well were stimulated with 10 μg/ml of native peptide in ELISPOT plates coated with anti-IFN-γ antibody. At 48 hours after incubation, the assay was developed and the frequency of cytokine-producing T cells that recognized the PSMA$_{288-297}$ peptide was automatically counted. The data is represented in FIG. 23 as frequency of specific T cells normalized to 0.5 million responder cells (mean of triplicates+SD). The data show that irrespective of the number of splenocytes/well, the frequency of native epitope-specific T cells was considerably higher in the mouse group immunized with the I297V analog.

Example 38

Ex Vivo Cytotoxicity Against Human Tumor Cells

HHD transgenic mice (n=4) were immunized with plasmid expressing the PSMA$_{288-297}$ epitope by direct inoculation into the inguinal lymph nodes with 25 μg in 25 μl of PBS to each lymph node at day 0, 3, 14 and 17. This was followed by two peptide boosts (same amount) at day 28 and 31, with the analog I297V. One week after the boost, splenocytes were stimulated ex vivo with the native PSMA$_{288-297}$ peptide and tested overnight against $^{51}$Cr-labeled human tumor cells (Lncap, A2$^+$ PSMA$^+$; or 624.38 A2$^+$ PSMA$^-$ or control 624.28 cells A2$^-$ PSMA$^-$) at various E:T ratios. The resulting immunity was effective in mediating cytotoxicity against LNCAP (FIG. 24).

Example 39

Validation of the Antigenicity of PRAME$_{425-433}$

HHD transgenic mice (n=4) were immunized with PRAME$_{425-433}$ peptide (25 μg in 25 μl of PBS, plus 12.5 μg of pI:C to each lymph node) at day 0, 3, 14 and 17. One week after the boost, splenocytes were stimulated ex vivo with the native PRAME$_{425-433}$ peptide and tested against $^{51}$Cr-labeled human tumor cells (PRAME$^+$ A2$^+$ 624.38 melanoma cells; or negative control 624.38 cells, deficient in A2 expression) at various E:T ratios. The results, expressed as % specific lysis (mean±SEM), showed that PRAME-specific T cells were able to lyse human tumor cells, confirming display of the PRAME$_{425-433}$ epitope on MHC class I of tumor cells in a fashion allowing immune mediated attack (FIG. 25).

Examples 40-48

Testing of PRAME$_{425-433}$ Analogs

The analogs listed in FIGS. 26-28 were tested for various properties such as improved affinity and stability of binding, cross-reactivity with the native epitope, and immunogenicity as follows in Examples 40-48. Using the procedures described in Example 31, the HLA-A*0201 binding characteristics of PRAME$_{425-433}$ and 69 analogs were assessed in comparison to each other. The positive control for binding was melan-A$_{26-35}$ A27L. The observed affinities of the analogs are reported as % binding (compared to the positive control) and ED$_{50}$, and stability of binding as half time of dissociation. Cross reactivity with the native epitope was assessed by using the analog peptides to stimulate IFN-gamma secretion from a T cell line specific for the native epitope, essentially as described in Example 6. The data shown in FIGS. 26-28 were generated by stimulating with analog peptide at approximately 0.3 μM. The results were collected from three separate experiments and were normalized to the amount of IFN-γ elicited by the native peptide in each. In some cases, the reported values are the average of two determinations. An asterisk "*" indicates that IFN-γ production was not distinguishable from background.

Example 40

Cross-Reactivity and Functional Avidity of Analogs Substituted at a Single Position (FIG. 26)

Single substitutions of Val, Met, Ile, Nle, Nva, and Abu were made for the Leu at the P2 primary anchor position. All of these analogs exhibited % binding within 20% of the native peptide. The ED50 for the Met analog had an affinity comparable to the native peptide while the Nva and Ile analogs' affinities were reduced within about 3-fold, but were still comparable to the PSMA$_{288-287}$ epitope. All of the P2 substitutions maintained binding stability at least similar to the native peptide. The Met, Nle, and Nva analogs elicited IFN-γ production within twofold of the native peptide and the Val analog somewhat less.

Single substitution of Lys, Phe, Tyr, Thr, Orn (ornithine), and Hse (homoserine) were made for the Ser at the P1 position. All of these analogs exhibited % binding within 20% of the native peptide except for the Phe analog which exceeded that range on the high side. The ED50 for the Lys analog was reduced by almost 6-fold, but the other five analogs had affinities within threefold of the native peptide. Stability of binding was generally similar to the native peptide with the Phe P1 analog showing greatest binding stability in this group with a half time of dissociation of 17.7 hours compared to 12.2 hours for the native peptide. With the exception of the Lys P1 analog, which elicited 40% of the IFN-γ of the native peptide, all of these analogs were considered cross-reactive as they elicited IFN-γ production within twofold of the native peptide.

Single substitutions of Val, Ile, Ala, Nle, Nva, Abu, were made to the PΩ anchor position, as well as modifying the carboxy-terminus by the addition of an amide group. All of these analogs exhibited % binding within 20% of the native peptide. ED50 measurements ranged from more than 10-fold less for the Ala substitution to a comparable value for the Nle substitution; the Nva substitution and C-terminal amide were also within 3-fold of the ED50 for native peptide. Stability of binding was also generally similar with outliers of the Nva analog at the high end, t1/2 of 17.2 hours, and the C-terminal amide at the low end with a significantly reduced t1/2 of only 3 hours. The Val, Ile, Ala, and Abu PΩ analogs exhibited less preferred cross-reactivity, but the others elicited IFN-γ production within twofold of the native peptide.

Single substitutions at positions primarily affecting TCR interactions were also made: Nle, Nva, and Abu at P3 and P6, and Ala, Ser, and Sar at P8. The P6 Nva analog produced IFN-γ within twofold of that of the native peptide, though the P6 Abu analog was close at 44%.

Example 41

Cross-Reactivity and Functional Avidity of Analogs Substituted at Two Positions

Double substitution analogs were created at P1 and P2, P2 and PΩ, and P1 and PΩ using various combinations of the single substitutions above (FIGS. 27A and 27B). None of the P1-P2 double substitutions examined had radical changes to binding affinity or stability, but none exhibited significant cross-reactivity in the IFN-γ assay. A similar pattern was seen with the P2-PΩ double substitution analogs, however, the L426Nva L433Nle analog exhibited a significant level of cross-recativity with the native peptide in the IFN-γ assay along with its similar, somewhat improved binding characteristics. Finally, for the P1-PΩ double substitutions, the examined analogs also conformed to the general pattern of having at least similar binding characteristics, but eliciting negligible IFN-γ in the cross-reactivity assay. The exceptions in this grouping were the S425F L433Nle analog, which exhibited somewhat improved binding stability and significant cross-reactivity, and the S425F L433Nle analog, which had a more that fourfold reduced $ED_{50}$, a nearly doubled halftime of dissociation, and elicited more IFN-γ than the native peptide.

Example 42

Cross-Reactivity and Functional Avidity of Analogs Substituted at Three Positions Four triple substitution analogs were investigated, having Phe or Thr at P1, Nva or Met at P2, and Nle at PΩ. The S425T L426M L433Nle analog had similar affinity whereas the affinity was improved for the other three analogs. Both analogs with P2 Nva substitutions displayed increased stability of binding and significant levels of cross-reactivity. See FIG. 28.

Example 43

Cross-Reactive Immunogenicity of the L426Nva L433Nle Analog

Two groups of HHD transgenic mice (n=8) were immunized with a pCTLR2 plasmid expressing $PRAME_{425-433}$, described in example 49 below, by direct inoculation into the inguinal lymph nodes of 25 μg in 25 μl of PBS to each lymph node at day 0, 3, 14 and 17. This was followed by two peptide boosts (2.5 μg) at day 28 and 31, of native peptide or the PRAME epitope analog L426Nva L433Nle.

Mice were sacrificed at 10 days after the last boost, and splenocytes prepared and assessed for IFN-γ production after in vitro stimulation at $0.5\times10^6$ cells/well, with 10 μg/ml of native peptide. At 48 hours after incubation, the supernatant was harvested and the concentration of IFN-γ produced in response to the $PRAME_{425-433}$ peptide was measured by ELISA. The data are presented in FIG. 29 and show a significant enhancement of IFN-γ production in mice boosted with the $PRAME_{425-433}$ L426Nva L433Nle analog.

Example 44

In Vivo Cytotoxicity Induced by the L426Nva L433Nle Analog

Two groups of HHD transgenic mice (n=8) were immunized as described in Example 43 above.

To evaluate the in vivo responses obtained against the native epitope, splenocytes were isolated from littermate control HHD mice and incubated with 20 μg/mL or 1 μg/ml of native peptide for 2 hours. Cells were then stained with $CFSE^{hi}$ and $CFSE^{med}$ fluorescence (4.0 μM or 1 μM, respectively, for 15 minutes) and intravenously co-injected into immunized mice with an equal number of control splenocytes stained with $CFSE^{lo}$ fluorescence (0.4 μM). Eighteen hours later the specific elimination of target cells was measured by removing the spleens and PBMC from challenged animals and measuring CFSE fluorescence by flow cytometry. The relative depletion of the populations corresponding to peptide loaded splenocytes was calculated relative to the control (unloaded) population and expressed as % specific lysis. The results in FIG. 30 showed preserved induction of cytotoxicity when the analog replaced the natural peptide as a booster agent. The trend indicates that the analog can improve on induction of cytotoxic immunity.

Example 45

In Vivo Cytotoxicity and Tetramer Staining

Seven groups of HHD transgenic mice (n=4) were immunized with a plasmid, pCTLR2, expressing $PRAME_{425-433}$ by direct inoculation into the inguinal lymph nodes of 25 μg in 25 μl of PBS to each lymph node at day 0, 3, 14 and 17. This was followed by two peptide boosts (2.5 μg) at day 28 and 31, of native peptide, negative control (EAAGIGILTV peptide (SEQ ID NO. 100)), or $PRAME_{425-433}$ epitope analogs bearing mutations at the primary and/or secondary anchor residues —S425F, L426Nva L433Nle, S425T L433Nle, and S425T L426Nva L433Nle.

To evaluate the in vivo response against native peptide, splenocytes were isolated from littermate control HHD mice and incubated with 0.2 µg/ml or 20 µg/ml of native peptide for 2 hours. These cells were then stained with CFSE fluorescence (1 and 2.5 µM, respectively, for 15 minutes) and intravenously co-injected into immunized mice with an equal number of control splenocytes stained with CFSE$^{lo}$ fluorescence (0.4 µM). Eighteen hours later, the specific elimination of target cells was measured by removing the spleen from challenged animals and measuring CFSE fluorescence in the resulting cell suspensions, by flow cytometry. The relative depletion of the populations corresponding to peptide-loaded splenocytes was calculated relative to the control (unloaded) population and expressed as % specific lysis. In addition, the frequency of PRAME$_{425-433}$-specific T cells was evaluated by tetramer/CD8 co-staining.

The boost with analogs encompassing mutations at primary or secondary anchor residues showed comparable immune activity as compared to the native peptide, based on in vivo cytotoxicity and tetramer staining. The analogs were capable of amplifying the immune response, as shown by comparison with the "EAA" group, boosted with an irrelevant peptide. In that regard, analogs comprising S425F, L33Nle, L426Nva L433Nle, S425T L433Nle, or S425T L426Nva L433Nle were all capable of expanding the immunity against the native epitope, as assessed by in vivo cytotoxicity. However, only the L433Nle, L426Nva L433Nle, and S425T L426Nva L433Nle analogs expanded the subset of T cells specific against the native epitope to a level significantly higher than in mice primed with plasmid and boosted with the negative control peptide (FIG. 31).

Example 46

Ex Vivo Cytokine Production

Three groups of HHD transgenic mice (n=4) were immunized with a plasmid, pCTLR2, expressing PRAME$_{425-433}$ by direct inoculation into the inguinal lymph nodes of 25 µg in 25 µl of PBS to each lymph node at day 0, 3, 14 and 17. This was followed by two peptide boosts (2.5 µg) at day 28 and 31, of the PRAME epitope analogs L426Nva L433Nle and S425T L426Nva L433Nle or the negative control peptide Melan A (EAAGIGILTV (SEQ ID NO. 100)).

Mice were sacrificed at 10 days after the last boost, and splenocytes prepared and assessed for IFN-γ production by ELISA at 48 hours after incubation with 10 µg/ml of native peptide. The data are presented in FIG. 32 as cytokine concentration in pg/ml (mean of triplicates±SD). The data showed ex vivo cytokine production by splenocytes from mice boosted with both analogs, and greater response to L426Nva L433Nle than to S425T L426Nva L433Nle.

Example 47

Ex Vivo Cytotoxicity Against a Human Tumor Cell Line after Peptide Boost with Analog HHD transgenic mice (n=4) were immunized with a plasmid, pCTLR2, expressing PRAME$_{425-433}$ by direct inoculation into the inguinal lymph nodes of 25 µg in 25 µl of PBS to each lymph node at day 0, 3, 14 and 17. This was followed by two peptide boosts (2.5 µg) at day 28 and 31, with the analog L426Nva L433Nle. One week after the boost, splenocytes were stimulated ex vivo with the native peptide and tested against $^{51}$Cr-labeled human tumor cells (PRAME$^+$ 624.38 melanoma cells pretreated or not with IFN-γ; or negative control 624.38 cells, deficient in HLA-A2 expression) at various E:T ratios. The analog L426Nva L433Nle elicited immune responses that mediated significant cytotoxicity against human tumor cells expressing A2 (624.38), slightly elevated upon their pre-treatment with IFNγ. In contrast, no significant activity was measured against A2-624.28 control cells. See FIG. 33.

Example 48

In Vitro Immunization to PRAME$_{425-433}$

In vitro immunization was carried out according to the general scheme presented in FIG. 34. Peripheral blood mononuclear cells (PBMCs) were obtained from healthy donors (HLA-A*0201$^+$) by Ficoll-separation. Fresh PBMCs (2.5× 10$^6$), together with 5 ng/ml PRAME$_{425-433}$ or peptide analog were plated in T-cell culture medium. Subsequently 20 IU/ml of interleukin-2 was added to each well after 72 and 96 hours and additional peptide (5 ng/ml) was added at day 7. Cultures were maintained for an additional 10 days before effector cells were harvested and used in tetramer staining. IVS PBMCs were labeled with PRAME$_{425-433}$ tetramer and analyzed on the FACSCalibur (BD, San Jose, Calif.). Quadrants were set based on negative controls, stained with irrelevant HBV tetramer and SSX2 tetramer, and a minimum of 10,000 gated events were captured. Tetramer-positive cells were expressed as a percentage of the lymphocyte population. PRAME$_{425-433}$-specific tetramers were significantly enhanced following IVS with peptide analog as compared with native peptide. See FIG. 35. This demonstrates that the analog can be a preferable immunogen.

Example 49 pCTLR2, a Plasmid Expressing the PRAME425-433 Epitope pCTLR2 is a recombinant DNA plasmid vaccine encoding one polypeptide with an HLA A2-specific CTL epitope from PRAME, amino acid residues 425-433, SLLQHLIGL (SEQ ID NO. 71), and an epitope cluster region of PRAME, amino acids 422-509. The cDNA sequence for the polypeptide in the plasmid is under the control of promoter/enhancer sequence from cytomegalovirus (CMVp), which allows efficient transcription of messenger for the polypeptide upon uptake by antigen presenting cells. The bovine growth hormone polyadenylation signal (BGH polyA) at the 3' end of the encoding sequence provides signal for polyadenylation of the messenger to increase its stability as well as translocation out of nucleus into the cytoplasm. To facilitate plasmid transport into the nucleus, a nuclear import sequence (NIS) from Simian virus 40 was inserted in the plasmid backbone. One copy of CpG immunostimulatory motif was engineered into the plasmid to further boost immune responses. Lastly, two prokaryotic genetic elements in the plasmid are responsible for amplification in *E. coli*, the kanamycin resistance gene (Kan R) and the pMB bacterial origin of replication. (See FIG. 36).

Immunogen Translation Product Sequence

The amino acid sequence of the encoded polypeptide (150 amino acid residues in length) is given below.

malqsllqhliglsnlthylypvple-syedihgtlhlerlaylharlrellcelgrpsmvwlsanpcp hcgdrtfydpepil-cpcfmpnkrsllqhliglgdaaysllqh-liglispekeeqyiasllqhliglkrpsikrsllqhligl (SEQ ID NO: 196).

The first 89 amino acid residues are an epitope cluster region representing PRAME 422-509. Within this epitope cluster region, a number of potential HLA A2-specific CTL epitopes have been found using a variety of epitope prediction algorithms. Amino acid residues 90-150 are an epitope liberation (Synchrotope™) sequence with four copies of PRAME 425-433 CTL epitope (boldface) embedded. Flanking the defined PRAME CTL epitope are short amino acid sequences that have been shown to play an important role in the processing of the PRAME CTL epitope. In addition, the amino acid sequence ispekeeqyia (SEQ ID NO. 197) (corresponding to PRAME amino acid 276-286, in italics) was engineered into the string-of-beads region to facilitate the detection of expression of encoded polypeptide.

Using a variety of immunological assays, including tetramer, ELISPOT, ELISA, and cytotoxicity, strong CTL responses specific for epitope $PRAME_{425-433}$ have been detected from HLA-A2 transgenic mice immunized with the pCTLR2 plasmid, suggesting immunogenic potency for pCTLR2. These data indicated that the plasmid was taken up by antigen presenting cells, the encoded polypeptide synthesized and proteolytically processed to produce the nonamer epitope peptide, and the nonamer epitope peptide HLA-A2 bound for presentation.

Plasmid Construction

Stepwise ligation of sets of long complementary oligonucleotides resulted in generation of cDNA encoding amino acid residues in the "String-of-Beads" epitope liberation sequence (amino acids 90-150). These cDNA bore appropriate cohesive ends for restriction enzymes that can be used for further ligation with cDNA encoding the PRAME epitope cluster region (amino acid 1-89), which were amplified by performing PCR on cDNA encoding PRAME as template. The entire insert was then ligated into vector backbone between Afl II and EcoR I sites. The entire coding sequence was verified by DNA sequencing.

Example 50

Generation of Antigen Specific T Cell Responses

H-2 class I-negative, HLA-A2.1-transgenic HHD mice were housed under pathogen-free conditions and used for evaluation of the immunogenicity of HLA-A2.1-restricted human tumor-associated cytotoxic T lymphocyte (CTL) epitopes. Female mice 8-12 weeks of age were used for intralymphatic immunization and for isolation of splenocytes for in vivo cytotoxicity studies. The mice were immunized via bilateral inguinal lymph node injection. Mice were anesthetized by inhalation of isofluorane and surgeries were conducted under aseptic conditions. Following preparation for surgery, an incision 0.5 cm in length was made in the inguinal fold and the inguinal lymph node was exposed. A maximum volume of 25 μl (25 μg) of plasmid DNA vaccine or peptide was injected directly into the lymph node using a 0.5 mL insulin syringe. The wound was closed with sterile 6-0 nylon skin sutures.

Example 51

Ex Vivo Cytotoxicity Against Human Tumor Cells

HHD transgenic mice (n=4/group) were immunized with the plasmid pSEM (described more fully in U.S. patent application Ser. No. 10/292,413 (Pub. No.20030228634 A1), which is incorporated herein by reference in its entirety) expressing melan-$A_{26-35}$ A27L epitope analog by direct inoculation into the inguinal lymph nodes with 25 μg in 25 μl of PBS/each lymph node at day 0, 3, 14 and 17. This was followed by two additional peptide boosts (same amount) at day 28 and 31, with the analogs A27L, A27Nva, or A27L V35Nva. One week after the boost, splenocytes were stimulated ex vivo with the native melan-$A_{26-35}$ peptide and tested against $^{51}$Cr-labeled human tumor cells (624.38 cells) at various E:T ratios. The resulting immunity after boosting with the A27L or A27Nva analogs was comparable and more effective than the native peptide EAAGIGILTV (SEQ ID NO. 100) (FIG. 37). Because the priming plasmid expresses the A27L analog, the experiment had a potential bias in favor of that peptide. Thus, the substantial cytotoxicity obtained with the A27Nva analog may be an underestimate of it potency if priming made use of that same sequence.

Example 52

Tetramer Analysis

Enumeration of CD8+ antigen-specific T cells requires cognate recognition of the T cell receptor (TCR) by a Class I MHC/peptide complex. This can be done using Class I MHC tetramers which are composed of a complex of four HLA MHC Class I molecules each bound to the specific peptide and conjugated with a fluorescent protein. Thus, tetramer assays allow quantitation of the total T cell population specific for a given peptide complexed in a particular MHC molecule. Furthermore, because binding does not depend on functional pathways, this population includes all specific CD8+ T cells regardless of functional status. The CTL response in immunized animals was measured by co-staining mononuclear cells isolated from peripheral blood after density centrifugation (Lympholyte Mammal, Cedarlane Labs) with HLA-A*0201 MART1 (ELAGIGILTV (SEQ ID NO. 100))-PE MHC tetramer (Beckman Coulter, T01008) or a Tyrosinase$_{369-377}$ (YMDGTMSQV (SEQ ID NO. 94)) specific tetramer reagent (HLA-A*0201 Tyrosinase-PE, Beckman Coulter) and FITC conjugated rat anti-mouse CD8a (Ly-2) monoclonal antibody (BD Biosciences). Data was collected using a BD FACS Calibur flow cytometer and analysed using cellquest software by gating on the lymphocyte population and calculating the percent of tetramer$^+$ cells within the CD8$^+$ CTL population.

Example 53

Tetramer Staining (Plasmid Priming, Peptide Boost—Native Versus Analog)

Two groups of HHD transgenic mice (n=8) were immunized with plasmid expressing Tyrosinase 369-377 by direct inoculation into the inguinal lymph nodes with 25 μg in 25 μl of PBS/each lymph node at day 0, 3, 14 and 17. This was followed by two additional peptide boosts (similar amount) at day 28 and 31, of natural peptide or the 377Nva analog. Ten days later, the immune response was monitored using a Tyrosinase$_{369-377}$ specific tetramer reagent (HLA-A*0201 Tyrosinase-PE, Beckman Coulter). Individual mice were bled via the retro-orbital sinus vein and PBMC were isolated using density centrifugation (Lympholyte Mammal, Cedarlane Labs) at 2000 rpm for 25 minutes. PBMC were co-stained with a mouse specific antibody to CD8 (BD Biosciences) and the Tyrosinase tetramer reagent and specific percentages were determined by flow cytometry using a FACS caliber flow cytometer (BD Biosciences). The percentages of Tyrosinase specific CD8+ cells show that replacement of the native peptide with the analog preserved the expansion of Tyrosinase-specific subset. The trend indicates that the analog can improve on the expansion of Tyrosinase specific T cells (FIG. 38).

Example 54

In Vivo Cytotoxicity and Tetramer Staining (Head to Head Comparison Between Native Peptide and a Panel of Analog Candidates)

Four groups of HHD transgenic mice (n=6) were immunized with plasmid (pSEM) expressing Tyrosinase$_{369-377}$ and Melan-A$_{26-35}$ A27L epitopes by direct inoculation into the inguinal lymph nodes of 25 µg of plasmid in 25 µl of PBS per lymph node at day 0, 3, 14 and 17. This was followed by two peptide boosts (similar amount) at days 28 and 31, of Melan-A$_{26-35}$ A27L into the left inguinal lymph node and Tyrosinase$_{369-377}$ analogs, bearing substitutions at the primary and/or secondary anchor residues, into the right lymph node. As controls, mice immunized with plasmid only or native mice were used.

To evaluate the in vivo response against natural Tyrosinase and Melan A epitopes, splenocytes were isolated from littermate control HHD mice and incubated separately with 20 µg/ml of natural peptide (Melan-A$_{26-35}$ or Tyrosinase$_{369-377}$) for 2 hours in HL-1 serum free medium (Cambrex) at a concentration of 20×10$^6$ cells/mL. These cells were then stained with CFSE (Vybrant CFDA SE cell tracer kit, Molecular Probes) (1 and 2.5 µM respectively, for 15 minutes) and intravenously co-injected into immunized or naïve control HHD mice with an equal number of control non-peptide coated splenocytes stained with CFSE$^{lo}$ fluorescence (0.4 µM). Eighteen hours later the specific elimination of target cells was measured by removing the spleen from challenged animals and measuring CFSE fluorescence in the resulting cell suspensions by flow cytometry. The relative depletion of the populations corresponding to peptide-loaded splenocytes was calculated relative to the control (unloaded) population and expressed as % specific lysis. In addition, the frequency of Tyrosinase$_{369-377}$- and Melan-A$_{26-35}$-specific T cells, was evaluated by tetramer/CD8 co-staining (HLA-A*0201-tetramers, Beckman Coulter).

The tyrosinase analog V377Nva was capable of expanding the population of tyrosinase-specific T cells and amplifying cytotoxic immunity, similarly to the native peptide and greater than the Tyrosinase analog M370V V377Nva (FIG. 39).

Example 55

Ex Vivo Cytotoxicity Against Human Tumor Cells

HHD transgenic mice (n=4/group) were immunized (according to the general protocol in FIG. 40) with plasmid (pSEM) expressing the Tyrosinase$_{369-377}$ epitope by direct inoculation into the inguinal lymph nodes of 25 µg of plasmid in 25 µl of PBS per lymph node at day 0, 3, 14 and 17. This was followed by two peptide boosts (same amount) at day 28 and 31, with the native peptide or analogs bearing substitutions at primary anchor residues P2 and PΩ (370 and 377). One week after the boost, splenocytes were stimulated ex vivo with the native Tyrosinase$_{369-377}$ peptide and assayed against $^{51}$Cr-labeled human tumor cells (624.38 cells) at various E:T ratios. Both the native peptide and the M370V V377Nva analog generated robust cytotoxicity against 624.38 cells (FIG. 41). Whereas there was some dilution of cytolytic activity with the native peptide, there was none with the analog, thereby reinforcing the indication of greater immunogenicity gained from the tetramer results in Example 52. Together with the preceding example, this observation illustrates the usefulness of complementing more stringent assays (in vivo cytotoxicity and tetramer staining) with more sensitive assays (ex vivo cytotoxicity after in vitro stimulation) to outline potentially useful analogs.

Example 56

Binding and Stability (Half-Life) Characterization of Native Peptides and Analogs by Itopia System Because the binding and the stability of the peptides bound to the MHC 1 complexes are essential to get a good immune response, native epitopes and analogs thereof were tested for their binding and stability (T$_{1/2}$) to A0201 restricted MHC Class 1 molecules using iTopia Epitope discovery System (also discussed in Example 31). The binding and offrate (T$_{1/2}$) was determined for six native epitopes and their analogs which were designed to enhance the immune response. The native peptides and analogs were as follows: NY-ESO-1$_{157-165}$, NY-ESO-1$_{157-165}$ (L158Nva, C165V)), Melan-A$_{26-35}$, Melan-A$_{26-35}$ (A27Nva), SSX-2$_{41-49}$, SSX-2$_{41-49}$ (A42V), Prame$_{425-433}$, Prame$_{425-433}$ (L426Nva, L433Nle), Tyrosinase$_{369-377}$, Tyrosinase$_{369-377}$ (V377Nva), PSMA$_{288-297}$ and PSMA$_{288-297}$(I297V).

Table-10 (below) shows the average values of peptide binding and stability or half-life of six analogs and their native peptides. The analogs of SSX-2$_{41-49}$ and NY-ESO-1$_{157-165}$ showed substantial increase in the percent binding compared to the native peptides. The analogs of Melan-A$_{26-35}$, Psma$_{288-297}$, Prame$_{425-433}$ and Tyrosinase$_{369-377}$ showed a marginal increase in the percentage binding of the peptides compared to the native peptides.

Melan A$_{26-35}$ (A27Nva) showed substantial increase in the stability (half-life) compared to the native peptide. Significant increase in the stability was observed for other analogs Psma$_{288-297}$ (I297V), NY-ESO-1$_{157-165}$ (L158Nva, C165V), Prame$_{425-433}$ (L236Nva, L433Nle) and SSX-2$_{41-47}$ (A42V). No significant differences were observed in the half-life of the analog Tyrosinase$_{369-377}$ (V377Nva) compared to the native peptide. The differences observed in the half life of the analogs may be due to the difference in the mechanism of binding of each analog to the MHC1 molecules

TABLE 10

THE AVERAGE VALUES OF PERCENT BINDING AND THE STABILITY (HALF-LIFE) OF NATIVE PEPTIDES AND THEIR ANALOGS.

| # | Peptide Name | Half-Life (T½) | % Peptide Binding at T0 |
|---|---|---|---|
| 1 | Melan-A 26-35 | 1.85 | 74 |
| 2 | Melan-A 26-35 (A27Nva) | 13.55 | 79 |
| 3 | PSMA 288-297 | 7.34 | 85 |
| 4 | PSMA 288-297(I297V) | 16.72 | 92 |
| 5 | Nyeso-1 157-165 | 12.74 | 63 |
| 6 | Nyeso-1 157-165 (L158Nva, C165V)) | 16.98 | 100 |
| 7 | PRAME 425-433 | 12.42 | 79 |
| 8 | Prame 425-433 (L426Nva, L433Nle) | 16.87 | 89 |
| 9 | SSX2 41-49 | 9.90 | 55 |
| 10 | SSX2 41-49 (A42V) | 15.01 | 71 |

TABLE 10-continued

THE AVERAGE VALUES OF PERCENT BINDING AND THE STABILITY (HALF-LIFE) OF NATIVE PEPTIDES AND THEIR ANALOGS.

| # | Peptide Name | Half-Life (T½) | % Peptide Binding at T0 |
|---|---|---|---|
| 11 | Tyrosinase 369-377 | 14.39 | 73 |
| 12 | Tyrosinase 369-377 (V377Nva) | 14.74 | 77 |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the invention extends beyond the specifically disclosed embodiments to other alternative embodiments and/or uses and modifications and equivalents thereof.

Many variations and alternative elements of the invention have been disclosed. Still further variations and alternate elements will be apparent to one of skill in the art. Among these variations, without limitation, are the specific number of antigens in a screening panel or targeted by a therapeutic product, the type of antigen, the type of cancer, and the particular antigen(s) specified. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar referents used in the context of describing a particular embodiment of the invention (especially in the context of certain of the following claims) may be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans may employ such variations as appropriate, and the invention may be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed may be within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An isolated peptide consisting essentially of the sequence P0-P1-P2-P3-P4-P5-P6-P7-P8-P9-P10, in which:
   P0 is X, XX, or XXX, wherein X specifies any amino acid or no amino acid; and
   P1 is S; and
   P2 is M, Nva, or Nle; and
   P3 is L; and
   P4 is Q; and
   P5 is H; and
   P6 is L; and
   P7 is I; and
   P8 is G, A, S, or Sar; and
   P9 is V, Nle, or Nva; and
   P10 is X, XX, or XXX, wherein X specifies any amino acid or no amino acid.

2. The isolated peptide of claim 1 consisting essentially of the sequence:
   S{Nva, Nle, or M}LQHLIG{Nva, Nle, or V}(SEQ ID NO: 79).

3. The isolated peptide of claim 1 consisting essentially of the sequence: S {Nva}LQHLIG{Nle}(SEQ ID NO: 87).

4. A class MHC-peptide complex, wherein the peptide has the sequence of the peptide of claim 1.

5. A polypeptide comprising the peptide sequence of claim 1 embedded within a liberation sequence.

6. An immunogenic composition comprising the peptide of claim 1.

7. A nucleic acid encoding the polypeptide of claim 5.

8. A nucleic acid means for expressing the peptide of claim 1.

9. An composition comprising the nucleic acid of claim 7 or 8.

10. A method of inducing, maintaining, or amplifying a CTL response in a mammal comprising intranodal administration of the composition of claim 6.

11. A method of entraining a class I MHC-restricted T cell response in a mammal comprising intranodal administration of the composition of claim 6 and an immunopotentiating agent.

12. A method of inducing, maintaining, or entraining a CTL response in a mammal comprising intranodal administration of the composition of claim 9.

13. An isolated peptide comprising the sequence:
   S{Nva, Nle, or M}LQHLIG{Nva, Nle, or V}(SEQ ID NO: 79).

14. The isolated peptide of claim 13 comprising the sequence: S{Nva}LQHLIG{Nle}(SEQ ID NO: 87).

15. An isolated peptide consisting of the sequence P0-P1-P2-P3-P4-P5-P6-P7-P8-P9-P10, in which:
   P0 is X, XX, or XXX, wherein X specifies any amino acid or no amino acid; and
   P1 is S; and
   P2 is M, Nva, or Nle; and
   P3 is L; and
   P4 is Q; and P5 is H; and
P6 is L; and
P7 is I; and
P8 is G; and
P9 is V, Nle, or Nva; and
P10 is X, XX, or XXX, wherein X specifies any amino acid or no amino acid.

16. The isolated peptide of claim 13 or 15 consisting of the sequence: S {Nva, Nle, or M}LQHLIG{Nva, Nle, or V}(SEQ ID NO: 79).

17. The isolated peptide of claim 16 consisting of the sequence: S{Nva}LQHLIG{Nle}(SEQ ID NO: 87).

18. A class I MHC-peptide complex, wherein the peptide has the sequence of the peptide of claim 13 or 15.

19. A polypeptide comprising the peptide sequence of claim 13 or 15 embedded within a liberation sequence.

20. An immunogenic composition comprising the peptide of claim 13 or 15.

21. A nucleic acid encoding the polypeptide of claim 19.

22. A nucleic acid means for expressing the peptide of claim 13 or 15.

23. An composition comprising the nucleic acid of claim 21 or 22.

24. A method of inducing, maintaining, or amplifying a CTL response in a mammal comprising intranodal administration of the composition of claim 20.

25. A method of entraining a class I MHC-restricted T cell response in a mammal comprising intranodal administration of the composition of claim 20 and an immunopotentiating agent.

26. A method of inducing, maintaining, or entraining a CTL response in a mammal comprising intranodal administration of the composition of claim 23.

* * * * *

SEQUENCE LISTING

<160> NUMBER OF SEQ ID NOS: 407

<210> SEQ ID NO 1
<211> LENGTH: 10
<212> TYPE: PRT
<213> ORGANISM: Artificial Sequence
<220> FEATURE:
<223> OTHER INFORMATION: Analog of MHC class I-restricted T cell epitope

<400> SEQUENCE: 1

Gly Ile Pro Ser Ile Pro Val His Pro Ile
 1               5                   10

<210> SEQ ID NO 2
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (2)...(2)
<223> OTHER INFORMATION: Xaa = L, V, M, I, D-Ala, D-Val, Nal-2, Aib, Abu,
      Nle or Nva

<400> SEQUENCE: 2

Lys Xaa Ser Glu Lys Ile Phe Tyr Val
 1               5

<210> SEQ ID NO 3
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (1)...(1)
<223> OTHER INFORMATION: Xaa = F, Phg, Y, Phe(4-F), Phe(4-NO2),
      O-methyl-Tyr, or beta (3-benzothienyl-Ala)

<400> SEQUENCE: 3

Xaa Ala Ser Glu Lys Ile Phe Tyr Val
 1               5

<210> SEQ ID NO 4
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (1)...(1)
<223> OTHER INFORMATION: Xaa = Y, F, or W
<220> FEATURE:
<221> NAME/KEY: VARIANT
<222> LOCATION: (2)...(2)
<223> OTHER INFORMATION: Xaa = V, M, or I

<400> SEQUENCE: 4

Xaa Xaa Ser Glu Lys Ile Phe Tyr Val
 1               5

<210> SEQ ID NO 5

```
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (1)...(1)
<223> OTHER INFORMATION: Xaa = F or W

<400> SEQUENCE: 5

Xaa Leu Ser Glu Lys Ile Phe Tyr Val
 1               5

<210> SEQ ID NO 6
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (2)...(2)
<223> OTHER INFORMATION: Xaa = A, V or L

<400> SEQUENCE: 6

Lys Xaa Ser Glu Lys Ile Phe Tyr Val
 1               5

<210> SEQ ID NO 7
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (2)...(2)
<223> OTHER INFORMATION: Xaa = L or V
<220> FEATURE:
<221> NAME/KEY: AMIDATION
<222> LOCATION: (9)...(9)
<223> OTHER INFORMATION: NH2 on Val

<400> SEQUENCE: 7

Lys Xaa Ser Glu Lys Ile Phe Tyr Val
 1               5

<210> SEQ ID NO 8
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (9)...(9)
<223> OTHER INFORMATION: Xaa = I, A, Nva, Abu or MeVal

<400> SEQUENCE: 8

Phe Val Ser Glu Lys Ile Phe Tyr Xaa
 1               5

<210> SEQ ID NO 9
<211> LENGTH: 9
<212> TYPE: PRT
<213> ORGANISM: Artificial Sequence
```

```
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (4)...(4)
<223> OTHER INFORMATION: Xaa = Q, Nle or Nva

<400> SEQUENCE: 9

Phe Val Ser Xaa Lys Ile Phe Tyr Val
 1               5

<210> SEQ ID NO 10
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (6)...(6)
<223> OTHER INFORMATION: Xaa = L, V, Nle or Nva

<400> SEQUENCE: 10

Phe Val Ser Glu Lys Xaa Phe Tyr Val
 1               5

<210> SEQ ID NO 11
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (8)...(8)
<223> OTHER INFORMATION: Xaa = F or Phe(4-F)

<400> SEQUENCE: 11

Phe Val Ser Glu Lys Ile Phe Xaa Val
 1               5

<210> SEQ ID NO 12
<211> LENGTH: 10
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (10)...(10)
<223> OTHER INFORMATION: Xaa = I or L

<400> SEQUENCE: 12

Lys Ala Ser Glu Lys Ile Phe Tyr Val Xaa
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (10)...(10)
<223> OTHER INFORMATION: Xaa = I, L, V, or Nle
```

```
<400> SEQUENCE: 13

Lys Val Ser Glu Lys Ile Phe Tyr Val Xaa
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (10)...(10)
<223> OTHER INFORMATION: Xaa = L, V, Nle or Nva

<400> SEQUENCE: 14

Lys Leu Ser Glu Lys Ile Phe Tyr Val Xaa
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (2)...(2)
<223> OTHER INFORMATION: Xaa = L, V, M, Abu, Nle or Nva

<400> SEQUENCE: 15

Lys Xaa Ser Glu Lys Ile Phe Tyr Val
1               5

<210> SEQ ID NO 16
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (1)...(1)
<223> OTHER INFORMATION: Xaa = Phe or Phg

<400> SEQUENCE: 16

Xaa Ala Ser Glu Lys Ile Phe Tyr Val
1               5

<210> SEQ ID NO 17
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)

<400> SEQUENCE: 17

Tyr Val Ser Glu Lys Ile Phe Tyr Val
1               5

<210> SEQ ID NO 18
<211> LENGTH: 9
<212> TYPE: PRT
<213> ORGANISM: Artificial Sequence
```

```
<220> FEATURE:
<223> OTHER INFORMATION: Analog of MHC class I-restricted T cell epitope
      SSX-

```
<400> SEQUENCE: 22

Lys Xaa Ser Glu Lys Ile Phe Tyr Val
1               5

<210> SEQ ID NO 23
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)
<220> FEATURE:
<221> NAME/KEY: VARIANT
<222> LOCATION: (1)...(1)
<223> OTHER INFORMATION: Xaa = F or Y

<400> SEQUENCE: 23

Xaa Ala Ser Glu Lys Ile Phe Tyr Val
1               5

<210> SEQ ID NO 24
<211> LENGTH: 9
<212> TYPE: PRT
<213> ORGANISM: Artificial Sequence
<220> FEATURE:
<223> OTHER INFORMATION: Analog of MHC class I-restricted T cell epitope
      SSX-2(41-49)

<400> SEQUENCE: 24

Phe Val Ser Glu Lys Ile Phe Tyr Ile
1               5

<210> SEQ ID NO 25
<211> LENGTH: 9
<212> TYPE: PRT
<213> ORGANISM: Homo sapiens

<400> SEQUENCE: 25

Ser Leu Leu Met Trp Ile Thr Gln Cys
1               5

<210> SEQ ID NO 26
<211> LENGTH: 9
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (9)...(9)
<223> OTHER INFORMATION: Xaa = C, V, I, L, or A

<400> SEQUENCE: 26

Ser Leu Leu Met Trp Ile Thr Gln Xaa
1               5

<210> SEQ ID NO 27
<211> LENGTH: 9
<212> TYPE: PRT
<213> ORGANISM: Artificial Sequence
<220> FEATURE:
<223> OTHER INFORMATION: Analog of NY-ESO-1 (157-165)

<400> SEQUENCE: 27

Phe Val Leu Met Trp Ile Thr Gln Ala
1               5
```

<210> SEQ ID NO 28
<211> LENGTH: 9
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (9)...(9)
<223> OTHER INFORMATION: Xaa = L or I

<400> SEQUENCE: 28

Phe Ile Leu Met Trp Ile Thr Gln Xaa
1               5

<210> SEQ ID NO 29
<211> LENGTH: 8
<212> TYPE: PRT
<213> ORGANISM: Artificial Sequence
<220> FEATURE:
<223> OTHER INFORMATION: Analog of NY-ESO-1 (157-165)

<400> SEQUENCE: 29

Tyr Val Leu Met Trp Ile Thr Leu
1               5

<210> SEQ ID NO 30
<211> LENGTH: 8
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (8)...(8)
<223> OTHER INFORMATION: Xaa = I or L

<400> SEQUENCE: 30

Tyr Leu Leu Met Trp Ile Thr Xaa
1               5

<210> SEQ ID NO 31
<211> LENGTH: 10
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (1)...(1)
<223> OTHER INFORMATION: Xaa = S or Y
<220> FEATURE:
<221> NAME/KEY: VARIANT
<222> LOCATION: (9)...(9)
<223> OTHER INFORMATION: Xaa = C or V
<220> FEATURE:
<221> NAME/KEY: VARIANT
<222> LOCATION: (10)...(10)
<223> OTHER INFORMATION: Xaa = L, I, or Nle

<400> SEQUENCE: 31

Xaa Leu Leu Met Trp Ile Thr Gln Xaa Xaa
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Analog of NY-ESO-1 (157-165)

```
<220> FEATURE:
<221> NAME/KEY: VARIANT
<222> LOCATION: (9)...(9)
<223> OTHER INFORMATION: Xaa = C, V, L or A

<400> SEQUENCE: 32

Ser Ile Leu Met Trp Ile Thr Gln Xaa
1               5

<210> SEQ ID NO 33
<211> LENGTH: 9
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (9)...(9)
<223> OTHER INFORMATION: Xaa = Nva or Nle

<400> SEQUENCE: 33

Tyr Leu Leu Met Trp Ile Thr Gln Xaa
1               5

<210> SEQ ID NO 34
<211> LENGTH: 9
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (2)...(2)
<223> OTHER INFORMATION: Xaa = L or V
<220> FEATURE:
<221> NAME/KEY: VARIANT
<222> LOCATION: (9)...(9)
<223> OTHER INFORMATION: Xaa = V, L, or I

<400> SEQUENCE: 34

Phe Xaa Leu Met Trp Ile Thr Gln Xaa
1               5

<210> SEQ ID NO 35
<211> LENGTH: 9
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (2)...(2)
<223> OTHER INFORMATION: Xaa = I, Nva, or Nle

<400> SEQUENCE: 35

Tyr Xaa Leu Met Trp Ile Thr Gln Val
1               5

<210> SEQ ID NO 36
<211> LENGTH: 9
<212> TYPE: PRT
<213> ORGANISM: Artificial Sequence
<220> FEATURE:
<223> OTHER INFORMATION: Analog of NY-ESO-1 (157-165)

<400> SEQUENCE: 36

Tyr Leu Leu Leu Trp Ile Thr Gln Val
1               5
```

```
<210> SEQ ID NO 37
<211> LENGTH: 9
<212> TYPE: PRT
<213> ORGANISM: Artificial Sequence
<220> FEATURE:
<223> OTHER INFORMATION: Analog of NY-ESO-1 (157-165)

<400> SEQUENCE: 37

Thr Val Leu Met Trp Ile Thr Gln Val
 1               5

<210> SEQ ID NO 38
<211> LENGTH: 9
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (1)...(1)
<223> OTHER INFORMATION: Xaa = S or F

<400> SEQUENCE: 38

Xaa Val Leu Met Trp Ile Thr Gln Val
 1               5

<210> SEQ ID NO 39
<211> LENGTH: 8
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (8)...(8)
<223> OTHER INFORMATION: Xaa = Nva

<400> SEQUENCE: 39

Ser Leu Met Trp Ile Thr Gln Xaa
 1               5

<210> SEQ ID NO 40
<211> LENGTH: 9
<212> TYPE: PRT
<213> ORGANISM: Artificial Sequence
<220> FEATURE:
<223> OTHER INFORMATION: Analog of NY-ESO-1 (157-165)
<220> FEATURE:
<221> NAME/KEY: VARIANT
<222> LOCATION: (2)...(2)
<223> OTHER INFORMATION: Xaa = Nva

<400> SEQUENCE: 40

Ser Xaa Leu Met Trp Ile Thr Gln Val
 1               5

<210> SEQ ID NO 41
<211> LENGTH: 9
<212> TYPE: PRT
<213> ORGANISM: Artificial Sequence
<220> FEATURE:
<223> OTHER INFORMATION: Analog of MHC class I-restricted T cell epitope

<400> SEQUENCE: 41

Lys Val Ser Glu Lys Ile Phe Tyr Val
 1               5

<210> SEQ ID NO 42
<211> LENGTH: 10
```

```
<212> TYPE: PRT
<213> ORGANISM: Artificial Sequence
<220> FEATURE:
<223> OTHER INFORMATION: T cell peptide epitope analog

<400> SEQUENCE: 42

Gly Leu Pro Ser Ile Pro Val His Pro Ile
1               5                   10

<210> SEQ ID NO 43
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = S, Sar, or Abu

<400> SEQUENCE: 43

Xaa Leu Pro Ser Ile Pro Val His Pro Ile
1               5                   10

<210> SEQ ID NO 44
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = M or Nle

<400> SEQUENCE: 44

Gly Xaa Pro Ser Ile Pro Val His Pro Ile
1               5                   10

<210> SEQ ID NO 45
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = L, I, Nva or Nle

<400> SEQUENCE: 45

Gly Xaa Trp Ser Ile Pro Val His Pro Ile
1               5                   10

<210> SEQ ID NO 46
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva or V

<400> SEQUENCE: 46

Gly Leu Trp Ser Ile Pro Val His Pro Xaa
1               5                   10
```

```
<210> SEQ ID NO 47
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = A or S

<400> SEQUENCE: 47

Gly Leu Pro Ser Ile Pro Val His Xaa Ile
1               5                   10

<210> SEQ ID NO 48
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = V, L, Nva or Nle

<400> SEQUENCE: 48

Gly Leu Pro Ser Ile Pro Val His Pro Xaa
1               5                   10

<210> SEQ ID NO 49
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle
<220> FEATURE:
<221> NAME/KEY: VARIANT
<222> LOCATION: (10)...(10)
<223> OTHER INFORMATION: Xaa = Nva or Nle

<400> SEQUENCE: 49

Gly Xaa Pro Ser Ile Pro Val His Pro Xaa
1               5                   10

<210> SEQ ID NO 50
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
<220> FEATURE:
<221> NAME/KEY: VARIANT
<222> LOCATION: (10)...(10)
<223> OTHER INFORMATION: Xaa = Nva

<400> SEQUENCE: 50

Gly Xaa Pro Ser Ile Pro Val His Pro Xaa
1               5                   10

<210> SEQ ID NO 51
<211> LENGTH: 10
<212> TYPE: PRT
```

```
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = V, Nva or Nle

<400> SEQUENCE: 51

Gly Xaa Pro Ser Ile Pro Val His Pro Val
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Sar or Abu
<220> FEATURE:
<221> NAME/KEY: VARIANT
<222> LOCATION: (10)...(10)
<223> OTHER INFORMATION: Xaa = V or Nva

<400> SEQUENCE: 52

Xaa Leu Pro Ser Ile Pro Val His Pro Xaa
 1               5                  10

<210> SEQ ID NO 53
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = V, I, Nva, or Nle

<400> SEQUENCE: 53

Ala Xaa Trp Ser Ile Pro Val His Pro Ile
 1               5                  10

<210> SEQ ID NO 54
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = V or Nva

<400> SEQUENCE: 54

Ala Val Pro Ser Ile Pro Val His Pro Xaa
 1               5                  10

<210> SEQ ID NO 55
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
```

```
<400> SEQUENCE: 55

Ala Xaa Pro Ser Ile Pro Val His Pro Val
1               5                   10

<210> SEQ ID NO 56
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = V or Nva

<400> SEQUENCE: 56

Ala Leu Trp Ser Ile Pro Val His Pro Xaa
1               5                   10

<210> SEQ ID NO 57
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = V or Nva

<400> SEQUENCE: 57

Gly Val Trp Ser Ile Pro Val His Pro Xaa
1               5                   10

<210> SEQ ID NO 58
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 58

Gly Xaa Trp Ser Ile Pro Val His Pro Val
1               5                   10

<210> SEQ ID NO 59
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Abu

<400> SEQUENCE: 59

Xaa Leu Pro Ser Ile Pro Val His Pro Ile
1               5                   10

<210> SEQ ID NO 60
<211> LENGTH: 10
<212> TYPE: PRT
<213> ORGANISM: Artificial Sequence
```

```
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = V, Nva or Abu

<400> SEQUENCE: 60

Gly Xaa Pro Ser Ile Pro Val His Pro Ile
 1               5                   10

<210> SEQ ID NO 61
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = V or Nva

<400> SEQUENCE: 61

Gly Leu Pro Ser Ile Pro Val His Pro Xaa
 1               5                   10

<210> SEQ ID NO 62
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa =  I or Nva

<400> SEQUENCE: 62

Gly Leu Trp Ser Ile Pro Val His Pro Xaa
 1               5                   10

<210> SEQ ID NO 63
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle
<220> FEATURE:
<221> NAME/KEY: VARIANT
<222> LOCATION: (10)...(10)
<223> OTHER INFORMATION: Xaa = Nva

<400> SEQUENCE: 63

Gly Xaa Pro Ser Ile Pro Val His Pro Xaa
 1               5                   10

<210> SEQ ID NO 64
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle or Nva
```

```
<400> SEQUENCE: 64

Gly Xaa Pro Ser Ile Pro Val His Pro Val
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = A or Abu
<220> FEATURE:
<221> NAME/KEY: VARIANT
<222> LOCATION: (10)...(10)
<223> OTHER INFORMATION: Xaa = V or Nva

<400> SEQUENCE: 65

Xaa Leu Pro Ser Ile Pro Val His Pro Xaa
 1               5                  10

<210> SEQ ID NO 66
<211> LENGTH: 11
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
<220> FEATURE:
<221> NAME/KEY: VARIANT
<222> LOCATION: (10)...(10)
<223> OTHER INFORMATION: Xaa = I or V

<400> SEQUENCE: 66

Gly Xaa Trp Pro Ser Ile Pro Val His Pro Xaa
 1               5                  10

<210> SEQ ID NO 67
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva or Nle

<400> SEQUENCE: 67

Ala Xaa Trp Ser Ile Pro Val His Pro Ile
 1               5                  10

<210> SEQ ID NO 68
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = V or Nva

<400> SEQUENCE: 68

Ala Xaa Pro Ser Ile Pro Val His Pro Val
```

-continued

<210> SEQ ID NO 69
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 69

Gly Leu Trp Ser Ile Pro Val His Pro Ile
1               5                   10

<210> SEQ ID NO 70
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 70

Gly Leu Pro Ser Ile Pro Val His Pro Val
1               5                   10

<210> SEQ ID NO 71
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 71

Ser Leu Leu Gln His Leu Ile Gly Leu
1               5

<210> SEQ ID NO 72
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = K, F, Y, T, Orn, or Hse

<400> SEQUENCE: 72

Xaa Leu Leu Gln His Leu Ile Gly Leu
1               5

<210> SEQ ID NO 73
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = V, M, I, Nva, Nle, or Abu

<400> SEQUENCE: 73

Ser Xaa Leu Gln His Leu Ile Gly Leu
1               5

<210> SEQ ID NO 74
<211> LENGTH: 9
<212> TYPE: PRT

```
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (3)...(3)
<223> OTHER INFORMATION: Xaa = Nva, Nle or Abu

<400> SEQUENCE: 74

Ser Leu Xaa Gln His Leu Ile Gly Leu
 1               5

<210> SEQ ID NO 75
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (6)...(6)
<223> OTHER INFORMATION: Xaa = Nva, Nle or Abu

<400> SEQUENCE: 75

Ser Leu Leu Gln His Xaa Ile Gly Leu
 1               5

<210> SEQ ID NO 76
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (8)...(8)
<223> OTHER INFORMATION: Xaa = A, S or Sar

<400> SEQUENCE: 76

Ser Leu Leu Gln His Leu Ile Xaa Leu
 1               5

<210> SEQ ID NO 77
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = V, I, A, Nle, Nva, Abu or L-NH2

<400> SEQUENCE: 77

Ser Leu Leu Gln His Leu Ile Gly Xaa
 1               5

<210> SEQ ID NO 78
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = F, Y, T, Orn or Hse
<220> FEATURE:
<221> NAME/KEY: VARIANT
<222> LOCATION: (2)...(2)
<223> OTHER INFORMATION: Xaa = Nva, Nle, M or I
```

```
<400> SEQUENCE: 78

Xaa Xaa Leu Gln His Leu Ile Gly Leu
 1               5

<210> SEQ ID NO 79
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva, Nle or M
<220> FEATURE:
<221> NAME/KEY: VARIANT
<222> LOCATION: (9)...(9)
<223> OTHER INFORMATION: Xaa = Nva, Nle or V

<400> SEQUENCE: 79

Ser Xaa Leu Gln His Leu Ile Gly Xaa
 1               5

<210> SEQ ID NO 80
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = K, F, Y, T, Orn or Hse

<400> SEQUENCE: 80

Xaa Leu Leu Gln His Leu Ile Gly Val
 1               5

<210> SEQ ID NO 81
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = F or T
<220> FEATURE:
<221> NAME/KEY: VARIANT
<222> LOCATION: (9)...(9)
<223> OTHER INFORMATION: Xaa = Nle

<400> SEQUENCE: 81

Xaa Leu Leu Gln His Leu Ile Gly Xaa
 1               5

<210> SEQ ID NO 82
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = F or T
<220> FEATURE:
<221> NAME/KEY: VARIANT
<222> LOCATION: (2)...(2)
```

```
<223> OTHER INFORMATION: Xaa = Nva or M
<220> FEATURE:
<221> NAME/KEY: VARIANT
<222> LOCATION: (9)...(9)
<223> OTHER INFORMATION: Xaa = Nle

<400> SEQUENCE: 82

Xaa Xaa Leu Gln His Leu Ile Gly Xaa
 1               5

<210> SEQ ID NO 83
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = F, Y, T, Orn, or Hse

<400> SEQUENCE: 83

Xaa Leu Leu Gln His Leu Ile Gly Leu
 1               5

<210> SEQ ID NO 84
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva, Nle, or M

<400> SEQUENCE: 84

Ser Xaa Leu Gln His Leu Ile Gly Leu
 1               5

<210> SEQ ID NO 85
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nle, Nva, or L-NH2

<400> SEQUENCE: 85

Ser Leu Leu Gln His Leu Ile Gly Xaa
 1               5

<210> SEQ ID NO 86
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (6)...(6)
<223> OTHER INFORMATION: Xaa = Nva or Abu

<400> SEQUENCE: 86

Ser Leu Leu Gln His Xaa Ile Gly Leu
 1               5
```

<210> SEQ ID NO 87
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa =Nva
<220> FEATURE:
<221> NAME/KEY: VARIANT
<222> LOCATION: (9)...(9)
<223> OTHER INFORMATION: Xaa = Nle

<400> SEQUENCE: 87

Ser Xaa Leu Gln His Leu Ile Gly Xaa
 1               5

<210> SEQ ID NO 88
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = F or T
<220> FEATURE:
<221> NAME/KEY: VARIANT
<222> LOCATION: (2)...(2)
<223> OTHER INFORMATION: Xaa = L or Nva
<220> FEATURE:
<221> NAME/KEY: VARIANT
<222> LOCATION: (9)...(9)
<223> OTHER INFORMATION: Xaa = Nle

<400> SEQUENCE: 88

Xaa Xaa Leu Gln His Leu Ile Gly Xaa
 1               5

<210> SEQ ID NO 89
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = L or Nva
<220> FEATURE:
<221> NAME/KEY: VARIANT
<222> LOCATION: (9)...(9)
<223> OTHER INFORMATION: Xaa = Nle

<400> SEQUENCE: 89

Ser Xaa Leu Gln His Leu Ile Gly Xaa
 1               5

<210> SEQ ID NO 90
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
<220> FEATURE:

```
<221> NAME/KEY: VARIANT
<222> LOCATION: (9)...(9)
<223> OTHER INFORMATION: Xaa = Nle

<400> SEQUENCE: 90

Thr Xaa Leu Gln His Leu Ile Gly Xaa
 1               5

<210> SEQ ID NO 91
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = A, L, Nva, or Nle
<220> FEATURE:
<221> NAME/KEY: VARIANT
<222> LOCATION: (10)...(10)
<223> OTHER INFORMATION: Xaa = V, Nva, or Nle

<400> SEQUENCE: 91

Glu Xaa Ala Gly Ile Gly Ile Leu Thr Xaa
 1               5                  10

<210> SEQ ID NO 92
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = M, V, Nva or Nle
<220> FEATURE:
<221> NAME/KEY: VARIANT
<222> LOCATION: (9)...(9)
<223> OTHER INFORMATION: Xaa = V, Nva or Nle

<400> SEQUENCE: 92

Tyr Xaa Asp Gly Thr Met Ser Gln Xaa
 1               5

<210> SEQ ID NO 93
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = A or L

<400> SEQUENCE: 93

Glu Xaa Ala Gly Ile Gly Ile Leu Thr Val
 1               5                  10

<210> SEQ ID NO 94
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 94

Tyr Met Asp Gly Thr Met Ser Gln Val
```

-continued

```
<210> SEQ ID NO 95
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 95

Glu Leu Ala Gly Ile Gly Ile Leu Thr Xaa
 1               5                  10

<210> SEQ ID NO 96
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 96

Glu Xaa Ala Gly Ile Gly Ile Leu Thr Val
 1               5                  10

<210> SEQ ID NO 97
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nva

<400> SEQUENCE: 97

Tyr Val Asp Gly Thr Met Ser Gln Xaa
 1               5

<210> SEQ ID NO 98
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 98

Tyr Val Asp Gly Thr Met Ser Gln Val
 1               5

<210> SEQ ID NO 99
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nva

<400> SEQUENCE: 99
```

```
Tyr Met Asp Gly Thr Met Ser Gln Xaa
 1               5
```

<210> SEQ ID NO 100
<211> LENGTH: 10
<212> TYPE: PRT
<213> ORGANISM: Homo sapiens

<400> SEQUENCE: 100

```
Glu Ala Ala Gly Ile Gly Ile Leu Thr Val
 1               5                   10
```

<210> SEQ ID NO 101
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 101

```
Ser Xaa Pro Pro Pro Gly Thr Arg Val
 1               5
```

<210> SEQ ID NO 102
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 102

```
Lys Leu Ser Glu Lys Ile Phe Tyr Val
 1               5
```

<210> SEQ ID NO 103
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 103

```
Lys Val Ser Glu Lys Ile Phe Tyr Val
 1               5
```

<210> SEQ ID NO 104
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 104

```
Lys Ile Ser Glu Lys Ile Phe Tyr Val
 1               5
```

<210> SEQ ID NO 105
<211> LENGTH: 9
<212> TYPE: PRT
<213> ORGANISM: Artificial Sequence
<220> FEATURE:
<223> OTHER INFORMATION: T cell peptide epitope analog

```
<400> SEQUENCE: 105

Lys Met Ser Glu Lys Ile Phe Tyr Val
1               5

<210> SEQ ID NO 106
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = D-Ala

<400> SEQUENCE: 106

Lys Xaa Ser Glu Lys Ile Phe Tyr Val
1               5

<210> SEQ ID NO 107
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = D-Leu

<400> SEQUENCE: 107

Lys Xaa Ser Glu Lys Ile Phe Tyr Val
1               5

<210> SEQ ID NO 108
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = D-Val

<400> SEQUENCE: 108

Lys Xaa Ser Glu Lys Ile Phe Tyr Val
1               5

<210> SEQ ID NO 109
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nal-1

<400> SEQUENCE: 109

Lys Xaa Ser Glu Lys Ile Phe Tyr Val
1               5

<210> SEQ ID NO 110
<211> LENGTH: 9
<212> TYPE: PRT
<213> ORGANISM: Artificial Sequence
<220> FEATURE:
```

```
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nal-2

<400> SEQUENCE: 110

Lys Xaa Ser Glu Lys Ile Phe Tyr Val
 1               5

<210> SEQ ID NO 111
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Abu

<400> SEQUENCE: 111

Lys Xaa Ser Glu Lys Ile Phe Tyr Val
 1               5

<210> SEQ ID NO 112
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 112

Lys Xaa Ser Glu Lys Ile Phe Tyr Val
 1               5

<210> SEQ ID NO 113
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 113

Lys Xaa Ser Glu Lys Ile Phe Tyr Val
 1               5

<210> SEQ ID NO 114
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Aib

<400> SEQUENCE: 114

Lys Xaa Ser Glu Lys Ile Phe Tyr Val
 1               5
```

```
<210> SEQ ID NO 115
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 115

Phe Ala Ser Glu Lys Ile Phe Tyr Val
 1               5

<210> SEQ ID NO 116
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 116

Trp Ala Ser Glu Lys Ile Phe Tyr Val
 1               5

<210> SEQ ID NO 117
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 117

Tyr Ala Ser Glu Lys Ile Phe Tyr Val
 1               5

<210> SEQ ID NO 118
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = D-Lys

<400> SEQUENCE: 118

Xaa Ala Ser Glu Lys Ile Phe Tyr Val
 1               5

<210> SEQ ID NO 119
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Phg

<400> SEQUENCE: 119

Xaa Ala Ser Glu Lys Ile Phe Tyr Val
 1               5

<210> SEQ ID NO 120
<211> LENGTH: 9
<212> TYPE: PRT
<213> ORGANISM: Artificial Sequence
<220> FEATURE:
```

```
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Cha

<400> SEQUENCE: 120

Xaa Ala Ser Glu Lys Ile Phe Tyr Val
 1               5

<210> SEQ ID NO 121
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Phe(4-F)

<400> SEQUENCE: 121

Xaa Ala Ser Glu Lys Ile Phe Tyr Val
 1               5

<210> SEQ ID NO 122
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Phe(4-NO2)

<400> SEQUENCE: 122

Xaa Ala Ser Glu Lys Ile Phe Tyr Val
 1               5

<210> SEQ ID NO 123
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = O-methyl-Tyr

<400> SEQUENCE: 123

Xaa Ala Ser Glu Lys Ile Phe Tyr Val
 1               5

<210> SEQ ID NO 124
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = beta-(3-benzothienyl)Ala

<400> SEQUENCE: 124

Xaa Ala Ser Glu Lys Ile Phe Tyr Val
 1               5
```

-continued

<210> SEQ ID NO 125
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 125

Tyr Leu Ser Glu Lys Ile Phe Tyr Val
1 5

<210> SEQ ID NO 126
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 126

Tyr Val Ser Glu Lys Ile Phe Tyr Val
1 5

<210> SEQ ID NO 127
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 127

Tyr Met Ser Glu Lys Ile Phe Tyr Val
1 5

<210> SEQ ID NO 128
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 128

Tyr Ile Ser Glu Lys Ile Phe Tyr Val
1 5

<210> SEQ ID NO 129
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 129

Phe Leu Ser Glu Lys Ile Phe Tyr Val
1 5

<210> SEQ ID NO 130
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 130

Phe Val Ser Glu Lys Ile Phe Tyr Val
1 5

<210> SEQ ID NO 131
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 131

Phe Met Ser Glu Lys Ile Phe Tyr Val
 1               5

<210> SEQ ID NO 132
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 132

Phe Ile Ser Glu Lys Ile Phe Tyr Val
 1               5

<210> SEQ ID NO 133
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 133

Trp Leu Ser Glu Lys Ile Phe Tyr Val
 1               5

<210> SEQ ID NO 134
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 134

Trp Val Ser Glu Lys Ile Phe Tyr Val
1 5

<210> SEQ ID NO 135
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 135

Trp Met Ser Glu Lys Ile Phe Tyr Val
1 5

<210> SEQ ID NO 136
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 136

Trp Ile Ser Glu Lys Ile Phe Tyr Val
1 5

<210> SEQ ID NO 137

```
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = D-Lys

<400> SEQUENCE: 137

Xaa Lys Ser Glu Lys Ile Phe Tyr Val
 1               5

<210> SEQ ID NO 138
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = D-Lys

<400> SEQUENCE: 138

Xaa Val Ser Glu Lys Ile Phe Tyr Val
 1               5

<210> SEQ ID NO 139
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 139

Phe Val Ser Glu Lys Ile Phe Tyr Leu
 1               5

<210> SEQ ID NO 140
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 140

Phe Val Ser Glu Lys Ile Phe Tyr Ile
 1               5

<210> SEQ ID NO 141
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 141

Phe Val Ser Glu Lys Ile Phe Tyr Ala
 1               5

<210> SEQ ID NO 142
<211> LENGTH: 9
<212> TYPE: PRT
<213> ORGANISM: Artificial Sequence
<220> FEATURE:
<223> OTHER INFORMATION: T cell peptide epitope analog
```

```
<400> SEQUENCE: 142

Phe Val Ser Glu Lys Ile Phe Tyr Met
 1               5

<210> SEQ ID NO 143
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nle

<400> SEQUENCE: 143

Phe Val Ser Glu Lys Ile Phe Tyr Xaa
 1               5

<210> SEQ ID NO 144
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nva

<400> SEQUENCE: 144

Phe Val Ser Glu Lys Ile Phe Tyr Xaa
 1               5

<210> SEQ ID NO 145
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = MeVal

<400> SEQUENCE: 145

Phe Val Ser Glu Lys Ile Phe Tyr Xaa
 1               5

<210> SEQ ID NO 146
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Aib

<400> SEQUENCE: 146

Phe Val Ser Glu Lys Ile Phe Tyr Xaa
 1               5

<210> SEQ ID NO 147
<211> LENGTH: 9
<212> TYPE: PRT
<213> ORGANISM: Artificial Sequence
<220> FEATURE:
```

```
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Abu

<400> SEQUENCE: 147

Phe Val Ser Glu Lys Ile Phe Tyr Xaa
 1               5

<210> SEQ ID NO 148
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 148

Lys Val Ser Glu Lys Ile Phe Tyr Ile
 1               5

<210> SEQ ID NO 149
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 149

Lys Leu Ser Glu Lys Ile Phe Tyr Ile
 1               5

<210> SEQ ID NO 150
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = D-Ala
<220> FEATURE:
<221> NAME/KEY: VARIANT
<222> LOCATION: (9)...(9)
<223> OTHER INFORMATION: Xaa = D-Val

<400> SEQUENCE: 150

Lys Xaa Ser Glu Lys Ile Phe Tyr Xaa
 1               5

<210> SEQ ID NO 151
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 151

Lys Ala Ser Glu Lys Ile Phe Tyr Ile
 1               5

<210> SEQ ID NO 152
<211> LENGTH: 9
<212> TYPE: PRT
<213> ORGANISM: Artificial Sequence
<220> FEATURE:
<223> OTHER INFORMATION: T cell peptide epitope analog
```

```
<400> SEQUENCE: 152

Phe Val Ser Asp Lys Ile Phe Tyr Val
1               5

<210> SEQ ID NO 153
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 153

Phe Val Ser Asn Lys Ile Phe Tyr Val
1               5

<210> SEQ ID NO 154
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 154

Phe Val Ser Ser Lys Ile Phe Tyr Val
1               5

<210> SEQ ID NO 155
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 155

Phe Val Ser Thr Lys Ile Phe Tyr Val
1               5

<210> SEQ ID NO 156
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 156

Phe Val Ser Gln Lys Ile Phe Tyr Val
1               5

<210> SEQ ID NO 157
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (4)...(4)
<223> OTHER INFORMATION: Xaa = Nle

<400> SEQUENCE: 157

Phe Val Ser Xaa Lys Ile Phe Tyr Val
1               5

<210> SEQ ID NO 158
<211> LENGTH: 9
<212> TYPE: PRT
<213> ORGANISM: Artificial Sequence
```

```
<220> FEATURE:
<223> OTHER INFORMATION: T cell peptide epitope analog
<220> FEATURE:
<221> NAME/KEY: VARIANT
<222> LOCATION: (4)...(4)
<223> OTHER INFORMATION: Xaa = Nva

<400> SEQUENCE: 158

Phe Val Ser Xaa Lys Ile Phe Tyr Val
 1               5

<210> SEQ ID NO 159
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 159

Phe Val Ser Glu Lys Leu Phe Tyr Val
 1               5

<210> SEQ ID NO 160
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 160

Phe Val Ser Glu Lys Val Phe Tyr Val
 1               5

<210> SEQ ID NO 161
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 161

Phe Val Ser Glu Lys Met Phe Tyr Val
 1               5

<210> SEQ ID NO 162
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (6)...(6)
<223> OTHER INFORMATION: Xaa = Nle

<400> SEQUENCE: 162

Phe Val Ser Glu Lys Xaa Phe Tyr Val
 1               5

<210> SEQ ID NO 163
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (6)...(6)
<223> OTHER INFORMATION: Xaa = Nva
```

-continued

<400> SEQUENCE: 163

Phe Val Ser Glu Lys Xaa Phe Tyr Val
1 5

<210> SEQ ID NO 164
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 164

Phe Val Ser Glu Lys Ile Phe Thr Val
1 5

<210> SEQ ID NO 165
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 165

Phe Val Ser Glu Lys Ile Phe Phe Val
1 5

<210> SEQ ID NO 166
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 166

Phe Val Ser Glu Lys Ile Phe Ser Val
1 5

<210> SEQ ID NO 167
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (8)...(8)
<223> OTHER INFORMATION: Xaa = Phe4-F

<400> SEQUENCE: 167

Phe Val Ser Glu Lys Ile Phe Xaa Val
1 5

<210> SEQ ID NO 168
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (8)...(8)
<223> OTHER INFORMATION: Xaa = Phg

<400> SEQUENCE: 168

Phe Val Ser Glu Lys Ile Phe Xaa Val
1 5

```
<210> SEQ ID NO 169
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 169

Phe Val Ser Glu Lys Leu Phe Thr Val
 1               5

<210> SEQ ID NO 170
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 170

Phe Val Ser Glu Lys Leu Phe Ser Val
 1               5

<210> SEQ ID NO 171
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 171

Phe Val Ser Glu Lys Leu Phe Thr Ala
 1               5

<210> SEQ ID NO 172
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 172

Phe Val Ser Glu Lys Leu Phe Ser Ala
 1               5

<210> SEQ ID NO 173
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: AMIDATION
<222> LOCATION: (9)...(9)
<223> OTHER INFORMATION: NH2 on Val

<400> SEQUENCE: 173

Lys Ala Ser Glu Lys Ile Phe Tyr Val
 1               5

<210> SEQ ID NO 174
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: AMIDATION
<222> LOCATION: (9)...(9)
```

```
<223> OTHER INFORMATION: NH2 on Val

<400> SEQUENCE: 174

Lys Leu Ser Glu Lys Ile Phe Tyr Val
 1               5

<210> SEQ ID NO 175
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: AMIDATION
<222> LOCATION: (9)...(9)
<223> OTHER INFORMATION: NH2 on Val

<400> SEQUENCE: 175

Lys Val Ser Glu Lys Ile Phe Tyr Val
 1               5

<210> SEQ ID NO 176
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = MeLeu

<400> SEQUENCE: 176

Phe Val Ser Glu Lys Ile Phe Tyr Xaa
 1               5

<210> SEQ ID NO 177
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 177

Lys Ala Ser Glu Lys Ile Phe Tyr Val Tyr
 1               5                  10

<210> SEQ ID NO 178
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 178

Lys Ala Ser Glu Lys Ile Phe Tyr Val Ile
 1               5                  10

<210> SEQ ID NO 179
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 179

Lys Ala Ser Glu Lys Ile Phe Tyr Val Leu
 1               5                  10
```

-continued

```
<210> SEQ ID NO 180
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 180

Lys Ala Ser Glu Lys Ile Phe Tyr Val Val
1               5                   10

<210> SEQ ID NO 181
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nle

<400> SEQUENCE: 181

Lys Ala Ser Glu Lys Ile Phe Tyr Val Xaa
1               5                   10

<210> SEQ ID NO 182
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 182

Lys Ala Ser Glu Lys Ile Phe Tyr Val Xaa
1               5                   10

<210> SEQ ID NO 183
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 183

Lys Val Ser Glu Lys Ile Phe Tyr Val Ile
1               5                   10

<210> SEQ ID NO 184
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 184

Lys Leu Ser Glu Lys Ile Phe Tyr Val Ile
1               5                   10

<210> SEQ ID NO 185
<211> LENGTH: 10
<212> TYPE: PRT
<213> ORGANISM: Artificial Sequence
```

```
<220> FEATURE:
<223> OTHER INFORMATION: T cell peptide epitope analog

<400> SEQUENCE: 185

Lys Val Ser Glu Lys Ile Phe Tyr Val Leu
1               5                   10

<210> SEQ ID NO 186
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 186

Lys Leu Ser Glu Lys Ile Phe Tyr Val Leu
1               5                   10

<210> SEQ ID NO 187
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 187

Lys Val Ser Glu Lys Ile Phe Tyr Val Val
1               5                   10

<210> SEQ ID NO 188
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 188

Lys Leu Ser Glu Lys Ile Phe Tyr Val Val
1               5                   10

<210> SEQ ID NO 189
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nle

<400> SEQUENCE: 189

Lys Val Ser Glu Lys Ile Phe Tyr Val Xaa
1               5                   10

<210> SEQ ID NO 190
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nle

<400> SEQUENCE: 190

Lys Leu Ser Glu Lys Ile Phe Tyr Val Xaa
```

```
<210> SEQ ID NO 191
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 191

Lys Val Ser Glu Lys Ile Phe Tyr Val Xaa
 1               5                  10

<210> SEQ ID NO 192
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 192

Lys Leu Ser Glu Lys Ile Phe Tyr Val Xaa
 1               5                  10

<210> SEQ ID NO 193
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 193

Lys Val Ser Glu Lys Ile Phe Tyr Ile Ile
 1               5                  10

<210> SEQ ID NO 194
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 194

Lys Leu Ser Glu Lys Ile Phe Tyr Ile Ile
 1               5                  10

<210> SEQ ID NO 195
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 195

Lys Ala Ser Glu Lys Ile Phe Tyr Ile Ile
 1               5                  10

<210> SEQ ID NO 196
<211> LENGTH: 150
<212> TYPE: PRT
```

<213> ORGANISM: Artificial Sequence
<220> FEATURE:
<223> OTHER INFORMATION: Amino acid sequence encoded by plasmid pCTLR2

<400> SEQUENCE: 196

```
Met Ala Leu Gln Ser Leu Leu Gln His Leu Ile Gly Leu Ser Asn Leu
 1               5                  10                  15

Thr His Val Leu Tyr Pro Val Pro Leu Glu Ser Tyr Glu Asp Ile His
            20                  25                  30

Gly Thr Leu His Leu Glu Arg Leu Ala Tyr Leu His Ala Arg Leu Arg
        35                  40                  45

Glu Leu Leu Cys Glu Leu Gly Arg Pro Ser Met Val Trp Leu Ser Ala
 50                  55                  60

Asn Pro Cys Pro His Cys Gly Asp Arg Thr Phe Tyr Asp Pro Glu Pro
 65                  70                  75                  80

Ile Leu Cys Pro Cys Phe Met Pro Asn Lys Arg Ser Leu Leu Gln His
                85                  90                  95

Leu Ile Gly Leu Gly Asp Ala Ala Tyr Ser Leu Leu Gln His Leu Ile
               100                 105                 110

Gly Leu Ile Ser Pro Glu Lys Glu Gln Tyr Ile Ala Ser Leu Leu
           115                 120                 125

Gln His Leu Ile Gly Leu Lys Arg Pro Ser Ile Lys Arg Ser Leu Leu
130                 135                 140

Gln His Leu Ile Gly Leu
145                 150
```

<210> SEQ ID NO 197
<211> LENGTH: 11
<212> TYPE: PRT
<213> ORGANISM: Artificial Sequence
<220> FEATURE:
<223> OTHER INFORMATION: Amino acid sequence encoded by plasmid pCTLR2

<400> SEQUENCE: 197

```
Ile Ser Pro Glu Lys Glu Glu Gln Tyr Ile Ala
 1               5                  10
```

<210> SEQ ID NO 198
<211> LENGTH: 8
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 198

```
Ile Xaa Gly Val Leu Val Gly Val
 1               5
```

<210> SEQ ID NO 199
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = D-Leu
<220> FEATURE:
<221> NAME/KEY: VARIANT

```
<222> LOCATION: (9)...(9)
<223> OTHER INFORMATION: Xaa = D-Val

<400> SEQUENCE: 199

Lys Xaa Ser Glu Lys Ile Phe Tyr Xaa
 1               5

<210> SEQ ID NO 200
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = D-Val
<220> FEATURE:
<221> NAME/KEY: VARIANT
<222> LOCATION: (9)...(9)
<223> OTHER INFORMATION: Xaa = D-Val

<400> SEQUENCE: 200

Lys Xaa Ser Glu Lys Ile Phe Tyr Xaa
 1               5

<210> SEQ ID NO 201
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 201

Tyr Leu Leu Met Trp Ile Thr Gln Cys
 1               5

<210> SEQ ID NO 202
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 202

Phe Leu Leu Met Trp Ile Thr Gln Cys
 1               5

<210> SEQ ID NO 203
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 203

Lys Leu Leu Met Trp Ile Thr Gln Cys
 1               5

<210> SEQ ID NO 204
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 204

Phe Val Leu Met Trp Ile Thr Gln Cys
```

-continued 1 5

<210> SEQ ID NO 205
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 205

Phe Ile Leu Met Trp Ile Thr Gln Cys
1 5

<210> SEQ ID NO 206
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 206

Tyr Val Leu Met Trp Ile Thr Gln Cys
1 5

<210> SEQ ID NO 207
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 207

Tyr Ile Leu Met Trp Ile Thr Gln Cys
1 5

<210> SEQ ID NO 208
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 208

Tyr Leu Leu Met Trp Ile Thr Gln Val
1 5

<210> SEQ ID NO 209
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 209

Tyr Leu Leu Met Trp Ile Thr Gln Leu
1 5

<210> SEQ ID NO 210
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 210

Tyr Leu Leu Met Trp Ile Thr Gln Ala
1 5

```
<210> SEQ ID NO 211
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 211

Tyr Leu Leu Met Trp Ile Thr Gln Ile
 1               5

<210> SEQ ID NO 212
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 212

Phe Leu Leu Met Trp Ile Thr Gln Val
 1               5

<210> SEQ ID NO 213
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 213

Phe Leu Leu Met Trp Ile Thr Gln Leu
 1               5

<210> SEQ ID NO 214
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 214

Phe Leu Leu Met Trp Ile Thr Gln Ala
 1               5

<210> SEQ ID NO 215
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 215

Phe Leu Leu Met Trp Ile Thr Gln Ile
 1               5

<210> SEQ ID NO 216
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 216

Lys Leu Leu Met Trp Ile Thr Gln Val
 1               5
```

```
<210> SEQ ID NO 217
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 217

Lys Leu Leu Met Trp Ile Thr Gln Leu
 1               5

<210> SEQ ID NO 218
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 218

Lys Leu Leu Met Trp Ile Thr Gln Ala
 1               5

<210> SEQ ID NO 219
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 219

Lys Leu Leu Met Trp Ile Thr Gln Ile
 1               5

<210> SEQ ID NO 220
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Abu

<400> SEQUENCE: 220

Tyr Leu Leu Met Trp Ile Thr Gln Xaa
 1               5

<210> SEQ ID NO 221
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nva

<400> SEQUENCE: 221

Tyr Leu Leu Met Trp Ile Thr Gln Xaa
 1               5

<210> SEQ ID NO 222
<211> LENGTH: 9
<212> TYPE: PRT
<213> ORGANISM: Artificial Sequence
<220> FEATURE:
```

```
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nle

<400> SEQUENCE: 222

Tyr Leu Leu Met Trp Ile Thr Gln Xaa
1               5

<210> SEQ ID NO 223
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 223

Tyr Val Leu Met Trp Ile Thr Gln Val
1               5

<210> SEQ ID NO 224
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 224

Tyr Val Leu Met Trp Ile Thr Gln Leu
1               5

<210> SEQ ID NO 225
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 225

Tyr Val Leu Met Trp Ile Thr Gln Ala
1               5

<210> SEQ ID NO 226
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 226

Tyr Val Leu Met Trp Ile Thr Gln Ile
1               5

<210> SEQ ID NO 227
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 227

Tyr Ile Leu Met Trp Ile Thr Gln Val
1               5

<210> SEQ ID NO 228
<211> LENGTH: 9
```

-continued

<212> TYPE: PRT
<213> ORGANISM: Artificial Sequence
<220> FEATURE:
<223> OTHER INFORMATION: T cell peptide epitope analog

<400> SEQUENCE: 228

Tyr Ile Leu Met Trp Ile Thr Gln Leu
1               5

<210> SEQ ID NO 229
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 229

Tyr Ile Leu Met Trp Ile Thr Gln Ala
1               5

<210> SEQ ID NO 230
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 230

Tyr Ile Leu Met Trp Ile Thr Gln Ile
1               5

<210> SEQ ID NO 231
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 231

Phe Val Leu Met Trp Ile Thr Gln Val
1               5

<210> SEQ ID NO 232
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 232

Phe Val Leu Met Trp Ile Thr Gln Leu
1               5

<210> SEQ ID NO 233
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 233

Phe Val Leu Met Trp Ile Thr Gln Ala
1               5

<210> SEQ ID NO 234
<211> LENGTH: 9
<212> TYPE: PRT

```
<213> ORGANISM: Artificial Sequence
<220> FEATURE:
<223> OTHER INFORMATION: T cell peptide epitope analog

<400> SEQUENCE: 234

Phe Val Leu Met Trp Ile Thr Gln Ile
1               5

<210> SEQ ID NO 235
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 235

Phe Ile Leu Met Trp Ile Thr Gln Val
1               5

<210> SEQ ID NO 236
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 236

Phe Ile Leu Met Trp Ile Thr Gln Leu
1               5

<210> SEQ ID NO 237
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 237

Phe Ile Leu Met Trp Ile Thr Gln Ala
1               5

<210> SEQ ID NO 238
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 238

Phe Ile Leu Met Trp Ile Thr Gln Ile
1               5

<210> SEQ ID NO 239
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 239

Tyr Leu Leu Ala Trp Ile Thr Gln Val
1               5

<210> SEQ ID NO 240
<211> LENGTH: 9
<212> TYPE: PRT
<213> ORGANISM: Artificial Sequence
```

-continued

<220> FEATURE:
<223> OTHER INFORMATION: T cell peptide epitope analog

<400> SEQUENCE: 240

Tyr Leu Leu Val Trp Ile Thr Gln Val
1 5

<210> SEQ ID NO 241
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 241

Tyr Leu Leu Ile Trp Ile Thr Gln Val
1 5

<210> SEQ ID NO 242
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 242

Tyr Leu Leu Leu Trp Ile Thr Gln Val
1 5

<210> SEQ ID NO 243
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 243

Tyr Leu Leu Asn Trp Ile Thr Gln Val
1 5

<210> SEQ ID NO 244
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 244

Tyr Leu Leu Asn Trp Ile Thr Gln Val
1 5

<210> SEQ ID NO 245
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 245

Tyr Leu Leu Met Trp Ala Thr Gln Val
1 5

<210> SEQ ID NO 246
<211> LENGTH: 9
<212> TYPE: PRT
<213> ORGANISM: Artificial Sequence
<220> FEATURE:

-continued

<223> OTHER INFORMATION: T cell peptide epitope analog

<400> SEQUENCE: 246

Tyr Leu Leu Met Trp Leu Thr Gln Val
1               5

<210> SEQ ID NO 247
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 247

Tyr Leu Leu Met Trp Val Thr Gln Val
1               5

<210> SEQ ID NO 248
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 248

Tyr Leu Leu Met Trp Asn Thr Gln Val
1               5

<210> SEQ ID NO 249
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 249

Tyr Leu Leu Met Trp Ile Thr Ala Val
1               5

<210> SEQ ID NO 250
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 250

Tyr Leu Leu Met Trp Ile Thr Glu Val
1               5

<210> SEQ ID NO 251
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 251

Tyr Leu Leu Met Trp Ile Thr Asp Val
1               5

<210> SEQ ID NO 252
<211> LENGTH: 9
<212> TYPE: PRT
<213> ORGANISM: Artificial Sequence
<220> FEATURE:
<223> OTHER INFORMATION: T cell peptide epitope analog

```
<400> SEQUENCE: 252

Tyr Leu Leu Met Trp Ile Thr Asn Val
1               5

<210> SEQ ID NO 253
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 253

Tyr Leu Leu Met Trp Ile Thr Thr Val
1               5

<210> SEQ ID NO 254
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 254

Tyr Leu Leu Met Trp Ile Thr Ser Val
1               5

<210> SEQ ID NO 255
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: AMIDATION
<222> LOCATION: (9)...(9)
<223> OTHER INFORMATION: NH2 on Val

<400> SEQUENCE: 255

Tyr Leu Leu Met Trp Ile Thr Gln Val
1               5

<210> SEQ ID NO 256
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: AMIDATION
<222> LOCATION: (9)...(9)
<223> OTHER INFORMATION: NH2 on Leu

<400> SEQUENCE: 256

Tyr Leu Leu Met Trp Ile Thr Gln Leu
1               5

<210> SEQ ID NO 257
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: AMIDATION
<222> LOCATION: (9)...(9)
<223> OTHER INFORMATION: NH2 on Ala

<400> SEQUENCE: 257
```

-continued

Tyr Leu Leu Met Trp Ile Thr Gln Ala
1 5

<210> SEQ ID NO 258
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 258

Ser Leu Leu Met Trp Ile Thr Gln Val
1 5

<210> SEQ ID NO 259
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 259

Ser Leu Leu Met Trp Ile Thr Gln Leu
1 5

<210> SEQ ID NO 260
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 260

Ser Leu Leu Met Trp Ile Thr Gln Ala
1 5

<210> SEQ ID NO 261
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 261

Ser Leu Leu Met Trp Ile Thr Gln Ile
1 5

<210> SEQ ID NO 262
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 262

Ser Leu Leu Met Trp Ile Thr Gln Cys Phe
1 5 10

<210> SEQ ID NO 263
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 263

```
Ser Leu Leu Met Trp Ile Thr Gln Cys Leu
1               5                   10

<210> SEQ ID NO 264
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 264

Tyr Leu Leu Met Trp Ile Thr Gln Val Leu
1               5                   10

<210> SEQ ID NO 265
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 265

Tyr Leu Leu Met Trp Ile Thr Gln Val Ile
1               5                   10

<210> SEQ ID NO 266
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 266

Tyr Leu Leu Met Trp Ile Thr Gln Val Val
1               5                   10

<210> SEQ ID NO 267
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nle

<400> SEQUENCE: 267

Tyr Leu Leu Met Trp Ile Thr Gln Val Xaa
1               5                   10

<210> SEQ ID NO 268
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 268

Tyr Leu Leu Met Trp Ile Thr Gln Val Xaa
1               5                   10

<210> SEQ ID NO 269
<211> LENGTH: 9
```

```
<212> TYPE: PRT
<213> ORGANISM: Artificial Sequence
<220> FEATURE:
<223> OTHER INFORMATION: T cell peptide epitope analog

<400> SEQUENCE: 269

Ser Val Leu Met Trp Ile Thr Gln Leu
 1               5

<210> SEQ ID NO 270
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 270

Ser Val Leu Met Trp Ile Thr Gln Ile
 1               5

<210> SEQ ID NO 271
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 271

Ser Val Leu Met Trp Ile Thr Gln Val
 1               5

<210> SEQ ID NO 272
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 272

Ser Ile Leu Met Trp Ile Thr Gln Leu
 1               5

<210> SEQ ID NO 273
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 273

Tyr Xaa Leu Met Trp Ile Thr Gln Val
 1               5

<210> SEQ ID NO 274
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 274

Trp Val Leu Met Trp Ile Thr Gln Val
 1               5
```

```
<210> SEQ ID NO 275
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 275

Ser Val Leu Met Trp Ile Thr Gln Ala
 1               5

<210> SEQ ID NO 276
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 276

Ser Val Leu Met Trp Ile Thr Gln Cys
 1               5

<210> SEQ ID NO 277
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 277

Thr Val Leu Met Trp Ile Thr Gln Val
 1               5

<210> SEQ ID NO 278
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 278

Tyr Xaa Leu Met Trp Ile Thr Gln Val
 1               5

<210> SEQ ID NO 279
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 279

Ser Ile Leu Met Trp Ile Thr Gln Cys
 1               5

<210> SEQ ID NO 280
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 280
```

Ser Ile Leu Met Trp Ile Thr Gln Ala
1               5

<210> SEQ ID NO 281
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 281

Ser Ile Leu Met Trp Ile Thr Gln Val
1               5

<210> SEQ ID NO 282
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 282

Ser Leu Leu Gln His Leu Ile Gly Leu
1               5

<210> SEQ ID NO 283
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 283

Ser Val Leu Gln His Leu Ile Gly Leu
1               5

<210> SEQ ID NO 284
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 284

Ser Met Leu Gln His Leu Ile Gly Leu
1               5

<210> SEQ ID NO 285
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 285

Ser Ile Leu Gln His Leu Ile Gly Leu
1               5

<210> SEQ ID NO 286
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

```
<400> SEQUENCE: 286

Ser Xaa Leu Gln His Leu Ile Gly Leu
1               5

<210> SEQ ID NO 287
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 287

Ser Xaa Leu Gln His Leu Ile Gly Leu
1               5

<210> SEQ ID NO 288
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Abu

<400> SEQUENCE: 288

Ser Xaa Leu Gln His Leu Ile Gly Leu
1               5

<210> SEQ ID NO 289
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 289

Lys Leu Leu Gln His Leu Ile Gly Leu
1               5

<210> SEQ ID NO 290
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 290

Phe Leu Leu Gln His Leu Ile Gly Leu
1               5

<210> SEQ ID NO 291
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 291

Tyr Leu Leu Gln His Leu Ile Gly Leu
1               5
```

```
<210> SEQ ID NO 292
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 292

Thr Leu Leu Gln His Leu Ile Gly Leu
 1               5

<210> SEQ ID NO 293
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Orn

<400> SEQUENCE: 293

Xaa Leu Leu Gln His Leu Ile Gly Leu
 1               5

<210> SEQ ID NO 294
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Hse

<400> SEQUENCE: 294

Xaa Leu Leu Gln His Leu Ile Gly Leu
 1               5

<210> SEQ ID NO 295
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 295

Ser Leu Leu Gln His Leu Ile Gly Val
 1               5

<210> SEQ ID NO 296
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 296

Ser Leu Leu Gln His Leu Ile Gly Ile
 1               5

<210> SEQ ID NO 297
<211> LENGTH: 9
<212> TYPE: PRT
<213> ORGANISM: Artificial Sequence
<220> FEATURE:
```

```
<223> OTHER INFORMATION: T cell peptide epitope analog

<400> SEQUENCE: 297

Ser Leu Leu Gln His Leu Ile Gly Ala
 1               5

```
<213> ORGANISM: Artificial Sequence
<220> FEATURE:
<223> OTHER INFORMATION: T cell peptide epitope analog

<400> SEQUENCE: 302

Ser Leu Leu Gln His Leu Ile Ala Leu
 1               5

<210> SEQ ID NO 303
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 303

Ser Leu Leu Gln His Leu Ile Ser Leu
 1               5

<210> SEQ ID NO 304
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (8)...(8)
<223> OTHER INFORMATION: Xaa = Sar

<400> SEQUENCE: 304

Ser Leu Leu Gln His Leu Ile Xaa Leu
 1               5

<210> SEQ ID NO 305
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (3)...(3)
<223> OTHER INFORMATION: Xaa = Nle

<400> SEQUENCE: 305

Ser Leu Xaa Gln His Leu Ile Gly Leu
 1               5

<210> SEQ ID NO 306
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (3)...(3)
<223> OTHER INFORMATION: Xaa = Nva

<400> SEQUENCE: 306

Ser Leu Xaa Gln His Leu Ile Gly Leu
 1               5

<210> SEQ ID NO 307
<211> LENGTH: 9
<212> TYPE: PRT
<213> ORGANISM: Artificial Sequence
<220> FEATURE:
```

```
<223> OTHER INFORMATION: T cell peptide epitope analog
<220> FEATURE:
<221> NAME/KEY: VARIANT
<222> LOCATION: (3)...(3)
<223> OTHER INFORMATION: Xaa = Abu

<400> SEQUENCE: 307

Ser Leu Xaa Gln His Leu Ile Gly Leu
 1               5

<210> SEQ ID NO 308
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (6)...(6)
<223> OTHER INFORMATION: Xaa = Nle

<400> SEQUENCE: 308

Ser Leu Leu Gln His Xaa Ile Gly Leu
 1               5

<210> SEQ ID NO 309
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (6)...(6)
<223> OTHER INFORMATION: Xaa = Nva

<400> SEQUENCE: 309

Ser Leu Leu Gln His Xaa Ile Gly Leu
 1               5

<210> SEQ ID NO 310
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (6)...(6)
<223> OTHER INFORMATION: Xaa = Abu

<400> SEQUENCE: 310

Ser Leu Leu Gln His Xaa Ile Gly Leu
 1               5

<210> SEQ ID NO 311
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 311

Phe Xaa Leu Gln His Leu Ile Gly Leu
 1               5
```

-continued

<210> SEQ ID NO 312
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 312

Tyr Xaa Leu Gln His Leu Ile Gly Leu
1 5

<210> SEQ ID NO 313
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 313

Thr Xaa Leu Gln His Leu Ile Gly Leu
1 5

<210> SEQ ID NO 314
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Hse
<220> FEATURE:
<221> NAME/KEY: VARIANT
<222> LOCATION: (2)...(2)
<223> OTHER INFORMATION: Xaa = Nva

<400> SEQUENCE: 314

Xaa Xaa Leu Gln His Leu Ile Gly Leu
1 5

<210> SEQ ID NO 315
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Orn
<220> FEATURE:
<221> NAME/KEY: VARIANT
<222> LOCATION: (2)...(2)
<223> OTHER INFORMATION: Xaa = Nva

<400> SEQUENCE: 315

Xaa Xaa Leu Gln His Leu Ile Gly Leu
1 5

<210> SEQ ID NO 316
<211> LENGTH: 9

```
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 316

Phe Xaa Leu Gln His Leu Ile Gly Leu
 1               5

<210> SEQ ID NO 317
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 317

Tyr Xaa Leu Gln His Leu Ile Gly Leu
 1               5

<210> SEQ ID NO 318
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 318

Thr Xaa Leu Gln His Leu Ile Gly Leu
 1               5

<210> SEQ ID NO 319
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Hse
<220> FEATURE:
<221> NAME/KEY: VARIANT
<222> LOCATION: (2)...(2)
<223> OTHER INFORMATION: Xaa = Nle

<400> SEQUENCE: 319

Xaa Xaa Leu Gln His Leu Ile Gly Leu
 1               5

<210> SEQ ID NO 320
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
```

```
<223> OTHER INFORMATION: Xaa = Orn
<220> FEATURE:
<221> NAME/KEY: VARIANT
<222> LOCATION: (2)...(2)
<223> OTHER INFORMATION: Xaa = Nle

<400> SEQUENCE: 320

Xaa Xaa Leu Gln His Leu Ile Gly Leu
 1               5

<210> SEQ ID NO 321
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 321

Phe Met Leu Gln His Leu Ile Gly Leu
 1               5

<210> SEQ ID NO 322
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 322

Tyr Met Leu Gln His Leu Ile Gly Leu
 1               5

<210> SEQ ID NO 323
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 323

Thr Met Leu Gln His Leu Ile Gly Leu
 1               5

<210> SEQ ID NO 324
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Hse

<400> SEQUENCE: 324

Xaa Met Leu Gln His Leu Ile Gly Leu
 1               5

<210> SEQ ID NO 325
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Orn
```

```
<400> SEQUENCE: 325

Xaa Met Leu Gln His Leu Ile Gly Leu
 1               5

<210> SEQ ID NO 326
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 326

Phe Ile Leu Gln His Leu Ile Gly Leu
 1               5

<210> SEQ ID NO 327
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 327

Tyr Ile Leu Gln His Leu Ile Gly Leu
 1               5

<210> SEQ ID NO 328
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 328

Thr Ile Leu Gln His Leu Ile Gly Leu
 1               5

<210> SEQ ID NO 329
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Hse

<400> SEQUENCE: 329

Xaa Ile Leu Gln His Leu Ile Gly Leu
 1               5

<210> SEQ ID NO 330
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Orn

<400> SEQUENCE: 330

Xaa Ile Leu Gln His Leu Ile Gly Leu
 1               5
```

```
<210> SEQ ID NO 331
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
<220> FEATURE:
<221> NAME/KEY: VARIANT
<222> LOCATION: (9)...(9)
<223> OTHER INFORMATION: Xaa = Nva

<400> SEQUENCE: 331

Ser Xaa Leu Gln His Leu Ile Gly Xaa
 1               5

<210> SEQ ID NO 332
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
<220> FEATURE:
<221> NAME/KEY: VARIANT
<222> LOCATION: (9)...(9)
<223> OTHER INFORMATION: Xaa = Nle

<400> SEQUENCE: 332

Ser Xaa Leu Gln His Leu Ile Gly Xaa
 1               5

<210> SEQ ID NO 333
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 333

Ser Xaa Leu Gln His Leu Ile Gly Val
 1               5

<210> SEQ ID NO 334
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle
<220> FEATURE:
<221> NAME/KEY: VARIANT
<222> LOCATION: (9)...(9)
<223> OTHER INFORMATION: Xaa = Nva

<400> SEQUENCE: 334

Ser Xaa Leu Gln His Leu Ile Gly Xaa
 1               5
```

```
<210> SEQ ID NO 335
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle
<220> FEATURE:
<221> NAME/KEY: VARIANT
<222> LOCATION: (9)...(9)
<223> OTHER INFORMATION: Xaa = Nle

<400> SEQUENCE: 335

Ser Xaa Leu Gln His Leu Ile Gly Xaa
 1               5

<210> SEQ ID NO 336
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 336

Ser Xaa Leu Gln His Leu Ile Gly Val
 1               5

<210> SEQ ID NO 337
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nva

<400> SEQUENCE: 337

Ser Met Leu Gln His Leu Ile Gly Xaa
 1               5

<210> SEQ ID NO 338
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nle

<400> SEQUENCE: 338

Ser Met Leu Gln His Leu Ile Gly Xaa
 1               5

<210> SEQ ID NO 339
<211> LENGTH: 9
<212> TYPE: PRT
<213> ORGANISM: Artificial Sequence
<220> FEATURE:
<223> OTHER INFORMATION: T cell peptide epitope analog
```

<400> SEQUENCE: 339

Ser Met Leu Gln His Leu Ile Gly Val
1               5

<210> SEQ ID NO 340
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 340

Lys Leu Leu Gln His Leu Ile Gly Val
1               5

<210> SEQ ID NO 341
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 341

Phe Leu Leu Gln His Leu Ile Gly Val
1               5

<210> SEQ ID NO 342
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 342

Tyr Leu Leu Gln His Leu Ile Gly Val
1               5

<210> SEQ ID NO 343
<211> LENGTH: 9
<212> TYPE: PRT
<213> ORGANISM: Artificial Sequence
<220> FEATURE:
<223> OTHER INFORMATION: T cell peptide epitope analog

<400> SEQUENCE: 343

Thr Leu Leu Gln His Leu Ile Gly Val
1               5

<210> SEQ ID NO 344
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Orn

<400> SEQUENCE: 344

Xaa Leu Leu Gln His Leu Ile Gly Val
1               5

<210> SEQ ID NO 345
<211> LENGTH: 9
<212> TYPE: PRT

```
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Hse

<400> SEQUENCE: 345

Xaa Leu Leu Gln His Leu Ile Gly Val
 1               5

<210> SEQ ID NO 346
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nle

<400> SEQUENCE: 346

Phe Leu Leu Gln His Leu Ile Gly Xaa
 1               5

<210> SEQ ID NO 347
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nle

<400> SEQUENCE: 347

Thr Leu Leu Gln His Leu Ile Gly Xaa
 1               5

<210> SEQ ID NO 348
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
<220> FEATURE:
<221> NAME/KEY: VARIANT
<222> LOCATION: (9)...(9)
<223> OTHER INFORMATION: Xaa = Nle

<400> SEQUENCE: 348

Phe Xaa Leu Gln His Leu Ile Gly Xaa
 1               5

<210> SEQ ID NO 349
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
```

```
<220> FEATURE:
<221> NAME/KEY: VARIANT
<222> LOCATION: (9)...(9)
<223> OTHER INFORMATION: Xaa = Nle

<400> SEQUENCE: 349

Thr Xaa Leu Leu Gln His Leu Ile Gly Xaa
 1               5                   10

<210> SEQ ID NO 350
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nle

<400> SEQUENCE: 350

Phe Met Leu Gln His Leu Ile Gly Xaa
 1               5

<210> SEQ ID NO 351
<211> LENGTH: 9
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (9)...(9)
<223> OTHER INFORMATION: Xaa = Nle

<400> SEQUENCE: 351

Thr Met Leu Gln His Leu Ile Gly Xaa
 1               5

<210> SEQ ID NO 352
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 352

Gly Leu Pro Ser Ile Pro Val His Pro Ile
 1               5                   10

<210> SEQ ID NO 353
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 353

Gly Met Pro Ser Ile Pro Val His Pro Ile
 1               5                   10

<210> SEQ ID NO 354
<211> LENGTH: 10
<212> TYPE: PRT
<213> ORGANISM: Artificial Sequence
<220> FEATURE:
<223> OTHER INFORMATION: Analog of MHC class I-restricted T cell epitope

<400> SEQUENCE: 354
```

```
Gly Gln Pro Ser Ile Pro Val His Pro Ile
1               5                   10

<210> SEQ ID NO 355
<211> LENGTH: 10
<212> TYPE: PRT
<213> ORGANISM: Artificial Sequence
<220> FEATURE:
<223> OTHER INFORMATION: Analog of MHC class I-restricted T cell epitope

<400> SEQUENCE: 355

Gly Val Pro Ser Ile Pro Val His Pro Ile
1               5                   10

<210> SEQ ID NO 356
<211> LENGTH: 10
<212> TYPE: PRT
<213> ORGANISM: Artificial Sequence
<220> FEATURE:
<223> OTHER INFORMATION: Analog of MHC class I-restricted T cell epitope

<400> SEQUENCE: 356

Gly Val Pro Ser Ile Pro Val His Pro Ile
1               5                   10

<210> SEQ ID NO 357
<211> LENGTH: 10
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: Xaa = Nva
<220> FEATURE:
<223> OTHER INFORMATION: T cell peptide epitope analog

<400> SEQUENCE: 357

Gly Xaa Pro Ser Ile Pro Val His Pro Ile
1               5                   10

<210> SEQ ID NO 358
<211> LENGTH: 10
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: Xaa = Nle
<220> FEATURE:
<223> OTHER INFORMATION: T cell peptide epitope analog

<400> SEQUENCE: 358

Gly Xaa Pro Ser Ile Pro Val His Pro Ile
1               5                   10

<210> SEQ ID NO 359
<211> LENGTH: 10
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: Xaa = Abu
<220> FEATURE:
<223> OTHER INFORMATION: T cell peptide epitope analog

<400> SEQUENCE: 359

Gly Xaa Pro Ser Ile Pro Val His Pro Ile
```

```
<210> SEQ ID NO 360
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 360

Ala Leu Pro Ser Ile Pro Val His Pro Ile
 1               5                  10

<210> SEQ ID NO 361
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 361

Ser Leu Pro Ser Ile Pro Val His Pro Ile
 1               5                  10

<210> SEQ ID NO 362
<211> LENGTH: 10
<212> TYPE: PRT
<213> ORGANISM: Artificial Sequence
<220> FEATURE:
<221> NAME/KEY: VARIANT
<222> LOCATION: (1)...(1)
<223> OTHER INFORMATION: Xaa = Sar
<220> FEATURE:
<223> OTHER INFORMATION: T cell peptide epitope analog

<400> SEQUENCE: 362

Xaa Leu Pro Ser Ile Pro Val His Pro Ile
 1               5                  10

<210> SEQ ID NO 363
<211> LENGTH: 10
<212> TYPE: PRT
<213> ORGANISM: Artificial Sequence
<220> FEATURE:
<221> NAME/KEY: VARIANT
<222> LOCATION: (1)...(1)
<223> OTHER INFORMATION: Xaa = Abu
<220> FEATURE:
<223> OTHER INFORMATION: T cell peptide epitope analog

<400> SEQUENCE: 363

Xaa Leu Pro Ser Ile Pro Val His Pro Ile
 1               5                  10

<210> SEQ ID NO 364
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 364

Gly Leu Pro Ser Ile Pro Val His Pro Val
 1               5                  10

<210> SEQ ID NO 365
<211> LENGTH: 10
<212> TYPE: PRT
```

```
<213> ORGANISM: Artificial Sequence
<220> FEATURE:
<223> OTHER INFORMATION: T cell peptide epitope analog

<400> SEQUENCE: 365

Gly Leu Pro Ser Ile Pro Val His Pro Leu
 1               5                  10

<210> SEQ ID NO 366
<211> LENGTH: 10
<212> TYPE: PRT
<213> ORGANISM: Artificial Sequence
<220> FEATURE:
<221> NAME/KEY: VARIANT
<222> LOCATION: (10)...(10)
<223> OTHER INFORMATION: Xaa = Nva
<220> FEATURE:
<223> OTHER INFORMATION: T cell peptide epitope analog

<400> SEQUENCE: 366

Gly Leu Pro Ser Ile Pro Val His Pro Xaa
 1               5                  10

<210> SEQ ID NO 367
<211> LENGTH: 10
<212> TYPE: PRT
<213> ORGANISM: Artificial Sequence
<220> FEATURE:
<221> NAME/KEY: VARIANT
<222> LOCATION: (10)...(10)
<223> OTHER INFORMATION: Xaa = Nle
<220> FEATURE:
<223> OTHER INFORMATION: T cell peptide epitope analog

<400> SEQUENCE: 367

Gly Leu Pro Ser Ile Pro Val His Pro Xaa
 1               5                  10

<210> SEQ ID NO 368
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 368

Gly Leu Pro Ser Ile Pro Val His Ala Ile
 1               5                  10

<210> SEQ ID NO 369
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 369

Gly Leu Pro Ser Ile Pro Val His Leu Ile
 1               5                  10

<210> SEQ ID NO 370
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 370
```

```
Gly Leu Pro Ser Ile Pro Val His Ser Ile
1               5                   10

<210> SEQ ID NO 371
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 371

Gly Leu Pro Ser Ile Pro Val His Thr Ile
1               5                   10

<210> SEQ ID NO 372
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 372

Gly Leu Trp Ser Ile Pro Val His Pro Ile
1               5                   10

<210> SEQ ID NO 373
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 373

Gly Leu Pro Ser Ile Pro Val His Pro Ile
1               5                   10

<210> SEQ ID NO 374
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
<220> FEATURE:
<221> NAME/KEY: VARIANT
<222> LOCATION: (10)...(10)
<223> OTHER INFORMATION: Xaa = Nle

<400> SEQUENCE: 374

Gly Xaa Pro Ser Ile Pro Val His Pro Xaa
1               5                   10

<210> SEQ ID NO 375
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle
<220> FEATURE:
<221> NAME/KEY: VARIANT
<222> LOCATION: (10)...(10)
<223> OTHER INFORMATION: Xaa = Nva
```

```
<400> SEQUENCE: 375

Gly Xaa Pro Ser Ile Pro Val His Pro Xaa
 1               5                  10

<210> SEQ ID NO 376
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
<220> FEATURE:
<221> NAME/KEY: VARIANT
<222> LOCATION: (10)...(10)
<223> OTHER INFORMATION: Xaa = Nva

<400> SEQUENCE: 376

Gly Xaa Pro Ser Ile Pro Val His Pro Xaa
 1               5                  10

<210> SEQ ID NO 377
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle
<220> FEATURE:
<221> NAME/KEY: VARIANT
<222> LOCATION: (10)...(10)
<223> OTHER INFORMATION: Xaa = Nle

<400> SEQUENCE: 377

Gly Xaa Pro Ser Ile Pro Val His Pro Xaa
 1               5                  10

<210> SEQ ID NO 378
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 378

Gly Xaa Pro Ser Ile Pro Val His Pro Val
 1               5                  10

<210> SEQ ID NO 379
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 379

Gly Xaa Pro Ser Ile Pro Val His Pro Val
```

-continued

```
1               5                   10

<210> SEQ ID NO 380
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 380

Gly Val Pro Ser Ile Pro Val His Pro Val
1               5                   10

<210> SEQ ID NO 381
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 381

Gly Ile Pro Ser Ile Pro Val His Pro Val
1               5                   10

<210> SEQ ID NO 382
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 382

Gly Val Pro Ser Ile Pro Val His Pro Xaa
1               5                   10

<210> SEQ ID NO 383
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 383

Gly Ile Pro Ser Ile Pro Val His Pro Xaa
1               5                   10

<210> SEQ ID NO 384
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 384

Ala Leu Pro Ser Ile Pro Val His Pro Val
1               5                   10

<210> SEQ ID NO 385
<211> LENGTH: 10
<212> TYPE: PRT
```

-continued

```
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 385

Ala Leu Pro Ser Ile Pro Val His Pro Xaa
 1               5                  10

<210> SEQ ID NO 386
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Abu

<400> SEQUENCE: 386

Xaa Leu Pro Ser Ile Pro Val His Pro Val
 1               5                  10

<210> SEQ ID NO 387
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (1)...(1)
<223> OTHER INFORMATION: Xaa = Abu
<220> FEATURE:
<221> NAME/KEY: VARIANT
<222> LOCATION: (10)...(10)
<223> OTHER INFORMATION: Xaa = Nva

<400> SEQUENCE: 387

Xaa Leu Pro Ser Ile Pro Val His Pro Xaa
 1               5                  10

<210> SEQ ID NO 388
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 388

Gly Leu Trp Ser Ile Pro Val His Pro Val
 1               5                  10

<210> SEQ ID NO 389
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 389

Gly Leu Trp Ser Ile Pro Val His Pro Xaa
```

-continued

```
<210> SEQ ID NO 390
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 390

Gly Xaa Trp Ser Ile Pro Val His Pro Ile
 1               5                  10

<210> SEQ ID NO 391
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 391

Gly Val Trp Ser Ile Pro Val His Pro Ile
 1               5                  10

<210> SEQ ID NO 392
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 392

Gly Xaa Trp Ser Ile Pro Val His Pro Ile
 1               5                  10

<210> SEQ ID NO 393
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 393

Gly Ile Trp Ser Ile Pro Val His Pro Ile
 1               5                  10

<210> SEQ ID NO 394
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 394

Gly Leu Pro Ser Ile Pro Val His Pro Ile
 1               5                  10

<210> SEQ ID NO 395
<211> LENGTH: 10
<212> TYPE: PRT
```

```
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 395

Ala Xaa Trp Ser Ile Pro Val His Pro Ile
 1               5                  10

<210> SEQ ID NO 396
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 396

Ala Val Trp Ser Ile Pro Val His Pro Ile
 1               5                  10

<210> SEQ ID NO 397
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nle

<400> SEQUENCE: 397

Ala Xaa Trp Ser Ile Pro Val His Pro Ile
 1               5                  10

<210> SEQ ID NO 398
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 398

Ala Ile Trp Ser Ile Pro Val His Pro Ile
 1               5                  10

<210> SEQ ID NO 399
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 399

Ala Xaa Pro Ser Ile Pro Val His Pro Val
 1               5                  10

<210> SEQ ID NO 400
<211> LENGTH: 10
<212> TYPE: PRT
<213> ORGANISM: Artificial Sequence
<220> FEATURE:
```

<223> OTHER INFORMATION: T cell peptide epitope analog

<400> SEQUENCE: 400

Ala Val Pro Ser Ile Pro Val His Pro Val
1               5                   10

<210> SEQ ID NO 401
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 401

Ala Val Pro Ser Ile Pro Val His Pro Xaa
1               5                   10

<210> SEQ ID NO 402
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva

<400> SEQUENCE: 402

Gly Xaa Trp Ser Ile Pro Val His Pro Val
1               5                   10

<210> SEQ ID NO 403
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 403

Gly Val Trp Ser Ile Pro Val His Pro Val
1               5                   10

<210> SEQ ID NO 404
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (2)...(2)
<223> OTHER INFORMATION: Xaa = Nva
<220> FEATURE:
<221> NAME/KEY: VARIANT
<222> LOCATION: (10)...(10)
<223> OTHER INFORMATION: Xaa = Nva

<400> SEQUENCE: 404

Gly Xaa Trp Ser Ile Pro Val His Pro Xaa
1               5                   10

<210> SEQ ID NO 405
<211> LENGTH: 10
<212> TYPE: PRT

```
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 405

Gly Val Trp Ser Ile Pro Val His Pro Xaa
 1               5                  10

<210> SEQ ID NO 406
<211> LENGTH: 10
<212> TYPE: PRT
<213> ORGANISM: Artificial Sequence
<220> FEATURE:
<223> OTHER INFORMATION: T cell peptide epitope analog

<400> SEQUENCE: 406

Ala Leu Trp Ser Ile Pro Val His Pro Val
 1               5                  10

<210> SEQ ID NO 407
<211> LENGTH: 10
<212> TYPE: PRT
<213> ORGANISM: Artificial Sequence
<220> FEATURE:
<223> OTHER INFORMATION: T cell peptide epitope analog
<220> FEATURE:
<221> NAME/KEY: VARIANT
<222> LOCATION: (10)...(10)
<223> OTHER INFORMATION: Xaa = Nva

<400> SEQUENCE: 407

Ala Leu Trp Ser Ile Pro Val His Pro Xaa
 1               5                  10
```